United States Patent
Cheng et al.

(10) Patent No.: US 8,791,131 B2
(45) Date of Patent: Jul. 29, 2014

(54) IMIDAZO[1,5]NAPHTHYRIDINE COMPOUNDS, THEIR PHARMACEUTICAL USE AND COMPOSITIONS

(75) Inventors: Hengmiao Cheng, San Diego, CA (US); Ted William Johnson, San Diego, CA (US); Jacqui Elizabeth Hoffman, San Diego, CA (US); Lisa Chen Guo, San Diego, CA (US); Zhengyu Liu, Carlsbad, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/121,900

(22) PCT Filed: Sep. 18, 2009

(86) PCT No.: PCT/IB2009/054103
§ 371 (c)(1),
(2), (4) Date: Mar. 30, 2011

(87) PCT Pub. No.: WO2010/038165
PCT Pub. Date: Apr. 8, 2010

(65) Prior Publication Data
US 2011/0190326 A1 Aug. 4, 2011

Related U.S. Application Data

(60) Provisional application No. 61/101,564, filed on Sep. 30, 2008, provisional application No. 61/187,077, filed on Jun. 15, 2009.

(51) Int. Cl.
| | | |
|---|---|---|
| A61K 31/4709 | (2006.01) | |
| A61K 31/506 | (2006.01) | |
| A61P 35/00 | (2006.01) | |
| C07D 471/22 | (2006.01) | |

(52) U.S. Cl.
USPC .............. 514/274; 514/293; 544/316; 546/82

(58) Field of Classification Search
None
See application file for complete search history.

(56) References Cited

FOREIGN PATENT DOCUMENTS

| WO | WO 2006/122806 | 11/2006 |
| WO | WO 2007/106854 | 9/2007 |

OTHER PUBLICATIONS

Richard B. Silverman, The Organic Chemistry of Drug Design and Drug Action, Chapter 2: Drug Discovery, Design, and Development, Academic Press, p. 5-51 (1992).*
Sabatini, et al., "RAFT1: A Mammalian Protein That Binds to FKBP12 in a Rapamycin-Dependent Fashion and Is Homologous to Yeast TORs," *Cell*, 1994, 35-43, vol. 78.
Samuels, et al., "High Frequency of Mutations of the *PIK3CA* Gene in Human Cancers," *Science*, 2004, 554, vol. 304.
Sarbassov, et al., "Rictor, a Novel Binding Partner of mTOR, Defines a Rapamycin-Insensitive and Raptor-Independent Pathway that Regulates the Cytoskeleton", *Current Biology*, 2004, 1296-1302, vol. 14.
Schmelzle, et al., "TOR, a Central Controller of Cell Growth," *Cell*, 2000, 253-262, vol. 103.
Shaw, et al., "Ras, PI(3)K and mTOR Signalling Controls Tumour Cell Growth", *Nature*, 2006, 424-430, vol. 441.
Stirdivant, et al., "Cloning and Mutagenesis of the pII0α Subunit of Human Phosphoinositide 3′-Hydroxykinase," *Bioorganic & Medicinal Chemistry*, 1997, 65-74, vol. 5, No. 1.
Verheijen, et al., "Phosphatidylinositol 3-kinase (PI3K) inhibitors as anticancer drugs," *Drugs of the Future*, 2007, 537-547, vol. 32, No. 6.
Vivanco, et al., The Phosphatidylinositol 3-Kinase—AKT Pathway in Human Cancer, *Nature Reviews Cancer*, 2002, 489-501, vol. 2.
International Search Report.
Broderick, et al., "Mutations of PIK3CA in Anaplastic Oligodendrogliomas, High-Grade Astrocytomas, and Medulloblastomas," *Cancer Research*, 2004, 5048-5050, vol. 64.
Faivre, et al., "Current Development of mTOR Inhibitors as Anticancer Agents," *Nature Reviews Drug Discovery*, 2006, 671-688, vol. 5.
Fruman, et al., "Phosphoinositide Kinases," *Annu. Rev. Biochem.*, 1998, 481-507, vol. 67.
Katso, et al., "Cellular Function of Phosphoinositide 3-Kinases: Implications for Development, Immunity, Homeostasis, and Cancer," *Annu. Rev. Cell Dev. Biol.*, 2001, 615-75, vol. 17.
Knight, et al., "A Pharmacological Map of the PI3-K Family Defines a Role for p110a in Insulin Signaling", *Cell*, 2006, 733-747, vol. 125.
Rosner, et al., "The mTOR Pathway and its Role in Human Genetic Diseases", *Mutation Research*, 2008, 284-292, vol. 659.

* cited by examiner

*Primary Examiner* — Janet L Andres
*Assistant Examiner* — Timothy R Rozof
(74) *Attorney, Agent, or Firm* — David Rubin

(57) ABSTRACT

The present invention is directed to compounds of Formula (I),

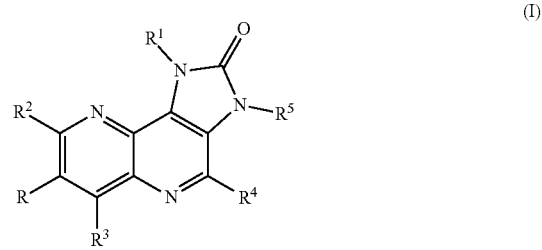

and to salts thereof, their synthesis, and their use as PI3-Kα inhibitors and/or PI3-Kα/mTOR dual inhibitors.

28 Claims, No Drawings

IMIDAZO[1,5]NAPHTHYRIDINE COMPOUNDS, THEIR PHARMACEUTICAL USE AND COMPOSITIONS

This application is a 371 application of PCT/IB2009/054103, filed on Sep. 18, 2009, which claims the benefit of U.S. Provisional Application No. 61/101,564 filed on Sep. 30, 2008, and U.S. Provisional Application No. 61/187,077 filed on Jun. 15, 2009, the contents of which is hereby incorporated by reference in its entirety.

FIELD OF THE INVENTION

The present invention relates to novel imidazo[1,5]naphthyridine compounds including their pharmaceutically acceptable salts as modulators or inhibitors of the phosphoinositide 3-kinase alpha (PI3-Kα) enzyme and/or PI3-Kα/mammalian target of rapamycin protein kinase (mTOR) dual inhibitors. The invention also relates to processes for the preparation of, intermediates used in the preparation of, pharmaceutical compositions containing and the uses of such compounds in treating diseases or conditions mediated by PI3-Kα and/or PI3-Kα/mTOR, such as for example, disease states associated with abnormal cell growth such as cancer.

BACKGROUND OF THE INVENTION

Activation of the PI3K pathway is a frequent event in human tumors, promoting cell proliferation, survival, and resistance to chemotherapy and radiotherapy. (Shaw et al. Ras, PI(3)K and mTOR signalling controls tumour cell growth. *Nature.* 441 (2006), pp. 424-430; Verheijen et al. Phosphatidylinositol 3-kinase (PI3K) inhibitors as anticancer drugs. *Drugs of the Future,* 32 (2007), pp. 537-547.) Phosphoinositide 3-kinases (PI3-Ks) and mammalian target of rapamycin protein kinase (mTOR) are the key kinases in the PI3K signaling pathway.

PI3-Ks catalyze the synthesis of the phosphatidylinositol (PI) second messengers PI(3)P, PI(3,4)$P_2$, and PI(3,4,5)$P_3$ (PIP$_3$). (Fruman et al., Phosphoinositide kinases, *Annu. Rev. Biochem.* 67 (1998), pp. 481-507; Knight et al., A Pharmacological Map of the PI3-K Family Defines a Role for p110α in Insulin Signaling, Cell 125 (2006), pp. 733-747.) In the appropriate cellular context, these three lipids control diverse physiological processes including cell growth, survival, differentiation, and chemotaxis. (Katso et al., Cellular function of phoinositide 3-kinases: implications for development, homeostasis, and cancer, *Annu. Rev. Cell Dev. Biol.* 17 (2001), pp. 615-675.) The PI3-K family comprises at least 15 different enzymes, sub-classified by structural homology, with distinct substrate specificities, expression patterns, and modes of regulation. The main PI3-kinase isoform in cancer is the Class I PI3-Kα, consisting of catalytic (p110α) and adapter (p85) subunits. (Stirdivant et al., Cloning and mutagenesis of the p110α subunit of human phosphoinositide 3'-hydroxykinase, *Bioorg. Med. Chem.* 5 (1997), pp. 65-74.) The 3-phosphorylated phospholipids (PIP$_3$s) generated by PI3-Ks act as second messengers recruiting kinases with lipid binding domains (including plekstrin homology (PH) regions), such as AKT and phosphoinositide-dependent kinase-1 (PDK1). (Vivanco & Sawyers, The Phosphatidylinositol 3-Kinase—AKT Pathway In Human Cancer, *Nature Reviews Cancer* 2 (2002), pp. 489-501.) Binding of AKT to membrane PIP$_3$s causes the translocation of AKT to the plasma membrane, bringing AKT into contact with PDK1, which is responsible for activating AKT. The tumor-suppressor phosphatase, PTEN, dephosphorylates PIP$_3$ and therefore acts as a negative regulator of AKT activation. Functional loss of PTEN (the most commonly mutated tumour-suppressor gene in cancer after p53), oncogenic mutations in the PIK3CA gene encoding PI3-Kα, amplification of the PIK3CA gene and overexpression of AKT have been established in many malignancies. (see, for example, Samuels, et al., High frequency of mutations of the PIK3CA gene in human cancers, *Science* 304 (2004), p. 554; Broderick et al., Mutations in PIK3CA in anaplastic oligodendrogliomas, high-grade astrocytomas, and medulloblastomas, Cancer Research 64 (2004), pp. 5048-5050.) PI3-Kα is thus an attractive target for cancer drug development since such agents would be expected to inhibit proliferation and surmount resistance to cytotoxic agents in cancer cells.

mTOR is a serine/threonine kinase that controls the protein translation machinery and hence cell proliferation. (Faivre et al. Current development of mTOR inhibitors as anticancer agents. *Nat Rev Drug Disc.* 5 (2006), pp. 671-688; Rosner et al. The mTOR pathway and its role in human genetic disease. *Mutation Research* 3 (2008), pp. 284-292; Hall and Schmelzle Cell, TOR, a central controller of cell growth. *Cell* 103 (2000), pp 253-252.) mTOR is active in two complexes: mTORC1, which is sensitive to inhibition by the immune suppressant rapamycin, and mTORC2, which is not inhibited by rapamycin. (Sabatini et al. RAFT1 a mammalian protein that binds to FKBP12 in a rapamycin-dependent fashion and is homologous to yeast TORS. *Cell* 78 (1994), pp. 35-43); Sarbassov et al. Rictor, a novel binding partener of mTOR, defines a rapamycin-insensitive and raptor-independent pathway that regulates the cytoskeleton. *Curr. Biol.* 14 (2004), pp. 1296-1302.) The protein kinase activities of the two mTOR complexes can be regulated by signaling from growth factor receptors, via PI3K, or by the level of nutrients, particularly amino acids, available to the cell. In both cases mTOR regulation involves a protein complex comprised of TSC1 and TSC2. During growth factor signaling, RTKs activate PI3K, which in turn activates the protein kinases AKT and PDK1, via formation of PIP3. AKT can directly phosphorylate TSC2, which leads to inhibition of the GAP activity of the TSC1/TSC2 complex towards the GTPase Rheb. This in turn leads to activation of Rheb, which is thought to directly activate mTOR. The TSC1/TSC2 complex can also be regulated by PI3K-independent signals. Activation of the AMPK kinase in response to energy deprivation, such as low glucose or amino acids, leads to activation of the TSC1/TSC2 complex and downregulation of mTOR. Similar mechanisms account for suppression of mTOR by hypoxia and Wnt signaling. TSC1/TSC2 therefore serves as a point of integration of diverse cellular signals converging on mTOR regulation. Once activated, the mTORC1 complex phosphorylates two key substrates, 4EBP1 and S6 kinase. Phosphorylated 4EBP1 binds to ribosomal initiation factors and activated S6 kinase phosphorylates the ribosomal protein S6. The net result is the stimulation of cap-dependent translation and the synthesis of proteins that are required for entry into the DNA synthesis phase of the cell cycle. mTORC1 is therefore seen as a gatekeeper of cell cycle progression, integrating extracellular growth signals and energy status to decide whether the cell has an appropriate environment for proliferation. The mTORC2 complex does not regulate translation, but activates AKT by phosphorylation, leading to further mTOR activation as well as substrates such as BAD and FOXO that stimulate cell survival. mTOR-activated proteins promote several hallmarks of cancer such as cell growth and proliferation, angiogenesis, and bioenergetics. Since mTOR acts as a neoplastic switch that is frequently turned on by many mutations found in cancer, inhibition of mTOR offers a promising strategy for cancer therapy. Given that the mTOR pathway is deregulated in a number of cancers, it is anticipated that mTOR inhibitors will have broad therapeutic application across many tumor types.

Hence, in some tumors, targeting both PI3-Kα and mTOR may provide additional benefit compared with selectively targeting PI3-Kα. There is a need to provide new PI3-Kα inhibitors and/or dual PI3-Kα/mTOR inhibitors that are good drug candidates. They should be bioavailable, be metabolically stable and possess favorable pharmacokinetic properties.

SUMMARY OF THE INVENTION

The present invention relates to novel compounds of Formula (I)

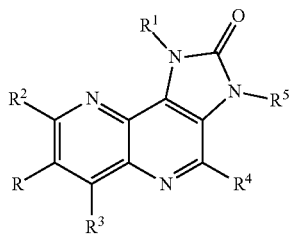

(I)

or a salt thereof,
wherein:
$R^1$ is H, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl is optionally substituted with at least one $R^6$ group;
$R^2$ is H, —$(CH_2)_nC(O)OR^7$, —$(CH_2)_nC(O)N(R^{8a}R^{8b})$, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl wherein the said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl or ($C_2$ to $C_9$) heteroaryl is optionally substituted with at least one $R^6$ group;
$R^3$ is H or ($C_1$ to $C_3$) alkyl;
R and $R^4$ are independently H, halo, cyano or ($C_1$ to $C_6$) alkyl;
$R^5$ is H or ($C_1$ to $C_6$) alkyl wherein the said ($C_1$ to $C_6$) alkyl is optionally substituted with at least one $R^6$ group;
each $R^6$ is independently —OH, halogen, $CF_3$, —$(CH_2)_n$ $NR^{8a}R^{8b}$, ($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, or ($C_2$ to $C_9$) heteroaryl is optionally substituted with at least one $R^{10}$ group;
each $R^7$ is independently H, or ($C_1$ to $C_6$) alkyl optionally substituted with at least one $R^{10}$ group;
$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each of the said ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl is optionally substituted with at least one $R^{10}$ group;
each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each of the said ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl is optionally substituted with at least one $R^{10}$ group;
each $R^{10}$ is independently —OH, halogen, $CF_3$, ($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_mS(O)_mNR^{11a}R^{11b}$, —$(CH_2)_nNR^{11a}S(O)_m R^{12}$, —$(CH_2)_nC(O)OR^7$, —$(CH_2)_nC(O)NR^{11a}R^{11b}$, —$(CH_2)_nOC(O)R^{12}$, —$(CH_2)_nNR^{11a}C(O)R^{12}$ or —$(CH_2)_n NR^{11a}C(O)NR^{11a}R^{11b}$;
$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;
each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;
each m is independently 1 or 2; and
each n is independently 0, 1, 2, 3, or 4.

One aspect of this embodiment is a compound according to Formula (I), as described above, or a salt thereof, wherein $R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to CO cycloalkyl, ($C_6$ to $C_{14}$) aryl, or ($C_2$ to $C_9$) cycloheteroalkyl is optionally substituted with at least one $R^6$ group.

A further aspect of this embodiment is a compound according to Formula (I), as described above, or a salt thereof, wherein $R^2$ is ($C_2$ to $C_9$) heteroaryl optionally substituted with at least one $R^6$ group.

A further aspect of this embodiment is a compound according to Formula (I), as described above, or a salt thereof, wherein $R^3$ is hydrogen.

A further aspect of this embodiment is a compound according to Formula (I), as described above, or a salt thereof, wherein $R^4$ is hydrogen.

A further aspect of this embodiment is a compound according to Formula (I), as described above, or a salt thereof, wherein R is hydrogen.

A further aspect of this embodiment is a compound according to Formula (I), as described above, or a salt thereof, wherein $R^5$ is hydrogen.

A further aspect of this embodiment is a compound according to Formula (I), as described above, or a salt thereof, wherein $R^5$ is methyl.

A further aspect of this embodiment is a compound according to Formula (I), as described above, or a salt thereof, wherein each $R^6$ is independently —OH, halogen, $CF_3$, —$(CH_2)_nNR^{8a}R^{8b}$, ($C_1$ to $C_6$) alkyl, ($C_1$ to $C_6$) alkoxy, ($C_6$ to $C_{14}$) aryl, —$(CH_2)_nC(O)R^9$, —$(CH_2)_nC(O)OR^7$, or —$(CH_2)_n C(O)NR^{8a}R^{8b}$, wherein each of the said ($C_1$ to $C_6$) alkyl or ($C_6$ to $C_{14}$) aryl is optionally substituted with at least one $R^{10}$ group.

A further aspect of this embodiment is a compound according to Formula (I), as described above, or a salt thereof, wherein each $R^7$ is independently ($C_1$ to $C_6$) alkyl optionally substituted with at least one $R^{10}$ group.

A further aspect of this embodiment is a compound according to Formula (I), as described above, or a salt thereof, wherein $R^{8a}$ and $R^{8b}$ are each independently H or ($C_1$ to $C_6$) alkyl optionally substituted with at least one $R^{10}$ group.

A further aspect of this embodiment is a compound according to Formula (I), as described above, or a salt thereof, wherein each $R^9$ is independently ($C_1$ to $C_6$) alkyl optionally substituted with at least one $R^{10}$ group.

A further aspect of this embodiment is a compound according to Formula (I), as described above, or a salt thereof, wherein each $R^{10}$ is independently —OH, $CF_3$, cyano, ($C_6$ to $C_{14}$) aryl, or —$(CH_2)_n NR^{11a}R^{11b}$.

A further aspect of this embodiment is a compound according to Formula (I), as described above, or a salt thereof, wherein R, $R^3$ and $R^4$ are hydrogen and $R^2$ is ($C_2$ to $C_9$) heteroaryl optionally substituted with at least one $R^6$ group.

A further aspect of this embodiment is a compound according to Formula (I), as described above, or a salt thereof, wherein R, $R^3$ and $R^4$ are hydrogen and $R^5$ is methyl.

A further aspect of this embodiment is a compound according to Formula (I), as described above, or a salt thereof, wherein R, $R^3$, $R^4$ and $R^5$ are hydrogen.

A further aspect of this embodiment is a compound according to Formula (I), as described above, or a salt thereof, wherein R, $R^3$ and $R^4$ are hydrogen and $R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to $C_8$) cycloalkyl, ($C_6$ to $C_{14}$) aryl, or ($C_2$ to $C_9$) cycloheteroalkyl is optionally substituted with at least one $R^6$ group.

A further aspect of this embodiment is a compound according to Formula (I), as described above, or a salt thereof, wherein R, $R^3$ and $R^4$ are hydrogen, $R^2$ is ($C_2$ to $C_9$) heteroaryl optionally substituted with at least one $R^6$ group and $R^5$ is hydrogen or methyl.

A further aspect of this embodiment is a compound according to Formula (I), as described above, or a salt thereof, wherein R, $R^3$ and $R^4$ are hydrogen, $R^2$ is ($C_2$ to $C_9$) heteroaryl optionally substituted with at least one $R^6$ group, $R^5$ is hydrogen or methyl, and $R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to $C_8$) cycloalkyl, ($C_6$ to $C_{14}$) aryl, or ($C_2$ to $C_9$) cycloheteroalkyl is optionally substituted with at least one $R^6$ group.

A further aspect of this embodiment is a compound according to Formula (I), as described above, or a salt thereof, wherein $R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to $C_8$) cycloalkyl, ($C_6$ to $C_{14}$) aryl, or ($C_2$ to $C_9$) cycloheteroalkyl is optionally substituted with at least one $R^6$ group; R, $R^3$ and $R^4$ are hydrogen; $R^2$ is ($C_2$ to $C_9$) heteroaryl optionally substituted with at least one $R^6$ group; $R^5$ is hydrogen or methyl; each $R^6$ is independently —OH, halogen, $CF_3$, —$(CH_2)_n NR^{8a}R^{8b}$, ($C_1$ to $C_6$) alkyl, ($C_1$ to $C_6$) alkoxy, of the said ($C_1$ to $C_6$) alkyl or ($C_6$ to $C_{14}$) aryl is optionally substituted with at least one $R^{10}$ group; each $R^7$ is independently ($C_1$ to $C_6$) alkyl optionally substituted with at least one $R^{10}$ group; $R^{8a}$ and $R^{8b}$ are each independently H or ($C_1$ to $C_6$) alkyl optionally substituted with at least one $R^{10}$ group; each $R^9$ is independently ($C_1$ to $C_6$) alkyl optionally substituted with at least one $R^{10}$ group; each $R^{10}$ is independently —OH, $CF_3$, cyano, ($C_6$ to $C_{14}$) aryl, or —$(CH_2)_n NR^{11a}R^{11b}$; and $R^{11a}$ and $R^{11b}$ are each independently H or ($C_1$ to $C_6$) alkyl.

A further aspect of this embodiment is a compound according to Formula (I),

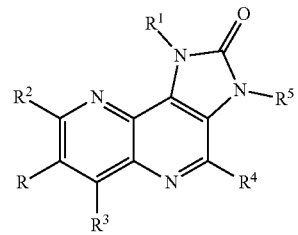

(I)

wherein:

$R^1$ is H, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, and ($C_2$ to $C_9$) heteroaryl is optionally substituted with at least one $R^6$ group;

$R^2$ is H, —$(CH_2)_n C(O)OR^7$, —$(CH_2)_n C(O)N(R^{8a}R^{8b})$, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl and ($C_2$ to $C_9$) heteroaryl is optionally substituted with at least one $R^6$ group;

$R^3$ is H or ($C_1$ to $C_3$) alkyl;

R and $R^4$ are independently H, halo, cyano or ($C_1$ to $C_6$) alkyl;

$R^5$ is H, or ($C_1$ to $C_6$) alkyl optionally substituted with at least one $R^6$ group;

each $R^6$ is independently —OH, halogen, $CF_3$, —$(CH_2)_n NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_n C(O)R^9$, —$(CH_2)_n S(O)_m R^9$, —$(CH_2)_n S(O)_m NR^{8a}R^{8b}$, —$(CH_2)_n NR^{8a}S(O)_m R^9$, —$(CH_2)_n C(O)OR^7$, —$(CH_2)_n C(O)NR^{8a}R^{8b}$, —$(CH_2)_n OC(O)R^9$, —$(CH_2)_n NR^{8a}C(O)R^9$ or —$(CH_2)_n NR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_n NR^{11a}R^{11b}$, —$(CH_2)_n C(O)R^{12}$, —$(CH_2)_n C(O)NR^{11a}R^{11b}$, —$(CH_2)_n S(O)_m R^{12}$, —$(CH_2)_n S(O)_m NR^{11a}R^{11b}$, —$(CH_2)_n NR^{11a}S(O)_m R^{12}$, —$(CH_2)_n OC(O)R^{12}$, —$(CH_2)_n NR^{11a}C(O)R^{12}$ or —$(CH_2)_n NR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_1$ to $C_6$) alkyl, ($C_3$ to $C_8$) cycloalkyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_6$ to $C_{14}$) aryl, ($C_2$ to $C_9$) cycloheteroalkyl, and ($C_2$ to $C_9$) heteroaryl is optionally substituted with at least one $R^6$ group;

$R^2$ is ($C_2$ to $C_9$) heteroaryl or ($C_6$ to $C_{14}$) aryl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_n$$NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_nS(O)_mNR^{11a}R^{11b}$, —$(CH_2)_nNR^{11a}S(O)_mR^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_1$ to $C_6$) alkyl, ($C_3$ to $C_8$) cycloalkyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_6$ to $C_{14}$) aryl, ($C_2$ to $C_9$) cycloheteroalkyl, and ($C_2$ to $C_9$) heteroaryl is optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_nS(O)_mNR^{11a}R^{11b}$, —$(CH_2)_nNR^{11a}S(O)_mR^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_6$ to $C_{14}$) aryl optionally substituted with at least one $R^6$ group;

$R^2$ is ($C_2$ to $C_9$) heteroaryl or ($C_6$ to $C_{14}$) aryl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, $-(CH_2)_nC(O)R^9$, $-(CH_2)_nS(O)_mR^9$, $-(CH_2)_nS(O)_mNR^{8a}R^{8b}$, $-(CH_2)_nNR^{8a}S(O)_mR^9$, $-(CH_2)_nC(O)OR^7$, $-(CH_2)_nC(O)NR^{8a}R^{8b}$, $-(CH_2)_nOC(O)R^9$, $-(CH_2)_nNR^{8a}C(O)R^9$ or $-(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, $-(CH_2)_nNR^{11a}R^{11b}$, $-(CH_2)_nC(O)R^{12}$, $-(CH_2)_nC(O)NR^{11a}R^{11b}$, $-(CH_2)_nS(O)_mR^{12}$, $-(CH_2)_nS(O)_mNR^{11a}R^{11b}$, $-(CH_2)_nNR^{11a}S(O)_mR^{12}$, $-(CH_2)_nOC(O)R^{12}$, $-(CH_2)_nNR^{11a}C(O)R^{12}$ or $-(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_6$ to $C_{14}$) aryl optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, $-(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, $-(CH_2)_nC(O)R^9$, $-(CH_2)_nS(O)_mR^9$, $-(CH_2)_nS(O)_mNR^{8a}R^{8b}$, $-(CH_2)_nNR^{8a}S(O)_mR^9$, $-(CH_2)_nC(O)OR^7$, $-(CH_2)_nC(O)NR^{8a}R^{8b}$, $-(CH_2)_nOC(O)R^9$, $-(CH_2)_nNR^{8a}C(O)R^9$ or $-(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, $-(CH_2)_nNR^{11a}R^{11b}$, $-(CH_2)_nC(O)R^{12}$, $-(CH_2)_nC(O)NR^{11a}R^{11b}$, $-(CH_2)_nS(O)_mR^{12}$, $-(CH_2)_nS(O)_mNR^{11a}R^{11b}$, $-(CH_2)_nNR^{11a}S(O)_m$R^{12}$, $-(CH_2)_nOC(O)R^{12}$, $-(CH_2)_nNR^{11a}C(O)R^{12}$ or $-(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_2$ to $C_9$) cycloheteroalkyl, optionally substituted with at least one $R^6$ group;

$R^2$ is ($C_2$ to $C_9$) heteroaryl or ($C_6$ to $C_{14}$) aryl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, $-(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, $-(CH_2)_nC(O)R^9$, $-(CH_2)_nS(O)_mR^9$, $-(CH_2)_nS(O)_mNR^{8a}R^{8b}$, $-(CH_2)_nNR^{8a}S(O)_mR^9$, $-(CH_2)_nC(O)OR^7$, $-(CH_2)_nC(O)NR^{8a}R^{8b}$, $-(CH_2)_nOC(O)R^9$, $-(CH_2)_nNR^{8a}C(O)R^9$ or $-(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, $-(CH_2)_nNR^{11a}R^{11b}$, $-(CH_2)_nC(O)R^{12}$, $-(CH_2)_nC(O)NR^{11a}R^{11b}$, $-(CH_2)_nS(O)_mR^{12}$, $-(CH_2)_nS(O)_mNR^{11a}R^{11b}$, $-(CH_2)_nNR^{11a}S(O)_m$ $R^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_2$ to $C_9$) cycloheteroalkyl, optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_nS(O)_mNR^{11a}R^{11b}$, —$(CH_2)_nNR^{11a}S(O)_mR^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is piperidinyl, optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_nNR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(OH_2)_nS(O)_mNR^{11a}R^{11b}$, —$(CH_2)_nNR^{11a}S(O)_m R^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is piperidinyl, optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H or —$CH_3$;

each $R^6$ is independently —OH, halogen, $CF_3$, —$(CH_2)_nNR^{8a}R^{8b}$, ($C_1$ to $C_6$) alkyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(OH_2)_nS(O)_mNR^{8a}R^{8b}$, or —$(CH_2)_nNR^{8a}C(O)NR^{8a}R^{8b}$, wherein each said ($C_1$ to $C_6$) alkyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_n NR^{11a}R^{11b}$, —$(CH_2)_n C(O)R^{12}$, —$(CH_2)_n C(O)NR^{11a}R^{11b}$, —$(CH_2)_n S(O)_m R^{12}$, —$(CH_2)_n S(O)_m NR^{11a}R^{11b}$, —$(CH_2)_n NR^{11a}S(O)_m R^{12}$, —$(CH_2)_n OC(O)R^{12}$, —$(CH_2)_n NR^{11a}C(O)R^{12}$ or —$(CH_2)_n NR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_3$ to $C_8$) cycloalkyl, optionally substituted with at least one $R^6$ group;

$R^2$ is ($C_2$ to $C_9$) heteroaryl or ($C_6$ to $C_{14}$) aryl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_n NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_n C(O)R^9$, —$(CH_2)_n S(O)_m R^9$, —$(CH_2)_n S(O)_m NR^{8a}R^{8b}$, —$(CH_2)_n NR^{8a}S(O)_m R^9$, —$(CH_2)_n C(O)OR^7$, —$(CH_2)_n C(O)NR^{8a}R^{8b}$, —$(CH_2)_n OC(O)R^9$, —$(CH_2)_n NR^{8a}C(O)R^9$ or —$(CH_2)_n NR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_n NR^{11a}R^{11b}$, —$(CH_2)_n C(O)R^{12}$, —$(CH_2)_n C(O)NR^{11a}R^{11b}$, —$(CH_2)_n S(O)_m R^{12}$, —$(CH_2)_n S(O)_m NR^{11a}R^{11b}$, —$(CH_2)_n NR^{11a}S(O)_m R^{12}$, —$(CH_2)_n OC(O)R^{12}$, —$(CH_2)_n NR^{11a}C(O)R^{12}$ or —$(CH_2)_n NR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein:

$R^1$ is ($C_3$ to $C_8$) cycloalkyl, optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_n NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_n C(O)R^9$, —$(CH_2)_n S(O)_m R^9$, —$(CH_2)_n S(O)_m NR^{8a}R^{8b}$, —$(CH_2)_n NR^{8a}S(O)_m R^9$, —$(CH_2)_n C(O)OR^7$, —$(CH_2)_n C(O)NR^{8a}R^{8b}$, —$(CH_2)_n OC(O)R^9$, —$(CH_2)_n NR^{8a}C(O)R^9$ or —$(CH_2)_n NR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_n NR^{11a}R^{11b}$, —$(CH_2)_n C(O)R^{12}$, —$(CH_2)_n C(O)NR^{11a}R^{11b}$, —$(CH_2)_n S(O)_m R^{12}$, —$(CH_2)_n S(O)_m NR^{11a}R^{11b}$, —$(CH_2)_n NR^{11a}S(O)_m R^{12}$, —$(CH_2)_n OC(O)R^{12}$, —$(CH_2)_n NR^{11a}C(O)R^{12}$ or —$(CH_2)_n NR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein $R^1$ is cyclohexyl optionally substituted with at least one $R^6$ group, or a pharmaceutically acceptable salt thereof.

A further aspect of this embodiment is a compound according to Formula (I), wherein:

$R^1$ is ($C_1$ to $C_6$) alkyl, optionally substituted with at least one $R^6$ group;

$R^2$ is ($C_2$ to $C_9$) heteroaryl or ($C_6$ to $C_{14}$) aryl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_n$$NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_n$$NR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_nS(O)_mNR^{11a}R^{11b}$, —$(CH_2)_nNR^{11a}S(O)_mR^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein $R^1$ is ($C_1$ to $C_6$) alkyl, optionally substituted with —OH, or a pharmaceutically acceptable salt thereof.

A further aspect of this embodiment is a compound according to Formula (I), wherein $R^1$ is 2-hydroxy-1-methylethyl, or a pharmaceutically acceptable salt thereof.

A further aspect of this embodiment is a compound according to Formula (I), wherein:

$R^1$ is ($C_1$ to $C_6$) alkyl, optionally substituted with at least one $R^6$ group;

$R^2$ is ($C_6$ to $C_{14}$) aryl, quinolinyl, pyridyl, pyrimidinyl, pyrazolyl, indolyl, pyrazolopyridinyl, or indazolyl, each of which is optionally substituted with at least one $R^6$ group;

R, $R^3$ and $R^4$ are H;

$R^5$ is H, or ($C_1$ to $C_6$) alkyl optionally substituted with at least one $R^6$ group;

each $R^6$ is independently —OH, halogen, $CF_3$, —$(CH_2)_n$$NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_n$$NR^{8a}C(O)R^9$ or —$(CH_2)_nNR^{8a}C(O)NR^{8a}R^{8b}$, wherein each said ($C_1$ to $C_6$) alkyl, ($C_2$ to $C_8$) alkenyl, ($C_2$ to $C_8$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each said ($C_1$ to $C_6$) alkyl, ($C_3$ to $C_8$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_nNR^{11a}R^{11b}$, —$(CH_2)_nC(O)R^{12}$, —$(CH_2)_nC(O)NR^{11a}R^{11b}$, —$(CH_2)_nS(O)_mR^{12}$, —$(CH_2)_nS(O)_mNR^{11a}R^{11b}$, —$(CH_2)_nNR^{11a}S(O)_mR^{12}$, —$(CH_2)_nOC(O)R^{12}$, —$(CH_2)_nNR^{11a}C(O)R^{12}$ or —$(CH_2)_nNR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4; or a pharmaceutically acceptable salt thereof.

A further aspect of this embodiment is a compound according to Formula (I), wherein $R^1$ is ($C_1$ to $C_6$) alkyl, optionally substituted with —OH, or a pharmaceutically acceptable salt thereof.

A further aspect of this embodiment is a compound according to Formula (I), wherein $R^2$ is quinolinyl optionally substituted with at least one $R^6$ group, or a pharmaceutically acceptable salt thereof.

A further aspect of this embodiment is a compound according to Formula (I), wherein $R^2$ is pyridyl optionally substituted with at least one $R^6$ group, or a pharmaceutically acceptable salt thereof.

A further aspect of this embodiment is a compound according to Formula (I), wherein R² is pyrimidinyl optionally substituted with at least one R⁶ group, or a pharmaceutically acceptable salt thereof.

A further aspect of this embodiment is a compound according to Formula (I), wherein R² is pyrazolyl optionally substituted with at least one R⁶ group, or a pharmaceutically acceptable salt thereof.

A further aspect of this embodiment is a compound according to Formula (I), wherein R² is indolyl optionally substituted with at least one R⁶ group, or a pharmaceutically acceptable salt thereof.

A further aspect of this embodiment is a compound according to Formula (I), wherein R² is pyrazolopyridinyl optionally substituted with at least one R⁶ group, or a pharmaceutically acceptable salt thereof.

A further aspect of this embodiment is a compound according to Formula (I), wherein R² is indazolyl optionally substituted with at least one R⁶ group, or a pharmaceutically acceptable salt thereof.

A further aspect of this embodiment is a compound according to Formula (I), wherein R² is ($C_6$ to $C_{14}$) aryl optionally substituted with at least one R⁶ group, or a pharmaceutically acceptable salt thereof.

A further aspect of this embodiment is a compound according to Formula (I), as described above, which is selected from the group consisting of: 2-methyl-2-[4-(2-oxo-8-quinolin-3-yl-2,3-dihydro-1H-imidazo[4,5-c]-1,5-naphthyridin-1-yl)phenyl]propanenitrile; 2-methyl-2-[4-(3-methyl-2-oxo-8-quinolin-3-yl-2,3-dihydro-1H-imidazo[4,5-c]-1,5-naphthyridin-1-yl)phenyl]propanenitrile; 2-{4-[8-(6-methoxypyridin-3-yl)-2-oxo-2,3-dihydro-1H-imidazo[4,5-c]-1,5-naphthyridin-1-yl]phenyl}-2-methylpropanenitrile; 2-{4-[8-(6-methoxypyridin-3-yl)-3-methyl-2-oxo-2,3-dihydro-1H-imidazo[4,5-c]-1,5-naphthyridin-1-yl]phenyl}-2-methylpropanenitrile; 2-methyl-2-{4-[8-(6-methylpyridin-3-yl)-2-oxo-2,3-dihydro-1H-imidazo[4,5-c]-1,5-naphthyridin-1-yl]phenyl}propanenitrile; 2-methyl-2-{4-[3-methyl-8-(6-methylpyridin-3-yl)-2-oxo-2,3-dihydro-1H-imidazo[4,5-c]-1,5-naphthyridin-1-yl]phenyl}propanenitrile; 2-(4-(8-(6-(dimethylamino)pyridin-3-yl)-2-oxo-2,3-dihydroimidazo[4,5-c][1,5]naphthyridin-1-yl)phenyl)-2-methylpropanenitrile; 2-(4-(8-(6-(dimethylamino)pyridin-3-yl)-3-methyl-2-oxo-2,3-dihydroimidazo[4,5-c][1,5]naphthyridin-1-yl)phenyl)-2-methylpropanenitrile; 2-(4-(8-(5-fluoro-6-methoxypyridin-3-yl)-3-methyl-2-oxo-2,3-dihydroimidazo[4,5-c][1,5]naphthyridin-1-yl)phenyl)-2-methylpropanenitrile; 2-(4-(8-(2-methoxypyrimidin-5-yl)-2-oxo-2,3-dihydroimidazo[4,5-c][1,5]naphthyridin-1-yl)phenyl)-2-methylpropanenitrile; 2-(4-(8-(2-methoxypyrimidin-5-yl)-3-methyl-2-oxo-2,3-dihydroimidazo[4,5-c][1,5]naphthyridin-1-yl)phenyl)-2-methylpropanenitrile; 2-Methyl-2-{4-[8-(1-methyl-1H-pyrazol-4-yl)-2-oxo-2,3-dihydro-1,3,5,9-tetraaza-cyclopenta[a]naphthalen-1-yl]-phenyl}-propionitrile; benzyl-4-(2-oxo-8-quinolin-3-yl-2,3-dihydro-1H-imidazo[4,5-c][1,5]naphthyridin-1-yl)piperidine-1-carboxylate; benzyl-4-(3-methyl-2-oxo-8-quinolin-3-yl-2,3-dihydro-1H-imidazo[4,5-c][1,5]naphthyridin-1-yl)piperidine-1-carboxylate; 1-(1-ethylpiperidin-4-yl)-3-methyl-8-quinolin-3-yl-1,3-dihydro-2H-imidazo[4,5-c][1,5]naphthyridin-2-one; 3-methyl-1-(1-propionylpiperidin-4-yl)-8-quinolin-3-yl-1,3-dihydro-2H-imidazo[4,5-c][1,5]naphthyridin-2-one; methyl-4-(3-methyl-2-oxo-8-quinolin-3-yl-2,3-dihydro-1H-imidazo[4,5-c][1,5]naphthyridin-1-yl)piperidine-1-carboxylate; N-methyl-4-(3-methyl-2-oxo-8-quinolin-3-yl-2,3-dihydro-1H-imidazo[4,5-c][1,5]naphthyridin-1-yl)piperidine-1-carboxamide; N-ethyl-4-(3-methyl-2-oxo-8-quinolin-3-yl-2,3-dihydro-1H-imidazo[4,5-c][1,5]naphthyridin-1-yl)piperidine-1-carboxamide; 1-(1-isobutyrylpiperidin-4-yl)-3-methyl-8-quinolin-3-yl-1,3-dihydro-2H-imidazo[4,5-c][1,5]naphthyridin-2-one; 1-[1-(N,N-dimethylglycyl)piperidin-4-yl]-3-methyl-8-quinolin-3-yl-1,3-dihydro-2H-imidazo[4,5-c][1,5]naphthyridin-2-one; ethyl 4-(3-methyl-2-oxo-8-quinolin-3-yl-2,3-dihydro-1H-imidazo[4,5-c][1,5]naphthyridin-1-yl)piperidine-1-carboxylate; isopropyl 4-(3-methyl-2-oxo-8-quinolin-3-yl-2,3-dihydro-1H-imidazo[4,5-c][1,5]naphthyridin-1-yl)piperidine-1-carboxylate; 3-methyl-1-(1-methylpiperidin-4-yl)-8-quinolin-3-yl-1,3-dihydro-2H-imidazo[4,5-c][1,5]naphthyridin-2-one; 1-benzyl-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-1,3-dihydro-2H-imidazo[4,5-c][1,5]naphthyridin-2-one; 1-(trans-4-hydroxycyclohexyl)-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-3-methyl-1,3-dihydro-2H-imidazo[4,5-c][1,5]naphthyridin-2-one; 1-(trans-4-hydroxycyclohexyl)-8-(6-methoxypyridin-3-yl)-3-methyl-1,3-dihydro-2H-imidazo[4,5-c][1,5]naphthyridin-2-one; 8-(6-methoxypyridin-3-yl)-3-methyl-1-(1-methyl piperidin-4-yl)-1,3-dihydro-2H-imidazo[4,5-c][1,5]naphthyridin-2-one; 1-(1-isopropylpiperidin-4-yl)-8-(6-methoxypyridin-3-yl)-3-methyl-1,3-dihydro-2H-imidazo[4,5-c][1,5]naphthyridin-2-one; 1-[1-(N,N-dimethylglycyl)piperidin-4-yl]-8-(6-methoxypyridin-3-yl)-3-methyl-1,3-dihydro-2H-imidazo[4,5-c][1,5]naphthyridin-2-one; 2-{4-[8-(6-methoxypyridin-3-yl)-3-methyl-2-oxo-2,3-dihydro-1H-imidazo[4,5-c][1,5]naphthyridin-1-yl]piperidin-1-yl}acetamide; 8-(6-methoxypyridin-3-yl)-3-methyl-1-(tetrahydro-2H-pyran-4-yl)-1,3-dihydro-2H-imidazo[4,5-c][1,5]naphthyridin-2-one; 3-methyl-8-quinolin-3-yl-1-[1-(2,2,2-trifluoroethyl)piperidin-4-yl]-1,3-dihydro-2H-imidazo[4,5-c][1,5]naphthyridin-2-one; 4-[8-(6-methoxypyridin-3-yl)-3-methyl-2-oxo-2,3-dihydro-1H-imidazo[4,5-c][1,5]naphthyridin-1-yl]-N-methylpiperidine-1-carboxamide; 1-[1-(2-hydroxy-2-methylpropanoyl)piperidin-4-yl]-3-methyl-8-quinolin-3-yl-1,3-dihydro-2H-imidazo[4,5-c][1,5]naphthyridin-2-one; 8-[6-(dimethylamino)pyridin-3-yl]-1-[1-(N,N-dimethylglycyl)piperidin-4-yl]-3-methyl-1,3-dihydro-2H-imidazo[4,5-c][1,5]naphthyridin-2-one; 3-methyl-1-[1-(2-methylalanyl)piperidin-4-yl]-8-quinolin-3-yl-1,3-dihydro-2H-imidazo[4,5-c][1,5]naphthyridin-2-one; 1-(trans-4-hydroxycyclohexyl)-3-methyl-8-quinolin-3-yl-1,3-dihydro-2H-imidazo[4,5-c][1,5]naphthyridin-2-one; 1-[trans-4-(2-hydroxyethoxy)cyclohexyl]-3-methyl-8-quinolin-3-yl-1,3-dihydro-2H-imidazo[4,5-c][1,5]naphthyridin-2-one; 1-[trans-4-(2-hydroxyethoxy)cyclohexyl]-8-(2-methoxypyrimidin-5-yl)-3-methyl-1,3-dihydro-2H-imidazo[4,5-c][1,5]naphthyridin-2-one; 8-[6-(dimethylamino)pyridin-3-yl]-1-[trans-4-(2-hydroxyethoxy)cyclohexyl]-3-methyl-1,3-dihydro-2H-imidazo[4,5-c][1,5]naphthyridin-2-one; 8-[6-(dimethylamino)pyridin-3-yl]-3-methyl-1-[1-(2,2,2-trifluoroethyl)piperidin-4-yl]-1,3-dihydro-2H-imidazo[4,5-c][1,5]naphthyridin-2-one; 1-[trans-4-(2-hydroxyethoxy)cyclohexyl]-3-methyl-8-(6-methylpyridin-3-yl)-1,3-dihydro-2H-imidazo[4,5-c][1,5]naphthyridin-2-one; 1-[1-(methoxyacetyl)piperidin-4-yl]-3-methyl-8-(6-methylpyridin-3-yl)-1,3-dihydro-2H-imidazo[4,5-c][1,5]naphthyridin-2-one; 1-{1-[(2S)-2-hydroxypropanoyl]piperidin-4-yl}-8-(2-methoxypyrimidin-5-yl)-3-methyl-1,3-dihydro-2H-imidazo[4,5-c][1,5]naphthyridin-2-one; trans-4-[8-(2-methoxypyrimidin-5-yl)-3-methyl-2-oxo-2,3- dihydro-1H-imidazo[4,5-c][1,5]naphthyridin-1-yl]cyclohexanecarboxamide; 1-[1-(methoxyacetyl)piperidin-4-yl]-8-(2-methoxypyrimidin-5-yl)-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(6-methylpyridin-3-yl)-1,3-dihydro-2H-imidazo[4,5-c][1,5]naphthyridin-2-one; 2-{4-[8-(2-methoxypyrimidin-5-yl)-3-methyl-2-oxo-2,3-dihydro-1H-imidazo[4,5-c][1,5]naphthyridin-1-yl]piperidin-1-yl}-N,N-dimethylacetamide; 3-methyl-8-(6-methylpyridin-3-yl)-1-(1-pyrimidin-2-ylpiperidin-4-yl)-1,3-dihydro-2H-imidazo[4,5-c][1,5]naphthyridin-2-one; 1-[1-(2-hydroxyethyl)piperidin-4-yl]-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(1H-pyrazol-4-yl)-1,3-dihydro-2H-imidazo[4,5-c][1,5]naphthyridin-2-one; 3-methyl-1-(1-methylpiperidin-4-yl)-8-(6-methylpyridin-3-yl)-1,3-dihydro-2H-imidazo[4,5-c][1,5]naphthyridin-2-one; 1-(1-glycoloyl piperidin-4-yl)-3-methyl-8-(6-methylpyridin-3-yl)-1,3-dihydro-2H-imidazo[4,5-c][1,5]naphthyridin-2-one; 1-(1-acetyl piperidin-4-yl)-3-methyl-8-(6-methylpyridin-3-yl)-1,3-dihydro-2H-imidazo[4,5-c][1,5]naphthyridin-2-one; 8-[6-(dimethylamino)pyridin-3-yl]-1-(trans-4-hydroxycyclohexyl)-3-methyl-1,3-dihydro-2H-imidazo[4,5-c][1,5]naphthyridin-2-one; 2-{4-[3-methyl-8-(6-methylpyridin-3-yl)-2-oxo-2,3-dihydro-1H-imidazo[4,5-c][1,5]naphthyridin-1-yl]piperidin-1-yl}acetamide; 1-[1-(N,N-dimethylglycyl)piperidin-4-yl]-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(6-methylpyridin-3-yl)-1,3-dihydro-2H-imidazo[4,5-c][1,5]naphthyridin-2-one; 1-(1-glycylpiperidin-4-yl)-3-methyl-8-(6-methylpyridin-3-yl)-1,3-dihydro-2H-imidazo[4,5-c][1,5]naphthyridin-2-one; N-methyl-4-[3-methyl-8-(6-methylpyridin-3-yl)-2-oxo-2,3-dihydro-1H-imidazo[4,5-c][1,5]naphthyridin-1-yl]piperidine-1-carboxamide; 4-[8-(2-methoxypyrimidin-5-yl)-3-methyl-2-oxo-2,3-dihydro-1H-imidazo[4,5-c][1,5]naphthyridin-1-yl]-N-methylpiperidine-1-carboxamide; 1-(1-acetyl piperidin-4-yl)-8-(2-methoxypyrimidin-5-yl)-3-methyl-1,3-dihydro-2H-imidazo[4,5-c][1,5]naphthyridin-2-one; 1-(1-glycoloylpiperidin-4-yl)-8-(2-methoxypyrimidin-5-yl)-3-methyl-1,3-dihydro-2H-imidazo[4,5-c][1,5]naphthyridin-2-one; 2-{4-[8-(2-methoxypyrimidin-5-yl)-3-methyl-2-oxo-2,3-dihydro-1H-imidazo[4,5-c][1,5]naphthyridin-1-yl]piperidin-1-yl}acetamide; 8-[6-(dimethylamino)pyridin-3-yl]-3-methyl-1-piperidin-4-yl-1,3-dihydro-2H-imidazo[4,5-c][1,5]naphthyridin-2-one; 3-methyl-1-[trans-4-(methylamino)cyclohexyl]-8-quinolin-3-yl-1,3-dihydro-2H-imidazo[4,5-c][1,5]naphthyridin-2-one; 1-(trans-4-aminocyclohexyl)-3-methyl-8-quinolin-3-yl-1,3-dihydro-2H-imidazo[4,5-c][1,5]naphthyridin-2-one; 1-(1-acetylpiperidin-4-yl)-8-[6-(dimethylamino)pyridin-3-yl]-3-methyl-1,3-dihydro-2H-imidazo[4,5-c][1,5]naphthyridin-2-one; 4-{8-[6-(dimethylamino)pyridin-3-yl]-3-methyl-2-oxo-2,3-dihydro-1H-imidazo[4,5-c][1,5]naphthyridin-1-yl}-N-methylpiperidine-1-carboxamide; 4-{8-[6-(dimethylamino)pyridin-3-yl]-3-methyl-2-oxo-2,3-dihydro-1H-imidazo[4,5-c][1,5]naphthyridin-1-yl}piperidine-1-carboxamide; 8-[6-(dimethylamino)pyridin-3-yl]-1-[1-(2-hydroxyethyl)piperidin-4-yl]-3-methyl-1,3-dihydro-2H-imidazo[4,5-c][1,5]naphthyridin-2-one; 3-methyl-8-(1H-pyrazol-4-yl)-1-(tetrahydro-2H-pyran-4-yl)-1,3-dihydro-2H-imidazo[4,5-c][1,5]naphthyridin-2-one; 3-methyl-8-(6-methylpyridin-3-yl)-1-(tetrahydro-2H-pyran-4-yl)-1,3-dihydro-2H-imidazo[4,5-c][1,5]naphthyridin-2-one; 8-(2-methoxypyrimidin-5-yl)-3-methyl-1-(tetrahydro-2H-pyran-4-yl)-1,3-dihydro-2H-imidazo[4,5-c][1,5]naphthyridin-2-one; 3-methyl-8-(1-methyl-1H-pyrazol-4-yl)-1-(tetrahydro-2H-pyran-4-yl)-1,3-dihydro-2H-imidazo[4,5-c][1,5]naphthyridin-2-one; 8-[6-(dimethylamino)pyridin-3-yl]-3-methyl-1-(tetrahydro-2H-pyran-4-yl)-1,3-dihydro-2H-imidazo[4,5-c][1,5]naphthyridin-2-one; 8-[6-(dimethylamino)pyridin-3-yl]-1-[1-(2,2-dimethylpropanoyl)piperidin-4-yl]-3-methyl-1,3-dihydro-2H-imidazo[4,5-c][1,5]naphthyridin-2-one; 8-[6-(dimethylamino)pyridin-3-yl]-1-[1-(2-methoxyethyl)piperidin-4-yl]-3-methyl-1,3-dihydro-2H-imidazo[4,5-c][1,5]naphthyridin-2-one; 8-[6-(dimethylamino)pyridin-3-yl]-3-methyl-1-(1-methyl piperidin-4-yl)-1,3-dihydro-2H-imidazo[4,5-c][1,5]naphthyridin-2-one; 8-[6-(dimethylamino)pyridin-3-yl]-1-[1-(2-hydroxy-2-methylpropanoyl)piperidin-4-yl]-3-methyl-1,3-dihydro-2H-imidazo[4,5-c][1,5]naphthyridin-2-one; 8-(2-aminopyrimidin-5-yl)-3-methyl-1-(tetrahydro-2H-pyran-4-yl)-1,3-dihydro-2H-imidazo[4,5-c][1,5]naphthyridin-2-one; 8-[6-(dimethylamino)pyridin-3-yl]-1-{1-[(2R)-2-hydroxypropanoyl]piperidin-4-yl}-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(1-methyl-1H-pyrazol-4-yl)-1,3-dihydro-2H-imidazo[4,5-c][1,5]naphthyridin-2-one; 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one; and N-methyl-4-[3-methyl-8-(1-methyl-1H-pyrazol-4-yl)-2-oxo-2,3-dihydro-1H-imidazo[4,5-c][1,5]naphthyridin-1-yl]piperidine-1-carboxamide, or a salt thereof.

A further aspect of this embodiment is a compound according to Formula (I), as described above, which is selected from the group consisting of: 1-(1-acetylpiperidin-4-yl)-3-methyl-8-quinolin-3-yl-1,3-dihydro-2H-imidazo[4,5-c][1,5]naphthyridin-2-one; 1-(trans-4-aminocyclohexyl)-3-methyl-8-quinolin-3-yl-1,3-dihydro-2H-imidazo[4,5-c][1,5]naphthyridin-2-one; 3-methyl-1-[trans-4-(methylamino)cyclohexyl]-8-quinolin-3-yl-1,3-dihydro-2H-imidazo[4,5-c][1,5]naphthyridin-2-one; 1-(trans-4-hydroxycyclohexyl)-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-3-methyl-1,3-dihydro-2H-imidazo[4,5-c][1,5]naphthyridin-2-one; 1-(trans-4-hydroxycyclohexyl)-8-(6-methoxypyridin-3-yl)-3-methyl-1,3-dihydro-2H-imidazo[4,5-c][1,5]naphthyridin-2-one; 8-(6-methoxypyridin-3-yl)-3-methyl-1-(1-methyl piperidin-4-yl)-1,3-dihydro-2H-imidazo[4,5-c][1,5]naphthyridin-2-one; 1-[1-(N,N-dimethylglycyl)piperidin-4-yl]-8-(6-methoxypyridin-3-yl)-3-methyl-1,3-dihydro-2H-imidazo[4,5-c][1,5]naphthyridin-2-one; 1-(1-acetylpiperidin-4-yl)-8-(2-methoxypyrimidin-5-yl)-3-methyl-1,3-dihydro-2H-imidazo[4,5-c][1,5]naphthyridin-2-one; 4-[8-(2-methoxypyrimidin-5-yl)-3-methyl-2-oxo-2,3-dihydro-1H-imidazo[4,5-c][1,5]naphthyridin-1-yl]-N-methylpiperidine-1-carboxamide; N-methyl-4-[3-methyl-8-(6-methylpyridin-3-yl)-2-oxo-2,3-dihydro-1H-imidazo[4,5-c][1,5]naphthyridin-1-yl]piperidine-1-carboxamide; 8-[6-(dimethylamino)pyridin-3-yl]-1-[1-(2-hydroxyethyl)piperidin-4-yl]-3-methyl-1,3-dihydro-2H-imidazo[4,5-c][1,5]naphthyridin-2-one; 3-methyl-8-(1H-pyrazol-4-yl)-1-(tetrahydro-2H-pyran-4-yl)-1,3-dihydro-2H-imidazo[4,5-c][1,5]naphthyridin-2-one; 1-(trans-4-hydroxycyclohexyl)-3-methyl-8-(6-methylpyridin-3-yl)-1,3-dihydro-2H-imidazo[4,5-c][1,5]naphthyridin-2-one; 1-(1-acetyl piperidin-4-yl)-3-methyl-8-(6-methylpyridin-3-yl)-1,3-dihydro-2H-imidazo[4,5-c][1,5]naphthyridin-2-one; 1-(1-glycoloylpiperidin-4-yl)-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(1H-pyrazol-4-yl)-1,3- dihydro-2H-imidazo[4,5-c][1,5]naphthyridin-2-one; 1-[1-(2-hydroxyethyl)piperidin-4-yl]-3-methyl-8-(6-methylpyridin-3-yl)-1,3-dihydro-2H-imidazo[4,5-c][1,5]naphthyridin-2-one; 8-(2-aminopyrimidin-5-yl)-3-methyl-1-(tetrahydro-2H-pyran-4-yl)-1,3-dihydro-2H-imidazo[4,5-c][1,5]naphthyridin-2-one; 1-[1-(2-hydroxy-2-methylpropanoyl)piperidin-4-yl]-3-methyl-8-(1-methyl-1H-pyrazol-4-yl)-1,3-dihydro-2H-imidazo[4,5-c][1,5]naphthyridin-2-one; 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(6-methylpyridin-3-yl)-1,3-dihydro-2H-imidazo[4,5-c][1,5]naphthyridin-2-one; 1-[1-(methoxyacetyl)piperidin-4-yl]-8-(2-methoxypyrimidin-5-yl)-3-methyl-1,3-dihydro-2H-imidazo[4,5-c][1,5]naphthyridin-2-one; trans-4-[8-(2-methoxypyrimidin-5-yl)-3-methyl-2-oxo-2,3-dihydro-1H-imidazo[4,5-c][1,5]naphthyridin-1-yl]cyclohexanecarboxamide; N-methyl-4-[3-methyl-8-(1-methyl-1H-pyrazol-4-yl)-2-oxo-2,3-dihydro-1H-imidazo[4,5-c][1,5]naphthyridin-1-yl]piperidine-1-carboxamide; 3-methyl-1-[1-(2-methylalanyl)piperidin-4-yl]-8-quinolin-3-yl-1,3-dihydro-2H-imidazo[4,5-c][1,5]naphthyridin-2-one; 1-[trans-4-(2-hydroxyethoxy)cyclohexyl]-8-(2-methoxypyrimidin-5-yl)-3-methyl-1,3-dihydro-2H-imidazo[4,5-c][1,5]naphthyridin-2-one; 1-{1-[(2S)-2-hydroxypropanoyl]piperidin-4-yl}-8-(2-methoxypyrimidin-5-yl)-3-methyl-1,3-dihydro-2H-imidazo[4,5-c][1,5]naphthyridin-2-one; 1-[1-(methoxyacetyl)piperidin-4-yl]-3-methyl-8-(6-methylpyridin-3-yl)-1,3-dihydro-2H-imidazo[4,5-c][1,5]naphthyridin-2-one; 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one; 8-(2-aminopyrimidin-5-yl)-1-(trans-4-hydroxycyclohexyl)-3-methyl-1,3-dihydro-2H-imidazo[4,5-c][1,5]naphthyridin-2-one; 1-[1-(2-hydroxy-2-methylpropanoyl)piperidin-4-yl]-8-(2-methoxypyrimidin-5-yl)-3-methyl-1,3-dihydro-2H-imidazo[4,5-c][1,5]naphthyridin-2-one; 1-[(1R)-2-hydroxy-1-methylethyl]-3-methyl-8-(6-methylpyridin-3-yl)-1,3-dihydro-2H-imidazo[4,5-c][1,5]naphthyridin-2-one; 1-[(1R)-2-hydroxy-1-methylethyl]-3-methyl-8-(1-methyl-1H-pyrazol-4-yl)-1,3-dihydro-2H-imidazo[4,5-c][1,5]naphthyridin-2-one; 1-[(1R)-2-hydroxy-1-methylethyl]-8-(6-methoxypyridin-3-yl)-3-methyl-1,3-dihydro-2H-imidazo[4,5-c][1,5]naphthyridin-2-one; 1-[(1R)-2-hydroxy-1-methylethyl]-3-methyl-8-quinolin-3-yl-1,3-dihydro-2H-imidazo[4,5-c][1,5]naphthyridin-2-one; 8-(2-aminopyrimidin-5-yl)-1-[(1R)-2-hydroxy-1-methylethyl]-3-methyl-1,3-dihydro-2H-imidazo[4,5-c][1,5]naphthyridin-2-one; 1-(trans-4-hydroxycyclohexyl)-8-(1H-indol-4-yl)-3-methyl-1,3-dihydro-2H-imidazo[4,5-c][1,5]naphthyridin-2-one; 1-[(1R)-2-hydroxy-1-methylethyl]-8-(1H-indol-4-yl)-3-methyl-1,3-dihydro-2H-imidazo[4,5-c][1,5]naphthyridin-2-one; 1-[(1R)-2-hydroxy-1-methylethyl]-3-methyl-8-(1H-pyrazolo[3,4-b]pyridin-5-yl)-1,3-dihydro-2H-imidazo[4,5-c][1,5]naphthyridin-2-one; 1-[(1S)-2-hydroxy-1-methylethyl]-3-methyl-8-(1-methyl-1H-pyrazol-4-yl)-1,3-dihydro-2H-imidazo[4,5-c][1,5]naphthyridin-2-one; 1-[(1S)-2-hydroxy-1-methylethyl]-3-methyl-8-quinolin-3-yl-1,3-dihydro-2H-imidazo[4,5-c][1,5]naphthyridin-2-one; 1-[(1S)-2-hydroxy-1-methylethyl]-8-(6-methoxypyridin-3-yl)-3-methyl-1,3-dihydro-2H-imidazo[4,5-c][1,5]naphthyridin-2-one; 1-(1-acetylpiperidin-4-yl)-8-(6-aminopyridin-3-yl)-3-methyl-1,3-dihydro-2H-imidazo[4,5-c][1,5]naphthyridin-2-one; 1-{4-[1-(1-acetylpiperidin-4-yl)-3-methyl-2-oxo-2,3-dihydro-1H-imidazo[4,5-c][1,5]naphthyridin-8-yl]phenyl}-3-methylurea; 1-[4-(1-{1-[(2S)-2-hydroxypropanoyl]piperidin-4-yl}-3-methyl-2-oxo-2,3-dihydro-1H-imidazo[4,5-c][1,5]naphthyridin-8-yl)phenyl]-3-methylurea; 1-{4-[1-(1-glycoloylpiperidin-4-yl)-3-methyl-2-oxo-2,3-dihydro-1H-imidazo[4,5-c][1,5]naphthyridin-8-yl]phenyl}-3-methylurea; 1-(1-acetylpiperidin-4-yl)-3-methyl-8-[4-(methylsulfonyl)phenyl]-1,3-dihydro-2H-imidazo[4,5-c][1,5]naphthyridin-2-one; 1-(1-acetylpiperidin-4-yl)-3-methyl-8-[3-(1H-pyrazol-1-yl)phenyl]-1,3-dihydro-2H-imidazo[4,5-c][1,5]naphthyridin-2-one; 1-(trans-4-hydroxycyclohexyl)-3-methyl-8-quinolin-5-yl-1,3-dihydro-2H-imidazo[4,5-c][1,5]naphthyridin-2-one; 1-(1-acetylpiperidin-4-yl)-3-methyl-8-quinolin-5-yl-1,3-dihydro-2H-imidazo[4,5-c][1,5]naphthyridin-2-one; 1-(trans-4-hydroxycyclohexyl)-3-methyl-8-(1H-pyrazolo[3,4-b]pyridin-4-yl)-1,3-dihydro-2H-imidazo[4,5-c][1,5]naphthyridin-2-one; 1-(1-acetylpiperidin-4-yl)-3-methyl-8-(1H-pyrazolo[3,4-b]pyridin-4-yl)-1,3-dihydro-2H-imidazo[4,5-c][1,5]naphthyridin-2-one; 1-(1-glycoloyl piperidin-4-yl)-3-methyl-8-(1H-pyrazolo[3,4-b]pyridin-4-yl)-1,3-dihydro-2H-imidazo[4,5-c][1,5]naphthyridin-2-one; 1-{1-[(2S)-2-hydroxypropanoyl]piperidin-4-yl}-3-methyl-8-(1H-pyrazolo[3,4-b]pyridin-4-yl)-1,3-dihydro-2H-imidazo[4,5-c][1,5]naphthyridin-2-one; 1-(1-acetyl piperidin-4-yl)-8-(1H-indazol-4-yl)-3-methyl-1,3-dihydro-2H-imidazo[4,5-c][1,5]naphthyridin-2-one; 1-{1-[(2S)-2-hydroxypropanoyl]piperidin-4-yl}-8-(1H-indazol-4-yl)-3-methyl-1,3-dihydro-2H-imidazo[4,5-c][1,5]naphthyridin-2-one; 1-(1-glycoloylpiperidin-4-yl)-8-(1H-indazol-4-yl)-3-methyl-1,3-dihydro-2H-imidazo[4,5-c][1,5]naphthyridin-2-one; 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one; 1-{1-[(2R)-2-hydroxypropanoyl]piperidin-4-yl}-3-methyl-8-(1H-pyrazolo[3,4-b]pyridin-5-yl)-1,3-dihydro-2H-imidazo[4,5-c][1,5]naphthyridin-2-one; 1-(1-acetylpiperidin-4-yl)-3-methyl-8-(1H-pyrazolo[3,4-b]pyridin-5-yl)-1,3-dihydro-2H-imidazo[4,5-c][1,5]naphthyridin-2-one; 1-[1-(methoxyacetyl)piperidin-4-yl]-3-methyl-8-(1H-pyrazolo[3,4-b]pyridin-5-yl)-1,3-dihydro-2H-imidazo[4,5-c][1,5]naphthyridin-2-one; 1-[1-(2-hydroxy-2-methylpropanoyl)piperidin-4-yl]-3-methyl-8-(1H-pyrazolo[3,4-b]pyridin-5-yl)-1,3-dihydro-2H-imidazo[4,5-c][1,5]naphthyridin-2-one; 1-(1-glycoloylpiperidin-4-yl)-3-methyl-8-(1H-pyrazolo[3,4-b]pyridin-5-yl)-1,3-dihydro-2H-imidazo[4,5-c][1,5]naphthyridin-2-one; 3-methyl-1-(1-methylpiperidin-4-yl)-8-(1H-pyrazolo[3,4-b]pyridin-5-yl)-1,3-dihydro-2H-imidazo[4,5-c][1,5]naphthyridin-2-one; 3-methyl-1-piperidin-4-yl-8-(1H-pyrazolo[3,4-b]pyridin-5-yl)-1,3-dihydro-2H-imidazo[4,5-c][1,5]naphthyridin-2-one; tert-butyl 4-(8-{4-[(ethylcarbamoyl)amino]phenyl}-3-methyl-2-oxo-2,3-dihydro-1H-imidazo[4,5-c][1,5]naphthyridin-1-yl)piperidine-1-carboxylate; 8-(6-methoxypyridin-3-yl)-3-methyl-1-(2-piperazin-1-ylethyl)-1,3-dihydro-2H-imidazo[4,5-c][1,5]naphthyridin-2-one; 1-(trans-4-hydroxycyclohexyl)-8-(1H-indazol-5-yl)-3-methyl-1,3-dihydro-2H-imidazo[4,5-c][1,5]naphthyridin-2-one; 1-(trans-4-hydroxycyclohexyl)-3-methyl-8-(1H-pyrazolo[3,4-b]pyridin-5-yl)-1,3-dihydro-2H-imidazo[4,5-c][1,5]naphthyridin-2-one; 8-(6-methoxypyridin-3-yl)-3-methyl-1-(2-morpholin-4-ylethyl)-1,3-dihydro-2H-imidazo[4,5-c][1,5]naphthyridin-2-one; 1-(2-methoxyethyl)-8-(6-methoxypyridin-3-yl)-3-methyl-1,3-dihydro-2H-imidazo[4,5-c][1,5]naphthyridin-2-one; 1-(3-methoxypropyl)-8-(6-methoxypyridin-3-yl)-3-methyl-1,3-dihydro-2H-imidazo[4,5-c][1,5]naphthyridin-2-one; 1-{1-[(2S)-2-hydroxypropanoyl]piperidin-4-yl}-8-(4-methoxyphenyl)-3-methyl-1,3-dihydro-2H-imidazo[4,5-c][1,5]naphthyridin-2- one; 1-(1-glycoloylpiperidin-4-yl)-8-(4-methoxyphenyl)-3-methyl-1,3-dihydro-2H-imidazo[4,5-c][1,5]naphthyridin-2-one; 1-(1-acetylpiperidin-4-yl)-8-(4-methoxyphenyl)-3-methyl-1,3-dihydro-2H-imidazo[4,5-c][1,5]naphthyridin-2-one; 1-{1-[(2S)-2-hydroxypropanoyl]piperidin-4-yl}-8-(3-methoxyphenyl)-3-methyl-1,3-dihydro-2H-imidazo[4,5-c][1,5]naphthyridin-2-one; 1-(1-glycoloylpiperidin-4-yl)-8-(3-methoxyphenyl)-3-methyl-1,3-dihydro-2H-imidazo[4,5-c][1,5]naphthyridin-2-one; 1-(1-acetylpiperidin-4-yl)-8-(3-methoxyphenyl)-3-methyl-1,3-dihydro-2H-imidazo[4,5-c][1,5]naphthyridin-2-one; 1-{1-[(2S)-2-hydroxypropanoyl]piperidin-4-yl}-8-(2-methoxyphenyl)-3-methyl-1,3-dihydro-2H-imidazo[4,5-c][1,5]naphthyridin-2-one; 1-(1-glycoloylpiperidin-4-yl)-8-(2-methoxyphenyl)-3-methyl-1,3-dihydro-2H-imidazo[4,5-c][1,5]naphthyridin-2-one; and 1-(1-acetylpiperidin-4-yl)-8-(2-methoxyphenyl)-3-methyl-1,3-dihydro-2H-imidazo[4,5-c][1,5]naphthyridin-2-one; or a salt thereof.

A further aspect of this embodiment is a compound according to Formula (I), as described above, which is selected from the group consisting of 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one; 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one; 1-{1-[(2S)-2-hydroxypropanoyl]piperidin-4-yl}-8-(1H-indazol-4-yl)-3-methyl-1,3-dihydro-2H-imidazo[4,5-c][1,5]naphthyridin-2-one; and 1-(1-acetylpiperidin-4-yl)-8-(1H-indazol-4-yl)-3-methyl-1,3-dihydro-2H-imidazo[4,5-c][1,5]naphthyridin-2-one; or a pharmaceutically acceptable salt thereof.

In a further embodiment is any of the aspects described above in combination with any of the other aspects described above which is not inconsistent therewith.

The present invention also relates to a pharmaceutical composition, comprising at least one compound as described herein, or a pharmaceutically acceptable salt thereof, and a pharmaceutically acceptable carrier or diluent.

The present invention also relates to a method of treating abnormal cell growth, or any PI3-Kα-mediated and/or PI3-Kα/mTOR-mediated disease or condition, in a mammal in need thereof, comprising the step of administering to said mammal a therapeutically effective amount of at least one compound as described herein, or a pharmaceutically acceptable salt thereof. For example, in one embodiment the abnormal cell growth is cancerous. In a further embodiment, the abnormal cell growth is non-cancerous.

The present invention further relates to a method of inhibiting PI3-Kα and/or PI3-Kα/mTOR enzymatic activity, comprising contacting a PI3-Kα enzyme and/or PI3-Kα/mTOR with a PI3-Kα-inhibiting and/or PI3-Kα/mTOR-inhibiting amount of at least one compound as described herein, or a pharmaceutically acceptable salt thereof.

The present invention further relates to the use of any of the compounds as described herein, or a pharmaceutically acceptable salt thereof, in the manufacture of a medicament for the treatment of abnormal cell growth in a mammal. The present invention further relates to the use of any of the compounds as described herein, or a pharmaceutically acceptable salt thereof, in the manufacture of a medicament for the treatment of abnormal cell growth in a mammal wherein the abnormal cell growth is cancerous or non-cancerous. In one embodiment, the abnormal cell growth is cancerous. In another embodiment, the abnormal cell growth is non-cancerous.

The present invention further relates to methods of making the compounds as described herein using the methods as shown in the specific examples herein and in the general synthetic methods as described herein.

The present invention further relates to any of the compounds described herein, or pharmaceutically acceptable salts thereof, for use as a medicament. The present invention further relates to the use of any of the compounds described above, or pharmaceutically acceptable salts thereof, for the manufacture of a medicament for the treatment of abnormal cell growth.

DEFINITIONS

As used herein, the terms "comprising" and "including" are used in their open, non-limiting sense.

The terms "halo" and/or "halogen" refer to fluorine, chlorine, bromine or iodine.

As used herein, the term "alkyl" is defined to include saturated aliphatic hydrocarbons including straight chains and branched chains. Preferably, the alkyl group has 1 to 20 carbon atoms. More preferably, the alkyl group has 1 to 10 carbon atoms. Most preferably, it is a lower alkyl having 1 to 6 carbon atoms. For example, as used herein, the term "($C_1$-$C_6$)alkyl," as well as the alkyl moieties of other groups referred to herein (e.g., ($C_1$-$C_6$)alkoxy), refers to a saturated aliphatic hydrocarbon radical including straight chain and branched chain groups of 1 to 6 carbon atoms. Examples of ($C_1$ to $C_6$) alkyl groups include methyl, ethyl, propyl, 2-propyl, n-butyl, iso-butyl, tert-butyl, pentyl, and the like. The terms "Me" and "methyl," as used herein, mean a —$CH_3$ group. The terms "Et" and "ethyl," as used herein, mean a —$C_2H_5$ group.

The term "($C_2$ to $C_8$) alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —$CH_2CH=CH_2$ group. The term, "C(R)=C(R)," as used herein, represents a carbon-carbon double bond in which each carbon is substituted by an R group.

As used herein, the term "($C_2$ to $C_8$) alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "($C_1$ to $C_8$) alkoxy", as used herein, means an O-alkyl group wherein said alkyl group contains from 1 to 8 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "($C_6$ to $C_{14}$) aryl", as used herein, means a group derived from an aromatic hydrocarbon containing from 6 to 14 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

"($C_2$ to $C_9$) heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_2$ to $C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (O-attached).

"($C_2$ to $C_9$) cycloheteroalkyl", as used herein, means a non-aromatic, monocyclic, bicyclic, tricyclic, spirocyclic, or tetracyclic group having a total of from 4 to 13 atoms in its ring system, and containing from 2 to 9 carbon atoms and from 1 to 4 heteroatoms each independently selected from O, S and N, and with the proviso that the ring of said group does not contain two adjacent O atoms or two adjacent S atoms. Furthermore, such $C_2$ to $C_9$ cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$ to $C_9$ cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such $C_2$ to $C_9$ cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl quinolizinyl, 3-oxopiperazinyl, 4-methylpiperazinyl, 4-ethylpiperazinyl, and 1-oxo-2,8,diazaspiro[4.5]dec-8-yl.

The term "($C_3$ to $C_8$) cycloalkyl group" means a saturated, monocyclic, fused, spirocyclic, or polycyclic ring structure having a total of from 3 to 8 carbon ring atoms. Examples of such groups include, but are not limited to, cyclopropyl, cyclobutyl, cyclopentyl, cyclopentenyl, cyclohexyl, cycloheptyl, and adamantyl.

The term "($C_5$ to $C_8$) cycloalkenyl" means an unsaturated, monocyclic, fused, spirocyclic ring structures having a total of from 5 to 8 carbon ring atoms. Examples of such groups include, but are not limited to, cyclopentenyl, cyclohexenyl.

The term cyano" refers to a —C≡N group.

An "aldehyde" group refers to a carbonyl group where R is hydrogen.

An "alkoxy" group refers to both an —O-alkyl and an —O-cycloalkyl group, as defined herein.

An "alkoxycarbonyl" refers to a —C(O)OR.

An "alkylaminoalkyl" group refers to an -alkyl-NR-alkyl group.

An "alkylsulfonyl" group refer to a —$SO_2$alkyl.

An "amino" group refers to an —$NH_2$ or an —NRR' group.

An "aminoalkyl" group refers to an -alkyl-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)Oaryl.

An "arylsulfonyl" group refers to a —$SO_2$aryl.

A "C-amido" group refers to a —C(O)NRR' group.

A "carbonyl" group refers to a —C(O)R.

A "C-carboxyl" group refers to a —C(O)OR groups.

A "carboxylic acid" group refers to a C-carboxyl group in which R is hydrogen.

A "cyano" group refers to a —CN group.

A "dialkylamionalkyl" group refers to an -(alkyl)N(alkyl)$_2$ group.

A "halo" or "halogen" group refers to fluorine, chlorine, bromine or iodine.

A "heteroalicycloxy" group refers to a heteroalicyclic-O group with heteroalicyclic as defined herein.

A "heteroaryloxyl" group refers to a heteroaryl-O group with heteroaryl as defined herein.

A "hydroxy" group refers to an —OH group.

An "N-amido" group refers to a —R'C(O)NR group.

An "N-carbamyl" group refers to a —ROC(O)NR-group.

A "nitro" group refers to a —$NO_2$ group.

An "N-Sulfonamido" group refers to a —NR—S(O)$_2$R group.

An "N-thiocarbamyl" group refers to a ROC(S)NR' group.

An "O-carbamyl" group refers to a —OC(O)NRR' group.

An "O-carboxyl" group refers to a RC(O)O group.

An "O-thiocarbamyl" group refers to a —OC(S)NRR' group.

An "oxo" group refers to a carbonyl moiety such that alkyl substituted by oxo refers to a ketone group.

A "perfluoroalkyl group" refers to an alkyl group where all of the hydrogen atoms have been replaced with fluorine atoms.

A "phosphonyl" group refers to a —P(O)(OR)$_2$ group.

A "silyl" group refers to a —Si(R)$_3$ group.

An "S-sulfonamido" group refers to a —S(O)$_2$NR-group.

A "sulfinyl" group refers to a —S(O)R group.

A "sulfonyl" group refers to a —S(O)$_2$R group.

A "thiocarbonyl" group refers to a —C(=S)—R group.

A "trihalomethanecarbonyl" group refers to a $Z_3$CC(O) group, where Z is halogen.

A "trihalomethanesulfonamido" group refers to a $Z_3$CS (O)$_2$ NR-group.

A "trihalomethanesulfonyl" group refers to a $Z_3$CS(O)$_2$ group.

A "trihalomethyl" group refers to a —$CZ_3$ group.

A "C-carboxyl" group refers to a —C(O)OR groups.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

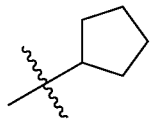 [SMILES: *C1CCCC1]

represents a cyclopentyl group, etc.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein the terms "Formula I" and "Formula I or pharmaceutically acceptable salts thereof" are defined to include all forms of the compound of Formula I, including hydrates, solvates, isomers including stereoisomers, tautomers, and isotopically labeled versions thereof, crystalline and non-crystalline forms, isomorphs, polymorphs, metabolites, and prodrugs thereof.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The term "solvate," is used to describe a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof. The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable. The term "pharmaceutically acceptable salt(s)", as used herein, unless otherwise indicated, includes salts of acidic or basic groups which may be present in the compounds of Formula I.

The term "pharmaceutically acceptable formulation," as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional agents that reduce abnormal cell growth.

The terms "inhibiting" and "modulating" PI3-Kα and/or PI3-Kα/mTOR activity mean inhibiting or modulating the PI3-Kα enzyme and/or the PI3-Kα and mTOR enzymes or either in vitro or in vivo, such as in a mammal, such as a human, by contacting the PI3-Kα enzyme and/or the PI3-Kα and mTOR enzymes with an amount of a compound of the present invention, or a pharmaceutically acceptable salt or solvate thereof, that will affect such inhibition or modulation.

The term "PI3-Kα-inhibiting amount" as used herein, refers to the amount of a compound of the present invention, or a pharmaceutically acceptable salt or solvate thereof, required to inhibit the enzymatic activity of PI3-Kα in vivo, such as in a mammal, or in vitro. The amount of such compounds required to cause such inhibition can be determined without undue experimentation using methods described herein and those known to those of ordinary skill in the art.

The term "PI3-Kα/mTOR-inhibiting amount" as used herein, refers to the amount of a compound of the present invention, or a pharmaceutically acceptable salt or solvate thereof, required to inhibit the enzymatic activity of PI3-Kα and mTOR in vivo, such as in a mammal, or in vitro. The amount of such compounds required to cause such inhibition can be determined without undue experimentation using methods described herein and those known to those of ordinary skill in the art.

The term "inhibiting PI3-Kα enzyme activity," as used herein, means decreasing the activity or functioning of the PI3-Kα enzyme either in vitro or in vivo, such as in a mammal, such as a human, by contacting the enzyme with a compound or pharmaceutically acceptable salt of the present invention.

The term "inhibiting PI3-Kα/mTOR enzyme activity," as used herein, means decreasing the activity or functioning of the PI3-Kα and mTOR enzymes either in vitro or in vivo, such as in a mammal, such as a human, by contacting the enzymes with a compound or pharmaceutically acceptable salt of the present invention.

The term "PI3-Kα" as used herein means PI3-Kα, or mutants thereof, or any of the known PI3-Kα isoformic splice variants.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer. The term "therapeutically effective amount," as used herein, means an amount of a compound of the present invention, or a salt thereof, that, when administered to a mammal in need of such treatment, is sufficient to effect treatment, as defined herein. Thus, a therapeutically effective amount of a compound of the present invention, or a salt thereof, is a quantity sufficient to modulate or inhibit the activity of the PI3-Kα enzyme and/or PI3-Kα/mTOR enzymes such that a disease condition that is mediated by activity of the PI3-Kα enzyme and/or PI3-Kα/mTOR enzymes is reduced or alleviated.

The terms "treat", "treating", and "treatment" with reference to abnormal cell growth, or to any PI3-Kα and/or PI3-Kα/mTOR mediated disease or condition, in a mammal, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition. With regard to abnormal cell growth, such as cancer, these terms simply mean that the life expectancy of an individual affected with abnormal cell growth will be increased or that one or more of the symptoms of the disease will be reduced. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). This includes the abnormal growth of: (1) tumor cells (tumors) that proliferate by expressing PI3-Kα and/or PI3-Kα/mTOR; (2) benign and malignant cells of other proliferative diseases in which PI3-Kα and/or PI3-Kα/mTOR occurs; (4) any tumors that proliferate by PI3-Kα and/or PI3-Kα/mTOR; (5) any tumors that proliferate by aberrant PI3-Kα and/or PI3-Kα/mTOR activation; and (6) benign and malignant cells of other proliferative diseases in which aberrant PI3-Kα and/or PI3-Kα/mTOR activation occurs.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

As used herein, the term "combination therapy" refers to the administration of a compound of Formula I together with an at least one additional pharmaceutical or medicinal agent (e.g., an anti-cancer agent), either sequentially or simultaneously.

DETAILED DESCRIPTION

1. Compounds of Formula I

The compounds of the present invention are useful for modulating or inhibiting PI3-Kα and/or PI3-Kα/mTOR activity. Accordingly, these compounds are useful for the prevention and/or treatment of disease states associated with abnormal cell growth such as cancer, alone or in combination with other anti-cancer agents.

In one embodiment, the invention also relates to the compounds described in the Examples section of the subject application, and pharmaceutically acceptable salts thereof.

2. Salts of the Compounds of Formula I

As noted above, the compounds of Formula I may exist in the form of salts such as, e.g., acid addition salts and base addition salts of the compounds of Formula I.

For example, the compounds of Formula I that are basic in nature are capable of forming a wide variety of salts with various inorganic and organic acids.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methanesulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate and pamoate [i.e., 1,1'-methylene-bis-(2-hydroxy-3-naphthoate)] salts.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The invention also relates to base addition salts of the compounds of Formula I. The chemical bases that may be used as reagents to prepare pharmaceutically acceptable base salts of the compounds of Formula I that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of Formula I are known to one of skill in the art.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of Formula I, or a pharmaceutically acceptable salt thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of the Formula I containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

In the case of agents that are solids, it is understood by those skilled in the art that the inventive compounds, agents and salts may exist in different crystal or polymorphic forms, all of which are intended to be within the scope of the present invention and specified formulas.

3. Prodrugs of the Compounds of Formula I

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some non-limiting examples of prodrugs in accordance with the invention include:

(i) where the compound of Formula I contains a carboxylic acid functionality which is functionalized into a suitably metabolically labile group (esters, carbamates, etc.) compound of Formula I (ii) where the compound of Formula I contains an alcohol functionality which is functionalized into a suitably metabolically labile group (ethers, esters, carbamates, acetals, ketals, etc.) compound of Formula I; and (iii) where the compound of Formula I contains a primary or secondary amino functionality, or an amide which are functionalized into a suitably metabolically labile group, e.g., a hydrolysable group (amides, carbamates, ureas, phosphonates, sulfonates, etc.). compound of Formula I.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug.

4. Isomers and Isotopes of the Compounds of Formula I

The compounds of Formula I may have asymmetric carbon atoms. The carbon-carbon bonds of the compounds of Formula I may be depicted herein using a solid line (—), a solid wedge ( ), or a dotted wedge ( ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present invention includes all tautomers of the compounds of Formula I.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of Formula I, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

5. Pharmaceutical Compositions of the Compounds of Formula I

The invention also relates to compositions comprising a compound of Formula I or a pharmaceutically acceptable salt thereof (e.g., pharmaceutical compositions). Accordingly, in one embodiment, the invention relates to a pharmaceutical composition comprising a compound of Formula I, or a pharmaceutically acceptable salt, a pharmaceutically acceptable carrier and, optionally, at least one additional medicinal or pharmaceutical agent. In one embodiment, the at least one additional medicinal or pharmaceutical agent is an anti-cancer agent as described below.

The pharmaceutically acceptable carrier may comprise a conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

In one preferred embodiment the composition comprises a therapeutically effective amount of a compound of Formula I and a pharmaceutically acceptable carrier.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated by PI3-Kα, a pharmaceutical composition of the invention is administered in a suitable formulation prepared by combining a therapeutically effective amount (i.e., a PI3-Kα modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal suffering from abnormal cell growth, such as a human, either alone or as part of a pharmaceutically acceptable formulation, once a day, twice a day, three times a day, or four times a day, or even more frequently.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

Administration of the compounds of Formula I may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

6. Therapeutic Use of the Compounds of Formula I

This invention also relates to a method for the treatment of abnormal cell growth in a mammal, including a human, comprising administering to said mammal an amount of a compound of the Formula (I), as defined above, or a pharmaceutically acceptable salt thereof, that is effective in treating abnormal cell growth.

The compounds of Formula I are potent inhibitors of by PI3-Kα and thus are all adapted to therapeutic use as antiproliferative agents (e.g., cancer), antitumor (e.g., effect against solid tumors) in mammals, particularly in humans. In particular, the compounds of Formula I are useful in the prevention and treatment of a variety of human hyperproliferative disorders including both malignant and benign abnormal cell growth.

The compounds, compositions and methods provided herein are useful for the treatment of cancers including but not limited to cancers of the:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

Still more specifically, examples of "cancer" when used herein in connection with the present invention include cancer selected from lung cancer (NSCLC and SCLC), breast cancer, ovarian cancer, colon cancer, rectal cancer, prostate cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

7. Combination Therapy of the Compounds of Formula I

As noted above, the compounds of Formula I may be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of Formula I, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of Formula I and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which can be used in conjunction with a compound of Formula I and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™) nabumetone (Relafen™), piroxicam (Feldene™), naproxen (Aleve™, Naprosyn™) diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™) squalamine (EVIZON™), thalidomide (Thalomid™), Ukrain™ (NSC 631570), Vitaxin™ (MEDI 522), and zoledronic acid (Zometa™)

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™) imatinib (Gleevec™), and PD325901 (Pfizer).

Additional examples of signal transduction inhibitors which may be used in conjunction with a compound of Formula I and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitor include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), lapatinib (Tycerb™), PF-299804 (Pfizer), pelitinib (EKB 569), and pertuzumab (Omnitarg™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and GI-4000 (GlobeImmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), and AG 024322 (Pfizer).

This invention contemplates the use of compounds of Formula I together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with a compound of Formula I, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with compounds of Formula I include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the compounds of Formula I together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of Formula I, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy)), bexarotene (Targretin™), Tesmilifene (DPPE—enhances efficacy of cytotoxics)), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof.

Further examples of classical antineoplastic agents used in combination therapy with a compound of Formula I, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Another embodiment of the present invention of particular interest relates to a method for the treatment of breast cancer in a human in need of such treatment, comprising administering to said human an amount of a compound of Formula I, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

In one embodiment the invention provides a method of treating colorectal cancer in a mammal, such as a human, in need of such treatment, by administering an amount of a compound of Formula I, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Another embodiment of the present invention of particular interest relates to a method for the treatment of renal cell carcinoma in a human in need of such treatment, comprising administering to said human an amount of a compound of Formula I, in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Another embodiment of the present invention of particular interest relates to a method for the treatment of melanoma in a human in need of such treatment, comprising administering to said human an amount of a compound of Formula I, in combination with one or more (preferably one to three) anticancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325, 901, Axitinib, bevacizumab (Avastin), thalidomide, sorafanib, vatalanib (PTK-787), Sutent, CpG-7909, AG-13736, Iressa, Lapatinib and Gleevec, wherein the amounts of the active agent together with the amounts of the combination anticancer agents is effective in treating melanoma.

Another embodiment of the present invention of particular interest relates to a method for the treatment of lung cancer in a human in need of such treatment, comprising administering to said human an amount of a compound of Formula I, in combination with one or more (preferably one to three) anticancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

8. Methods of Making the Compounds of Formula I

The invention also relates to methods of making the compounds of Formula I. Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

In each of the routes and synthetic schemes below, $R^1$, $R^2$, $R^3$, $R^4$, $R^5$ and R are as hereinbefore defined.

In one general synthetic process, compounds of the general structure represented by 10 can be prepared according to Method A.

Method A

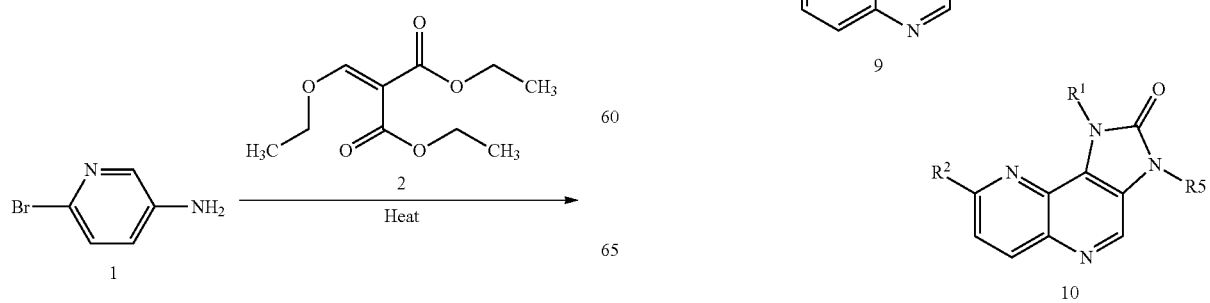

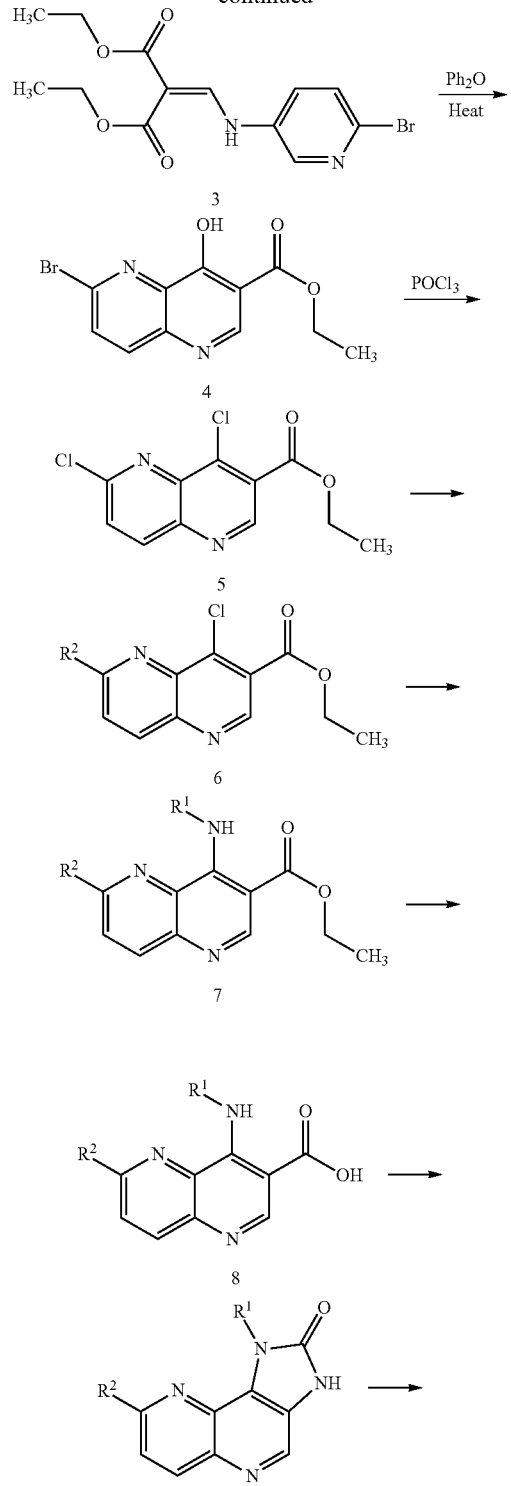

Following the modified procedure from *Synthesis*, (14), 2315-2320, 2005, described in detail in Example 1 below, compound 1 is treated with diethyl 2-(ethoxymethylene)malonate at elevated temperature to afford compound 3. Compound 3 is heated in phenyl ether ($Ph_2O$) to afford the cyclized compound 4. Treatment of compound 4 with $POCl_3$ yields 4,6-dichloro-[1,5]naphthyridine-3-carboxylic acid ethyl ester (compound 5).

Palladium catalyzed coupling of compound 5 with a boronic acid derivative $R^2B(OH)_2$ or a boronic acid ester derivative gives the compound of formula 6. Treatment of the compound of formula 6 with an amine of the formula $R^1NH_2$ generates the compound of formula 7. Hydrolysis of the ester in 7 gives the free acid 8. A compound of formula 8 is converted to a compound of formula 9 by treatment with diphenylphosphoryl azide (DPPA) and $Et_3N$ in a suitable solvent such as DMF at a temperature ranging from room temperature to 150° C. Treatment of the compound of formula 9 with an alkylating agent such as $R^5I$ in the presence of a base such as sodium hydride or $Cs_2CO_3$ gives the compound of formula 10.

In another general synthetic process, compounds of the general structure represented by 16 are prepared according to Method B.

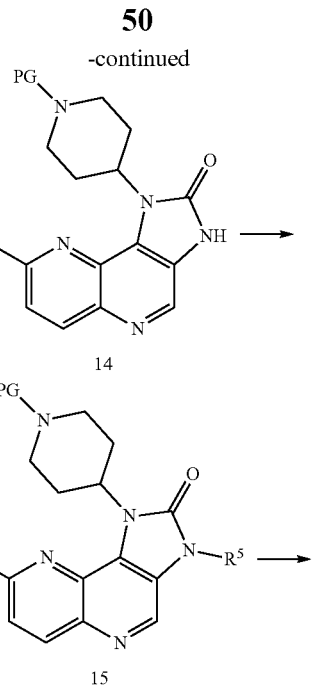

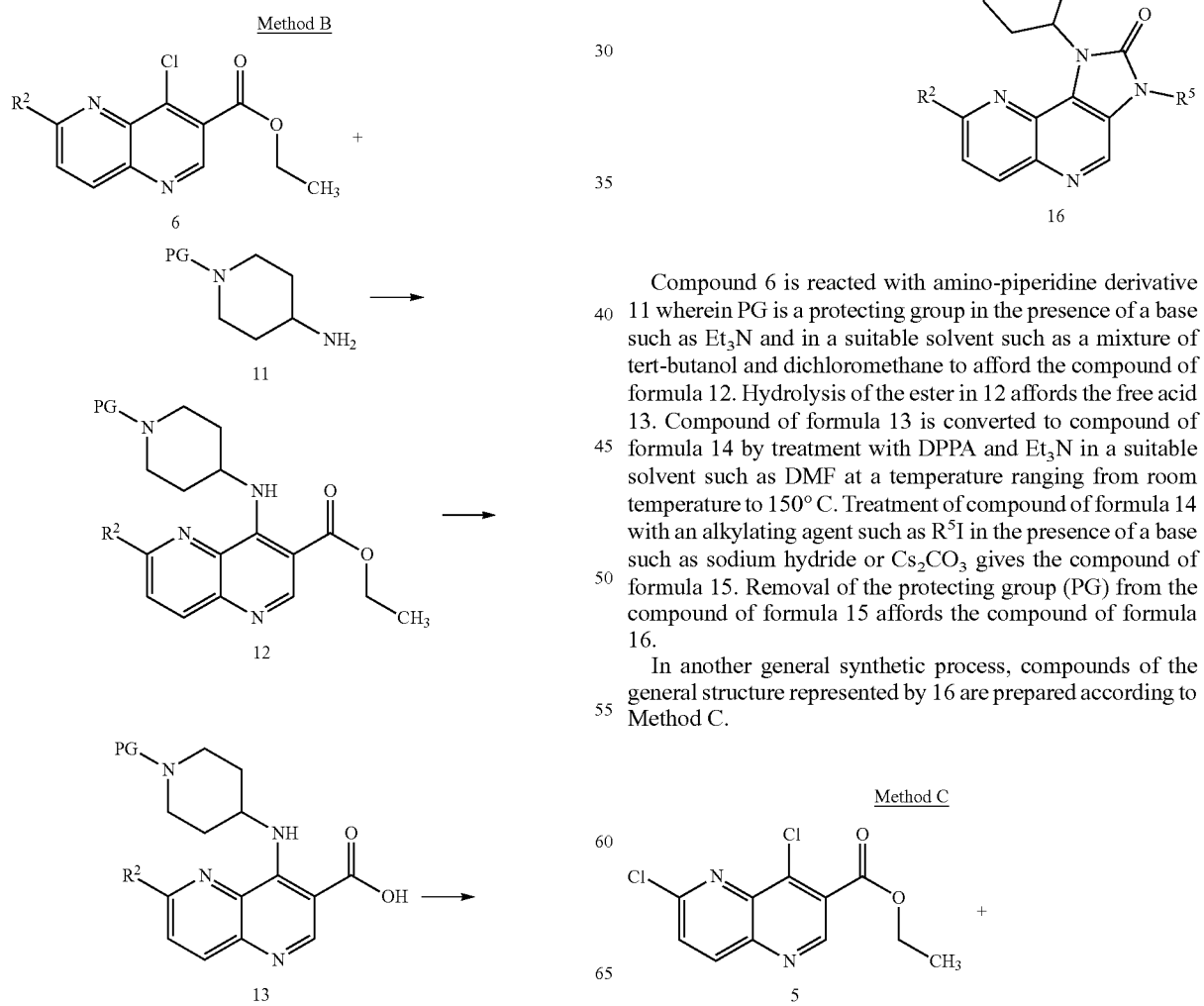

Compound 6 is reacted with amino-piperidine derivative 11 wherein PG is a protecting group in the presence of a base such as $Et_3N$ and in a suitable solvent such as a mixture of tert-butanol and dichloromethane to afford the compound of formula 12. Hydrolysis of the ester in 12 affords the free acid 13. Compound of formula 13 is converted to compound of formula 14 by treatment with DPPA and $Et_3N$ in a suitable solvent such as DMF at a temperature ranging from room temperature to 150° C. Treatment of compound of formula 14 with an alkylating agent such as $R^5I$ in the presence of a base such as sodium hydride or $Cs_2CO_3$ gives the compound of formula 15. Removal of the protecting group (PG) from the compound of formula 15 affords the compound of formula 16.

In another general synthetic process, compounds of the general structure represented by 16 are prepared according to Method C.

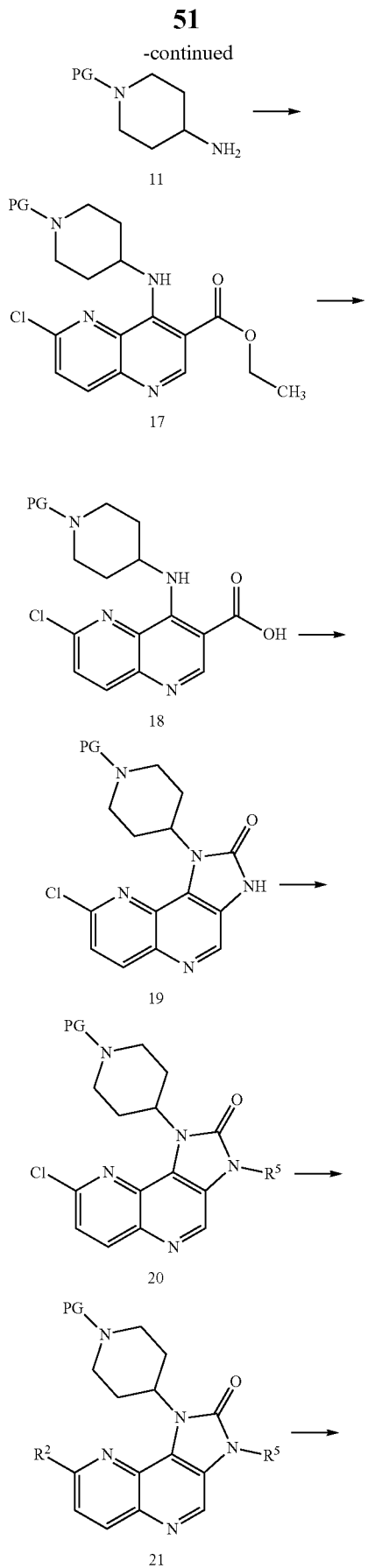

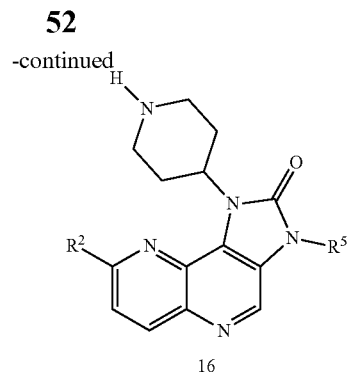

When compound 5 is reacted with amino-piperidine derivative 11 in the presence of a base such as $Et_3N$ and in a suitable solvent such as a mixture of tert-butanol and dichloromethane, the compound of formula 17 is obtained. Hydrolysis of the ester in 17 affords the free acid 18. Compound of formula 18 is converted to compound of formula 19 by treatment with diphenylphosphoryl azide (DPPA) and $Et_3N$ in a suitable solvent such as DMF at a temperature ranging from room temperature to 150° C. Treatment of compound of formula 19 with an alkylating agent such as $R^5I$ in the presence of a base such as sodium hydride or $Cs_2CO_3$ gave the compound of formula 20. Palladium catalyzed coupling of compound of formula 20 with a boronic acid derivative $R^2B(OH)_2$ or a boronic acid ester derivative gives the compound of formula 21. Removal of the protecting group from compound of formula 21 yields the compound of formula 16.

In another general synthetic process, compounds of the general structure represented by 22 are prepared according to Method D.

Method D

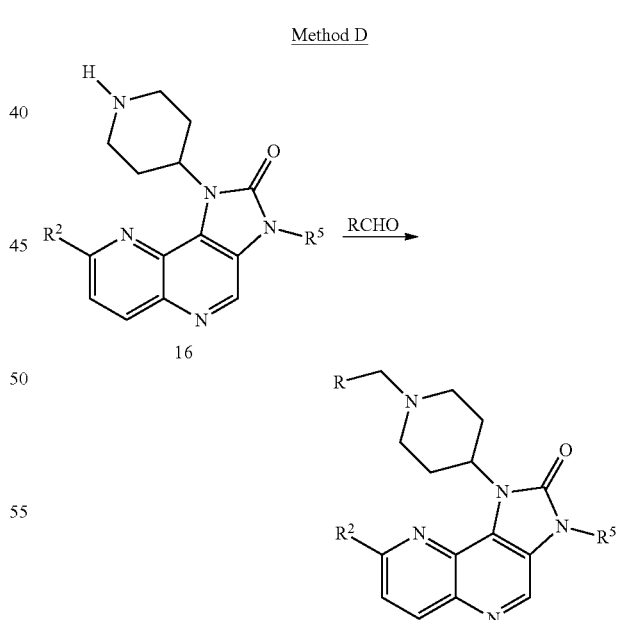

Compound of formula 16 is converted to compound of formula 22 under reductive amination conditions.

In another general synthetic process, compounds of the general structure represented by 23 are prepared according to Method E.

Method E

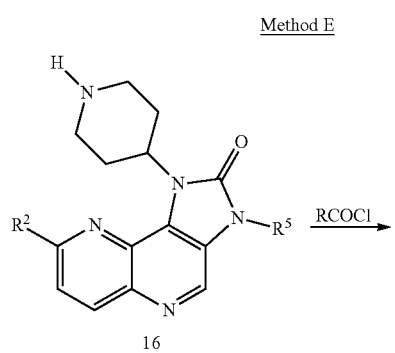

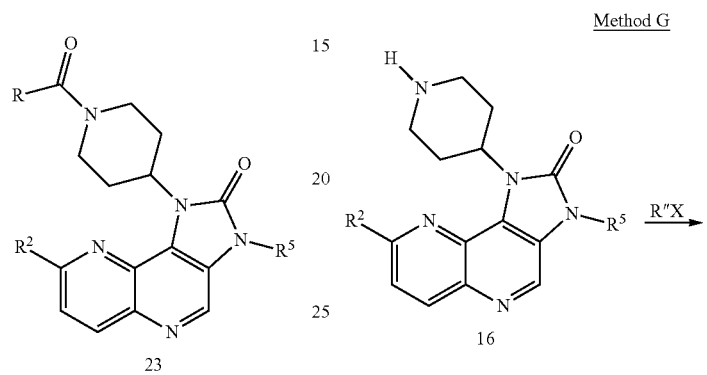

Compound of formula 16 is treated with acyl chloride in the presence of a base such as Et₃N, and in a suitable solvent such as dichloromethane to produce the compound of formula 23.

In another general synthetic process, compounds of the general structure represented by 24 are prepared according to Method F.

Method F

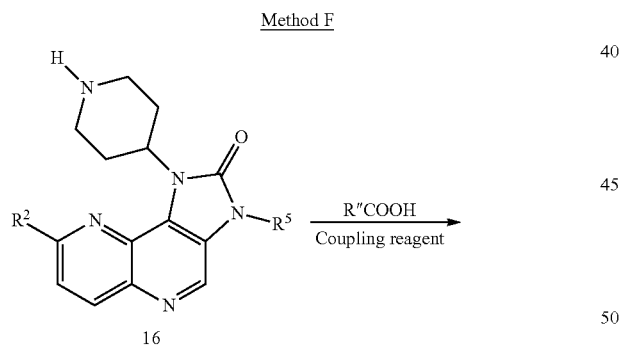

Compound of formula 16 is converted to the compound of formula 24 by reacting the piperidine amine in 16 with an acid R"COOH in the presence of a coupling reagent such as, for example, (2-(1H-7-azabenzotriazol-1-yl)-1,1,3,3-tetramethyl uronium hexafluorophosphate methanaminium) (HATU) or (1-ethyl-3-(3-dimethylaminopropyl)carbodiimide hydrochloride (EDC).

In another general synthetic process, compounds of the general structure represented by 25 are prepared according to Method G.

Method G

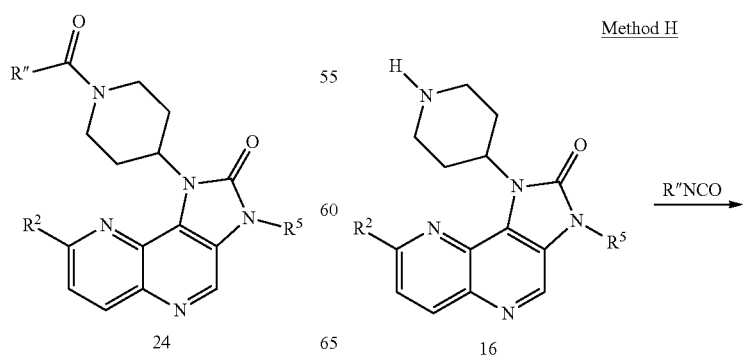

Compound of formula 16 is converted to the compound of formula 25 by reacting the piperidine amine in 16 with R"X, wherein X is a leaving group such as, for example, Cl, Br, I, in the presence of a base such as, for example, Et₃N.

In another general synthetic process, compounds of the general structure represented by 26 are prepared according to Method H.

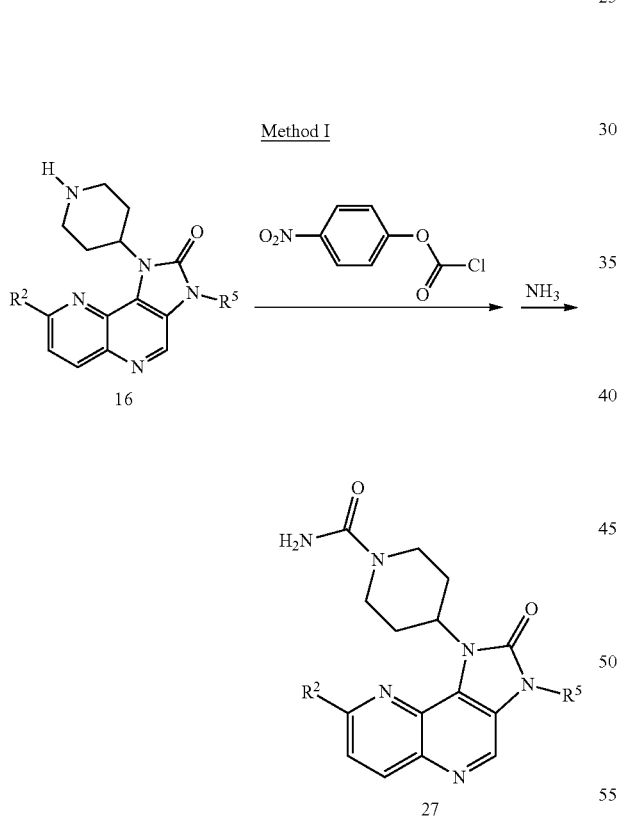

Compound of formula 16 is converted to the compound of formula 26 by reacting the piperidine amine in 16 with an isocyanate derivative R"NCO in the presence of an amine such as, for example, Et$_3$N and in a suitable solvent such as, for example, THF.

In another general synthetic process, compounds of the general structure represented by 27 are prepared according to Method I.

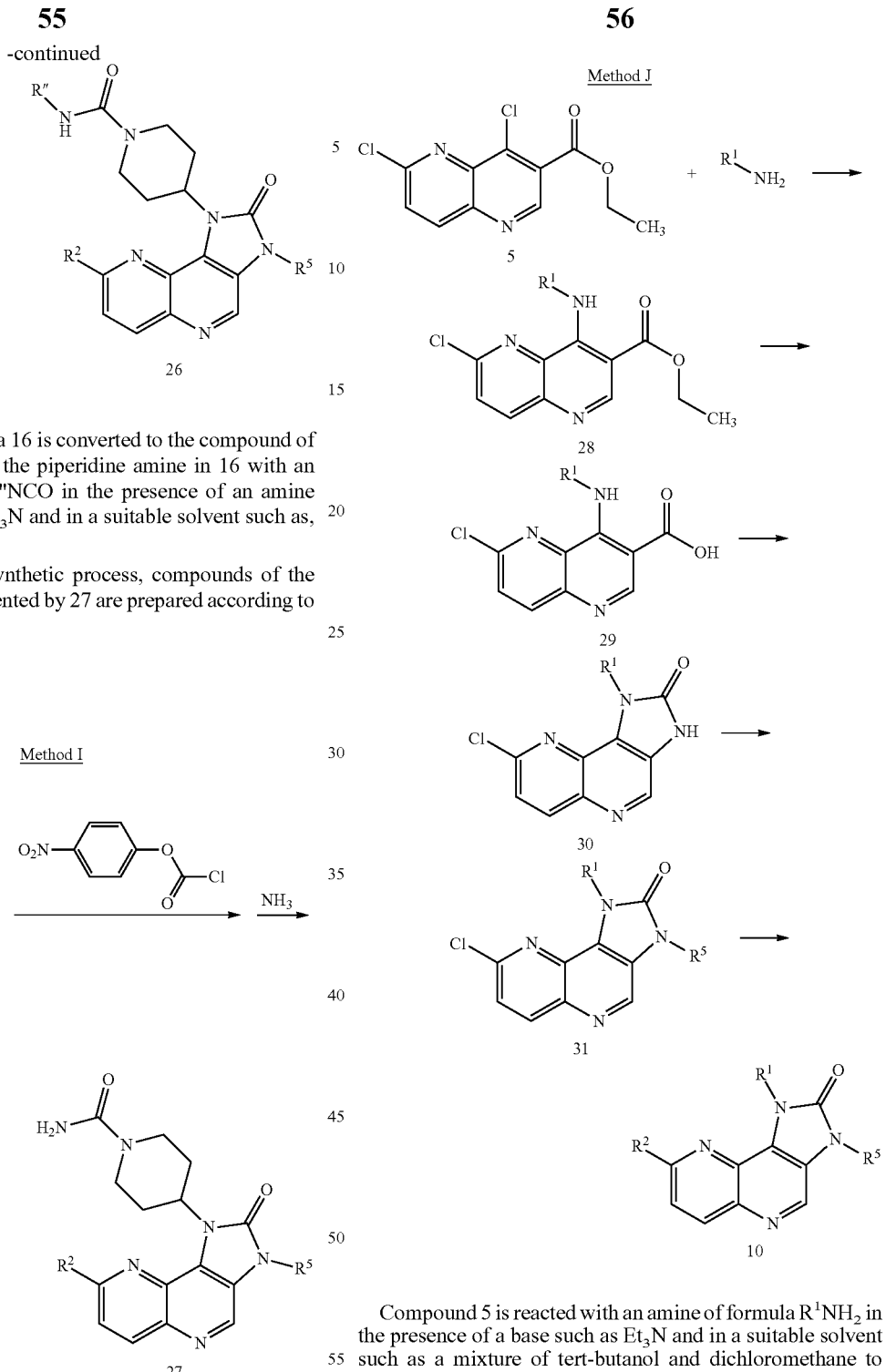

Compound of formula 16 is converted to the compound of formula 27 by first reacting the piperidine amine in 16 with 4-nitrophenyl chloroformate in the presence of an amine such as Et$_3$N and in a suitable solvent such as CH$_2$Cl$_2$, then treating the resultant carbamate with ammonia gas in DMSO in a sealed tube at an elevated temperature.

In another general synthetic process, compounds of the general structure represented by 10 are prepared according to Method J.

Compound 5 is reacted with an amine of formula R$^1$NH$_2$ in the presence of a base such as Et$_3$N and in a suitable solvent such as a mixture of tert-butanol and dichloromethane to afford the compound of formula 28. Hydrolysis of the ester in 28 affords the free acid 29. Compound of formula 29 is converted to compound of formula 30 upon treatment with DPPA and Et$_3$N in a suitable solvent such as DMF at a temperature ranging from room temperature to 150° C. Treatment of the compound of formula 30 with an alkylating agent such as R$^5$I in the presence of a base such as sodium hydride or Cs$_2$CO$_3$ gives the compound of formula 31. Palladium catalyzed coupling of compound 31 with a boronic acid or a boronic acid ester of formula R$^2$B(OR$^z$)$_2$, wherein R$^z$ is, for example, hydrogen or an alkyl group, to give the compound of formula 10.

In another general synthetic process, compounds of the general structure represented by 37 are prepared according to Method K.

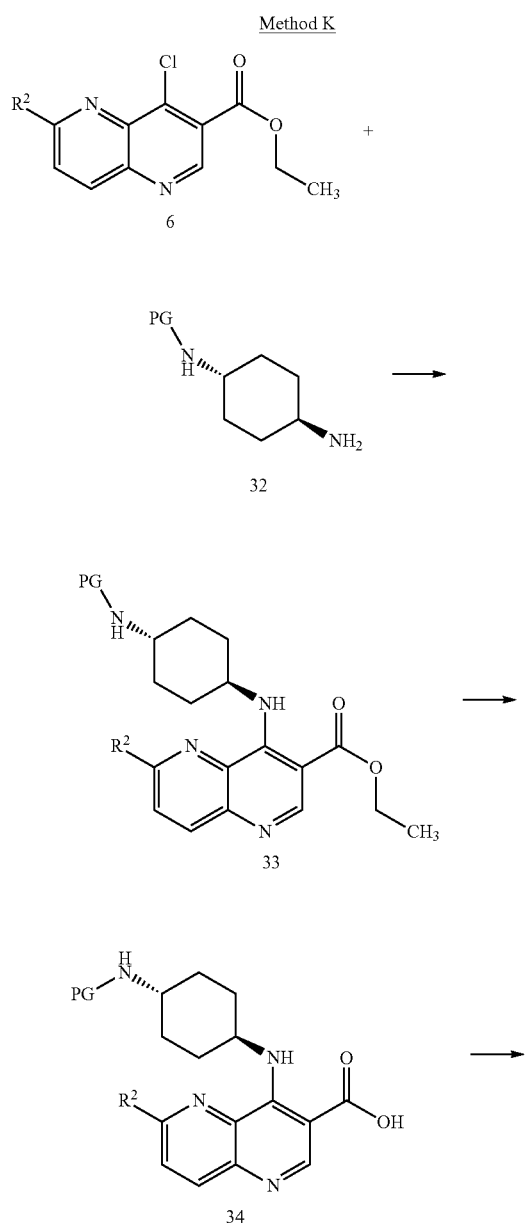

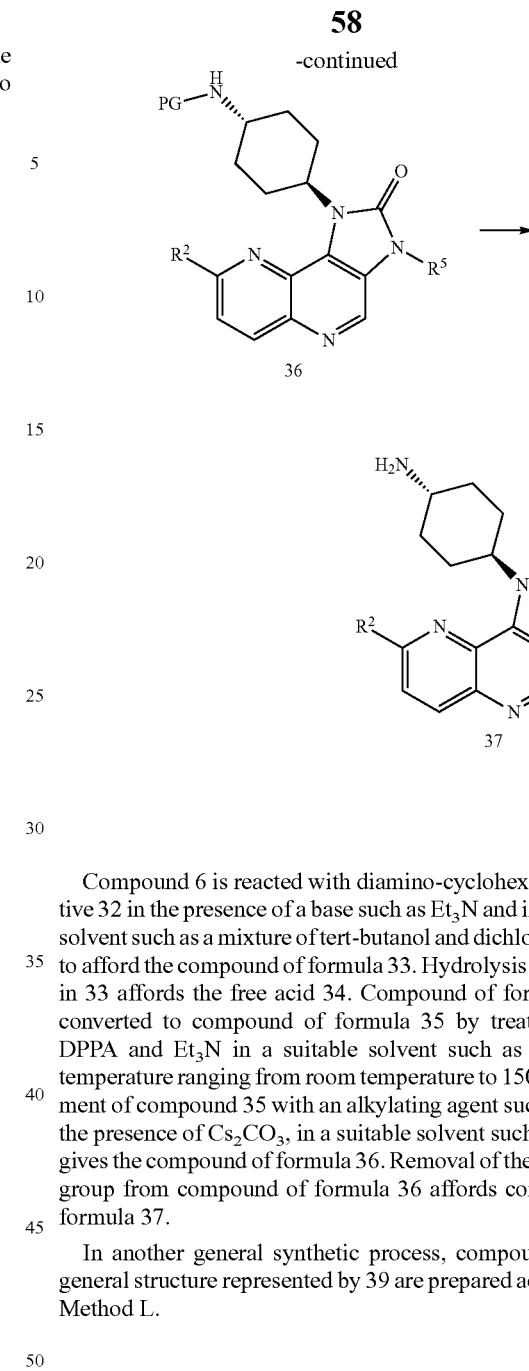

Compound 6 is reacted with diamino-cyclohexane derivative 32 in the presence of a base such as $Et_3N$ and in a suitable solvent such as a mixture of tert-butanol and dichloromethane to afford the compound of formula 33. Hydrolysis of the ester in 33 affords the free acid 34. Compound of formula 34 is converted to compound of formula 35 by treatment with DPPA and $Et_3N$ in a suitable solvent such as DMF at a temperature ranging from room temperature to 150° C. Treatment of compound 35 with an alkylating agent such as $R^5I$ in the presence of $Cs_2CO_3$, in a suitable solvent such as DMSO gives the compound of formula 36. Removal of the protecting group from compound of formula 36 affords compound of formula 37.

In another general synthetic process, compounds of the general structure represented by 39 are prepared according to Method L.

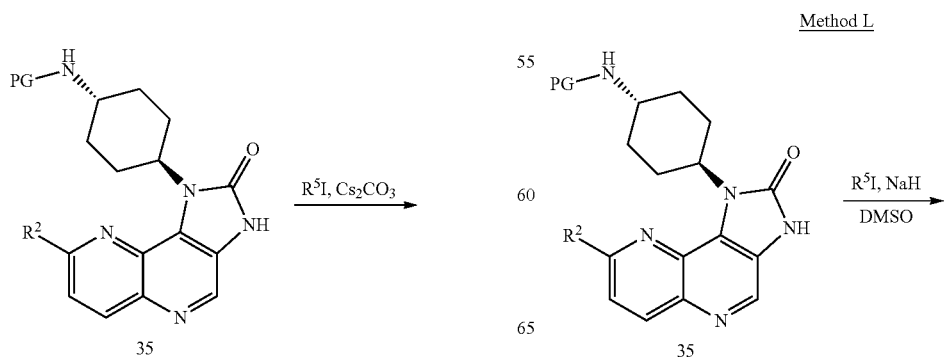

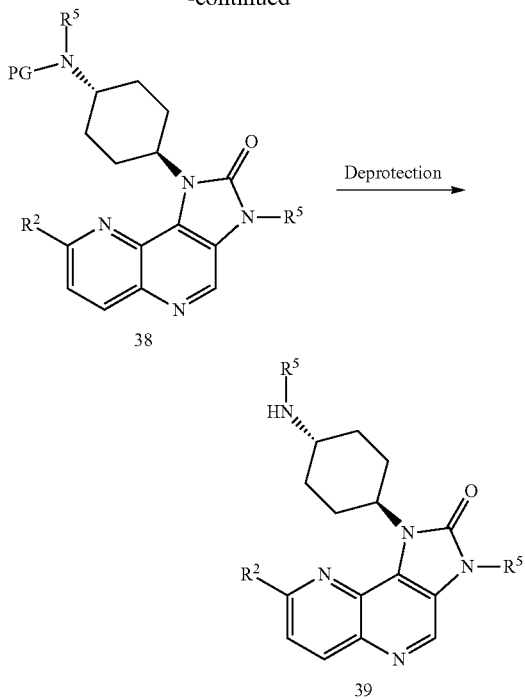

Treatment of compound 35 with an alkylating agent such as R⁵I in the presence of NaH, in a suitable solvent such as DMSO gives the compound of formula 38. Removal of the protecting group from compound 38 affords the compound of formula 39.

EXAMPLES

It is to be understood that the scope of the present invention is not limited in any way by the scope of the following examples and preparations. In the following examples molecules with a single chiral center, unless otherwise noted or indicated by the structural formula or chemical name, exist as a racemic mixture. Those molecules with two or more chiral centers, unless otherwise noted or indicated by the structural formula or chemical name, exist as a racemic mixture of diastereomers. Single enantiomers/diastereomers may be obtained by methods known to those skilled in the art.

Various starting materials and other reagents were purchased from commercial suppliers, such as Aldrich Chemical Company, and used without further purification, unless indicated otherwise. ¹H-NMR spectra were recorded on a Bruker instrument operating either at 300 MHz, or 400 MHz and ¹³C-NMR spectra were recorded operating at 75 MHz. NMR spectra were obtained as CDCl₃ solutions (reported in ppm), using chloroform as the reference standard (7.25 ppm and 77.00 ppm) or DMSO-D₆ (2.50 ppm and 39.51 ppm) or CD₃OD (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

The following abbreviations may be used herein: Et₂O (diethyl ether); DMF (N,N-dimethylformamide); THF (tetrahydrofuran); DCM (dichloromethane); DMA (dimethyl acetal); DBU (1,8-diazabicyclo[5.4.0]undec-7-ene); DPPA (diphenylphosphoryl azide); HATU (2-(1H-7-azabenzotriazol-1-yl)-1,1,3,3-tetra methyl uronium hexafluorophosphate methanaminium); EDC (1-ethyl-3-(3-dimethylaminopropyl) carbodiimide hydrochloride); LiHMDS or LHMDS (lithium hexamethyldisilazide); TBME (tert-butyl methyl ether); LDA (lithium diisopropylamide); DMSO (dimethylsulfoxide); MeOH (methanol); EtOH (ethanol); EtOAc (ethyl acetate); Ac (acetyl); Me (methyl); Et (ethyl); Ph (phenyl); MEM (minimal essential medium); PS (penicillin-streptomycin); Hepes (N-2-hydroxylethylpiperazine-N-2-ethane sulfonic acid); 2-ME (β-2-mercaptoethanol); PBS (phosphate-buffered saline); FBS (fetal bovine serum); TLC (thin-layer chromatography); Bu (butyl); CBZ (carbobenzyloxy); t-Bu (tert-butyl); BOO (tert-butyloxycarbonyl); r.t. or rt (room temperature); d (day); h or hr (hour); g (gram); mg (milligram); mL (milliliter); L (liter); LC-MS (liquid chromatography mass spectrometry); eq (equivalents)

Example 1

Preparation of 4,6-dichloro-[1,5]naphthyridine-3-carboxylic acid ethyl ester (Compound 5)

Compound 5 was synthesized in 3 steps shown in Method A, as follows.

Step 1

Compound 1 (400 g, 2.33 mol) and compound 2 (565 g, 2.80 mol) were mixed in EtOH (4 L) and the resultant mixture was refluxed for 5 hours. TLC (EtOAc/petroleum ether=1:3) indicated complete consumption of compound 1. The mixture was filtered and the cake was washed with petroleum ether (1 L×3) to give compound 3 (710 g, 89%) as an off-white solid.

¹H NMR (400 MHz, CDCl₃): δ 8.34-8.31 (d, 1H), 8.18-8.17 (d, 1H), 7.43-7.41 (d, 1H), 7.30-7.28 (dd, 1H), 4.27-4.22 (m, 2H), 4.21-4.16 (m, 2H), 1.32-1.29 (t, 3H), 1.28-1.24 (t, 3H).

Step 2

To a refluxing solvent of Ph₂O (3.5 L) was added compound 3 (680 g, 1.98 mol) in portions over 5 minutes. The resultant mixture was refluxed for 20 minutes. TLC (dichloromethane/MeOH=10:1) indicated complete consumption of compound 3. The reaction mixture was cooled to room temperature and poured into petroleum ether (15 L). The resulting precipitate was filtered and washed with petroleum ether (4 L×3) to give compound 4 (320 g, 50%) as a brown solid which was used directly for the next reaction step.

Step 3

A suspension of compound 4 (300 g, 1 mol) in POCl₃ (5 L) was refluxed for 3 hours. TLC (EtOAc/petroleum ether=1:4) indicated complete consumption of compound 4. The solvent was removed under reduced pressure. The residue was poured into ice-water (4 L) carefully, basified with K₂CO₃ to pH of above 8, and then extracted with dichloromethane (1 L×3). The combined organic layers were washed with brine (500 mL), dried over anhydrous Na₂SO₄ and concentrated in vacuo to give the residue, which was purified by column chromatography on silica gel eluted with DCM to give the title compound (101.7 g, 32.0%) as a white solid.

¹H NMR (400 MHz, DMSO): δ 1.452-1.500 (t, 3H), 4.492-4.564 (q, 2H), 7.725-7.755 (d, 1H), 8.379-8.408 (d, 1H), 9.229 (s, 1H).

Example 2
Preparation of 2-methyl-2-[4-(3-methyl-2-oxo-8-quinolin-3-yl-2,3-dihydro-1H-imidazo[4,5-c]-1,5-naphthyridin-1-yl)phenyl]propanenitrile (compound 102)
Compound 102 was synthesized according to Method A as follows.
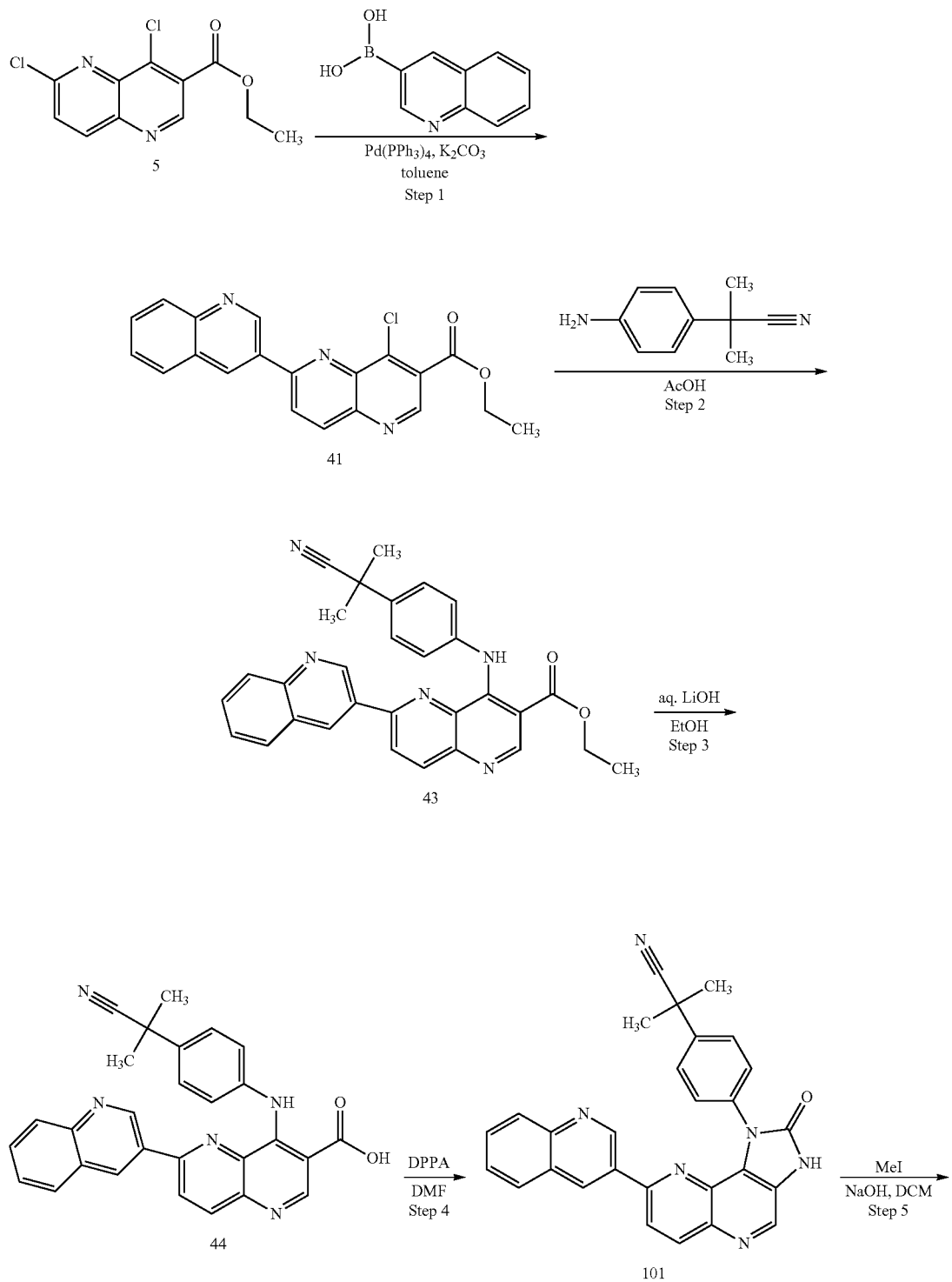

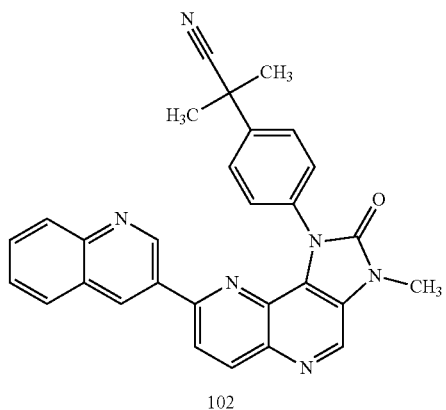

102

Step 1

To a stirred suspension of crude compound 5 (3.0 g, 0.0095 mol), compound 40 (1.6 g, 0.0095 mol) and 2 N Na$_2$CO$_3$ (14 mL) in toluene (45 mL) and EtOH (15 mL) was added a catalytic amount of Pd(PPh$_3$)$_4$ under nitrogen. The resulting mixture was refluxed overnight. TLC (EtOAc/petroleum ether 1:3) indicated the reaction was complete. The reaction mixture was cooled to room temperature and filtered. The filtrate was concentrated in vacuo to give a residue which was dissolved in dichloromethane (150 mL). After washing with water (50 mL×3) and brine (50 mL×3), the dichloromethane layer was dried over anhydrous Na$_2$SO$_4$ and concentrated in vacuo to give the crude product which was purified by column chromatography (silica gel, EtOAc/petroleum ether 1:3) to afford compound 41 (2.1 g, 62%) as an off white solid.

$^1$H NMR (400 MHz, CDCl$_3$): δ 9.80 (s, 1H), 9.18 (s, 1H), 8.90 (s, 1H), 8.52-8.50 (d, 1H), 8.36-8.31 (d, 1H), 8.16-8.14 (d, 1H), 7.97-7.95 (d, 1H), 7.78-7.74 (t, 1H), 7.59-7.52 (t, 1H), 4.52-4.46 (m, 2H), 1.46-1.42 (t, 3H).

Step 2

A mixture of compound 41 (2.1 g, 0.0058 mol) and compound 42 (1.0 g, 0.0062 mol) in acetic acid (30 mL) was stirred at room temperature overnight. TLC (dichloromethane/MeOH 20:1) indicated the reaction was complete. The reaction mixture was diluted with water (50 mL) and neutralized with 1 N NaOH to pH 8. The resulting mixture was extracted with dichloromethane (50 mL×3). The combined dichloromethane layers were dried over anhydrous Na$_2$SO$_4$ and concentrated in vacuo to give the crude product which was purified by column chromatography (silica gel, dichloromethane/MeOH 60:1) to afford compound 43 (2.0 g, 77%) as a yellow solid.

$^1$H NMR (400 MHz, DMSO): δ 10.11 (s, 1H), 9.44 (s, 1H), 9.07 (s, 1H), 8.89 (s, 1H), 8.63-8.61 (d, 1H), 8.44-8.42 (d, 1H), 8.04-8.02 (d, 2H), 7.82-7.79 (t, 1H), 7.67-7.65 (t, 1H), 7.51-7.49 (d, 2H), 7.33-7.31 (d, 2H), 3.95-3.92 (m, 2H), 1.68 (s, 6H), 1.12-1.09 (t, 3H).

Step 3

A mixture of compound 43 (2.0 g, 0.0041 mol) and lithium hydroxide monohydrate (0.23 g, 0.0055 mol) in EtOH (40 mL) and water (4 mL) was stirred at room temperature overnight. TLC (EtOAc) indicated the reaction was complete. The reaction mixture was concentrated in vacuo to give a residue which was dissolved into water (100 mL) and acidified with 1N HCl to pH 4. The resulting precipitate was filtered, washed with MeOH (10 mL×3) and then dried in vacuum (50° C., 0.4 bar) to give compound 44 (1.5 g, 83%) as a yellow solid.

Step 4

A mixture of compound 44 (0.4 g, 0.87 mmol) and Et$_3$N (0.18 g, 1.74 mmol) in DMF (15 mL) was stirred at room temperature for 30 minutes. DPPA (0.48 g, 1.74 mmol) was added dropwise to the mixture. After being stirred for 2 hours at room temperature, the resulting mixture was heated at 60° C. for 2 hours. TLC (dichloromethane/MeOH 10:1) indicated the reaction was complete. The reaction mixture was cooled to room temperature and poured into ice-water (100 mL). The aqueous layer was saturated with NaCl (50 g) and extracted with THF (40 mL×3). The combined THF layers were dried over anhydrous Na$_2$SO$_4$ and concentrated in vacuo to give a residue which was diluted with EtOAc (50 mL). The resulting precipitate was filtered, washed with EtOAc (40 mL×3) and then dried under air to give 2-methyl-2-[4-(2-oxo-8-quinolin-3-yl-2,3-dihydro-1H-imidazo[4,5-c]-1,5-naphthyridin-1-yl)phenyl]propanenitrile (Compound 101) (800 mg, 53%) as an off-white solid.

$^1$H NMR (400 MHz, DMSO): δ 8.89 (s, 1H), 8.82 (s, 2H), 8.51-8.48 (d, 1H), 8.41-8.39 (d, 1H), 8.02-7.95 (m, 2H), 7.82-7.77 (m, 3H), 7.70-7.67 (d, 2H), 7.64-7.60 (t, 1H), 1.89 (s, 6H).

LRMS m/z 457 (M+H)$^+$.

Step 5

To a stirred suspension of Compound 101 (0.2 g, 0.44 mmol), Bu$_4$NBr (14 mg, 0.044 mmol) and CH$_3$I (0.10 g, 0.66 mmol) in dichloromethane (10 mL) was added NaOH (0.026 g, 0.66 mmol) in H$_2$O (3.5 mL). The resulting mixture was stirred at room temperature overnight. TLC (EtOAc) indicated the reaction was complete. The reaction mixture was diluted with water (20 mL) and dichloromethane (50 mL). The separated aqueous layer was saturated with NaCl (40 g) and extracted with THF (40 mL×3). The combined organic layers were concentrated in vacuo to give a residue which was washed with DMSO (10 mL×3) and EtOAc (30 mL×3). The residue was dried under air to give the title Compound 102 (120 mg, 78%) as an off-white solid.

$^1$H NMR: (400 MHz, DMSO): δ 9.10 (s, 1H), 8.91 (s, 1H), 8.82 (s, 1H), 8.55-8.52 (d, 1H), 8.43-8.41 (d, 1H), 7.98 (m, 2H), 7.80-7.78 (d, 2H), 7.71-7.69 (d, 2H), 7.64 (m, 1H), 3.64 (s, 3H), 1.91 (s, 6H).

LRMS m/z 471 (M+H)$^+$.

Example 3

Preparation of 3-methyl-1-piperidin-4-yl-8-quinolin-3-yl-1,3-dihydro-2H-imidazo[4,5-c][1,5]naphthyridin-2-one (Compound 118)

Compound 118 was synthesized according to Method B as follows.

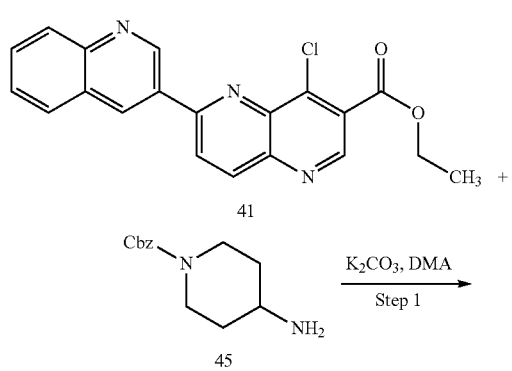

41

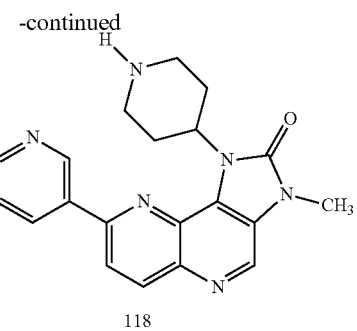

118

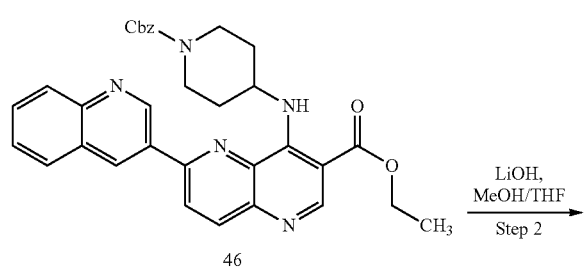

46

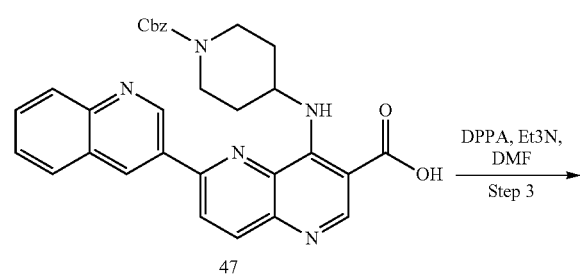

47

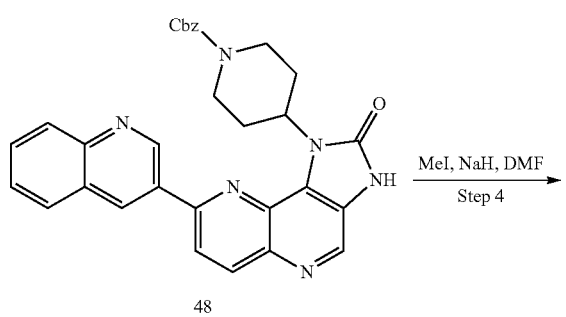

48

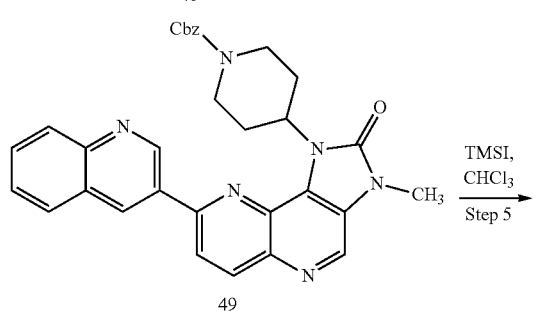

49

Step 1

A mixture of ethyl 4-chloro-6-quinolin-3-yl-1,5-naphthyridine-3-carboxylate (compound 41) (6.0 g, 17 mmol), 4-amino-1-N-Cbz-piperidine (compound 45) (4.1 g, 17 mmol), and potassium carbonate (4.6 g, 33 mmol) in N,N-dimethylacetamide (100 mL) was heated to 90° C. After 2 hours, the reaction was cooled to room temperature and filtered. The filtrate was concentrated and the residue was triturated with methanol to afford methyl 4-({1-[(benzyloxy)carbonyl]piperidin-4-yl}amino)-6-quinolin-3-yl-1,5-naphthyridine-3-carboxylate (compound 46) as a cream solid (8.2 g, 90%).

$^1$H NMR (400 MHz, DMSO-d6) ppm 1.47-1.66 (m, 2H) 2.16-2.29 (m, 2H) 3.04-3.28 (m, 2H) 3.90 (s, 3H) 3.95-4.05 (m, 2H) 5.10 (s, 2H) 5.55 (br s, 1H) 7.23-7.46 (m, 5H) 7.62-7.75 (m, 1H) 7.85 (ddd, J=8.46, 6.95, 1.26 Hz, 1H) 8.12 (d, J=9.60 Hz, 2H) 8.35 (d, J=8.84 Hz, 1H) 8.55 (d, J=8.84 Hz, 1H) 8.96 (s, 1H) 9.07 (d, J=1.77 Hz, 1H) 9.56 (br s, 1H) 9.65 (s, 1H).

LRMS m/z 553 (M+H)$^+$.

Step 2

A mixture of compound 46 (8.2 g, 15 mmol) and lithium hydroxide (480 mg, 20 mmol) in 2:1 ethanol:water (150 mL) was heated to 75° C. resulting in a solution. After 2 hours, the solution was cooled to room temperature and concentrated. The residue was taken up in water (200 mL) and the solution was acidified with 1 N HCl (20 mL). The precipitate was collected by filtration and dried at 60° C. under vacuum to afford 4-({1-[(benzyloxy)carbonyl]piperidin-4-yl}amino)-6-quinolin-3-yl-1,5-naphthyridine-3-carboxylic acid (compound 47) (7.8 g, 98%).

$^1$H NMR (400 MHz, DMSO-d6) ppm 1.43-1.59 (m, 2H) 2.06-2.23 (m, 2H) 3.11-3.26 (m, 2H) 3.87-3.95 (m, 3H) 5.09 (s, 2H) 5.47 (br s, 1H) 7.28-7.50 (m, 5H) 7.65-7.85 (m, 1H) 7.79-7.94 (m, 1H) 8.11 (t, J=6.95 Hz, 2H) 8.21 (d, J=8.84 Hz, 1H) 8.38 (d, J=8.84 Hz, 1H) 9.02 (d, J=6.06 Hz, 2H) 9.65 (d, J=1.77 Hz, 1H) 11.85 (br s, 1H).

LRMS m/z 534 (M+H)$^+$.

Step 3

A suspension of compound 47 (7.8 g, 15 mmol) and triethylamine (4.1 mL, 29 mmol) in N,N-dimethylformamide (200 mL) was stirred at room temperature for 2 hr. Diphenyl phosphoryl azide (6.5 mL, 29 mmol) was added dropwise to the suspension via a syringe pump. After stirring 2 hours at room temperature the mixture was heated to 60° C., resulting in a solution. After 1.5 hr the reaction was cooled to room temperature overnight. The precipitate was collected by filtration to afford the title compound (4.2 g, 54%). The filtrate was concentrated and the residue was triturated with methanol to afford benzyl 4-(2-oxo-8-quinolin-3-yl-2,3-dihydro-1H-imidazo[4,5-c][1,5]naphthyridin-1-yl)piperidine-1-carboxylate (compound 48) (2.7 g, 35%).

¹H NMR 400 MHz, DMSO-d6) ppm 1.83-2.06 (m, 2H) 2.60-2.88 (m, 2H) 2.88-3.18 (m, 2H) 4.17-4.42 (m, 2H) 5.18 (s, 2H) 6.25 (br. s, 1H) 7.25-7.44 (m, 5H) 7.67-7.74 (m, 1H) 7.78-7.89 (m, 1H) 8.11 (d, J=8.59 Hz, 2H) 8.48 (d, J=9.09 Hz, 1H) 8.55 (d, J=8.84, 1H) 8.75 (s, 1H) 9.17 (d, J=1.77 Hz, 1H) 9.81 (d, J=2.27 Hz, 1H) 11.75 (br s, 1H).

LRMS m/z 531 (M+H)⁺.

Step 4

A suspension of compound 48 (6.6 g, 12 mmol) in N,N-dimethylformamide (200 mL) was cooled to 0° C. Sodium hydride (1.0 g, 25 mmol) was added, resulting in bright orange slush. The reaction mixture was stirred for 1 hr at 0° C. before adding methyl iodide (890 mL, 14 mmol). After 3 hours, the reaction was quenched with methanol (100 mL) and the solids were collected by filtration to afford benzyl 4-(3-methyl-2-oxo-8-quinolin-3-yl-2,3-dihydro-1H-imidazo[4,5-c][1,5]naphthyridin-1-yl)piperidine-1-carboxylate (compound 49) (5.0 g, 73%).

¹H NMR (400 MHz, DMSO-d6) ppm 1.85-2.06 (m, 2H) 2.56-2.84 (m, 2H) 2.88-3.17 (m, 2H) 3.54 (s, 3H) 4.30-4.38 (m, 2H) 5.18 (s, 2H) 7.26-7.46 (m, 5H) 7.68-7.74 (m, 1H) 7.83-7.88 (m, 1H) 8.11 (d, J=8.34 Hz, 2H) 8.49 (d, J=8.84 Hz, 1H) 8.58 (d, J=9.09 Hz, 1H) 9.00 (s, 1H) 9.17 (d, J=2.02 Hz, 1H) 9.80 (d, J=2.27 Hz, 1H).

LRMS m/z 545 (M+H)⁺.

Step 5

To a cooled (0° C.) yellow solution of compound 49 (5.0 g, 9.2 mL) in chloroform (130 mL) was added iodotrimethylsilane (TMSI) (9.0 mL, 64 mmol), dropwise, turning to an orange mixture. After 3 hours the reaction was quenched with methanol and concentrated. The resulting residue was slurried in diethyl ether and filtered solids, and the solids were washed with diethyl ether to remove all benzyl iodide. To the solids was then added 2 N sodium hydroxide (20 mL) and water (150 mL). With stirring the orange suspension slowly turned to a cream suspension. The solids were collected by filtration and purified by flash chromatography eluting with chloroform/7 N ammonia in methanol (0-10%) to afford Compound 118 (3.6 g, 96%).

¹H NMR (400 MHz, DMSO-d6) ppm 2.15-2.31 (m, 2H) 2.82-2.97 (m, 2H) 3.00-3.20 (m, 2H) 3.56-3.66 (m, 2H) 3.59 (s, 1H) 6.26-6.44 (m, 1H) 7.80 (t, J=7.20 Hz, 1H) 7.89-8.01 (m, 1H) 8.21 (d, J=8.34 Hz, 1H) 8.26 (d, J=7.83 Hz, 1H) 8.66 (d, J=8.84 Hz, 1H) 8.76-8.83 (m, 1H) 8.76 (d, J=8.47 Hz) 9.20 (s, 1H) 9.27 (d, J=10.11 Hz, 1H) 9.38 (s, 1H) 9.83 (d, J=2.02 Hz, 1H).

LRMS m/z 411 (M+H)⁺.

Example 4

Preparation of 3-methyl-8-(6-methyl-pyridin-3-yl)-1-piperidin-4-yl-1,3-dihydro-1,3,5,9-tetraaza-cyclopenta[a]naphthalen-2-one (Compound 177)

Compound 177 was synthesized according to Method C as follows.

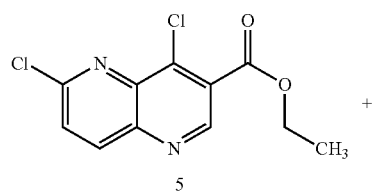

5

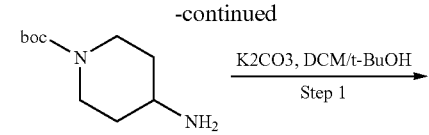
50

51

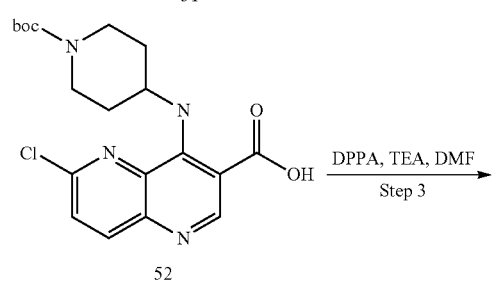
52

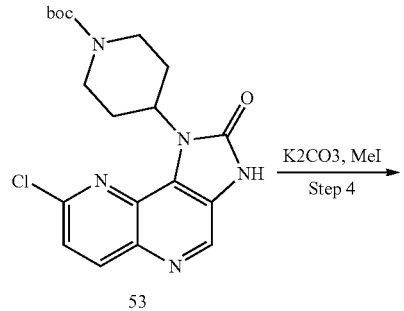
53

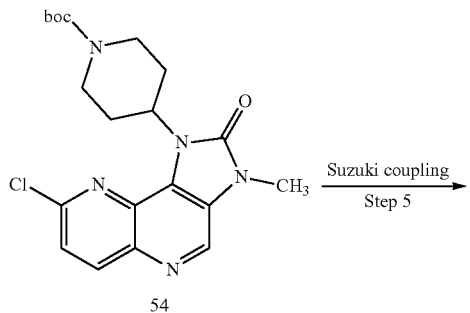
54

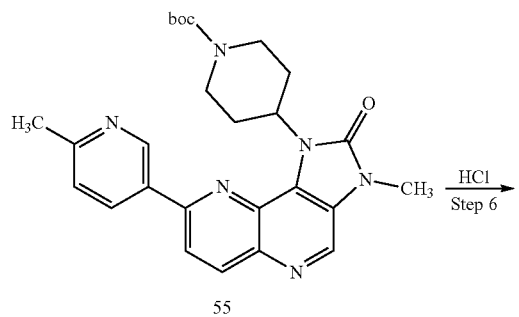
55

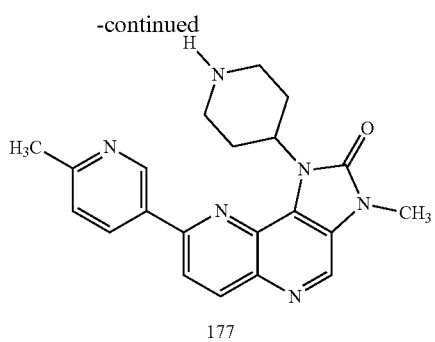

177

Step 1

To a suspension of compound 5 (5 g, 18.44 mmol) in 10 mL of dichloroethane and 10 mL of t-butanol were added 4-amino-piperidine-1-carboxylic acid tert-butyl ester (compound 50) (4.43 g, 1.2 eq.) and potassium carbonate (3.06 g, 1.2 eq.). The reaction mixture was stirred at room temperature overnight. LC mass indicated that the reaction was about half done. Another 1.2 eq of potassium carbonate was added and the reaction mixture was continued stirring for another day. LCMS indicated the completion. The reaction mixture was concentrated, and compound 51, as a crude product, was used in the next step without further purification.

Step 2

Compound 51, as the crude product mixture from step 1, was suspended in MeOH/THF/water (20/20/20 mL), and 2 M LiOH aqueous solution (27.7 mL, 3 eq.) was added. The resulting reaction mixture was stirred at 60° C. for 5 h. LC-MS indicated complete hydrolysis. After removal of the organic solvent, the aqueous residue was taken into water and acidified to pH 6 with 2 N HCl aqueous solution under vigorous stirring. The solid product was collected by vacuum-filtration, rinsed with water and MeOH, and further dried in vacuum oven to give 4-(1-tert-butoxycarbonyl-piperidin-4-ylamino)-6-chloro-[1,5]naphthyridine-3-carboxylic acid (compound 52) as a white solid (5.38 g, 73% yield in two steps), which was used in the next step without further purification.

$^1$H NMR (400 MHz, DMSO-d6) δ ppm 8.94 (s, 1H) 8.22 (d, J=8.59 Hz, 1H) 7.81 (d, J=8.59 Hz, 1H) 5.02 (br s, 1H) 3.91 (d, J=10.11 Hz, 2H) 2.99 (br s, 2H) 2.11 (dd, J=12.38, 2.53 Hz, 2H) 1.41 (s, 9H) 1.25-1.50 (m, 3H).

LRMS m/z 407.2 (M+H)$^+$.

Step 3

A suspension of compound 52 (5.38 g, 13.2 mmol) in anhydrous DMF (40 mL) was treated with Et$_3$N (3.69 ml, 2.0 eq.), stirred at r.t. for 30 minutes, and followed by the dropwise addition of DPPA (5.72 mL, 2 eq.). The resulting reaction solution was heated to 60° C. for 3 hours. After cooling to rt, the solid was collected by vacuum-filtration, rinsed with MeOH, and further dried to give 2.78 g (54% yield) of 4-(8-chloro-2-oxo-2,3-dihydro-1,3,5,9-tetraaza-cyclopenta[a]naphthalen-1-yl)-piperidine-1-carboxylic acid tert-butyl ester (compound 53) as a white solid, which was used in the next step without further purification. The filtrate was concentrated and the residue was triturated with ethyl acetate to give 2.27 g (42% yield) of the 2$^{nd}$ batch of compound 53.

$^1$H NMR (400 MHz, DMSO-d6) δ ppm 8.76 (s, 1H) 8.43 (d, J=8.84 Hz, 1H) 7.69 (d, J=8.84 Hz, 1H) 4.07-4.28 (m, 2H) 3.33 (s, 3H) 2.85 (br s, 2H) 2.66 (br s, 1H) 1.75 (d, J=10.11 Hz, 2H) 1.44 (s, 9H).

LC mass: 404.20 (AP+).

Step 4

A mixture of compound 53 (1.67 g, 4.14 mmol), MeI (0.52 mL, 2.0 eq), and potassium carbonate (2.29 g, 4.0 eq.) in anhydrous DMSO (10 mL) was stirred at rt overnight. LC-MS showed the reaction was complete. Water (30 mL) was added and the mixture was vigorously stirred. The solid product was collected by vacuum-filtration, rinsed with water and EtOAc, and further dried under vacuum at 60° C. to give 1.68 g of compound 54 (97% yield) as a clean, white solid.

$^1$H NMR (400 MHz, DMSO-d6) δ ppm 9.02 (s, 1H) 8.46 (d, J=8.84 Hz, 1H) 7.71 (d, J=8.84 Hz, 1H) 4.18 (br s, 2H) 3.53 (s, 3H) 2.88 (br s, 2H) 2.65 (br s, 2H) 1.77 (d, J=9.09 Hz, 2H) 1.44 (s, 9H).

LRMS m/z 418.2 (M+H)$^+$.

Step 5

A mixture of compound 54 (0.836 g, 2.00 mmol), 6-methylpyridin-3-ylboronic acid (0.548 g, 4.00 mmol), Pd(PPh$_3$)$_2$Cl$_2$ (85.1 mg, 0.12 mmol), and K$_2$CO$_3$ (0.829 g, 6.00 mmol) in dioxane/water (14/7 mL) was bubbled with nitrogen for 5 minutes, and heated in a sealed tube at 90° C. to furnish a brown mixture. Heating was continued for 3 h, and LC-MS showed complete reaction. Water (40 mL) was added, and the mixture was vigorously stirred. The solid was collected by vacuum-filtration and further dried. The crude solid product was dissolved in MeOH/CH$_2$Cl$_2$ (10/30 mL) and filtered through a pad of Celite to remove the insoluble materials. The filtrate containing compound 54 was used in the next step without further purification.

LRMS m/z 475.2 (M+H)$^+$.

Step 6

A solution of compound 55 (0.949 g, 2.00 mmol) in CH$_2$Cl$_2$/MeOH (30/10 mL) was treated with a stream of HCl gas gently for about 10 minutes and solid precipitated. The flask was tightly capped and the mixture was stirred at rt overnight. The solid was collected by vacuum-filtration and further dried to give the HCl salt of compound 177 (0.91 g, 94%).

$^1$H NMR (400 MHz, DMSO-d6) δ 2.18 (d, J=12.38 Hz, 2H), 2.75 (s, 3H), 2.81-2.99 (m, 2H), 3.13 (d, J=11.12 Hz, 2H), 3.47-3.62 (m, 5H), 4.15 (br s, 2H), 5.95-6.44 (m, 1H), 7.86 (d, J=8.08 Hz, 1H), 8.48 (d, J=8.84 Hz, 1H), 8.59-8.80 (m, 2H), 8.92 (d, J=6.06 Hz, 1H), 9.13 (s, 2H), 9.42 (d, J=2.02 Hz, 1H).

LRMS m/z 375.0 (M+H)$^+$.

Example 5

Preparation of 8-(6-methoxypyridin-3-yl)-3-methyl-1-(1-methylpiperidin-4-yl)-1,3-dihydro-2H-imidazo[4,5-c][1,5]naphthyridin-2-one (Compound 135)

Compound 135 was synthesized according to Method D as follows.

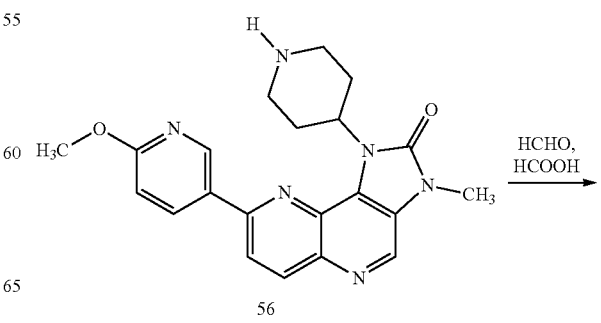

56

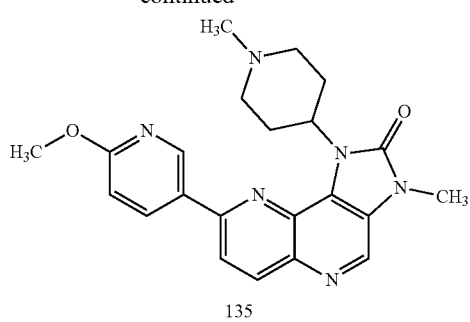

135

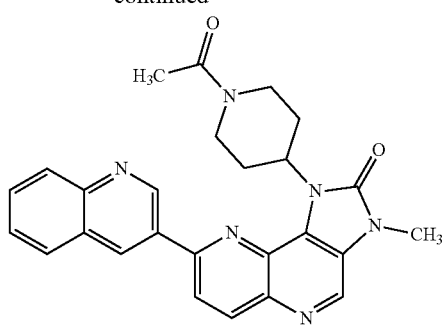

120

A solution of 8-(6-methoxypyridin-3-yl)-3-methyl-1-piperidin-4-yl-1,3-dihydro-2H-imidazo[4,5-c][1,5]naphthyridin-2-one (compound 56) (120 mg, 0.31 mmol), formaldehyde (37% in water, 0.23 mL, 3.1 mmol), and formic acid (0.12 mL, 3.1 mmol) in tetrahydrofuran (3.0 mL) was heated to reflux resulting in a solution. After 1 hour, the reaction was cooled to room temperature and concentrated. The residue was purified by flash chromatography eluting with chloroform/7 N ammonia in methanol (0-5%) to afford compound 135 (100 mg, 82%).

$^1$H NMR (400 MHz, DMSO-$d_6$) ppm 2.21-2.30 (m, 2H) 2.88 (d, J=4.55 Hz, 3H) 2.91-3.14 (m, 4H) 3.56 (s, 3H) 3.64-3.73 (m, 2H) 3.99 (s, 3H) 6.17-6.29 (m, 1H) 7.21 (d, J=8.59 Hz, 1H) 8.50 (d, J=9.09 Hz, 1H) 8.54 (dd, J=8.84, 2.53 Hz, 1H) 8.73 (d, J=9.09 Hz, 1H) 9.07 (d, J=2.27 Hz, 1H) 9.26 (s, 1H) 10.35 (br s, 1H).

LRMS m/z 405 (M+H)$^+$.

To a suspension of compound 118 (150 mg, 0.37 mmol) and triethylamine (0.10 mL, 0.73 mmol) in dimethylsulfoxide (2.0 mL) was added acetyl chloride (0.05 mL, 0.73 mol). Once the reaction was complete, water was added and the solids were filtered out and purified by flash chromatography eluting with chloroform/methanol (0-10%) to afford the title compound (27 mg). The impure fractions were combined and purified a second time by flash chromatography eluting with 1:1 ethyl acetate:chloroform/methanol (0-10%) to afford compound 120 (30 mg, 35% total yield).

$^1$H NMR (400 MHz, DMSO-$d_6$) ppm 1.92-2.08 (m, 2H) 2.12 (s, 3H) 2.61-2.83 (m, 2H) 3.21 (t, J=14.27 Hz, 1H) 3.53 (s, 3H) 4.09-4.17 (m, 1H) 4.66-4.76 (m, 1H) 6.21 (br s, 1H) 7.69-7.74 (m, 1H) 7.80-7.90 (m, 1H) 8.10 (dd, J=7.70, 4.67 Hz, 2H) 8.48 (d, J=8.84 Hz, 1H) 8.58 (d, J=8.84 Hz, 1H) 8.98 (s, 1H) 9.15 (d, J=1.52 Hz, 1H) 9.78 (d, J=2.02 Hz, 1H).

LRMS m/z 453 (M+H)$^+$.

Example 6

Preparation of 1-(1-acetylpiperidin-4-yl)-3-methyl-8-quinolin-3-yl-1,3-dihydro-2H-imidazo[4,5-c][1,5]naphthyridin-2-one (Compound 120)

Compound 120 was synthesized according to Method E as follows.

Example 7

Preparation of 1-(1-glycoloylpiperidin-4-yl)-8-(2-methoxypyrimidin-5-yl)-3-methyl-1,3-dihydro-2H-imidazo[4,5-c][1,5]naphthyridin-2-one (Compound 189)

Compound 189 was synthesized according to Method F as follows.

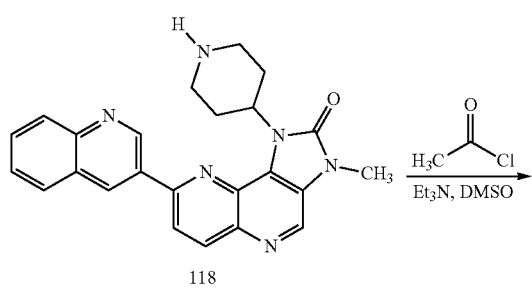

118

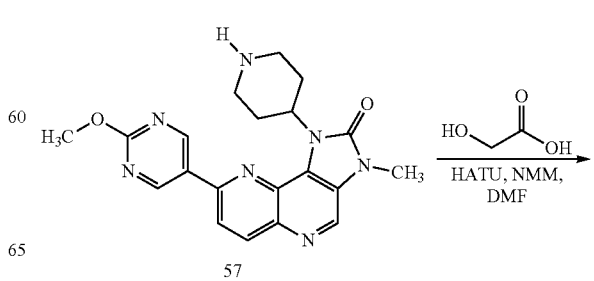

57

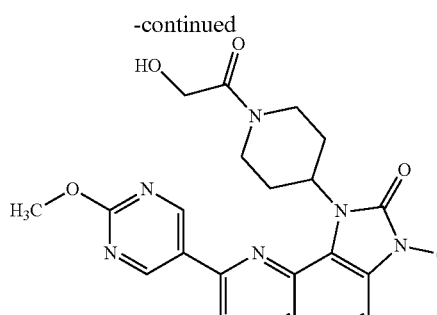

189

A solution of compound 57 (217 mg, 0.35 mmol), 2-hydroxyacetic acid (39.4 mg. 0.525 mmol), and N-methylmorpholine (NMM) (177 mg, 1.75 mmol) in anhydrous DMF (3 mL) was treated with HATU (160 mg, 0.42 mmol) at room temperature. The resulting reaction solution was stirred at room temperature under nitrogen overnight, and a mixture was obtained. The solid product was collected by vacuum-filtration, rinsed with MeOH, and further dried to give compound 189 (99 mg, 63%).

$^1$H NMR (400 MHz, DMSO-d$_6$) δ 1.92 (br s, 2H), 2.55 (d, J=5.05 Hz, 1H), 2.63-2.81 (m, 2H), 3.12 (t, J=10.36 Hz, 1H), 3.52 (s, 3H), 3.87-4.06 (m, 4H), 4.12-4.32 (m, 2H), 4.46-4.71 (m, 2H), 5.95 (br s, 1H), 8.26 (d, J=9.09 Hz, 1H), 8.46 (d, J=8.84 Hz, 1H), 8.95 (s, 1H), 9.35 (s, 2H).

LRMS m/z 450.0 (M+H)$^+$.

Example 8

Preparation of 2-{4-[8-(2-methoxypyrimidin-5-yl)-3-methyl-2-oxo-2,3-dihydro-1H-imidazo[4,5-c][1,5] naphthyridin-1-yl]piperidin-1-yl}acetamide (Compound 190)

Compound 190 was synthesized according to Method G as follows.

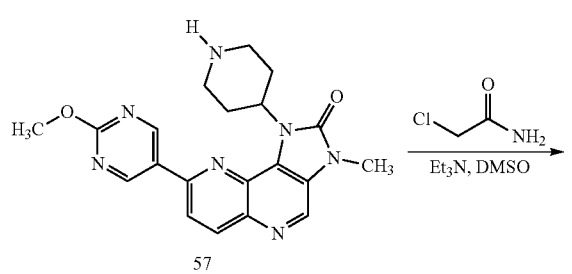

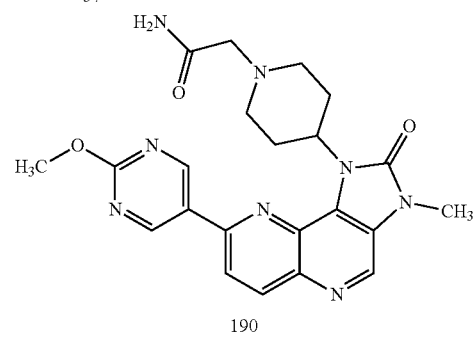

190

A solution of compound 57 (186 mg, 0.30 mmol), 2-chloroacetamide (84.2 mg, 0.90 mmol), and Et$_3$N (243 mg, 2.40 mmol) in anhydrous DMSO (2 mL) was stirred at room temperature overnight, and a mixture was obtained. The solid product was collected by vacuum-filtration, rinsed with MeOH, and further dried to give compound 190 (78 mg, 58%).

$^1$H NMR (400 MHz, DMSO-d$_6$) δ 1.76 (d, J=8.84 Hz, 2H), 2.20 (t, J=11.37 Hz, 2H), 2.73-3.18 (m, 6H), 3.54 (s, 3H), 4.03 (s, 3H), 5.21 (br s, 1H), 7.28 (br s, 1H), 7.41 (brs, 1H), 8.33 (d, 1H), 8.50 (d, J=8.84 Hz, 1H), 8.98 (s, 1H), 9.70 (s, 2H).

LRMS m/z 449.0 (M+H)$^+$.

Example 9

Preparation of 4-[8-(2-methoxypyrimidin-5-yl)-3-methyl-2-oxo-2,3-dihydro-1H-imidazo[4,5-c][1,5] naphthyridin-1-yl]-N-methylpiperidine-1-carboxamide (Compound 186)

Compound 186 was synthesized according to Method H as follows.

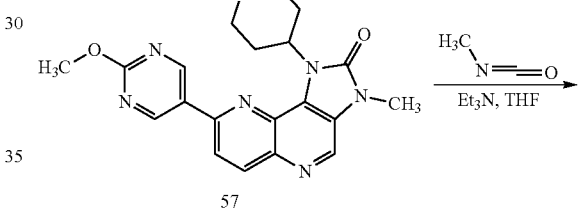

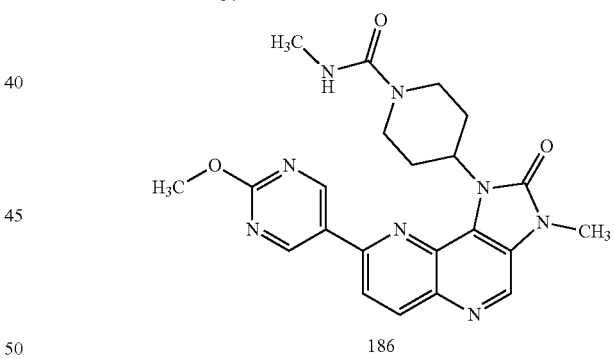

186

A mixture of compound 57 (248 mg, 0.40 mmol) in anhydrous THF (5 mL) was treated with Et$_3$N (202 mg, 2.00 mmol). The resulting mixture was stirred at rt for 30 minutes and followed by the addition of methyl isocyanate (68.5 mg. 1.20 mmol). The reaction mixture was stirred at room temperature for 2 h. MeOH was added and the mixture was stirred vigorously. The solid was collected by vacuum-filtration and further dried to give compound 186 (125 mg, 70%).

$^1$H NMR (400 MHz, DMSO-d$_6$) δ 1.87 (d, J=10.36 Hz, 2H), 2.53-2.65 (m, 5H), 2.76 (t, J=12.38 Hz, 2H), 3.53 (s, 3H), 4.03 (s, 3H), 4.22 (d, J=12.63 Hz, 2H), 5.94 (br s, 1H), 6.57 (d, J=4.29 Hz, 1H), 8.30 (d, J=8.84 Hz, 1H), 8.50 (d, 1H), 8.96 (s, 1H), 9.40 (s, 2H).

LRMS m/z 449.0 (M+H)$^+$.

Example 10

Preparation of 4-[3-methyl-8-(6-methylpyridin-3-yl)-2-oxo-2,3-dihydro-1H-imidazo[4,5-c][1,5]naphthyridin-1-yl]piperidine-1-carboxamide (Compound 167)

Compound 167 was synthesized according to Method I as follows.

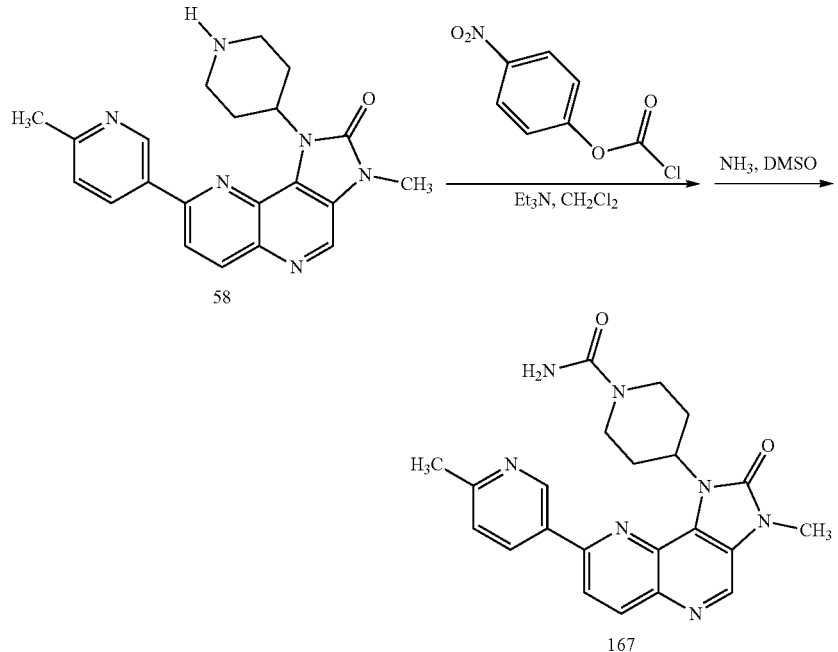

A mixture of compound 58 (194 mg, 0.40 mmol) in anhydrous CH$_2$Cl$_2$ (5 mL) was treated with Et$_3$N (202 mg, 2.00 mmol) and 4-nitrophenyl chloroformate (242 mg, 1.20 mmol). The reaction mixture was stirred at room temperature overnight and concentrated to give a solid residue, which was taken into anhydrous DMSO (10 mL) in a sealed tube, treated with a stream of NH$_3$ gas gently for about 10 minutes, tightly capped, and heated at 100° C. for 3 h. The mixture was concentrated to a low volume and purified by HPLC to yield compound 167 (22 mg, 13%).

$^1$H NMR (400 MHz, DMSO-d$_6$) δ 1.83 (d, J=7.07 Hz, 2H), 2.57 (s, 3H), 2.63-3.13 (m, 4H), 3.54 (s, 3H), 4.24 (d, J=11.37 Hz, 2H), 4.68-6.60 (m, 3H), 7.52 (d, J=8.08 Hz, 1H), 8.34 (d, J=9.09 Hz, 1H), 8.43-8.65 (m, 2H), 8.97 (s, 1H), 9.31 (d, J=1.77 Hz, 1H).

LRMS m/z 418.2 (M+H)$^+$.

Example 11

Preparation of 8-[6-(dimethylamino)pyridin-3-yl]-1-(trans-4-hydroxycyclohexyl)-3-methyl-1,3-dihydro-2H-imidazo[4,5-c][1,5]naphthyridin-2-one (Compound 175)

Compound 175 was synthesized according to Method J as follows.

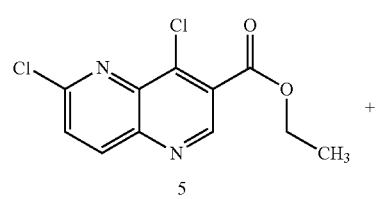

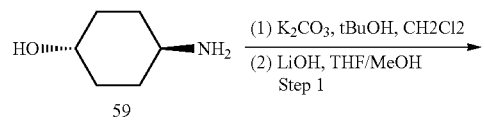

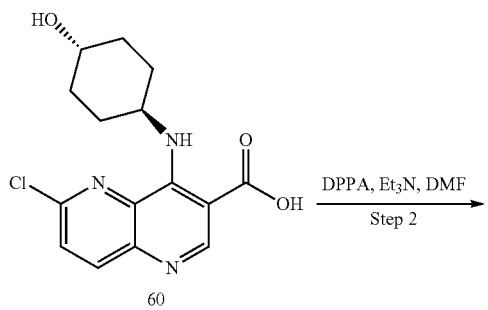

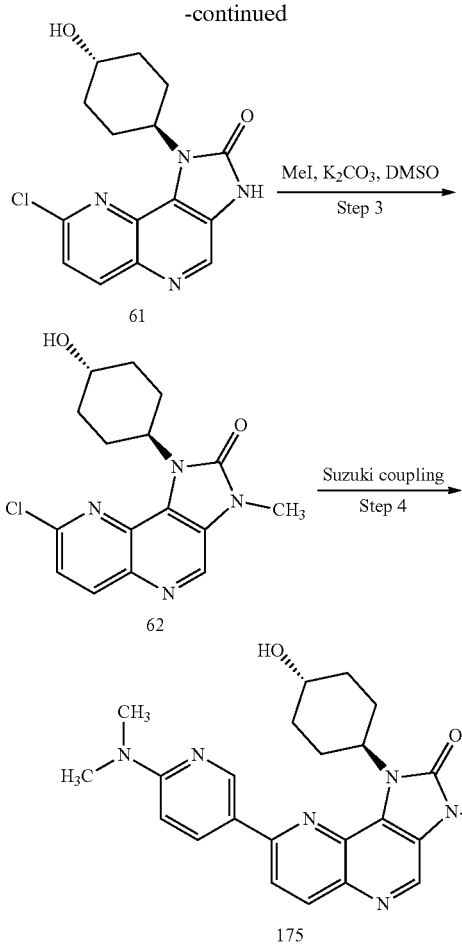

Step 1

A mixture of compound 5 (8.13 g, 30.0 mmol), trans-4-aminocyclohexanol (4.49 g, 39.0 mmol), and K₂CO₃ (12.4 g, 90.0 mmol) in t-BuOH/1,2-dichloroethane (70/70 mL) was heated on an oil-bath at 85° C. overnight. The reaction mixture was concentrated to give a solid residue, which was suspended in MeOH/THF/water (100/100/100 mL), and followed by the addition of LiOH (2.16 g, 90.0 mmol) in one portion. The resulting reaction mixture was stirred at 60° C. for 4 h. After removal of the organic solvent, the aqueous residue was taken into water (30 mL) and acidified to pH 6 with 2 N HCl aqueous solution. The solid product was collected by vacuum-filtration, rinsed with water and MeOH, and further dried to give 9.49 g (98%) of compound 60 as white solid.

$^1$H NMR (400 MHz, DMSO-$d_6$) δ 1.35 (brs, 4H), 1.89 (br s, 2H), 2.12 (br s, 2H), 3.50 (br s, 1H), 4.61 (br s, 1H), 4.86 (br s, 1H), 7.80 (d, J=8.59 Hz, 1H), 8.20 (d, J=8.84 Hz, 1H), 8.91 (br s, 1H), 9.79 (br s, 1H), 13.33 (br s, 1H).

LRMS (M+H)⁺ 322.0; 324.0.

Step 2

A suspension of 60 (9.49 g, 29.5 mmol) in anhydrous DMF (150 mL) was treated with Et₃N (5.97 g, 59.0 mmol). A solution was obtained, stirred at room temperature for 1 h, and followed by the dropwise addition of diphenylphosphoryl azide (DPPA) (16.7 g, 59.0 mmol). The resulting reaction solution was stirred at room temperature and a mixture was obtained. Stirring was continued for 1 h at room temperature and then heated at 60° C. for 3 h. After cooling to room temperature, the solid was collected by vacuum-filtration, rinsed with MeOH, and further dried to afford compound 61 (6.63 g, 71%).

$^1$H NMR (400 MHz, DMSO-$d_6$) δ 1.26-1.45 (m, 2H), 1.71 (br s, 2H), 1.99 (d, J=10.86 Hz, 2H), 2.59-2.76 (m, 2H), 3.67 (br s, 1H), 4.58-4.73 (m, 1H), 5.04 (br s, 1H), 7.60-7.71 (m, 1H), 8.31-8.43 (m, 1H), 8.73 (br s, 1H), 11.79 (brs, 1H).

LRMS (M+H)⁺319.0; 321.0.

Step 3

A mixture of 61 (6.63 g, 20.8 mmol), MeI (5.90 g, 41.6 mmol), and K₂CO₃ (11.5 g, 83.2 mmol) in anhydrous DMSO (50 mL) was stirred at room temperature overnight. Water (100 mL) was added and the mixture was vigorously stirred. The solid product was collected by vacuum-filtration, rinsed with water and EtOAc, and further dried to give compound 62 (5.28 g, 76%).

$^1$H NMR (400 MHz, CDCl₃) δ 1.52-1.64 (m, 2H), 1.70 (br s, 1H), 1.89 (d, J=7.07 Hz, 2H), 2.13-2.26 (m, 2H), 2.86 (br s, 2H), 3.61 (s, 3H), 3.99 (br s, 1H), 5.40 (br s, 1H), 7.51 (d, J=8.84 Hz, 1H), 8.33 (d, J=8.84 Hz, 1H), 8.72 (s, 1H).

LRMS (M+H)⁺333.0; 335.0.

Step 4

A mixture of 62 (166 mg, 0.50 mmol), 6-(dimethylamino)pyridin-3-yl boronic acid (184 mg, 1.00 mmol), Pd(PPh₃)₂Cl₂ (25 mg, 0.035 mmol), and K₂CO₃ (207 mg, 1.50 mmol) in dioxane/water (3/1.5 mL) was bubbled with nitrogen for 5 minutes, and heated in a sealed tube at 90° C. to furnish a dark brown solution. Heating was continued for 3 h. Water (5 mL) was added, and the solid was collected by vacuum-filtration. The crude product was dissolved in MeOH/CH₂Cl₂ and filtered through a pad of Celite. The filtrate was concentrated to give a solid, which was triturated with MeOH, collected by vacuum-filtration, rinsed with MeOH, and further dried to afford the title compound 175 (95 mg, 45%).

$^1$H NMR (400 MHz, DMSO-$d_6$) δ 1.29-1.47 (m, 2H), 1.85 (d, J=9.85 Hz, 2H), 2.04 (d, J=10.61 Hz, 2H), 2.59 (br s, 2H), 3.15 (s, 6H), 3.50 (s, 3H), 3.60 (br s, 1H), 4.76 (d, J=4.04 Hz, 1H), 5.99 (br s, 1H), 6.82 (d, J=9.09 Hz, 1H), 8.17 (d, J=8.84 Hz, 1H), 8.35 (d, J=9.09 Hz, 2H), 8.84 (s, 1H), 9.00 (d, J=2.02 Hz, 1H).

LRMS m/z 419.2 (M+H)⁺.

Example 12

Preparation of 1-(trans-4-aminocyclohexyl)-3-methyl-8-quinolin-3-yl-1,3-dihydro-2H-imidazo[4,5-c][1,5]naphthyridin-2-one (Compound 194)

Compound 194 was synthesized according to Method K as follows.

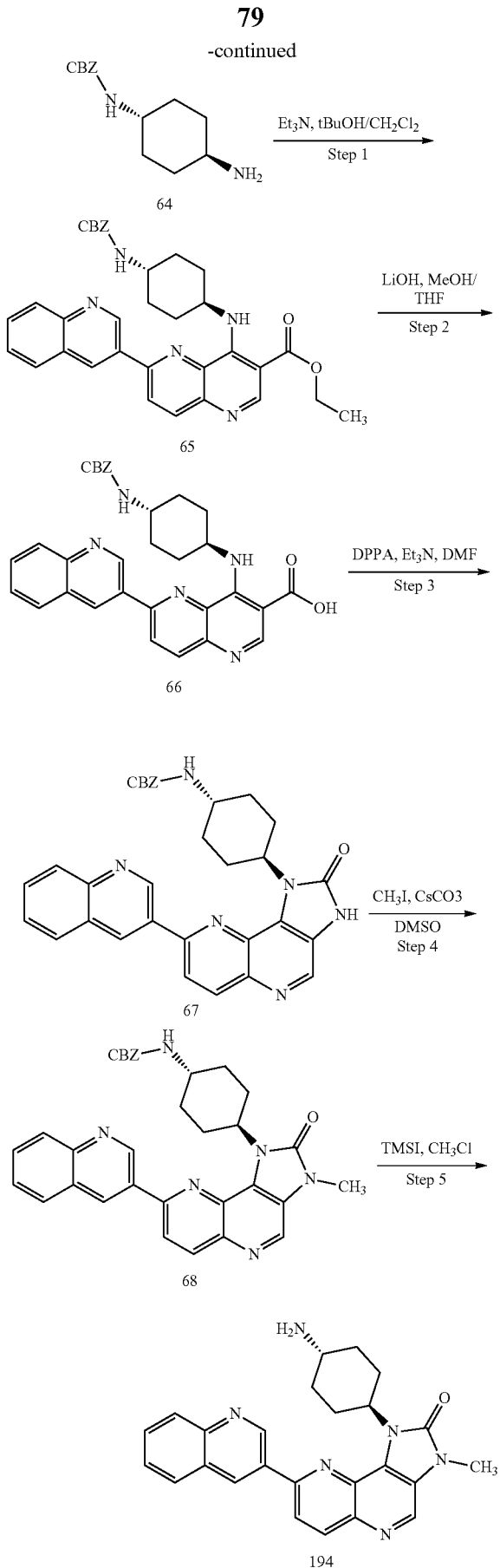

Step 1

A mixture of ethyl 4-chloro-6-(quinolin-3-yl)-1,5-naphthyridine-3-carboxylate (compound 63) (2.91 g, 8.00 mmol), N-Cbz-trans-1,4-cyclohexanediamine HCl (compound 64) (2.51 g, 8.80 mmol), and Et₃N (2.43 g, 24.0 mmol) in t-BuOH/1,2-dichloroethane (20/20 mL) was heated at 80° C. in a sealed tube to furnish a solution. Heating was continued overnight and the product precipitated. After cooling to room temperature, the solid was collected by vacuum-filtration, rinsed with MeOH, and further air-dried to give compound 65 (4.57 g, 99%).

$^1$H NMR (400 MHz, DMSO-d$_6$) δ 1.34 (t, J=7.07 Hz, 3H), 1.40-1.53 (m, 4H), 1.93 (d, J=9.09 Hz, 2H), 2.27 (br s, 2H), 3.05 (d, J=5.56 Hz, 1H), 3.38-3.48 (m, 1H), 4.32 (q, J=7.07 Hz, 2H), 5.02 (s, 2H), 5.20 (br s, 1H), 7.21-7.38 (m, 5H), 7.67 (t, J=7.71 Hz, 1H), 7.77-7.90 (m, 1H), 8.10 (d, J=9.09 Hz, 2H), 8.29 (d, J=8.84 Hz, 1H), 8.49 (d, J=8.84 Hz, 1H), 8.89 (s, 1H), 9.00 (s, 1H), 9.50 (br s, 1H), 9.62 (br s, 1H).

LRMS (M+H)$^+$ 576.2.

Step 2

A mixture of compound 65 (4.57 g, 7.94 mmol) in MeOH/THF/water (20/20/20 mL) was treated with LiOH (0.38 g, 16.0 mmol). The resulting reaction mixture was stirred at room temperature overnight, and the reaction was 60% complete by LC-MS. The reaction mixture was then heated at 60° C. for 2 h. After removal of organic solvent, the residue was suspended in water (20 mL) and acidified to pH 6 with 2 N HCl aqueous solution. The solid product was collected by vacuum-filtration, rinsed with water and MeOH, and further dried to give compound 66 (3.94 g, 91%).

$^1$H NMR (400 MHz, DMSO-d$_6$) δ 1.37-1.59 (m, 4H), 1.96 (d, J=10.86 Hz, 2H), 2.26-2.37 (m, 2H), 3.44 (br s, 2H), 5.02 (s, 2H), 5.33 (br s, 1H), 7.27-7.39 (m, 5H), 7.45 (d, J=7.33 Hz, 1H), 7.72 (br s, 1H), 7.82-7.93 (m, 1H), 8.15 (t, J=7.45 Hz, 2H), 8.44 (br s, 1H), 8.69 (d, J=9.35 Hz, 1H), 8.91-9.16 (m, 2H), 9.65 (s, 1H), 11.01 (br s, 1H).

LRMS (M+H)$^+$ 548.0.

Step 3

A suspension of compound 66 (3.94 g, 7.20 mmol) in anhydrous DMF (50 mL) was treated with Et₃N (1.46 g, 14.4 mmol). The resulting mixture was stirred at room temperature for 1 hr and followed by the dropwise addition of diphenylphosphoryl azide (3.96 g, 14.4 mmol). The reaction mixture was further stirred at room temperature for 1 h and then heated at 60° C. for 2 h. After cooling to room temperature, the solid was collected by vacuum-filtration, rinsed with MeOH, and further air-dried to afford compound 67 (3.48 g, 89%).

$^1$H NMR (400 MHz, DMSO-d$_6$) δ 1.32-1.61 (m, 2H), 1.97 (d, J=8.84 Hz, 2H), 2.09 (d, J=11.37 Hz, 2H), 2.62-2.74 (m, 2H), 3.44 (br s, 1H), 5.04 (s, 2H), 5.91 (br s, 1H), 7.30-7.42 (m, 5H), 7.53 (d, J=5.81 Hz, 1H), 7.67 (t, J=7.45 Hz, 1H), 7.79-7.87 (m, 1H), 8.12 (t, J=9.22 Hz, 2H), 8.40-8.46 (m, 1H), 8.48-8.54 (m, 1H), 8.71 (s, 1H), 9.12 (s, 1H), 9.74 (d, J=2.02 Hz, 1H), 11.67 (br s, 1H).

LRMS m/z 545.0 (M+H)$^+$.

Step 4

A mixture of compound 67 (272 mg, 0.50 mmol), MeI (85.2 mg, 0.60 mmol), and cesium carbonate (489 mg, 1.50 mmol) in anhydrous DMSO (4 mL) was stirred at rt overnight. The reaction was 60% complete by LC-MS. More MeI (85.2 mg, 0.60 mmol) was added and the reaction mixture was stirred at room temperature overnight. Water was added and the mixture was vigorously stirred. The solid product was collected by vacuum-filtration and further dried to give compound 68 (271 mg, 97%).

¹H NMR (400 MHz, DMSO-d₆) δ 1.35-1.55 (m, 2H), 1.98 (d, J=9.60 Hz, 2H), 2.09 (d, J=11.62 Hz, 2H), 2.65 (d, J=14.15 Hz, 2H), 3.44 (d, J=4.80 Hz, 1H), 3.53 (s, 3H), 5.04 (s, 2H), 5.99 (br s, 1H), 7.27-7.41 (m, 5H), 7.55 (d, J=4.04 Hz, 1H), 7.68 (t, J=7.33 Hz, 1H), 7.78-7.89 (m, 1H), 8.12 (t, J=8.84 Hz, 2H), 8.41-8.49 (m, 1H), 8.50-8.60 (m, 1H), 8.94 (s, 1H), 9.12 (d, J=1.01 Hz, 1H), 9.74 (d, J=2.02 Hz, 1H).

LRMS m/z 559.0 (M+H)⁺.

Step 5

A solution of compound 68 (256 mg, 0.458 mmol) in CH₃Cl (10 mL) was treated with TMSI (642 mg, 3.21 mmol) at room temperature dropwise. The resulting reaction mixture was stirred for 2 h and concentrated to give a solid residue, which was purified by HPLC to afford the title compound 194 (60 mg, 31%).

¹H NMR (400 MHz, DMSO-d₆) δ 1.42-1.71 (m, 2H), 2.05 (d, J=9.60 Hz, 2H), 2.17 (d, J=11.62 Hz, 2H), 2.60-2.82 (m, 2H), 3.08-3.21 (m, 2H), 3.54 (s, 3H), 7.31-7.76 (m, 3H), 7.84-7.97 (m, 1H), 8.15 (t, J=9.22 Hz, 2H), 8.47 (d, J=9.09 Hz, 1H), 8.59 (d, J=8.84 Hz, 1H), 9.00 (s, 1H), 9.16 (d, J=1.52 Hz, 1H), 9.75 (d, J=2.27 Hz, 1H).

LRMS m/z 425.0 (M+H)⁺.

Example 13

Preparation of 3-methyl-1-[trans-4-(methylamino) cyclohexyl]-8-quinolin-3-yl-1,3-dihydro-2H-imidazo [4,5-c][1,5]naphthyridin-2-one (Compound 193)

Compound 193 was synthesized according to Method L as follows.

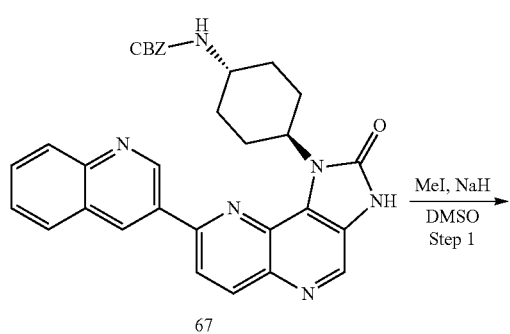

67

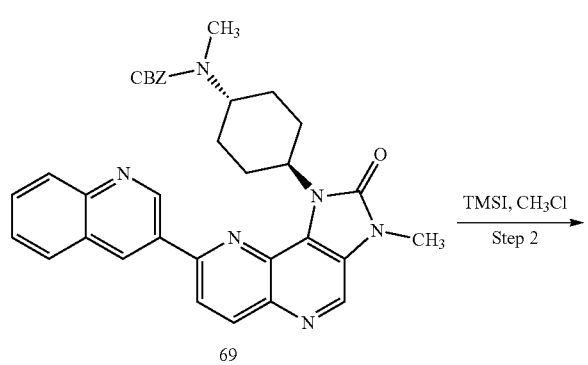

69

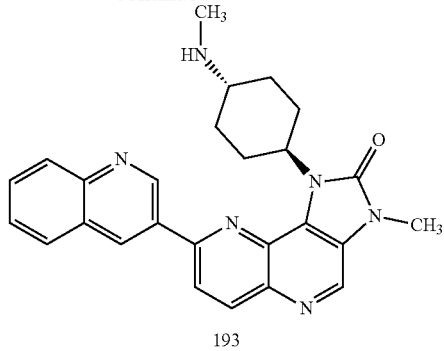

193

Step 1

A mixture of compound 67 (272 mg, 0.50 mmol) in anhydrous DMSO (4 mL) was treated with 60% NaH dispersion (50 mg, 1.25 mmol), and followed by the addition of MeI (85.2 mg, 0.60 mmol). The resulting mixture was stirred at room temperature overnight. LC-MS showed about 20% mono-methylated product and 80% di-methylated product. More MeI (85.2 mg, 0.60 mmol) was added and the reaction mixture was further stirred at room temperature overnight. Water was added, and the solid product was collected by vacuum-filtration, rinsed with water, MeOH, and further dried to give 290 mg (100%) of yellow solid as the crude product of compound 69. 60 mg was triturated with MeOH to give 36 mg of light yellow solid as the clean product of compound 69.

¹H NMR (400 MHz, DMSO-d₆) δ 1.76-1.94 (m, 4H), 2.07 (br s, 2H), 2.67 (d, J=1.77 Hz, 2H), 2.89 (s, 3H), 3.53 (s, 3H), 4.05 (br s, 1H), 5.04 (br s, 1H), 5.10 (br s, 1H), 6.13 (br s, 1H), 7.38 (br s, 5H), 7.70 (t, J=7.45 Hz, 1H), 7.84 (dd, J=15.16, 1.26 Hz, 1H), 8.09 (d, J=8.08 Hz, 2H), 8.44-8.51 (m, 1H), 8.53-8.63 (m, 1H), 8.98 (s, 1H), 9.15 (s, 1H), 9.82 (d, J=1.77 Hz, 1H).

LRMS m/z 573.0 (M+H)⁺.

Step 2

A solution of compound 69 (230 mg, 0.402 mmol) in CH₃Cl (10 mL) was treated with TMSI (563 mg, 2.81 mmol) dropwise at room temperature. The reaction mixture was stirred for 3 h and concentrated to give a solid residue, which was purified by HPLC to afford the title compound 193 (35 mg, 20%).

¹H NMR (400 MHz, DMSO-d₆) δ 1.36-1.61 (m, 2H), 2.08 (d, J=3.79 Hz, 2H), 2.27 (d, J=11.62 Hz, 2H), 2.60 (s, 3H), 2.68 (dd, J=3.66, 1.89 Hz, 2H), 3.03 (t, J=11.49 Hz, 1H), 3.29-3.39 (m, 1H), 3.56 (s, 3H), 5.96 (br s, 1H), 7.65-7.78 (m, 1H), 7.85-7.94 (m, 1H), 8.16 (dd, J=11.37, 8.34 Hz, 2H), 8.49 (d, J=9.09 Hz, 1H), 8.61 (d, J=8.84 Hz, 1H), 9.02 (s, 1H), 9.18 (s, 1H), 9.77 (d, J=1.77 Hz, 1H).

LRMS m/z 439.0 (M+H)⁺.

Example 14

Preparation of tert-butyl 4-(8-chloro-3-methyl-2-oxo-2,3-dihydro-1H-imidazol-[4,5-c][1,5]naphthyridin-1-yl)piperidine-1-carboxylate (compound 57)

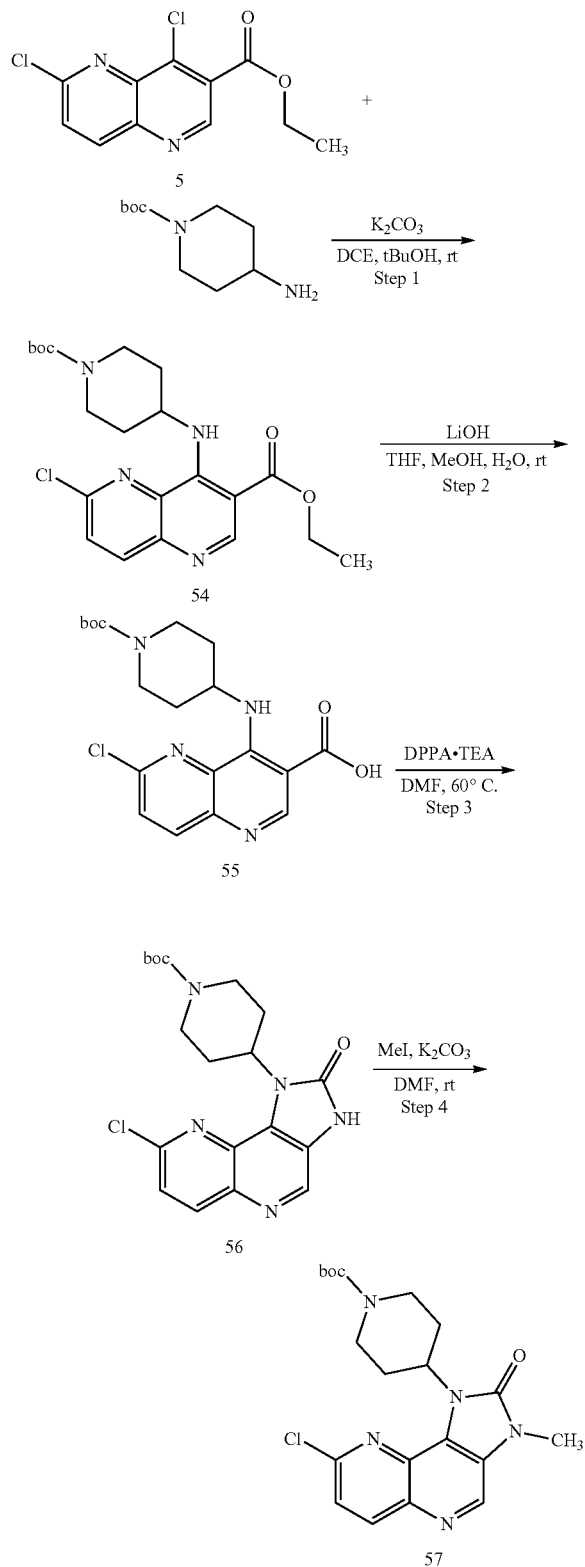

Step 1

To a 2 L round bottom flask was added ethyl 4,6-dichloro-1,5-naphthyridine-3-carboxylate 5 (150.1 g, 553.7 mmol), tert-butyl 4-aminopiperidine-1-carboxylate (133.0 g, 664 mmol, 1.2 eq), potassium carbonate (184 g, 1.33 mol, 2.4 eq), 1,2-dichloroethane (300 mL) and tert-butanol (300 mL). The reaction mixture was stirred at rt and monitored by LCMS. After ~90% conversion (~2 days), the reaction was concentrated to give 240.8 g of crude material 54 (ethyl 4-(1-(tert-butoxycarbonyl)piperidin-4-ylamino)-6-chloro-1,5-naphthyridine-3-carboxylate).

Step 2

Crude ethyl 4-(1-(tert-butoxycarbonyl)piperidin-4-ylamino)-6-chloro-1,5-naphthyridine-3-carboxylate (54) (240.8 g, 554 mmol) was suspended in a 1:1:1 mixture of MeOH:THF:$H_2O$ (500 mL each) and LiOH (39.8 g, 1.66 mol, 3 eq) was added. The mixture was maintained at rt and monitored by LCMS. After consumption of starting material, the volatiles were removed under vacuum and the resultant solution was neutralized by the addition of 6N HCl (~3 eq). The mixture was then carefully acidified to pH 3-5 with 5N HCl (aq). The resultant slurry was then filtered and the precipitate was rinsed with water and then methanol. The resultant precipitate was dried in a vac-oven overnight, to give 203.6 g (83%, over two steps) of 4-(1-(tert-butoxycarbonyl)piperidin-4-ylamino)-6-chloro-1,5-naphthyridine-3-carboxylic acid (55).

Step 3

A suspension of 4-(1-(tert-butoxycarbonyl)piperidin-4-ylamino)-6-chloro-1,5-naphthyridine-3-carboxylic acid (55) (103.7 g, 234 mmol) in anhydrous DMF (650 mL) was treated with triethyl amine (73 mL, 524 mmol, 2.24 eq) and stirred at rt for 45 min followed by the dropwise addition of diphenyl phosphoryl azide (60.7 mL, 281 mmol, 1.2 eq). The solution was heated to 60° C. for 1 h. The mixture was cooled to rt and water (~2 L) was added. The mixture was allowed to sit overnight. The resultant precipitate was filtered and washed with water (3×0.5 L). The precipitate was dried in a vac-oven overnight to give 79.4 g (84%) of tert-butyl 4-(8-chloro-2-oxo-2,3-dihydro-1H-imidazo[4,5-c][1,5]naphthyridin-1-yl)piperidine-1-carboxylate (56). $^1$H NMR (400 MHz, DMSO-$d_6$) δ ppm 1.44 (s, 9H) 1.75 (d, J=10.32 Hz, 2H) 2.57-2.75 (m, 2H) 2.76-2.99 (m, 2H) 4.19 (d, J=9.32 Hz, 2H) 5.02-5.50 (m, 1H) 7.68 (d, J=8.81 Hz, 1H) 8.41 (d, J=8.81 Hz, 1H) 8.75 (s, 1H) 11.77 (br s, 1H).

Step 4

To a DMF (1 L) solution of tert-butyl 4-(8-chloro-2-oxo-2,3-dihydro-1H-imidazo[4,5-c][1,5]naphthyridin-1-yl)piperidine-1-carboxylate (56) (157 g, 388.7 mmol) was added potassium carbonate (161 g, 1.17 mmol, 3.0 eq) followed by methyl iodide (36.3 mL, 82.8 g, 583 mmol, 1.5 eq) and the mixture stirred at rt. After 1 h, 2.5 L of water was added and the mixture was cooled below 8° C. The resultant precipitate was filtered, washed with water (2×1 L), and dried in a in vac-oven at 40° C. to give 154.5 g (95%) of tert-butyl 4-(8-chloro-3-methyl-2-oxo-2,3-dihydro-1H-imidazo[4,5-c][1,5]naphthyridin-1-yl)piperidine-1-carboxylate (57).

$^1$H NMR (400 MHz, DMSO-$d_6$) δ 1.44 (s, 9H) 1.77 (d, J=10.83 Hz, 2H) 2.54-2.75 (m, 2H) 2.77-2.98 (m, 2H) 3.53 (s, 3H) 4.05-4.31 (m, 2H) 4.92-5.73 (m, 1H) 7.70 (d, J=8.81 Hz, 1H) 8.45 (d, J=8.81 Hz, 1H) 9.01 (s, 1H).

The compounds of Examples 15, 16, and 17 were synthesized according to Method M as follows.

Example 15

Preparation of 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one (Compound 257)

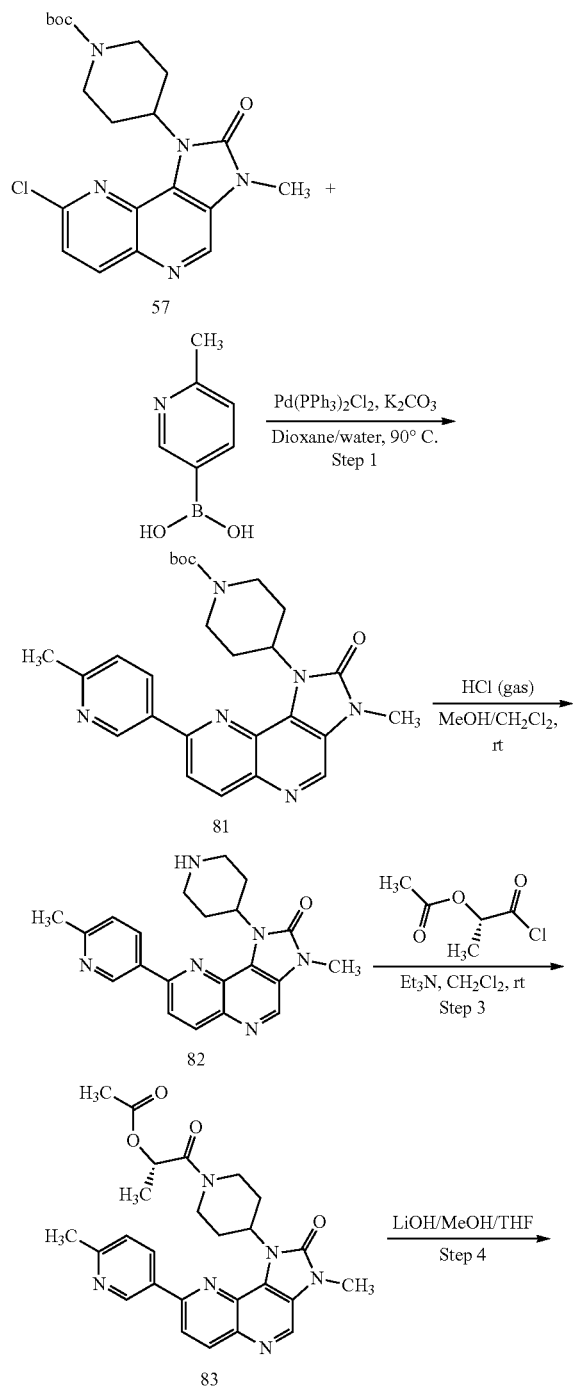

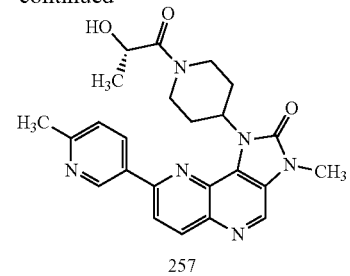

Step 1

To a mixture of compound 57 (0.500 g, 1.20 mmol), 6-methylpyridin-3-ylboronic acid (0.246 g, 1.5 mmol), Pd(PPh$_3$)$_2$Cl$_2$ (68.1 mg, 0.096 mmol), and K$_2$CO$_3$ (0.496 g, 3.59 mmol) in dioxane/water (10/5 mL) was bubbled with nitrogen for 5 minutes. The resultant reaction solution was then heated in a sealed tube at 90° C. to furnish a brown mixture. After the reaction mixture was heated for 3 h, LCMS showed the reaction was completed. Water (40 mL) was added, and the mixture was vigorously stirred. The solid was collected by vacuum-filtration and further dried. The crude solid product was dissolved in MeOH/CH$_2$Cl$_2$ (10/30 mL) and filtered through a pad of Celite to remove the insoluble materials. The filtrate was concentrated in vacuo to give a solid which was triturated with MeOH, collected by vacuum-filtration, rinsed with MeOH, and further dried to afford compound 81 (568 mg, 97%). $^1$H NMR (400 MHz, CDCl$_3$) δ 1.51 (s, 9H) 1.62-1.82 (m, 2H) 1.86-2.00 (m, 2H) 2.67 (s, 3H) 2.78-3.08 (m, 4H) 3.62 (s, 3H) 4.27-4.51 (m, 1H) 7.39 (d, J=8.08 Hz, 1H) 8.05 (d, J=8.84 Hz, 1H) 8.34-8.44 (m, 1H) 8.49 (d, J=9.09 Hz, 1H) 8.74 (s, 1H) 9.25 (s, 1H).

Step 2

A solution of compound 81 (0.550 g, 1.16 mmol) in CH$_2$Cl$_2$/MeOH (30/10 mL) was treated with a stream of HCl gas gently for about 10 minutes, and solid was precipitated. The flask was tightly capped and the mixture was stirred at room temperature overnight. The solid was collected by vacuum-filtration and further dried to give the HCl salt of compound 82 (0.420 g, 97%). $^1$H NMR (400 MHz, DMSO-d6) δ 2.13-2.28 (m, 2H) 2.86 (s, 3H) 2.89-3.00 (m, 2H) 3.23 (d, J=11.87 Hz, 2H) 3.43-3.56 (m, 2H) 3.58 (s, 3H) 6.17-6.32 (m, 1H) 8.11 (d, J=8.59 Hz, 1H) 8.68 (d, J=9.09 Hz, 1H) 8.88 (d, J=9.09 Hz, 2H) 9.18 (dd, J=8.46, 1.64 Hz, 1H) 9.34 (s, 1H) 9.50 (d, J=1.77 Hz, 1H).

Step 3

A mixture of compound 82 (600 mg, 1.6 mmol), (S)-(−)-2-acetoxypropionyl chloride (362 mg, 0.304 mmol) in anhydrous CH$_2$Cl$_2$ (10 mL) was treated with Et$_3$N (486 mg, 4.81 mmol) at room temperature. The resulting reaction mixture was stirred under nitrogen at room temperature for 30 min under nitrogen. After 30 mins, LC-MS showed the reaction was completed. The reaction mixture was concentrated to give the crude product as a yellow solid which was purified by Biotage (Si, 40M) using gradient 1-5% MeOH in CH$_2$Cl$_2$ to afford compound 83 as light yellow solid (650 mg, 83%). $^1$H NMR (300 MHz, CDCl$_3$) δ 1.47 (d, J=6.40 Hz, 3H) 1.95-2.11 (m, 4H) 2.14 (s, 3H) 2.68 (s, 3H) 2.76-2.91 (m, 2H) 2.91-3.04 (m, 1H) 3.23-3.37 (m, 1H) 3.62 (s, 3H) 3.94-4.20 (m, 1H) 5.50 (br s, 1H) 7.39 (d, J=8.10 Hz, 1H) 8.03 (d, J=9.04 Hz, 1H) 8.28 (dd, J=8.10, 2.07 Hz, 1H) 8.51 (d, J=8.85 Hz, 1H) 8.75 (s, 1H) 9.23 (br s, 1H).

Step 4

To a mixture of compound 83 (0.5 g, 1.02 mmol) in MeOH/THF (5/5 mL) was added 1.0 M LiOH aqueous solution (8.18 mL, 8.18 mmol). The resulting reaction mixture was stirred at room temperature for 3 h. LC-MS indicated complete hydrolysis. After removal of the organic solvent, the aqueous residue was taken into water and acidified to pH 6 with 1N HCl aqueous solution under vigorous stirring. The solid product was collected by vacuum-filtration, rinsed with water and MeOH to afford the product as light yellow solid. The solid compound was re-dissolved in EtOH (3 mL), Et$_2$O (5 mL) was then added which caused a precipitate to form. The solid was filtered and washed with Et$_2$O to give the title compound 84 (315 mg, 68%) as light yellow solid. $^1$H NMR (400 MHz, DMSO-d6) δ 1.24 (d, J=6.06 Hz, 3H) 1.80-2.06 (m, 2H) 2.56 (s, 3H) 2.63-2.85 (m, 3H) 3.06-3.28 (m, 2H) 3.53 (s, 3H) 4.20-4.40 (m, 1H) 4.46-4.62 (m, 1H) 4.62-4.77 (m, 1H) 5.18 (brs, 1H) 7.42-7.59 (m, 1H) 8.29 (d, J=8.84 Hz, 1H) 8.38-8.55 (m, 2H) 8.96 (s, 1H) 9.29 (br s, 1H).

Example 16

Preparation of 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one (Compound 216)

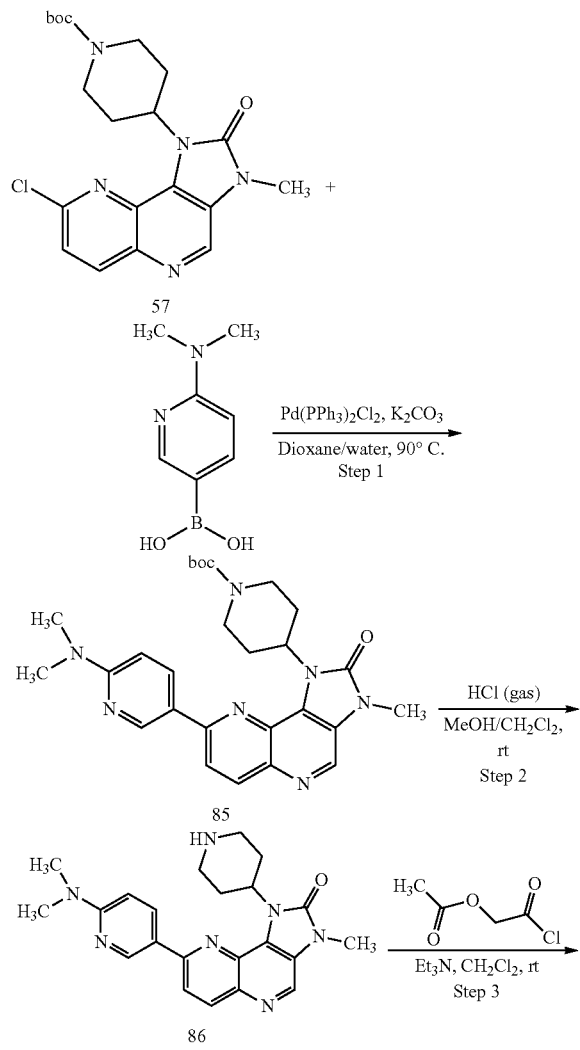

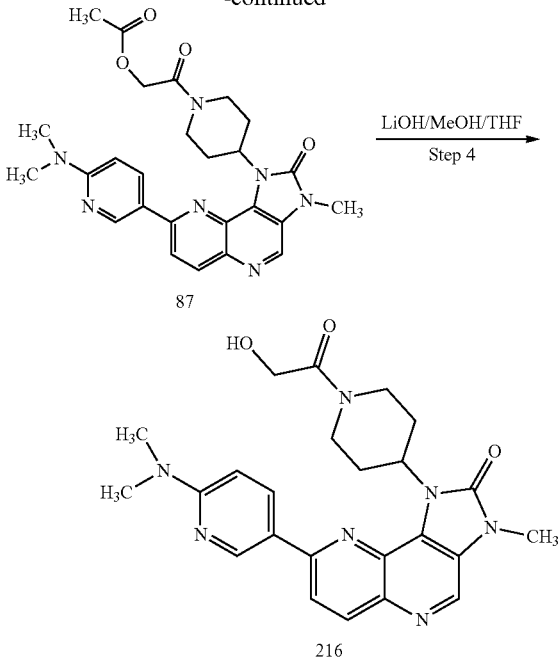

Step 1

To a mixture of compound 57 (0.500 g, 1.20 mmol), 6-(dimethylamino)pyridin-3-ylboronic acid (0.397 g, 2.39 mmol), Pd(PPh$_3$)$_2$Cl$_2$ (85.1 mg, 0.12 mmol), and K$_2$CO$_3$ (0.496 g, 3.59 mmol) in dioxane/water (10/5 mL) was bubbled with nitrogen for 5 minutes. The reaction mixture was then heated in a sealed tube at 90° C. to furnish a brown mixture. After the reaction mixture was heated for 3 h, LCMS showed the reaction was completed. Water (40 mL) was added, and the mixture was vigorously stirred. The solid was collected by vacuum-filtration and further dried. The crude solid product was dissolved in MeOH/CH$_2$Cl$_2$ (10 mL/30 mL) and filtered through a pad of Celite to remove the insoluble materials. The filtrate was then concentrated to give a solid. The solid was triturated with MeOH, collected by vacuum-filtration, and dried under high vacuum to afford compound 85 (602 mg, 91%). $^1$H NMR (300 MHz, CDCl$_3$) δ1.51 (s, 9H) 1.71-1.86 (m, 2H) 1.87-2.04 (m, 2H) 2.78-3.06 (m, 4H) 3.21 (s, 6H) 3.59 (s, 3H) 4.33-4.49 (m, 1H) 6.70 (d, J=9.04 Hz, 1H) 7.95 (d, J=9.04 Hz, 1H) 8.27-8.44 (m, 2H) 8.64 (s, 1H) 8.91 (d, J=2.07 Hz, 1H).

Step 2

A solution of compound 85 (0.550 g, 1.09 mmol) in CH$_2$Cl$_2$/MeOH (30/10 mL) was treated with a stream of HCl gas gently for about 10 minutes, and solid was precipitated. The flask was tightly capped and the mixture was stirred at room temperature overnight. The solid was collected by vacuum-filtration and further dried to give the HCl salt of compound 86 (0.420 g, 93%). $^1$H NMR (300 MHz, DMSO-d6) δ 2.07-2.28 (m, 2H) 2.74-3.01 (m, 2H) 3.38 (s, 6H) 3.41-3.54 (m, 4H) 3.57 (s, 3H) 6.20-6.37 (m, 1H) 7.47 (d, J=9.80 Hz, 1H) 8.56 (d, J=9.04 Hz, 1H) 8.75 (d, J=9.42 Hz, 1H) 8.81 (d, J=9.04 Hz, 1H) 8.86-8.93 (m, 1H) 9.06 (br s, 1H) 9.32 (s, 1H).

Step 3

To a mixture of compound 86 (500 mg, 1.24 mmol), 2-chloro-2-oxoethyl acetate (254 mg, 1.86 mmol) in anhydrous CH$_2$Cl$_2$ (10 mL) was treated with Et$_3$N (376 mg, 3.72 mmol) at room temperature. The resulting reaction mixture was stirred under nitrogen at room temperature for 30 min. After 30 min, LC-MS showed the reaction was completed. The reaction mixture was concentrated to give the crude product as a yellow solid. The crude product was purified by Biotage (Si, 40M) using gradient 1-5% MeOH in $CH_2Cl_2$ to provide compound 87 as light yellow solid (550 mg, 82%). $^1$H NMR (300 MHz, chloroform-d) δ 1.72 (s, 3H) 1.88-2.07 (m, 2H) 2.19 (s, 3H) 2.78-2.98 (m, 2H) 3.21 (s, 6H) 3.25-3.41 (m, 1H) 3.61 (s, 2H) 3.80-3.98 (m, 1H) 4.60-4.76 (m, 1H) 4.85-4.97 (m, 1H) 4.97-5.09 (m, 1H) 6.71 (d, J=9.04 Hz, 1H) 7.95 (d, J=9.23 Hz, 1H) 8.24 (dd, J=9.04, 2.64 Hz, 1H) 8.37 (d, J=9.04 Hz, 1H) 8.66 (s, 1H) 8.91 (d, J=2.07 Hz, 1H).

Step 4

To a mixture of compound 87 (0.4 g, 0.794 mmol) in MeOH/THF (5 mL/5 mL) was added 1.0 M LiOH aqueous solution (6.35 mL, 6.35 mmol). The resulting reaction mixture was stirred at room temperature for 3 h. LC-MS indicated complete hydrolysis. After removal of the organic solvent, the aqueous residue was taken into water and acidified to pH 6 with 1N HCl aqueous solution under vigorous stirring. The solid product was collected by vacuum-filtration, rinsed with water and MeOH to afford the product as light yellow solid. The solid compound was re-dissolved in EtOH (3 mL). The precipitate was formed after the addition of $Et_2O$ (5 mL). The solid was filtered and washed with $Et_2O$ to give the title compound 88 (250 mg, 68%) as light yellow solid. $^1$H NMR (400 MHz, DMSO-d6) δ 1.09-1.31 (m, 2H) 1.78-2.06 (m, 2H) 2.71-2.94 (m, 2H) 3.13 (s, 6H) 3.53 (s, 3H) 3.89-4.04 (m, 1H) 4.10-4.37 (m, 2H) 4.69 (br s, 2H) 6.75-6.88 (m, 1H) 8.16-8.25 (m, 1H) 8.29-8.41 (m, 2H) 8.88 (s, 1H) 8.97 (br s, 1H).

Example 17

Preparation of 1-{1-[(2S)-2-hydroxypropanoyl]piperidin-4-yl}-8-(1H-indazol-4-yl)-3-methyl-1,3-dihydro-2H-imidazo[4,5-c][1,5]naphthyridin-2-one (Compound 255)

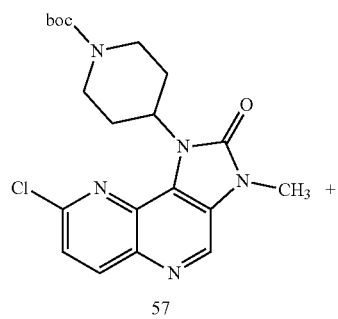

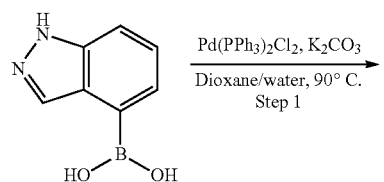

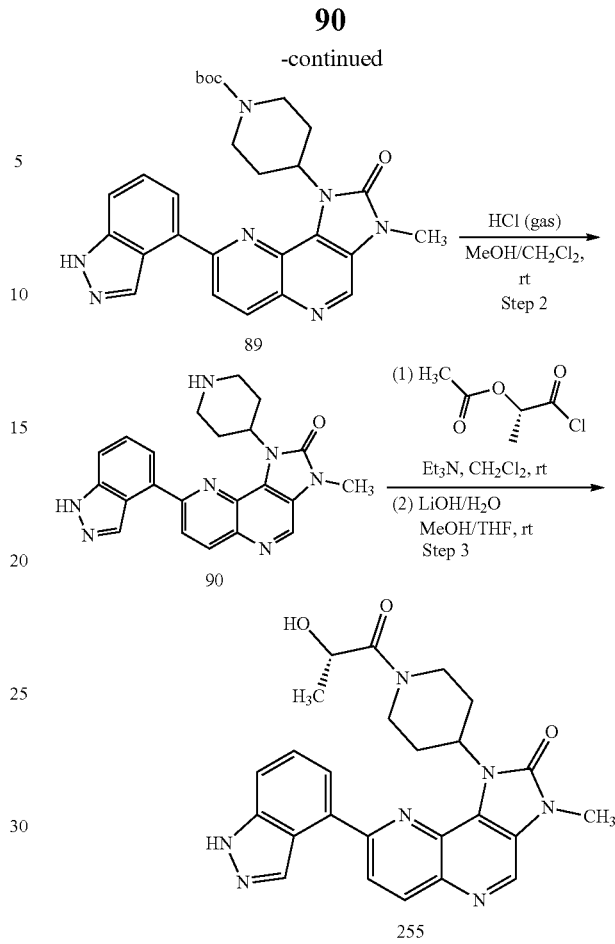

Step 1

A mixture of 57 (2.09 g, 5.00 mmol), 1H-indazol-4-ylboronic acid (1.21 g, 7.50 mmol), $Pd(PPh_3)_2Cl_2$ (213 mg, 0.30 mmol), and $K_2CO_3$ (2.07 g, 15.0 mmol) in dioxane/water (20/10 mL) was bubbled with nitrogen for 5 minutes. The reaction mixture was then heated in a sealed tube at 100° C. to give a brown solution, which turned to a gray suspension later. Heating was continued for 3 h. After cooling the mixture was diluted with water (50 mL) and vigorously stirred. The solid was collected by vacuum-filtration and further dried to give 2.49 g (99%) of 89 as a yellow solid. $^1$H NMR (400 MHz, $CDCl_3$) δ 1.48 (s, 9H), 1.94 (d, J=6.32 Hz, 2H), 2.84 (br s, 4H), 3.63 (s, 3H), 4.31 (br s, 2H), 6.33 (br s, 1H), 7.56-7.63 (m, 1H), 7.64-7.70 (m, 1H), 7.74 (d, J=7.07 Hz, 1H), 8.12 (d, J=8.84 Hz, 1H), 8.45-8.66 (m, 2H), 8.78 (s, 1H), 10.44 (br s, 1H).

Step 2

A solution of tert-butyl 4-(8-(1H-indazol-4-yl)-3-methyl-2-oxo-2,3-dihydroimidazo[4,5-c][1,5]naphthyridin-1-yl)piperidine-1-carboxylate (89) (2.49 g, 4.98 mmol) in MeOH/$CH_2Cl_2$ (15 mL/40 mL) was treated with a stream of HCl gas gently for about 15 minutes, and solid formed gradually. The flask was tightly capped, and the mixture was stirred at rt for 3 h. The solid was collected by vacuum-filtration and further dried to give 2.41 g (95%) of 90 as a yellow solid. $^1$H NMR (400 MHz, DMSO-$d_6$) δ 2.25 (d, J=12.38 Hz, 2H), 2.61-2.79 (m, 2H), 2.82-2.99 (m, 2H), 3.47 (d, J=11.62 Hz, 2H), 3.61 (s, 3H), 6.42 (t, J=12.00 Hz, 1H), 7.54-7.67 (m, 1H), 7.83 (t, J=7.33 Hz, 2H), 8.50-8.66 (m, 2H), 8.84 (d, J=9.35 Hz, 1H), 8.96 (d, J=9.09 Hz, 1H), 9.25-9.55 (m, 2H).

Step 3

A mixture of 8-(1H-indazol-4-yl)-3-methyl-1-(piperidin-4-yl)-1H-imidazo[4,5-c][1,5]naphthyridin-2(3H)-one trihydrochloride (90) (1.20 g, 2.36 mmol), and (S)-(−)-2-acetoxypropionyl chloride (1.06 g, 7.07 mmol) in anhydrous CH$_2$Cl$_2$ (10 mL) was treated with Et$_3$N (1.19 g, 11.8 mmol) at rt. The resulting reaction solution was stirred at rt under nitrogen for 1 h. Water (30 mL) and CH$_2$Cl$_2$ (40 mL) were added, and layers were separated. The aqueous layer was extracted with CH$_2$Cl$_2$ (20 mL). The organic extracts were washed with brine, dried over sodium sulfate, and concentrated to give a waxy, yellow solid (1.21 g, 100%). The solid was suspended in MeOH/THF (10 mL/10 mL), and followed by the addition of 2 M LiOH (5.9 mL, 11.8 mmol). The resulting reaction mixture was stirred at rt for 3 h. After removal of the organic solvent, the aqueous residue was diluted with water (10 mL) and adjusted to pH 7 with 2 M HCl. The resulting mixture was concentrated to a low volume and vigorously stirred to form more solid, which was collected by vacuum-filtration and further dried to give the crude product as a yellow solid. The crude product was dissolved in 10% MeOH/CH$_2$Cl$_2$ (150 mL) and filtered. The filtrate was concentrated to a low volume until solid formed. The mixture was stirred for 2 h while the solid was precipitating. The precipitated solid was collected by vacuum-filtration, rinsed with MeOH, and further dried to yield 362 mg (33%) of the title compound 255 as a pale yellow solid. $^1$H NMR (400 MHz, DMSO-d$_6$) δ 1.18 (d, J=6.32 Hz, 3H), 1.99 (br s, 2H), 2.55 (br s, 3H), 2.96 (t, J=12.63 Hz, 1H), 3.53 (s, 3H), 4.15 (d, J=12.38 Hz, 1H), 4.35-4.71 (m, 2H), 4.91 (br s, 1H), 6.35 (br s, 1H), 7.49-7.63 (m, 1H), 7.66-7.87 (m, 2H), 8.26 (d, J=9.09 Hz, 1H), 8.53 (d, J=8.84 Hz, 1H), 8.60 (s, 1H), 8.98 (s, 1H), 13.35 (s, 1H).

Example 18

Preparation of 1-(1-acetylpiperidin-4-yl)-8-(1H-indazol-4-yl)-3-methyl-1,3-dihydro-2H-imidazo[4,5-c][1,5]naphthyridin-2-one (Compound 254)

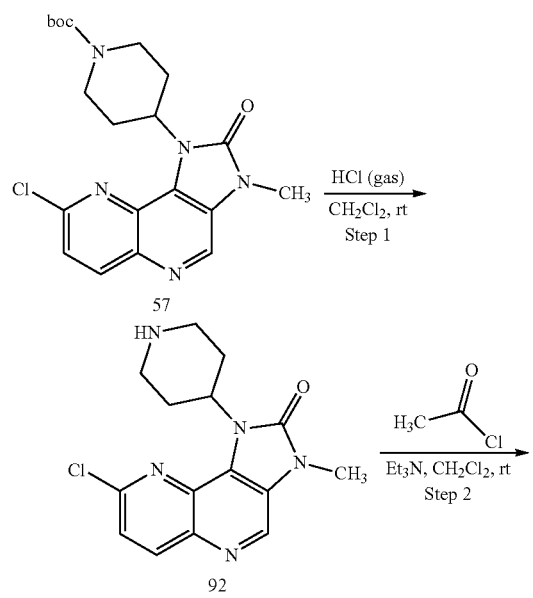

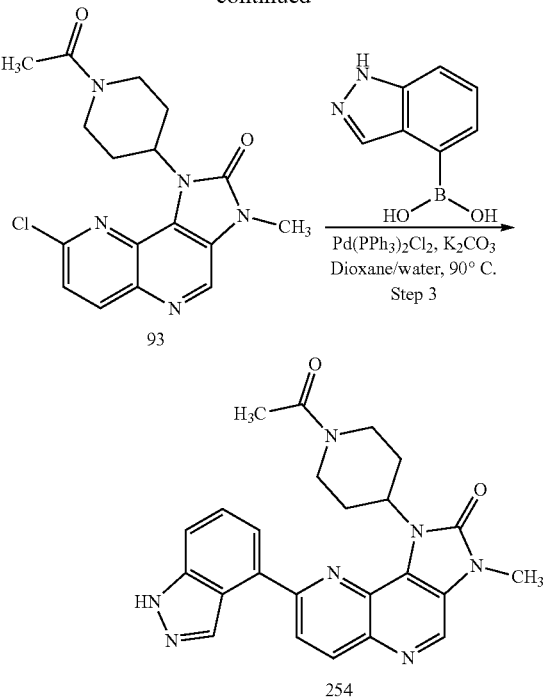

Step 1

A solution of 57 (4.18 g, 10.0 mmol) in CH$_2$Cl$_2$ (80 mL) was treated with a stream of HCl gas gently for about 10 minutes, and solid formed slowly. The flask was tightly capped, and the mixture was stirred at rt overnight. EtOAc (80 mL) was added, and the mixture was stirred vigorously. The solid was collected by vacuum-filtration and further dried to afford 3.91 g (100%) of 92 as a pale yellow solid. $^1$H NMR (400 MHz, DMSO-d$_6$) δ 2.12 (d, J=12.63 Hz, 2H), 2.67-2.87 (m, 2H), 2.88-3.08 (m, 2H), 3.38-3.69 (m, 5H), 4.81 (br s, 1H), 5.57-5.90 (m, 1H), 7.78 (d, J=9.09 Hz, 1H), 8.54 (d, J=8.84 Hz, 1H), 8.66-8.93 (m, 1H), 9.10 (s, 1H), 9.62 (d, J=9.85 Hz, 1H).

Step 2

A mixture of 8-chloro-3-methyl-1-(piperidin-4-yl)-1H-imidazo[4,5-c][1,5]naphthyridin-2(3H)-one HCl salt (92) (3.91 g, 10.0 mmol) in anhydrous CH$_2$Cl$_2$ (40 mL) was treated with Et$_3$N (6.07 g, 60.0 mmol). The resulting mixture was stirred at rt for 20 minutes, cooled in an ice-bath, and followed by the dropwise addition of acetyl chloride (4.71 g, 60.0 mmol) over a period of 10 minutes. Cooling bath was removed, and the reaction mixture was stirred at rt for 2 h. MeOH (5 mL) was added, and the mixture was stirred vigorously. The solid product was collected by vacuum-filtration and further dried to give a pale yellow solid, which was triturated with MeOH (40 mL) to remove Et$_3$N HCl salt. The solid was collected by vacuum-filtration and further dried to give 1.81 g of white solid as the first batch. The filtrate was concentrated and partitioned between CH$_2$Cl$_2$ (100 mL) and water (50 mL). The separated organic layer was washed with brine, dried over sodium sulfate, and concentrated to give 1.31 g of waxy, yellow solid as the second batch. Total yield of 93 from the two batches was 3.12 g (82%). $^1$H NMR (400 MHz, DMSO-d$_6$) δ 1.67-1.94 (m, 2H), 2.09 (s, 3H), 2.52-2.92 (m, 3H), 3.14-3.31 (m, 1H), 3.56 (s, 3H), 4.04 (d, J=13.64 Hz, 1H), 4.62 (d, J=11.37 Hz, 1H), 5.40 (br s, 1H), 7.83 (d, J=9.09 Hz, 1H), 8.59 (d, J=8.84 Hz, 1H), 9.19 (s, 1H).

Step 3

A mixture of 1-(1-acetylpiperidin-4-yl)-8-chloro-3-methyl-1H-imidazo[4,5-c][1,5]naphthyridin-2(3H)-one (93) (540 mg, 1.50 mmol), 1H-indazol-4-ylboronic acid (364 mg, 2.25 mmol), Pd(PPh₃)₂Cl₂ (74.4 mg, 0.105 mmol), and K₂CO₃ (622 mg, 4.50 mmol) in dioxane/water (8/4 mL) was bubbled with nitrogen for 5 minutes, and heated in a sealed tube at 90° C. overnight. After cooling the reaction mixture was partitioned between water (40 mL) and CH₂Cl₂/MeOH (100/5 mL). The aqueous layer was further extracted with CH₂Cl₂ (50 mL). The organic extract was washed with brine, dried over sodium sulfate, and concentrated to give a waxy, yellow solid, which was purified on ISCO purification system with a 40-gram column using 0-10% MeOH in CH₂Cl₂ to afford 450 mg (68%) of the title compound 254 as a waxy, pale yellow solid. ¹H NMR (400 MHz, CDCl₃) δ 1.88-2.04 (m, 2H), 2.08 (br s, 3H), 2.62 (t, J=12.51 Hz, 1H), 2.82 (br s, 1H), 3.02 (br s, 1H), 3.24 (t, J=12.25 Hz, 1H), 3.64 (s, 3H), 3.95 (d, J=13.14 Hz, 1H), 4.85 (d, J=12.88 Hz, 1H), 6.28 (br s, 1H), 7.54-7.64 (m, 1H), 7.70 (t, J=7.20 Hz, 2H), 8.12 (d, J=8.84 Hz, 1H), 8.56 (d, J=8.84 Hz, 2H), 8.79 (s, 1H), 11.02 (br s, 1H).

Compounds represented in Table 1 were prepared following the above described procedures. Compounds 101-116, 119-128, 130-134, 136-170, 172-176, 178-190, 192-194, 196-203, 205-206, and 208-228 were isolated as a free base, while Compounds 117, 118, 129, 135, 171, 177, 191, 195, 204 and 207 were isolated as hydrochlorides.

TABLE 1

| Ex. No. | Synthetic Method | Structure | Compound Name |
|---|---|---|---|
| 103 | A | 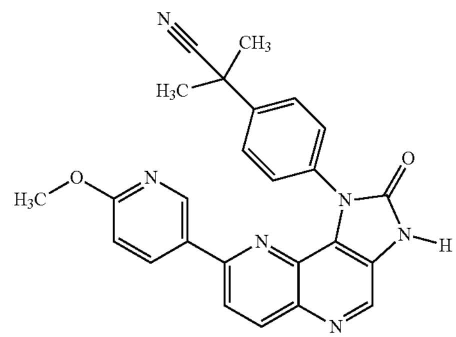 [SMILES: COc1ccc(-c2ccc3ncc4[nH]c(=O)n(-c5ccc(C(C)(C)C#N)cc5)c4c3n2)cn1] | 2-{4-[8-(6-methoxypyridin-3-yl)-2-oxo-2,3-dihydro-1H-imidazo[4,5-c]-1,5-naphthyridin-1-yl]phenyl}-2-methylpropanenitrile |
| 104 | A | 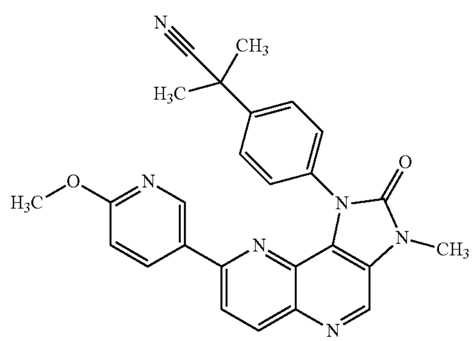 | 2-{4-[8-(6-methoxypyridin-3-yl)-3-methyl-2-oxo-2,3-dihydro-1H-imidazo[4,5-c]-1,5-naphthyridin-1-yl]phenyl}-2-methylpropanenitrile |
| 105 | A | 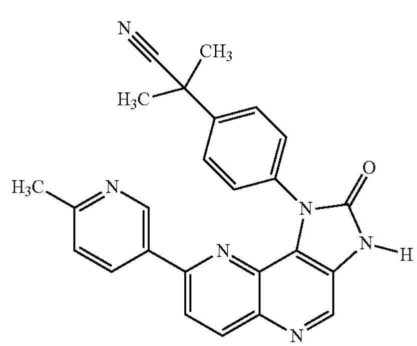 [SMILES: Cc1ccc(-c2ccc3ncc4[nH]c(=O)n(-c5ccc(C(C)(C)C#N)cc5)c4c3n2)cn1] | 2-methyl-2-{4-[8-(6-methylpyridin-3-yl)-2-oxo-2,3-dihydro-1H-imidazo[4,5-c]-1,5-naphthyridin-1-yl]phenyl}propanenitrile |

TABLE 1-continued

| Ex. No. | Synthetic Method | Structure | Compound Name |
|---|---|---|---|
| 106 | A | 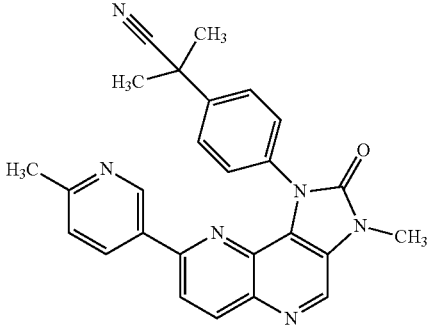 | 2-methyl-2-{4-[3-methyl-8-(6-methylpyridin-3-yl)-2-oxo-2,3-dihydro-1H-imidazo[4,5-c]-1,5-naphthyridin-1-yl]phenyl}propanenitrile |
| 107 | A | 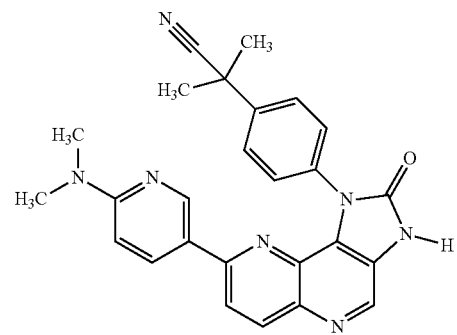 [SMILES: CN(C)c1ccc(-c2ccc3ncc4[nH]c(=O)n(-c5ccc(C(C)(C)C#N)cc5)c4c3n2)cn1] | 2-(4-(8-(6-(dimethylamino)pyridin-3-yl)-2-oxo-2,3-dihydroimidazo[4,5-c][1,5]naphthyridin-1-yl)phenyl)-2-methylpropanenitrile |
| 108 | A | 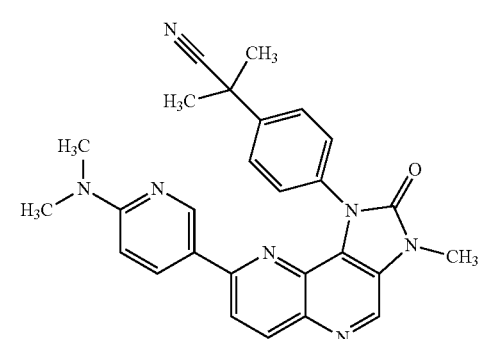 | 2-(4-(8-(6-(dimethylamino)pyridin-3-yl)-3-methyl-2-oxo-2,3-dihydroimidazo[4,5-c][1,5]naphthyridin-1-yl)phenyl)-2-methylpropanenitrile |
| 109 | A | 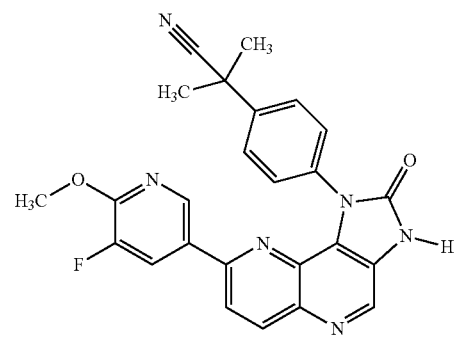 [SMILES: COc1ncc(-c2ccc3ncc4[nH]c(=O)n(-c5ccc(C(C)(C)C#N)cc5)c4c3n2)cc1F] | 2-(4-(8-(5-fluoro-6-methoxypyridin-3-yl)-2-oxo-2,3-dihydroimidazo[4,5-c][1,5]naphthyridin-1-yl)phenyl)-2-methylpropanenitrile |

TABLE 1-continued

| Ex. No. | Synthetic Method | Structure | Compound Name |
|---|---|---|---|
| 110 | A | 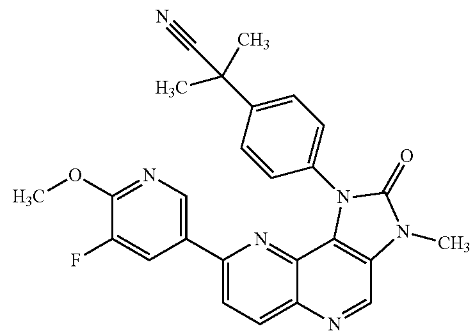 | 2-(4-(8-(5-fluoro-6-methoxypyridin-3-yl)-3-methyl-2-oxo-2,3-dihydroimidazo[4,5-c][1,5]naphthyridin-1-yl)phenyl)-2-methylpropanenitrile |
| 111 | A | 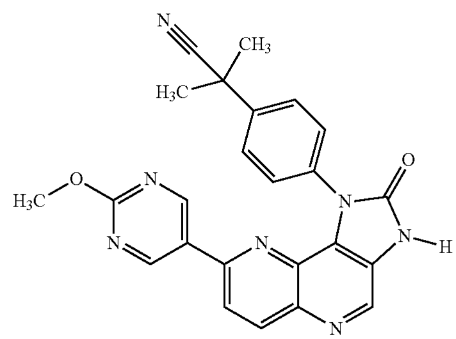 [SMILES: COc1ncc(-c2ccc3ncc4[nH]c(=O)n(-c5ccc(C(C)(C)C#N)cc5)c4c3n2)cn1] | 2-(4-(8-(2-methoxypyrimidin-5-yl)-2-oxo-2,3-dihydroimidazo[4,5-c][1,5]naphthyridin-1-yl)phenyl)-2-methylpropanenitrile |
| 112 | A | 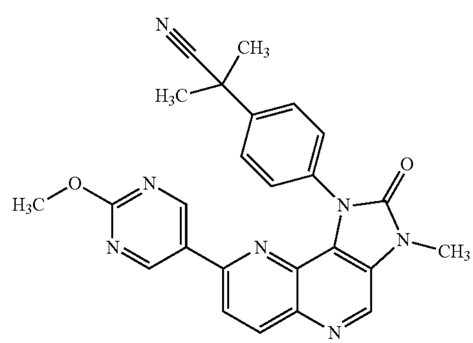 | 2-(4-(8-(2-methoxypyrimidin-5-yl)-3-methyl-2-oxo-2,3-dihydroimidazo[4,5-c][1,5]naphthyridin-1-yl)phenyl)-2-methylpropanenitrile |
| 113 | A | 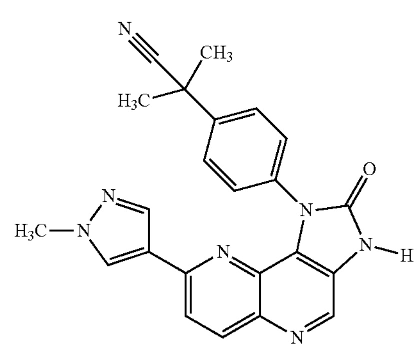 [SMILES: Cn1cc(-c2ccc3ncc4[nH]c(=O)n(-c5ccc(C(C)(C)C#N)cc5)c4c3n2)cn1] | 2-Methyl-2-{4-[8-(1-methyl-1H-pyrazol-4-yl)-2-oxo-2,3-dihydro-1,3,5,9-tetraaza-cyclopenta[a]naphthalen-1-yl]-phenyl}-propionitrile |

TABLE 1-continued

| Ex. No. | Synthetic Method | Structure | Compound Name |
|---|---|---|---|
| 114 | A | 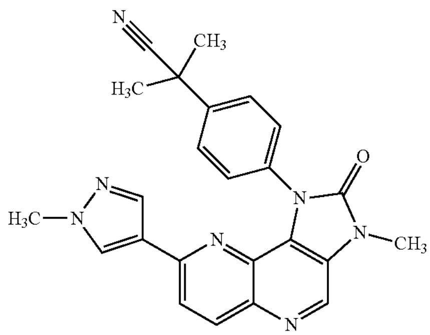 | 2-Methyl-2-{4-[3-methyl-8-(1-methyl-1H-pyrazol-4-yl)-2-oxo-2,3-dihydro-1,3,5,9-tetraaza-cyclopenta[a]naphthalen-1-yl]-phenyl}-propionitrile |
| 115 | B | 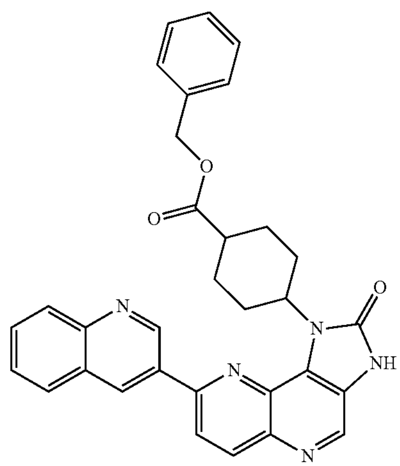 [SMILES: O=C(OCc1ccccc1)C1CCC(n2c(=O)[nH]c3cnc4ccc(-c5cnc6ccccc6c5)nc4c32)CC1] | benzyl4-(2-oxo-8-quinolin-3-yl-2,3-dihydro-1H-imidazo[4,5-c][1,5]naphthyridin-1-yl)piperidine-1-carboxylate |
| 116 | B | 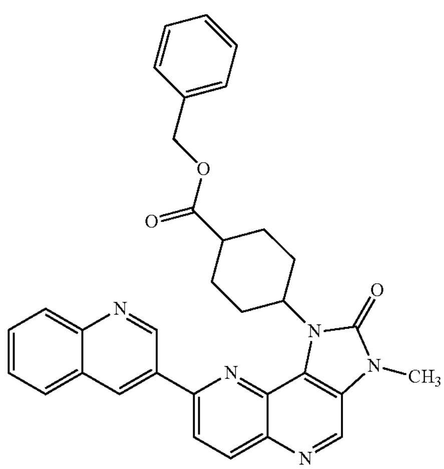 [SMILES: Cn1c(=O)n(C2CCC(C(=O)OCc3ccccc3)CC2)c2c3nc(-c4cnc5ccccc5c4)ccc3ncc21] | benzyl4-(3-methyl-2-oxo-8-quinolin-3-yl-2,3-dihydro-1H-imidazo[4,5-c][1,5]naphthyridin-1-yl)piperidine-1-carboxylate |
| 117 | B | 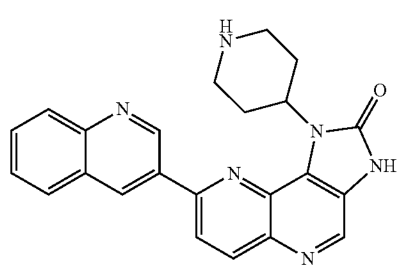 [SMILES: O=c1[nH]c2cnc3ccc(-c4cnc5ccccc5c4)nc3c2n1C1CCNCC1] | 1-piperidin-4-yl-8-quinolin-3-yl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 119 | G | 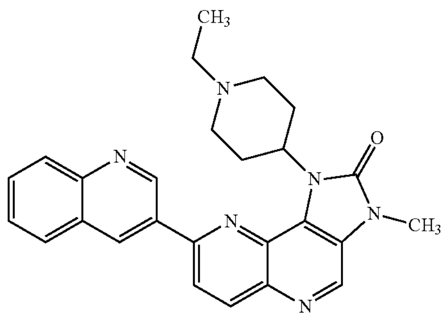 [SMILES: CCN1CCC(n2c(=O)n(C)c3cnc4ccc(-c5cnc6ccccc6c5)nc4c32)CC1] | 1-(1-ethylpiperidin-4-yl)-3-methyl-8-quinolin-3-yl-1,3-dihydro-2H-imidazo[4,5-c][1,5]naphthyridin-2-one |
| 121 | E | 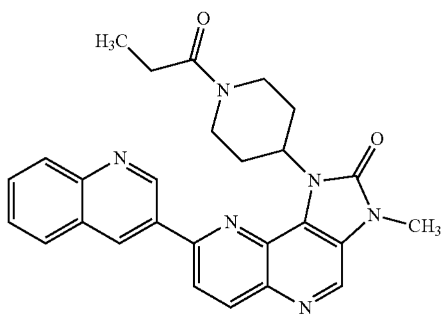 [SMILES: CCC(=O)N1CCC(n2c(=O)n(C)c3cnc4ccc(-c5cnc6ccccc6c5)nc4c32)CC1] | 3-methyl-1-(1-propionylpiperidin-4-yl)-8-quinolin-3-yl-1,3-dihydro-2H-imidazo[4,5-c][1,5]naphthyridin-2-one |
| 122 | E | 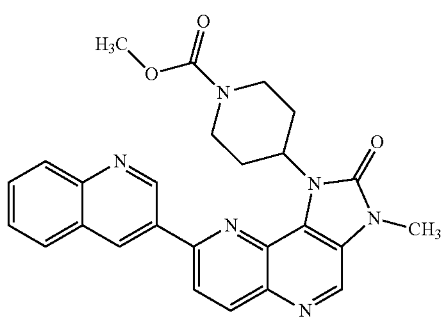 [SMILES: COC(=O)N1CCC(n2c(=O)n(C)c3cnc4ccc(-c5cnc6ccccc6c5)nc4c32)CC1] | methyl 4-(3-methyl-2-oxo-8-quinolin-3-yl-2,3-dihydro-1H-imidazo[4,5-c][1,5]napthyridin-1-yl)piperidine-1-carboxylate |
| 123 | H | 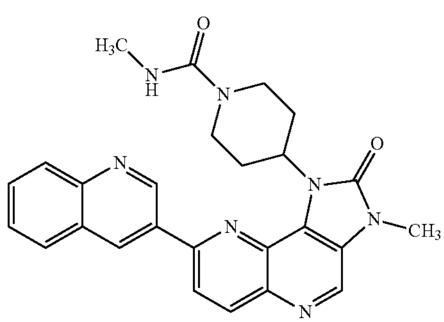 [SMILES: CNC(=O)N1CCC(n2c(=O)n(C)c3cnc4ccc(-c5cnc6ccccc6c5)nc4c32)CC1] | N-methyl-4-(3-methyl-2-oxo-8-quinolin-3-yl-2,3-dihydro-1H-imidazo[4,5-c][1,5]naphthyridin-1-yl)piperidine-1-carboxamide |
| 124 | H | 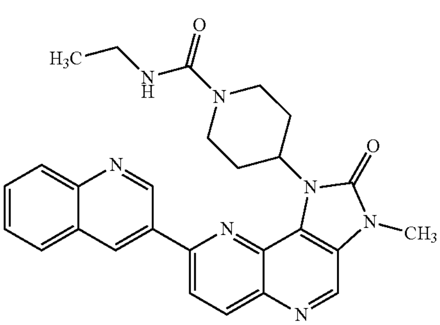 [SMILES: CCNC(=O)N1CCC(n2c(=O)n(C)c3cnc4ccc(-c5cnc6ccccc6c5)nc4c32)CC1] | N-ethyl-4-(3-methyl-2-oxo-8-quinolin-3-yl-2,3-dihydro-1H-imidazo[4,5-c][1,5]naphthyridin-1-yl)piperidine-1-carboxamide |

TABLE 1-continued

| Ex. No. | Synthetic Method | Structure | Compound Name |
|---|---|---|---|
| 125 | E | 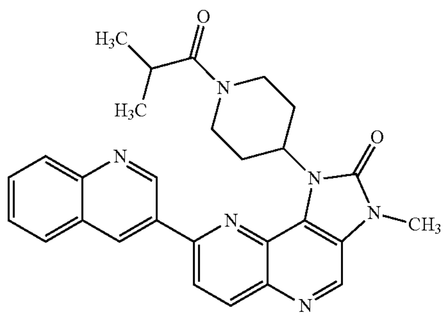 [SMILES: CC(C)C(=O)N1CCC(n2c(=O)n(C)c3cnc4ccc(-c5cnc6ccccc6c5)nc4c32)CC1] | 1-(1-isobutyrylpiperidin-4-yl)-3-methyl-8-quinolin-3-yl-1,3-dihydro-2H-imidazo[4,5-c][1,5]naphthyridin-2-one |
| 126 | F | 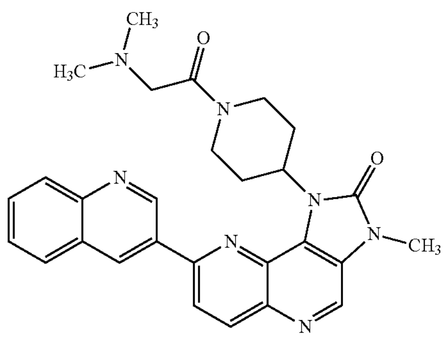 [SMILES: CN(C)CC(=O)N1CCC(n2c(=O)n(C)c3cnc4ccc(-c5cnc6ccccc6c5)nc4c32)CC1] | 1-[1-(N,N-dimethylglycyl)piperidin-4-yl]-3-methyl-8-quinolin-3-yl-1,3-dihydro-2H-imidazo[4,5-c][1,5]naphthyridin-2-one |
| 127 | E | 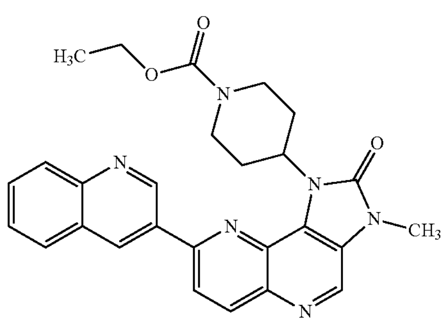 [SMILES: CCOC(=O)N1CCC(n2c(=O)n(C)c3cnc4ccc(-c5cnc6ccccc6c5)nc4c32)CC1] | ethyl 4-(3-methyl-2-oxo-8-quinolin-3-yl-2,3-dihydro-1H-imidazo[4,5-c][1,5]naphthyridin-1-yl)piperidine-1-carboxylate |
| 128 | E | 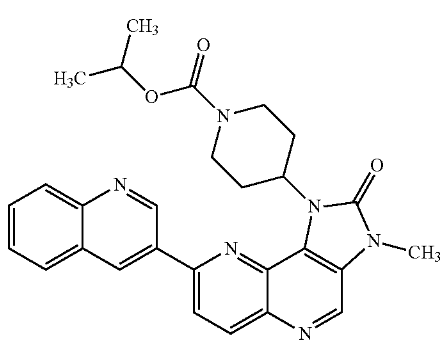 [SMILES: CC(C)OC(=O)N1CCC(n2c(=O)n(C)c3cnc4ccc(-c5cnc6ccccc6c5)nc4c32)CC1] | isopropyl 4-(3-methyl-2-oxo-8-quinolin-3-yl-2,3-dihydro-1H-imidazo[4,5-c][1,5]naphthyridin-1-yl)piperidine-1-carboxylate |

TABLE 1-continued

| Ex. No. | Synthetic Method | Structure | Compound Name |
|---|---|---|---|
| 129 | G | 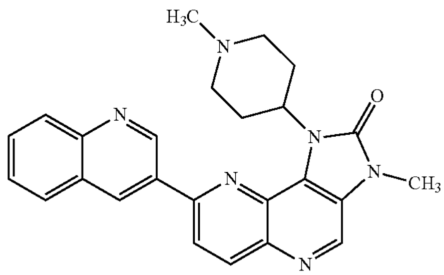 [SMILES: CN1CCC(n2c(=O)n(C)c3cnc4ccc(-c5cnc6ccccc6c5)nc4c32)CC1] | 3-methyl-1-(1-methylpiperidin-4-yl)-8-quinolin-3-yl-1,3-dihydro-2H-imidazo[4,5-c][1,5]naphthyridin-2-one |
| 130 | A | 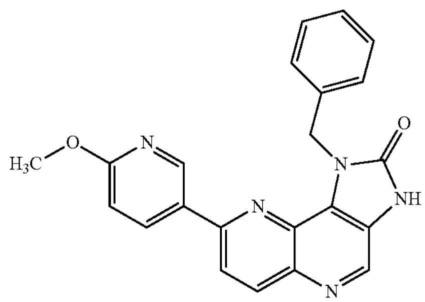 [SMILES: COc1ccc(-c2ccc3ncc4[nH]c(=O)n(Cc5ccccc5)c4c3n2)cn1] | 1-benzyl-8-(6-methoxypyridin-3-yl)-1,3-dihydro-2H-imidazo[4,5-c][1,5]naphthyridin-2-one |
| 131 | J | 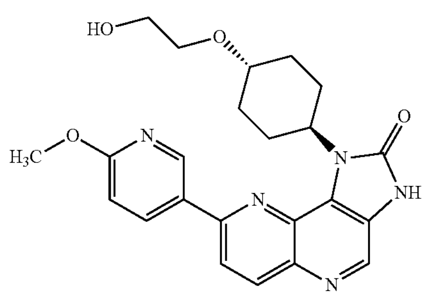 [SMILES: COc1ccc(-c2ccc3ncc4[nH]c(=O)n([C@H]5CC[C@H](OCCO)CC5)c4c3n2)cn1] | 1-[trans-4-(2-hydroxyethoxy)cyclohexyl]-8-(6-methoxypyridin-3-yl)-1,3-dihydro-2H-imidazo[4,5-c][1,5]naphthyridin-2-one |
| 132 | J | 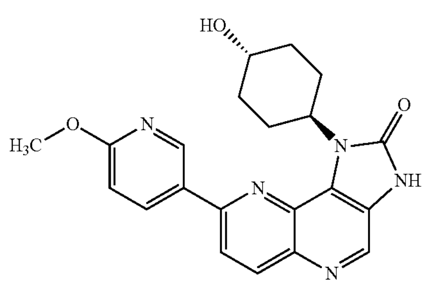 [SMILES: COc1ccc(-c2ccc3ncc4[nH]c(=O)n([C@H]5CC[C@H](O)CC5)c4c3n2)cn1] | 1-(trans-4-hydroxycyclohexyl)-8-(6-methoxypyridin-3-yl)-1,3-dihydro-2H-imidazo[4,5-c][1,5]naphthyridin-2-one |
| 133 | J | 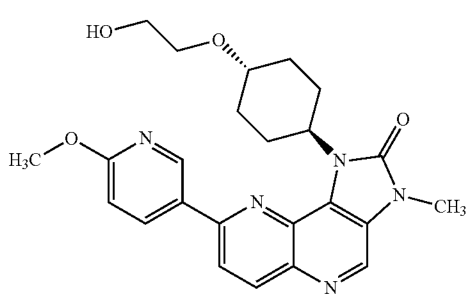 | 1-[trans-4-(2-hydroxyethoxy)cyclohexyl]-8-(6-methoxypyridin-3-yl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 134 | J | 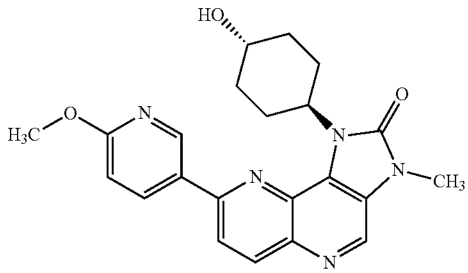 | 1-(trans-4-hydroxycyclohexyl)-8-(6-methoxypyridin-3-yl)-3-methyl-1,3-dihydro-2H-imidazo[4,5-c][1,5]naphthyridin-2-one |
| 136 | E | 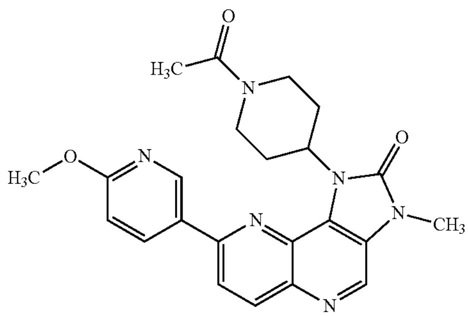 | 1-(1-acetylpiperidin-4-yl)-8-(6-methoxypyridin-3-yl)-3-methyl-1,3-dihydro-2H-imidazo[4,5-c][1,5]naphthyridin-2-one |
| 137 | G | 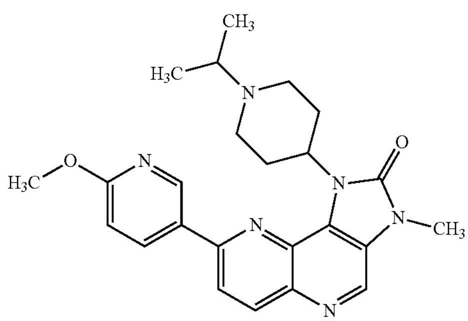 | 1-(1-isopropylpiperidin-4-yl)-8-(6-methoxypyridin-3-yl)-3-methyl-1,3-dihydro-2H-imidazo[4,5-c][1,5]naphthyridin-2-one |
| 138 | F | 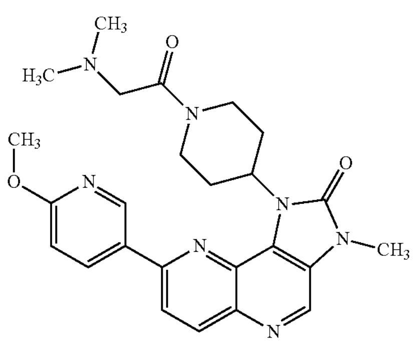 [SMILES: COc1ccc(-c2ccc3ncc4c(c3n2)n(C2CCN(C(=O)CN(C)C)CC2)c(=O)n4C)cn1] | 1-[1-(N,N-dimethylglycyl)piperidin-4-yl]-8-(6-methoxypyridin-3-yl)-3-methyl-1,3-dihydro-2H-imidazo[4,5-c][1,5]naphthyridin-2-one |
| 139 | G | 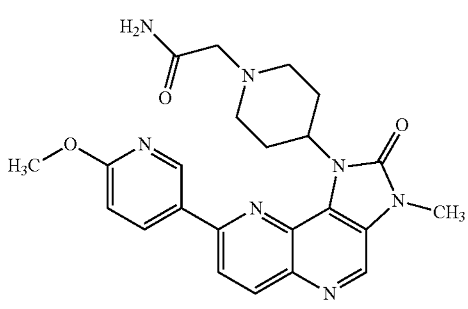 | 2-{4-[8-(6-methoxypyridin-3-yl)-3-methyl-2-oxo-2,3-dihydro-1H-imidazo[4,5-c][1,5]naphthyridin-1-yl]piperidin-1-yl}acetamide |

TABLE 1-continued

| Ex. No. | Synthetic Method | Structure | Compound Name |
|---|---|---|---|
| 140 | J | 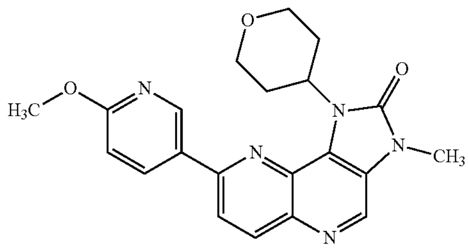 | 8-(6-methoxypyridin-3-yl)-3-methyl-1-(tetrahydro-2H-pyran-4-yl)-1,3-dihydro-2H-imidazo[4,5-c][1,5]naphthyridin-2-one |
| 141 | G | 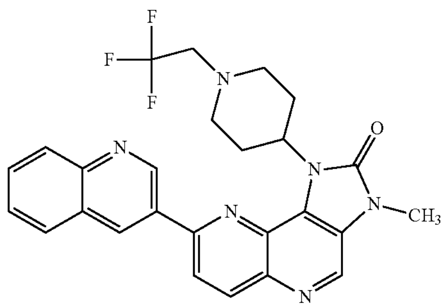 [SMILES: Cn1c(=O)n(C2CCN(CC(F)(F)F)CC2)c2c3nc(-c4cnc5ccccc5c4)ccc3ncc21] | 3-methyl-8-quinolin-3-yl-1-[1-(2,2,2-trifluoroethyl)piperidin-4-yl]-1,3-dihydro-2H-imidazo[4,5-c][1,5]naphthyridin-2-one |
| 142 | H | 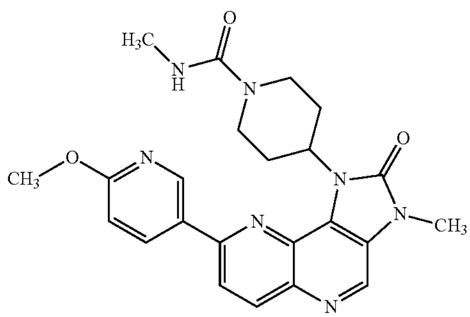 | 4-[8-(6-methoxypyridin-3-yl)-3-methyl-2-oxo-2,3-dihydro-1H-imidazo[4,5-c][1,5]naphthyridin-1-yl]-N-methylpiperidine-1-carboxamide |
| 143 | F | 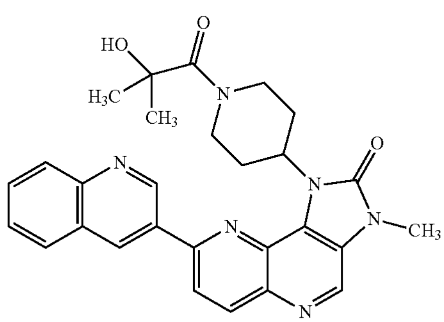 [SMILES: Cn1c(=O)n(C2CCN(C(=O)C(C)(C)O)CC2)c2c3nc(-c4cnc5ccccc5c4)ccc3ncc21] | 1-[1-(2-hydroxy-2-methylpropanoyl)piperidin-4-yl]-3-methyl-8-quinolin-3-yl-1,3-dihydro-2H-imidazo[4,5-c][1,5]naphthyridin-2-one |
| 144 | F | 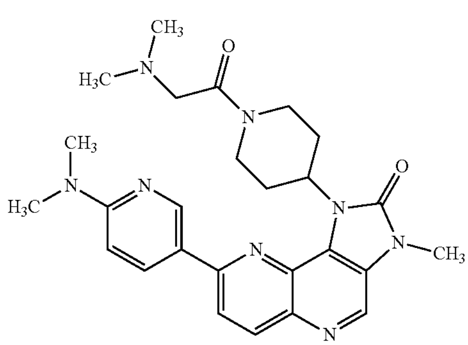 | 8-[6-(dimethylamino)pyridin-3-yl]-1-[1-(N,N-dimethylglycyl)piperidin-4-yl]-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 145 | F | 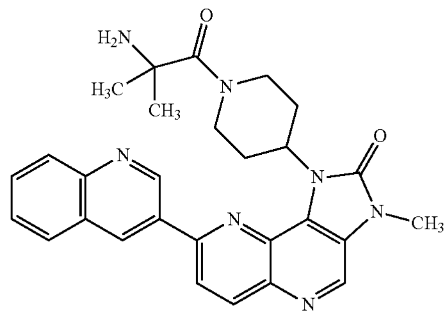 [SMILES: Cn1c(=O)n(C2CCN(C(=O)C(C)(C)N)CC2)c2c3nc(-c4cnc5ccccc5c4)ccc3ncc21] | 3-methyl-1-[1-(2-methylalanyl)piperidin-4-yl]-8-quinolin-3-yl-1,3-dihydro-2H-imidazo[4,5-c][1,5]naphthyridin-2-one |
| 146 | J | 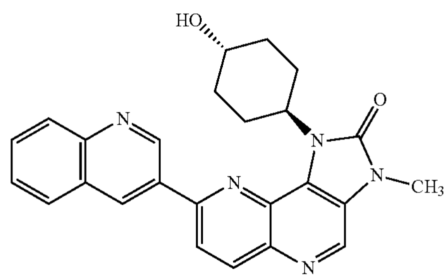 [SMILES: Cn1c(=O)n([C@H]2CC[C@H](O)CC2)c2c3nc(-c4cnc5ccccc5c4)ccc3ncc21] | 1-(trans-4-hydroxycyclohexyl)-3-methyl-8-quinolin-3-yl-1,3-dihydro-2H-imidazo[4,5-c][1,5]naphthyridin-2-one |
| 147 | J | 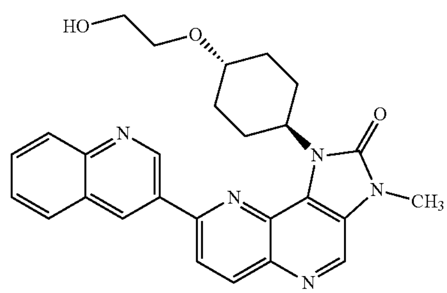 [SMILES: Cn1c(=O)n([C@H]2CC[C@H](OCCO)CC2)c2c3nc(-c4cnc5ccccc5c4)ccc3ncc21] | 1-[trans-4-(2-hydroxyethoxy)cyclohexyl]-3-methyl-8-quinolin-3-yl-1,3-dihydro-2H-imidazol[4,5-c][1,5]naphthyridin-2-one |
| 148 | J | 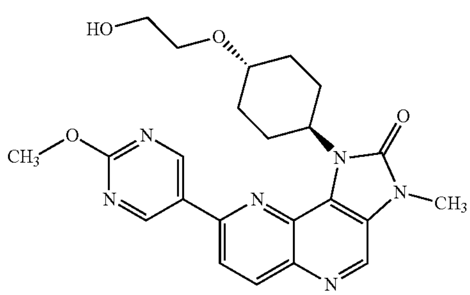 | 1-[trans-4-(2-hydroxyethoxy)cyclohexyl]-8-(2-methoxypyrimidin-5-yl)-3-methyl-1,3-dihydro-2H-imidazo[4,5-c][1,5]naphthyridin-2-one |
| 149 | J | 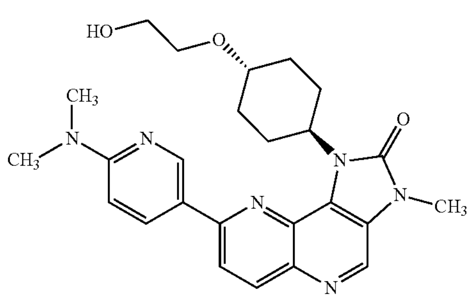 | 8-[6-(dimethylamino)pyridin-3-yl]-1-[trans-4-(2-hydroxyethoxy)cyclohexyl]-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 150 | G | 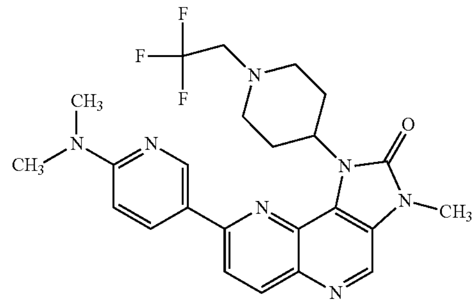 | 8-[6-(dimethylamino)pyridin-3-yl]-3-methyl-1-[1-(2,2,2-trifluoroethyl)piperidin-4-yl]-1,3-dihydro-2H-imidazo[4,5-c][1,5]naphthyridin-2-one |
| 151 | G | 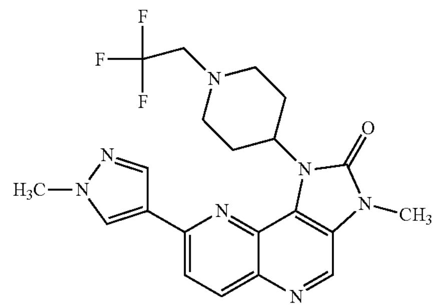 | 3-methyl-8-(1-methyl-1H-pyrazol-4-yl)-1-[1-(2,2,2-trifluoroethyl)piperidin-4-yl]-1,3-dihydro-2H-imidazo[4,5-c][1,5]naphthyridin-2-one |
| 152 | J | 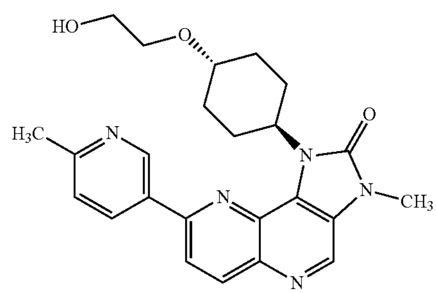 | 1-[trans-4-(2-hydroxyethoxy)cyclohexyl]-3-methyl-8-(6-methylpyridin-3-yl)-1,3-dihydro-2H-imidazo[4,5-c][1,5]naphthyridin-2-one |
| 153 | F | 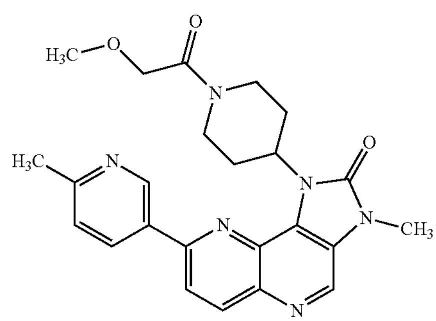 | 1-[1-(methoxyacetyl)piperidin-4-yl]-3-methyl-8-(6-methylpyridin-3-yl)-1,3-dihydro-2H-imidazo[4,5-c][1,5]naphthyridin-2-one |
| 154 | F | 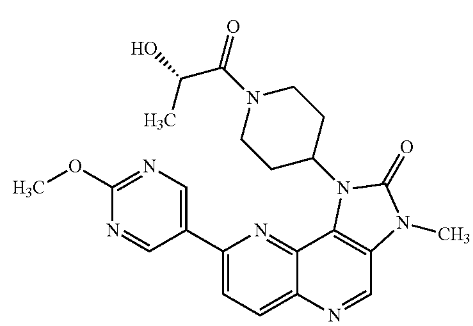 | 1-{1-[(2S)-2-hydroxypropanoyl]piperidin-4-yl}-8-(2-methoxypyrimidin-5-yl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 155 | F | 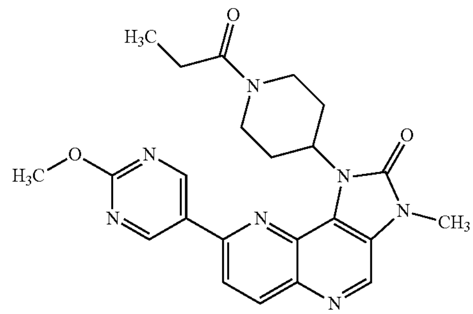 | 8-(2-methoxypyrimidin-5-yl)-3-methyl-1-(1-propionylpiperidin-4-yl)-1,3-dihydro-2H-imidazo[4,5-c][1,5]naphthyridin-2-one |
| 156 | J | 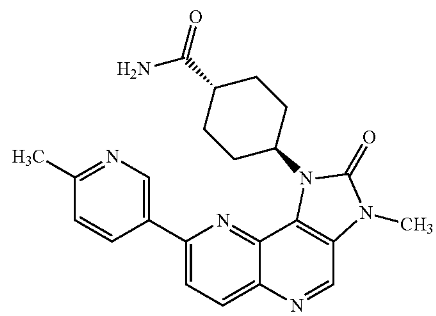 | trans-4-[3-methyl-8-(6-methylpyridin-3-yl)-2-oxo-2,3-dihydro-1H-imidazo[4,5-c][1,5]naphthyridin-1-yl]cyclohexanecarboxamide |
| 157 | J | 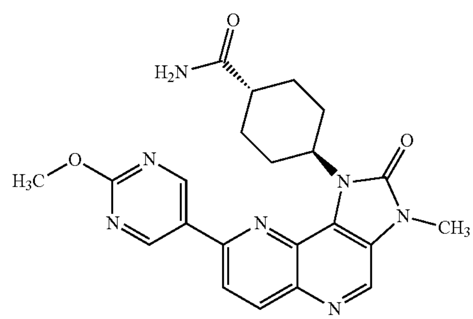 | trans-4-[8-(2-methoxypyrimidin-5-yl)-3-methyl-2-oxo-2,3-dihydro-1H-imidazo[4,5-c][1,5]naphthyridin-1-yl]cyclohexanecarboxamide |
| 158 | J | 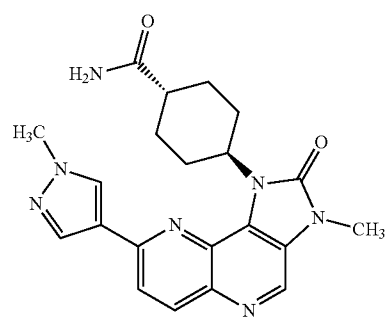 [SMILES: Cn1cc(-c2ccc3ncc4c(c3n2)n([C@H]2CC[C@H](C(N)=O)CC2)c(=O)n4C)cn1] | trans-4-[3-methyl-8-(1-methyl-1H-pyrazol-4-yl)-2-oxo-2,3-dihydro-1H-imidazo[4,5-c][1,5]naphthyridin-1-yl]cyclohexanecarboxamide |
| 159 | J | 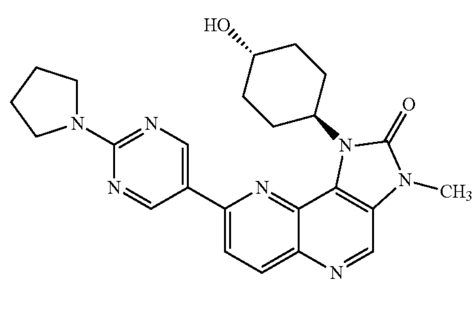 [SMILES: Cn1c(=O)n([C@H]2CC[C@H](O)CC2)c2c3nc(-c4cnc(N5CCCC5)nc4)ccc3ncc21] | 1-(trans-4-hydroxycyclohexyl)-3-methyl-8-(2-pyrrolidin-1-ylpyrimidin-5-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 160 | J | 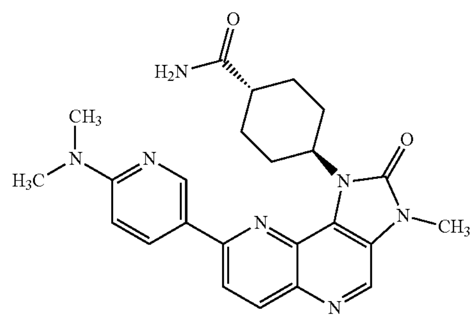 | trans-4-{8-[6-(dimethylamino)pyridin-3-yl]-3-methyl-2-oxo-2,3-dihydro-1H-imidazo[4,5-c][1,5]naphthyridin-1-yl}cyclohexanecarboxamide |
| 161 | F | 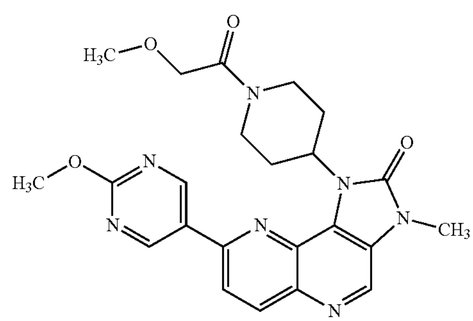 | 1-[1-(methoxyacetyl)piperidin-4-yl]-8-(2-methoxypyrimidin-5-yl)-3-methyl-1,3-dihydro-2H-imidazo[4,5-c][1,5]naphthyridin-2-one |
| 162 | F | 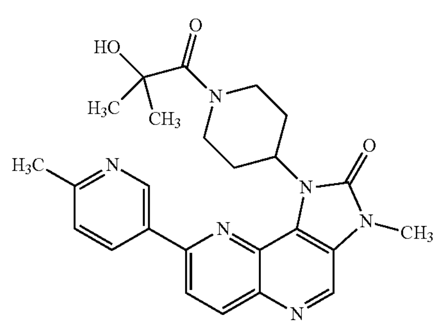 | 1-[1-(2-hydroxy-2-methylpropanoyl)piperidin-4-yl]-3-methyl-8-(6-methylpyridin-3-yl)-1,3-dihydro-2H-imidazo[4,5-c][1,5]naphthyridin-2-one |
| 163 | G | 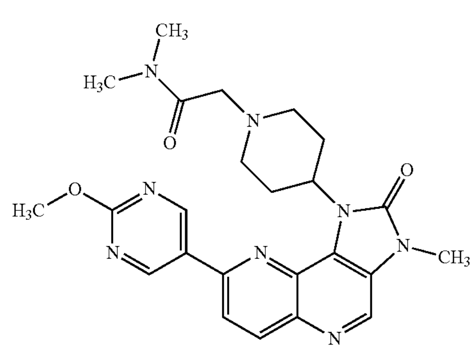 | 2-{4-[8-(2-methoxypyrimidin-5-yl)-3-methyl-2-oxo-2,3-dihydro-1H-imidazo[4,5-c][1,5]naphthyridin-1-yl]piperidin-1-yl}-N,N-dimethylacetamide |

TABLE 1-continued

| Ex. No. | Synthetic Method | Structure | Compound Name |
|---|---|---|---|
| 164 | J | 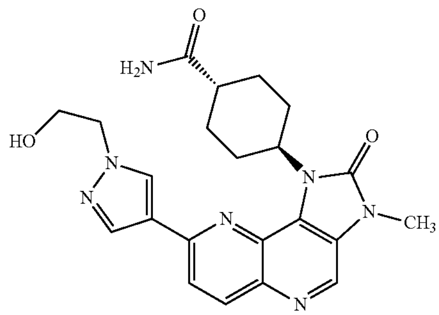 [SMILES: Cn1c(=O)n([C@H]2CC[C@H](C(N)=O)CC2)c2c3nc(-c4cnn(CCO)c4)ccc3ncc21] | 1-(trans-4-hydroxycyclohexyl)-8-[1-(2-hydroxyethyl)-1H-pyrazol-4-yl]-3-methyl-1,3-dihydro-2H-imidazo[4,5-c][1,5]naphthyridin-2-one |
| 165 | G | 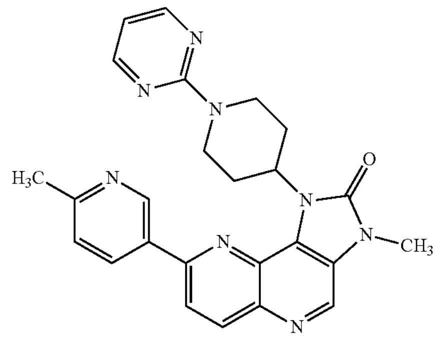 | 3-methyl-8-(6-methylpyridin-3-yl)-1-(1-pyrimidin-2-ylpiperidin-4-yl)-1,3-dihydro-2H-imidazo[4,5-c][1,5]naphthyridin-2-one |
| 166 | G | 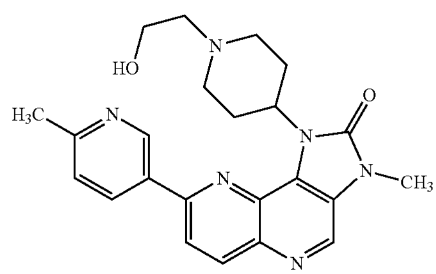 | 1-[1-(2-hydroxyethyl)piperidin-4-yl]-3-methyl-8-(6-methylpyridin-3-yl)-1,3-dihydro-2H-imidazo[4,5-c][1,5]naphthyridin-2-one |
| 168 | J | 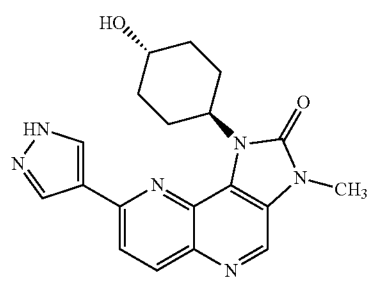 [SMILES: Cn1c(=O)n([C@H]2CC[C@H](O)CC2)c2c3nc(-c4cn[nH]c4)ccc3ncc21] | 1-(trans-4-hydroxycyclohexyl)-3-methyl-8-(1H-pyrazol-4-yl)-1,3-dihydro-2H-imidazo[4,5-c][1,5]naphthyridin-2-one |
| 169 | J | 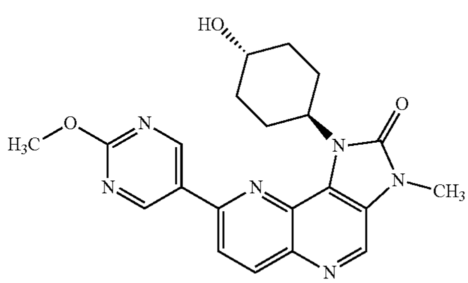 | 1-(trans-4-hydroxycyclohexyl)-8-(2-methoxypyrimidin-5-yl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 170 | J | 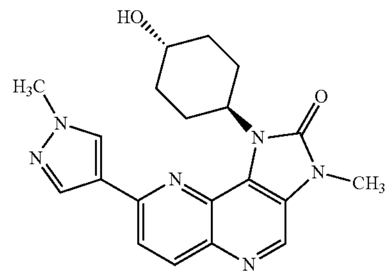 [SMILES: Cn1cc(-c2ccc3ncc4c(c3n2)n([C@H]2CC[C@H](O)CC2)c(=O)n4C)cn1] | 1-(trans-4-hydroxycyclohexyl)-3-methyl-8-(1-methyl-1H-pyrazol-4-yl)-1,3-dihydro-2H-imidazo[4,5-c][1,5]naphthyridin-2-one |
| 171 | D | 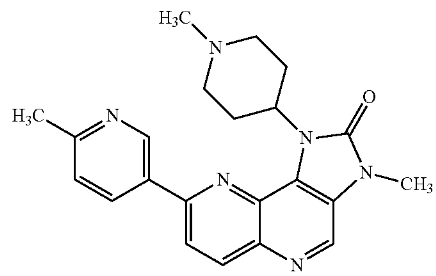 | 3-methyl-1-(1-methylpiperidin-4-yl)-8-(6-methylpyridin-3-yl)-1,3-dihydro-2H-imidazo[4,5-c][1,5]naphthyridin-2-one |
| 172 | F | 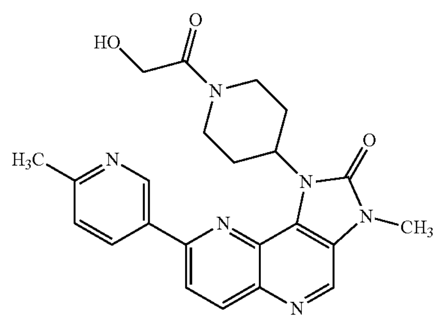 | 1-(1-glycoloylpiperidin-4-yl)-3-methyl-8-(6-methylpyridin-3-yl)-1,3-dihydro-2H-imidazo[4,5-c][1,5]naphthyridin-2-one |
| 173 | E | 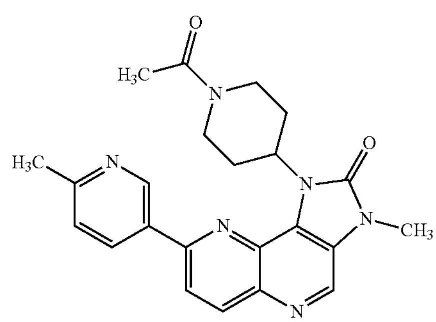 | 1-(1-acetylpiperidin-4-yl)-3-methyl-8-(6-methylpyridin-3-yl)-1,3-dihydro-2H-imidazo[4,5-c][1,5]naphthyridin-2-one |
| 174 | J | 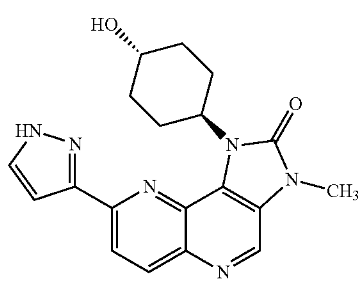 [SMILES: Cn1c(=O)n([C@H]2CC[C@H](O)CC2)c2c3nc(-c4cc[nH]n4)ccc3ncc21] | 1-(trans-4-hydroxycyclohexyl)-3-methyl-8-(1H-pyrazol-3-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 176 | G | 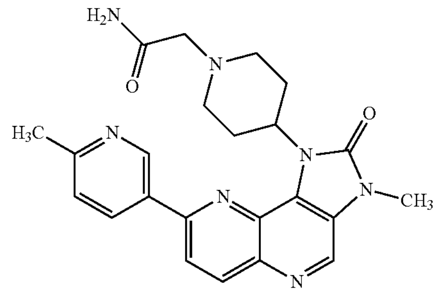 | 2-{4-[3-methyl-8-(6-methylpyridin-3-yl)-2-oxo-2,3-dihydro-1H-imidazo[4,5-c][1,5]naphthyridin-1-yl]piperidin-1-yl}acetamide |
| 178 | F | 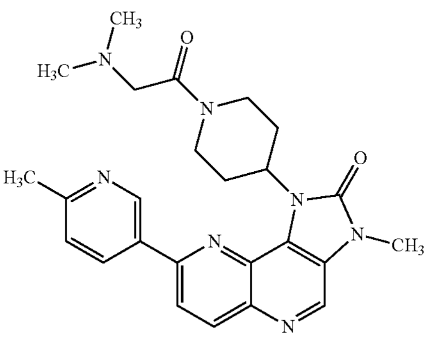 | 1-[1-(N,N-dimethylglycyl)piperidin-4-yl]-3-methyl-8-(6-methylpyridin-3-yl)-1,3-dihydro-2H-imidazo[4,5-c][1,5]naphthyridin-2-one |
| 179 | J | 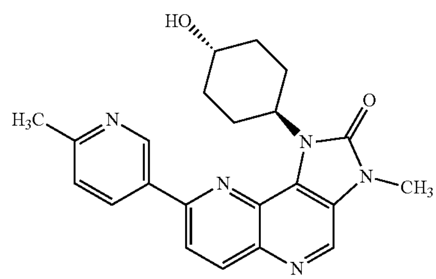 | 1-(trans-4-hydroxycyclohexyl)-3-methyl-8-(6-methylpyridin-3-yl)-1,3-dihydro-2H-imidazo[4,5-c][1,5]naphthyridin-2-one |
| 180 | F (followed by BOC deprotection) | 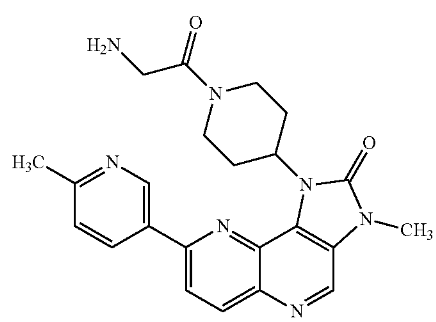 | 1-(1-glycylpiperidin-4-yl)-3-methyl-8-(6-methylpyridin-3-yl)-1,3-dihydro-2H-imidazo[4,5-c][1,5]naphthyridin-2-one |
| 181 | H | 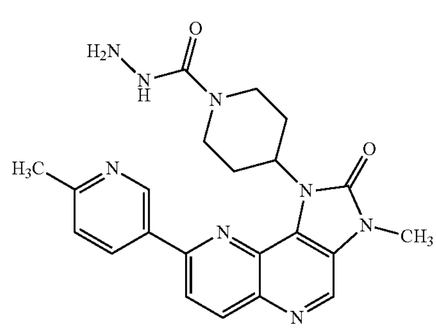 | N-methyl-4-[3-methyl-8-(6-methylpyridin-3-yl)-2-oxo-2,3-dihydro-1H-imidazo[4,5-c][1,5]naphthyridin-1-yl]piperidine-1-carboxamide |

TABLE 1-continued

| Ex. No. | Synthetic Method | Structure | Compound Name |
|---|---|---|---|
| 182 | D | 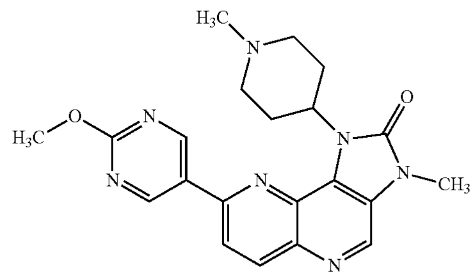 | 8-(2-methoxypyrimidin-5-yl)-3-methyl-1-(1-methylpiperidin-4-yl)-1,3-dihydro-2H-imidazo[4,5-c][1,5]naphthyridin-2-one |
| 183 | F | 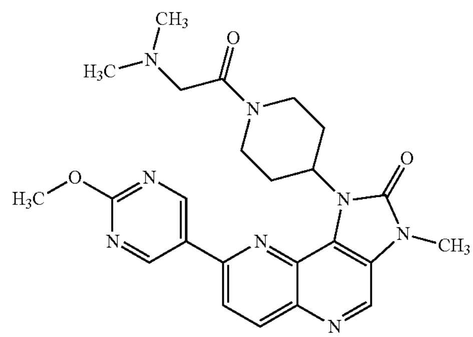 | 1-[1-(N,N-dimethylglycyl)piperidin-4-yl]-8-(2-methoxypyrimidin-5-yl)-3-methyl-1,3-dihydro-2H-imidazo[4,5-c][1,5]naphthyridin-2-one |
| 184 | F (followed by BOC deprotection) | 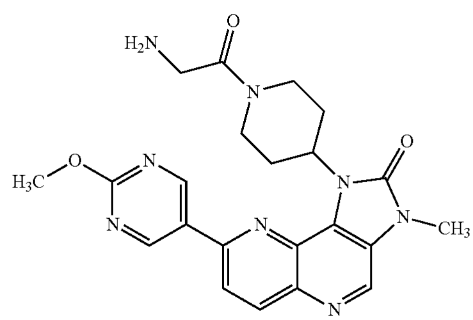 | 1-(1-glycylpiperidin-4-yl)-8-(2-methoxypyrimidin-5-yl)-3-methyl-1,3-dihydro-2H-imidazo[4,5-c][1,5]naphthyridin-2-one |
| 185 | G | 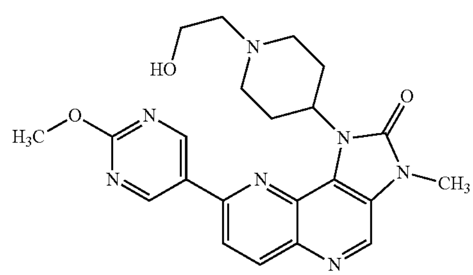 | 1-[1-(2-hydroxyethyl)piperidin-4-yl]-8-(2-methoxypyrimidin-5-yl)-3-methyl-1,3-dihydro-2H-imidazo[4,5-c][1,5]naphthyridin-2-one |
| 187 | E | 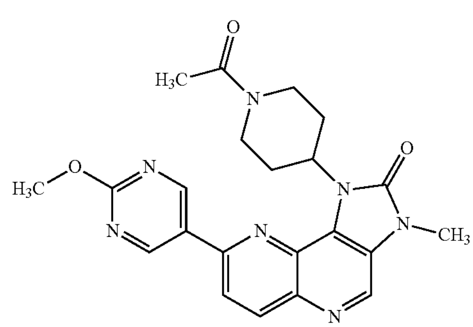 | 1-(1-acetylpiperidin-4-yl)-8-(2-methoxypyrimidin-5-yl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 188 | B | 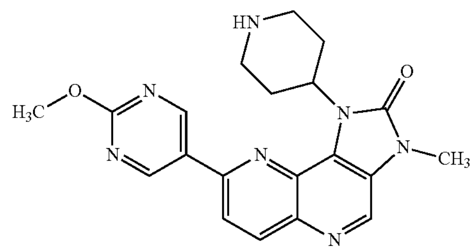 | 8-(2-methoxypyrimidin-5-yl)-3-methyl-1-piperidin-4-yl-1,3-dihydro-2H-imidazo[4,5-c][1,5]naphthyridin-2-one |
| 191 | B | 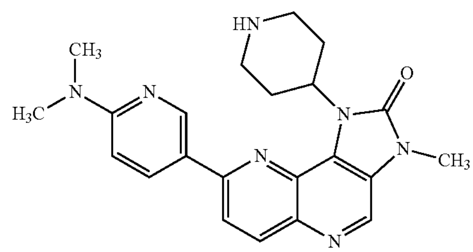 | 8-[6-(dimethylamino)pyridin-3-yl]-3-methyl-1-piperidin-4-yl-1,3-dihydro-2H-imidazo[4,5-c][1,5]naphthyridin-2-one |
| 192 | K | 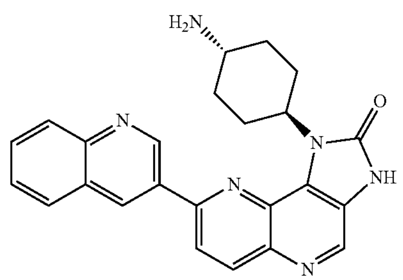 [SMILES: N[C@H]1CC[C@H](n2c(=O)[nH]c3cnc4ccc(-c5cnc6ccccc6c5)nc4c32)CC1] | 1-(trans-4-aminocyclohexyl)-8-quinolin-3-yl-1,3-dihydro-2H-imidazo[4,5-c][1,5]naphthyridin-2-one |
| 195 | E | 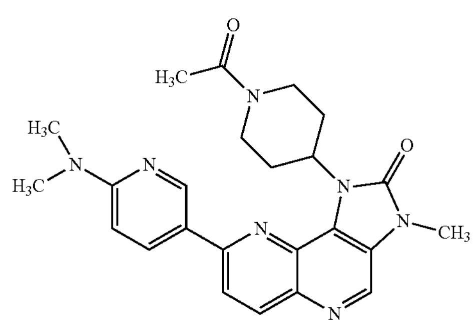 | 1-(1-acetylpiperidin-4-yl)-8-[6-(dimethylamino)pyridin-3-yl]-3-methyl-1,3-dihydro-2H-imidazo[4,5-c][1,5]naphthyridin-2-one |
| 196 | H | 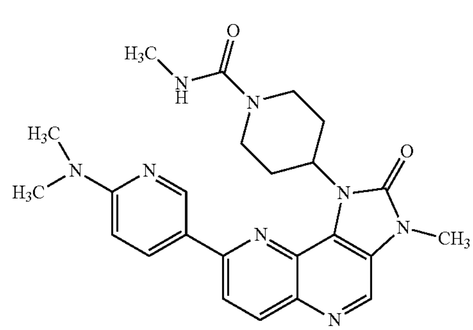 | 4-{8-[6-(dimethylamino)pyridin-3-yl]-3-methyl-2-oxo-2,3-dihydro-1H-imidazo[4,5-c][1,5]naphthyridin-1-yl}-N-methylpiperidine-1-carboxamide |

TABLE 1-continued

| Ex. No. | Synthetic Method | Structure | Compound Name |
|---|---|---|---|
| 197 | I | 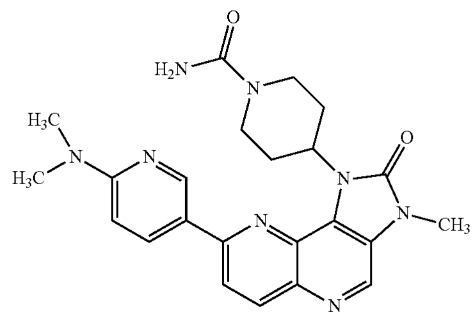 | 4-{8-[6-(dimethylamino)pyridin-3-yl]-3-methyl-2-oxo-2,3-dihydro-1H-imidazo[4,5-c][1,5]naphthyridin-1-yl}piperidine-1-carboxamide |
| 198 | G | 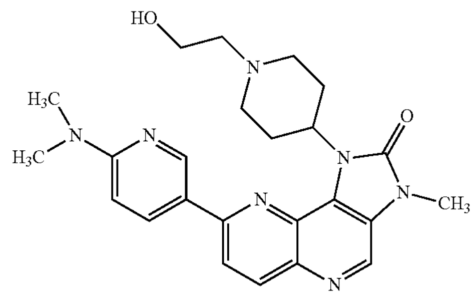 | 8-[6-(dimethylamino)pyridin-3-yl]-1-[1-(2-hydroxyethyl)piperidin-4-yl]-3-methyl-1,3-dihydro-2H-imidazo[4,5-c][1,5]naphthyridin-2-one |
| 199 | J | 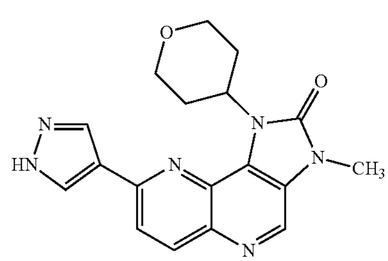 [SMILES: Cn1c(=O)n(C2CCOCC2)c2c3nc(-c4cn[nH]c4)ccc3ncc21] | 3-methyl-8-(1H-pyrazol-4-yl)-1-(tetrahydro-2H-pyran-4-yl)-1,3-dihydro-2H-imidazo[4,5-c][1,5]naphthyridin-2-one |
| 200 | J | 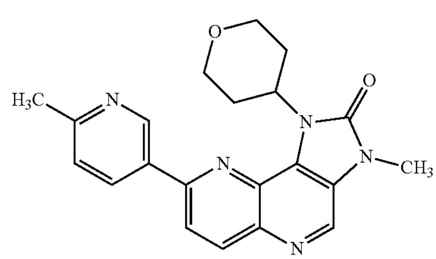 | 3-methyl-8-(6-methylpyridin-3-yl)-1-(tetrahydro-2H-pyran-4-yl)-1,3-dihydro-2H-imidazo[4,5-c][1,5]naphthyridin-2-one |
| 201 | J | 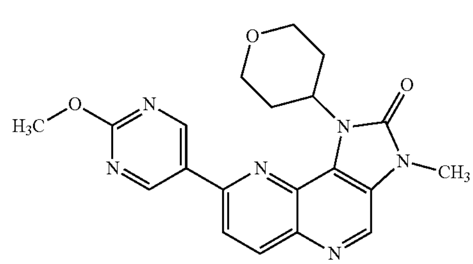 | 8-(2-methoxypyrimidin-5-yl)-3-methyl-1-(tetrahydro-2H-pyran-4-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 202 | J | 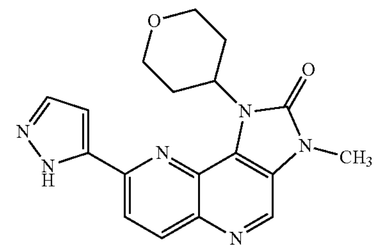 [SMILES: Cn1c(=O)n(C2CCOCC2)c2c3nc(-c4ccn[nH]4)ccc3ncc21] | 3-methyl-8-(1H-pyrazol-5-yl)-1-(tetrahydro-2H-pyran-4-yl)-1,3-dihydro-2H-imidazo[4,5-c][1,5]naphthyridin-2-one |
| 203 | J | 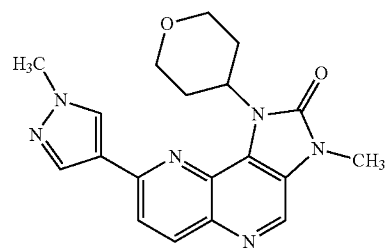 [SMILES: Cn1cc(-c2ccc3ncc4c(c3n2)n(C2CCOCC2)c(=O)n4C)cn1] | 3-methyl-8-(1-methyl-1H-pyrazol-4-yl)-1-(tetrahydro-2H-pyran-4-yl)-1,3-dihydro-2H-imidazo[4,5-c][1,5]naphthyridin-2-one |
| 204 | J | 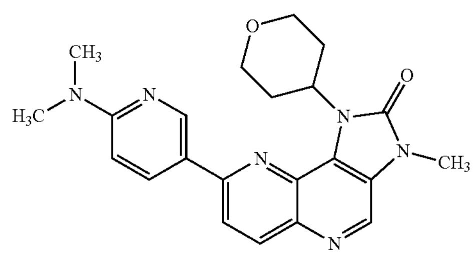 | 8-[6-(dimethylamino)pyridin-3-yl]-3-methyl-1-(tetrahydro-2H-pyran-4-yl)-1,3-dihydro-2H-imidazo[4,5-c][1,5]naphthyridin-2-one |
| 205 | F | 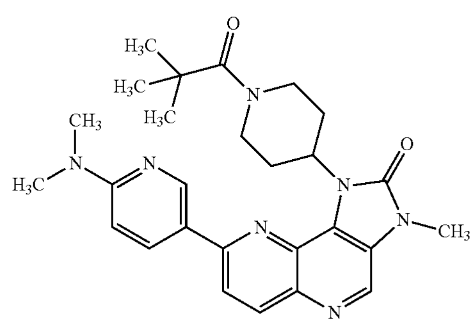 | 8-[6-(dimethylamino)pyridin-3-yl]-1-[1-(2,2-dimethylpropanoyl)piperidin-4-yl]-3-methyl-1,3-dihydro-2H-imidazo[4,5-c][1,5]naphthyridin-2-one |
| 206 | G | 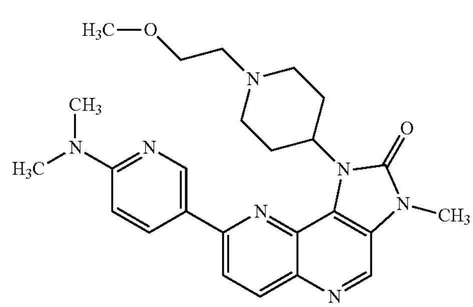 | 8-[6-(dimethylamino)pyridin-3-yl]-1-[1-(2-methoxyethyl)piperidin-4-yl]-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 207 | D | 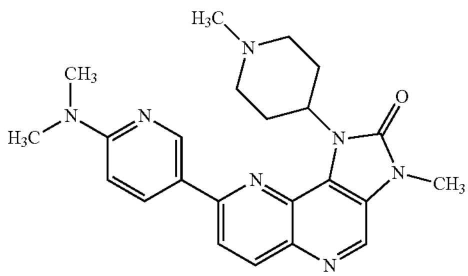 | 8-[6-(dimethylamino)pyridin-3-yl]-3-methyl-1-(1-methylpiperidin-4-yl)-1,3-dihydro-2H-imidazo[4,5-c][1,5]naphthyridin-2-one |
| 208 | J | 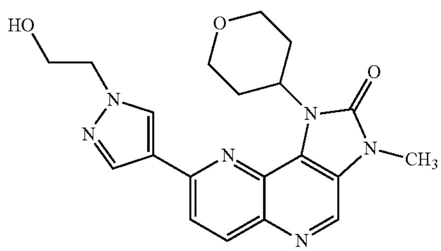 [SMILES: Cn1c(=O)n(C2CCOCC2)c2c3nc(-c4cnn(CCO)c4)ccc3ncc21] | 8-[1-(2-hydroxyethyl)-1H-pyrazol-4-yl]-3-methyl-1-(tetrahydro-2H-pyran-4-yl)-1,3-dihydro-2H-imidazo[4,5-c][1,5]naphthyridin-2-one |
| 209 | F | 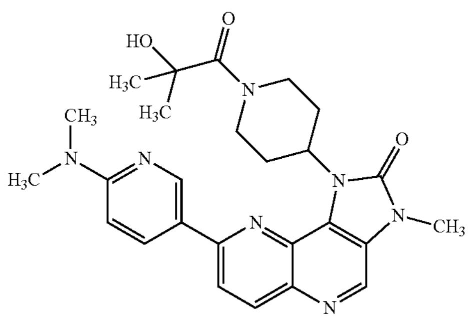 | 8-[6-(dimethylamino)pyridin-3-yl]-1-[1-(2-hydroxy-2-methylpropanoyl)piperidin-4-yl]-3-methyl-1,3-dihydro-2H-imidazo[4,5-c][1,5]naphthyridin-2-one |
| 210 | J | 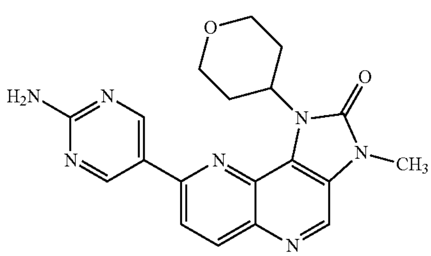 [SMILES: Cn1c(=O)n(C2CCOCC2)c2c3nc(-c4cnc(N)nc4)ccc3ncc21] | 8-(2-aminopyrimidin-5-yl)-3-methyl-1-(tetrahydro-2H-pyran-4-yl)-1,3-dihydro-2H-imidazo[4,5-c][1,5]naphthyridin-2-one |
| 211 | G | 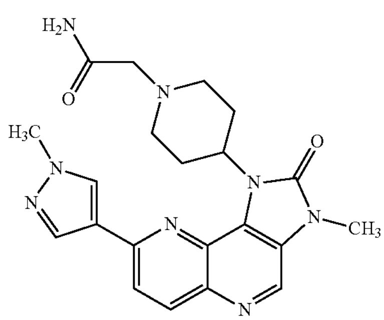 [SMILES: Cn1cc(-c2ccc3ncc4c(c3n2)n(C2CCN(CC(N)=O)CC2)c(=O)n4C)cn1] | 2-{4-[3-methyl-8-(1-methyl-1H-pyrazol-4-yl)-2-oxo-2,3-dihydro-1H-imidazo[4,5-c][1,5]naphthyridin-1-yl]piperidin-1-yl}acetamide |

TABLE 1-continued

| Ex. No. | Synthetic Method | Structure | Compound Name |
|---|---|---|---|
| 212 | G | 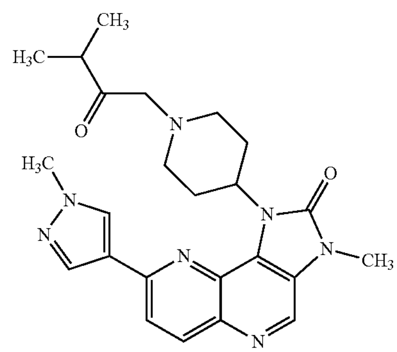 [SMILES: CC(C)C(=O)CN1CCC(n2c(=O)n(C)c3cnc4ccc(-c5cnn(C)c5)nc4c32)CC1] | N,N-dimethyl-2-{4-[3-methyl-8-(1-methyl-1H-pyrazol-4-yl)-2-oxo-2,3-dihydro-1H-imidazo[4,5-c][1,5]naphthyridin-1-yl]piperidin-1-yl}acetamide |
| 213 | F | 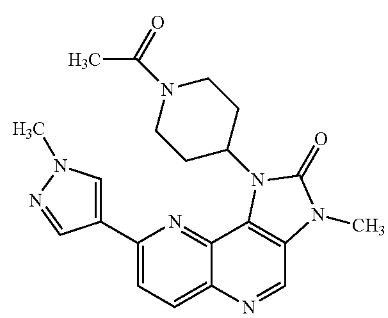 [SMILES: CC(=O)N1CCC(n2c(=O)n(C)c3cnc4ccc(-c5cnn(C)c5)nc4c32)CC1] | 1-(1-acetylpiperidin-4-yl)-3-methyl-8-(1-methyl-1H-pyrazol-4-yl)-1,3-dihydro-2H-imidazo[4,5-c][1,5]naphthyridin-2-one |
| 214 | F | 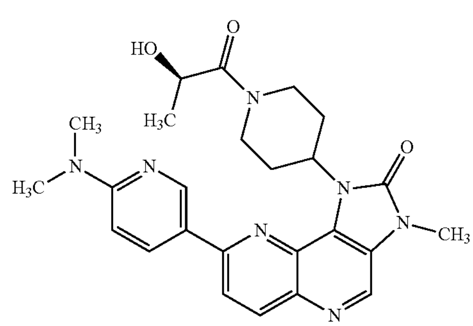 | 8-[6-(dimethylamino)pyridin-3-yl]-1-{1-[(2R)-2-hydroxypropanoyl]piperidin-4-yl}-3-methyl-1,3-dihydro-2H-imidazo[4,5-c][1,5]naphthyridin-2-one |
| 215 | F | 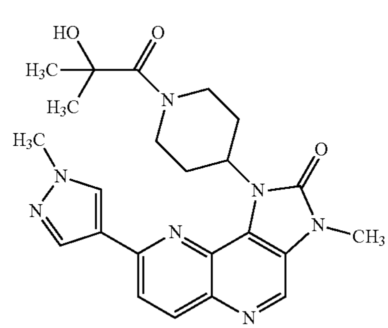 [SMILES: Cn1cc(-c2ccc3ncc4c(c3n2)n(C2CCN(C(=O)C(C)(C)O)CC2)c(=O)n4C)cn1] | 1-[1-(2-hydroxy-2-methylpropanoyl)piperidin-4-yl]-3-methyl-8-(1-methyl-1H-pyrazol-4-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 216 | F | 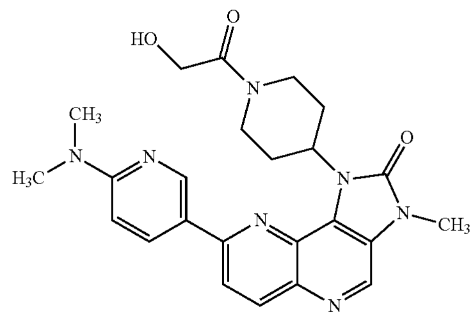 | 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one |
| 217 | H | 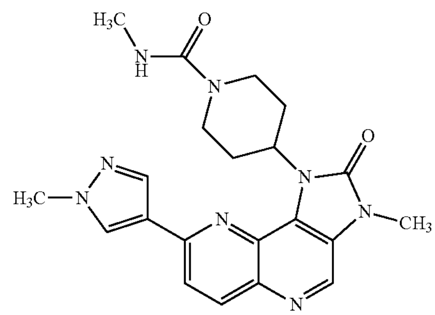 | N-methyl-4-[3-methyl-8-(1-methyl-1H-pyrazol-4-yl)-2-oxo-2,3-dihydro-1H-imidazo[4,5-c][1,5]naphthyridin-1-yl]piperidine-1-carboxamide |
| 218 | J | 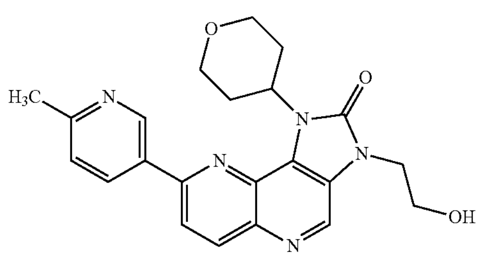 [SMILES: Cc1ccc(-c2ccc3ncc4c(c3n2)n(C2CCOCC2)c(=O)n4CCO)cn1] | 3-(2-hydroxyethyl)-8-(6-methylpyridin-3-yl)-1-(tetrahydro-2H-pyran-4-yl)-1,3-dihydro-2H-imidazo[4,5-c][1,5]naphthyridin-2-one |
| 219 | J | 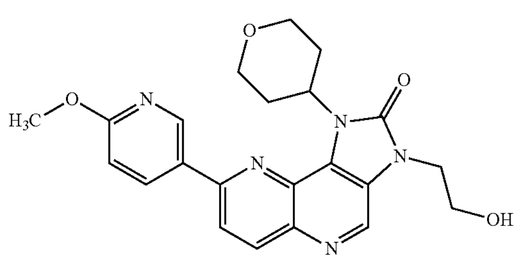 [SMILES: COc1ccc(-c2ccc3ncc4c(c3n2)n(C2CCOCC2)c(=O)n4CCO)cn1] | 3-(2-hydroxyethyl)-8-(6-methoxypyridin-3-yl)-1-(tetrahydro-2H-pyran-4-yl)-1,3-dihydro-2H-imidazo[4,5-c][1,5]naphthyridin-2-one |
| 220 | J | 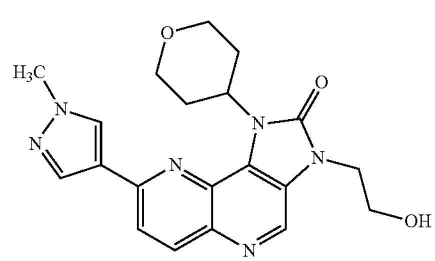 [SMILES: Cn1cc(-c2ccc3ncc4c(c3n2)n(C2CCOCC2)c(=O)n4CCO)cn1] | 3-(2-hydroxyethyl)-8-(1-methyl-1H-pyrazol-4-yl)-1-(tetrahydro-2H-pyran-4-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 221 | J | 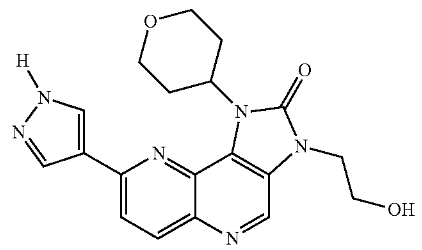 [SMILES: O=c1n(CCO)c2cnc3ccc(-c4cn[nH]c4)nc3c2n1C1CCOCC1] | 3-(2-hydroxyethyl)-8-(1H-pyrazol-4-yl)-1-(tetrahydro-2H-pyran-4-yl)-1,3-dihydro-2H-imidazo[4,5-c][1,5]naphthyridin-2-one |
| 222 | J | 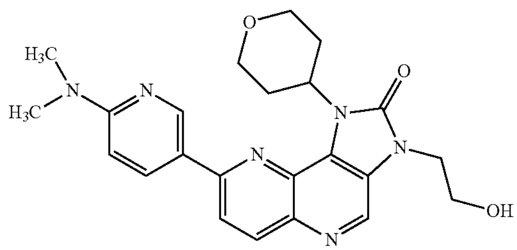 [SMILES: CN(C)c1ccc(-c2ccc3ncc4c(c3n2)n(C2CCOCC2)c(=O)n4CCO)cn1] | 8-[6-(dimethylamino)pyridin-3-yl]-3-(2-hydroxyethyl)-1-(tetrahydro-2H-pyran-4-yl)-1,3-dihydro-2H-imidazo[4,5-c][1,5]naphthyridin-2-one |
| 223 | J | 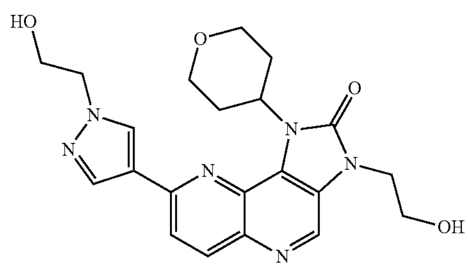 [SMILES: O=c1n(CCO)c2cnc3ccc(-c4cnn(CCO)c4)nc3c2n1C1CCOCC1] | 3-(2-hydroxyethyl)-8-[1-(2-hydroxyethyl)-1H-pyrazol-4-yl]-1-(tetrahydro-2H-pyran-4-yl)-1,3-dihydro-2H-imidazo[4,5-c][1,5]naphthyridin-2-one |
| 224 | J | 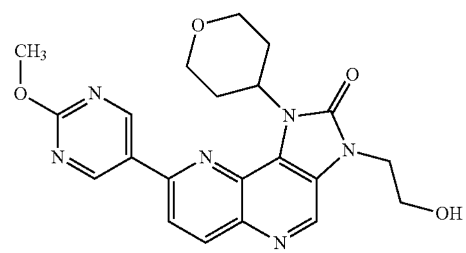 [SMILES: COc1ncc(-c2ccc3ncc4c(c3n2)n(C2CCOCC2)c(=O)n4CCO)cn1] | 3-(2-hydroxyethyl)-8-(2-methoxypyrimidin-5-yl)-1-(tetrahydro-2H-pyran-4-yl)-1,3-dihydro-2H-imidazo[4,5-c][1,5]naphthyridin-2-one |
| 225 | J | 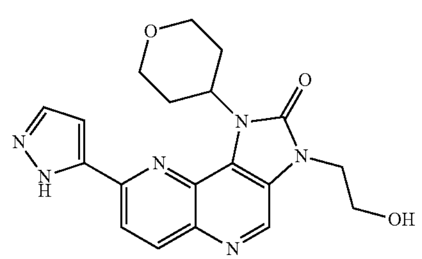 [SMILES: O=c1n(CCO)c2cnc3ccc(-c4ccn[nH]4)nc3c2n1C1CCOCC1] | 3-(2-hydroxyethyl)-8-(1H-pyrazol-5-yl)-1-(tetrahydro-2H-pyran-4-yl)-1,3-dihydro-2H-imidazo[4,5-c][1,5]naphthyridin-2-one |
| 226 | B | 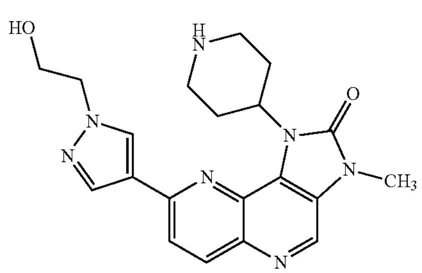 [SMILES: Cn1c(=O)n(C2CCNCC2)c2c3nc(-c4cnn(CCO)c4)ccc3ncc21] | 8-[1-(2-hydroxyethyl)-1H-pyrazol-4-yl]-3-methyl-1-piperidin-4-yl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 227 | C | 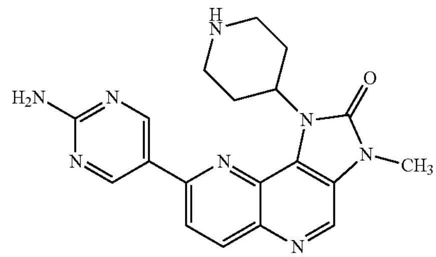 [SMILES: Cn1c(=O)n(C2CCNCC2)c2c3nc(-c4cnc(N)nc4)ccc3ncc21] | 8-(2-aminopyrimidin-5-yl)-3-methyl-1-piperidin-4-yl-1,3-dihydro-2H-imidazo[4,5-c][1,5]naphthyridin-2-one |
| 228 | F | 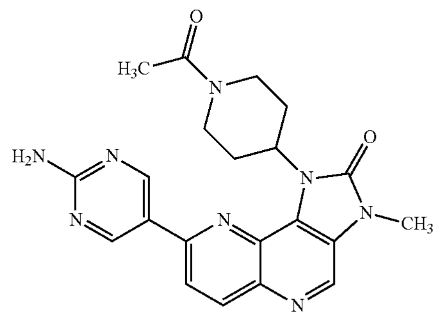 | 1-(1-acetylpiperidin-4-yl)-8-(2-aminopyrimidin-5-yl)-3-methyl-1,3-dihydro-2H-imidazo[4,5-c][1,5]naphthyridin-2-one |
| 229 | J | 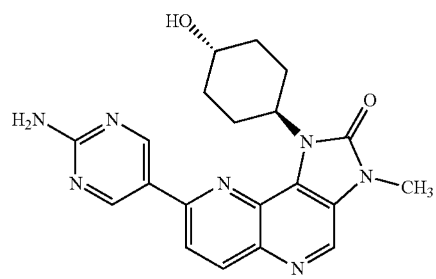 | 8-(2-aminopyrimidin-5-yl)-1-(trans-4-hydroxycyclohexyl)-3-methyl-1,3-dihydro-2H-imidazo[4,5-c][1,5]naphthyridin-2-one |
| 230 | F | 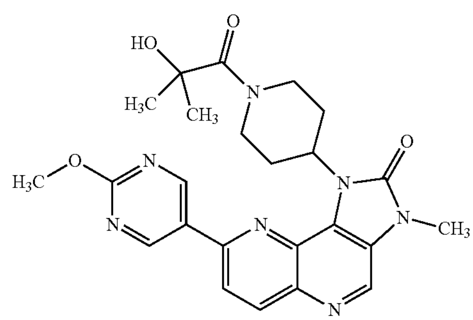 | 1-[1-(2-hydroxy-2-methylpropanoyl)piperidin-4-yl]-8-(2-methoxypyrimidin-5-yl)-3-methyl-1,3-dihydro-2H-imidazo[4,5-c][1,5]naphthyridin-2-one |
| 231 | J | 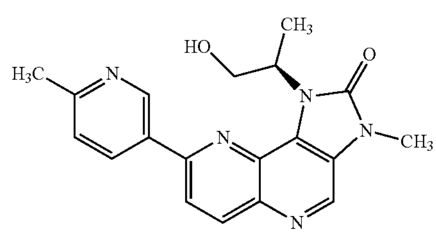 | 1-[(1R)-2-hydroxy-1-methylethyl]-3-methyl-8-(6-methylpyridin-3-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 232 | J | 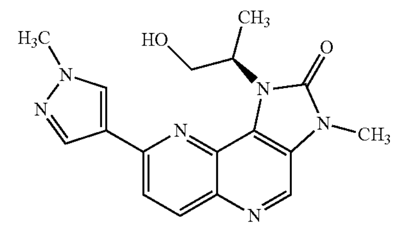 [SMILES: C[C@H](CO)n1c(=O)n(C)c2cnc3ccc(-c4cnn(C)c4)nc3c21] | 1-[(1R)-2-hydroxy-1-methylethyl]-3-methyl-8-(1-methyl-1H-pyrazol-4-yl)-1,3-dihydro-2H-imidazo[4,5-c][1,5]naphthyridin-2-one |
| 233 | J | 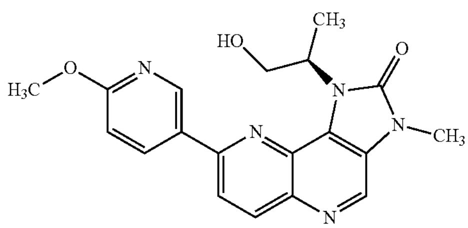 | 1-[(1R)-2-hydroxy-1-methylethyl]-8-(6-methoxypyridin-3-yl)-3-methyl-1,3-dihydro-2H-imidazo[4,5-c][1,5]naphthyridin-2-one |
| 234 | J | 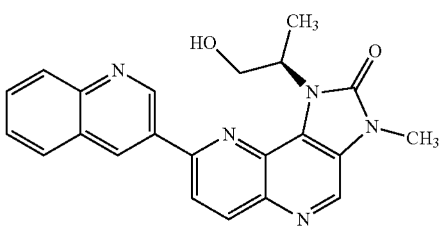 [SMILES: C[C@H](CO)n1c(=O)n(C)c2cnc3ccc(-c4cnc5ccccc5c4)nc3c21] | 1-[(1R)-2-hydroxy-1-methylethyl]-3-methyl-8-quinolin-3-yl-1,3-dihydro-2H-imidazo[4,5-c][1,5]naphthyridin-2-one |
| 235 | J | 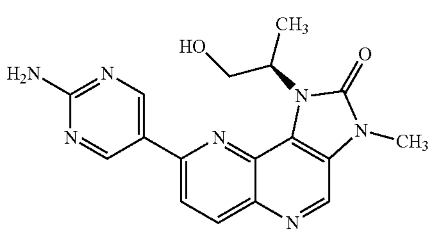 [SMILES: C[C@H](CO)n1c(=O)n(C)c2cnc3ccc(-c4cnc(N)nc4)nc3c21] | 8-(2-aminopyrimidin-5-yl)-1-[(1R)-2-hydroxy-1-methylethyl]-3-methyl-1,3-dihydro-2H-imidazo[4,5-c][1,5]naphthyridin-2-one |
| 236 | J | 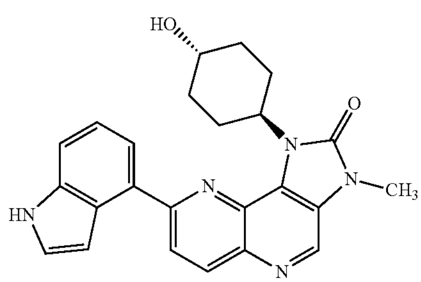 [SMILES: Cn1c(=O)n([C@H]2CC[C@H](O)CC2)c2c3nc(-c4cccc5[nH]ccc45)ccc3ncc21] | 1-(trans-4-hydroxycyclohexyl)-8-(1H-indol-4-yl)-3-methyl-1,3-dihydro-2H-imidazo[4,5-c][1,5]naphthyridin-2-one |
| 237 | J | 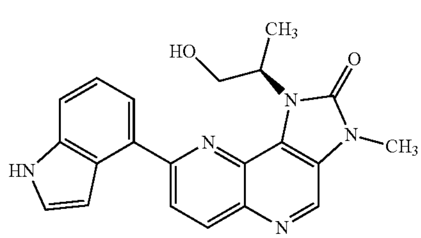 [SMILES: C[C@H](CO)n1c(=O)n(C)c2cnc3ccc(-c4cccc5[nH]ccc45)nc3c21] | 1-[(1R)-2-hydroxy-1-methylethyl]-8-(1H-indol-4-yl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 238 | J | 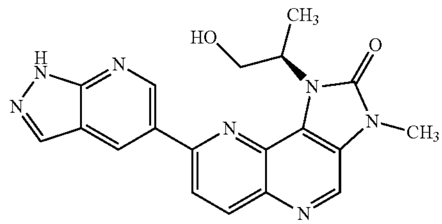 [SMILES: C[C@H](CO)n1c(=O)n(C)c2cnc3ccc(-c4cnc5[nH]ncc5c4)nc3c21] | 1-[(1R)-2-hydroxy-1-methylethyl]-3-methyl-8-(1H-pyrazolo[3,4-b]pyridin-5-yl)-1,3-dihydro-2H-imidazo[4,5-c][1,5]naphthyridin-2-one |
| 239 | J | 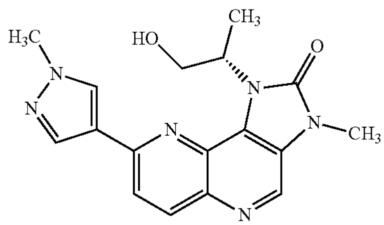 [SMILES: C[C@@H](CO)n1c(=O)n(C)c2cnc3ccc(-c4cnn(C)c4)nc3c21] | 1-[(1S)-2-hydroxy-1-methylethyl]-3-methyl-8-(1-methyl-1H-pyrazol-4-yl)-1,3-dihydro-2H-imidazo[4,5-c][1,5]naphthyridin-2-one |
| 240 | J | 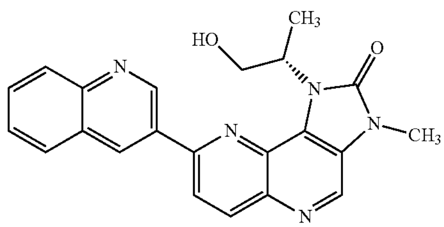 [SMILES: C[C@@H](CO)n1c(=O)n(C)c2cnc3ccc(-c4cnc5ccccc5c4)nc3c21] | 1-[(1S)-2-hydroxy-1-methylethyl]-3-methyl-8-quinolin-3-yl-1,3-dihydro-2H-imidazo[4,5-c][1,5]naphthyridin-2-one |
| 241 | J | 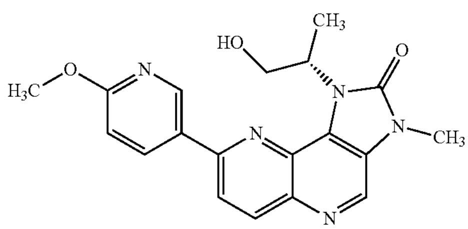 | 1-[(1S)-2-hydroxy-1-methylethyl]-8-(6-methoxypyridin-3-yl)-3-methyl-1,3-dihydro-2H-imidazo[4,5-c][1,5]naphthyridin-2-one |
| 242 | F | 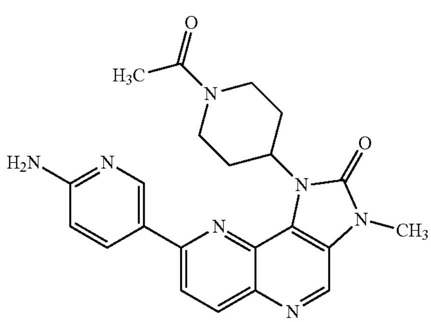 | 1-(1-acetylpiperidin-4-yl)-8-(6-aminopyridin-3-yl)-3-methyl-1,3-dihydro-2H-imidazo[4,5-c][1,5]naphthyridin-2-one |
| 243 | F | 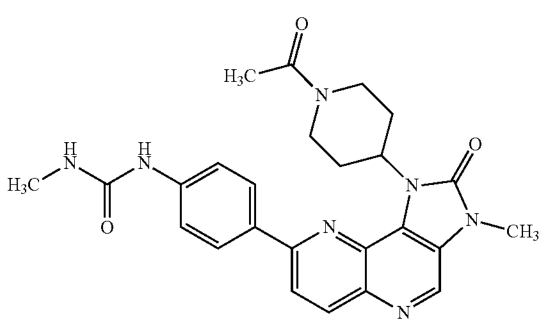 | 1-{4-[1-(1-acetylpiperidin-4-yl)-3-methyl-2-oxo-2,3-dihydro-1H-imidazo[4,5-c][1,5]naphthyridin-8-yl]phenyl}-3-methylurea |

TABLE 1-continued

| Ex. No. | Synthetic Method | Structure | Compound Name |
|---|---|---|---|
| 244 | M | 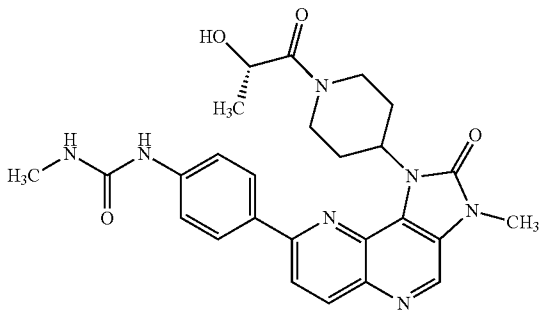 | 1-[4-(1-{1-[(2S)-2-hydroxypropanoyl]piperidin-4-yl}-3-methyl-2-oxo-2,3-dihydro-1H-imidazo[4,5-c][1,5]naphthyridin-8-yl)phenyl]-3-methylurea |
| 245 | M | 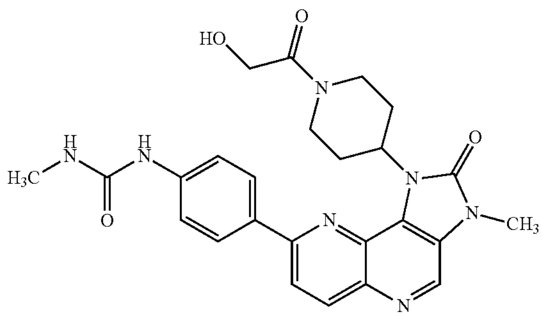 | 1-{4-[1-(1-glycoloylpiperidin-4-yl)-3-methyl-2-oxo-2,3-dihydro-1H-imidazo[4,5-c][1,5]naphthyridin-8-yl]phenyl}-3-methylurea |
| 246 | C | 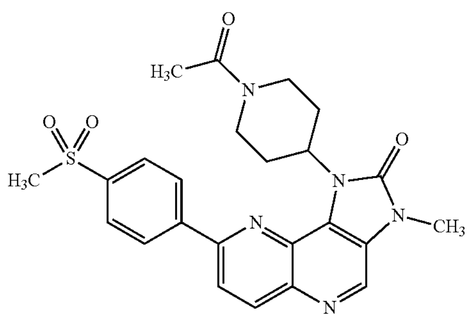 | 1-(1-acetylpiperidin-4-yl)-3-methyl-8-[4-(methylsulfonyl)phenyl]-1,3-dihydro-2H-imidazo[4,5-c][1,5]naphthyridin-2-one |
| 247 | C | 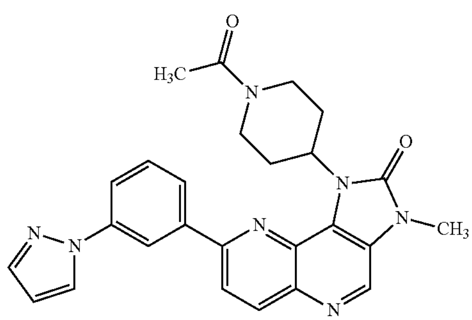 [SMILES: CC(=O)N1CCC(n2c(=O)n(C)c3cnc4ccc(-c5cccc(-n6cccn6)c5)nc4c32)CC1] | 1-(1-acetylpiperidin-4-yl)-3-methyl-8-[3-(1H-pyrazol-1-yl)phenyl]-1,3-dihydro-2H-imidazo[4,5-c][1,5]naphthyridin-2-one |
| 248 | J | 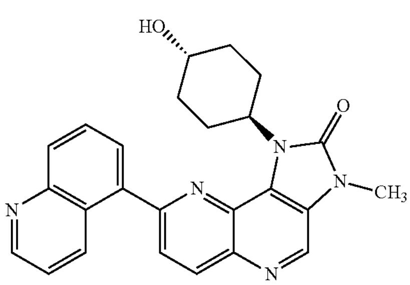 [SMILES: Cn1c(=O)n([C@H]2CC[C@H](O)CC2)c2c3nc(-c4cccc5ncccc45)ccc3ncc21] | 1-(trans-4-hydroxycyclohexyl)-3-methyl-8-quinolin-5-yl-1,3-dihydro-2H-imidazo[4,5-c][1,5]naphthyridin-2-one |

| Ex. No. | Synthetic Method | Structure | Compound Name |
|---|---|---|---|
| 249 | C | 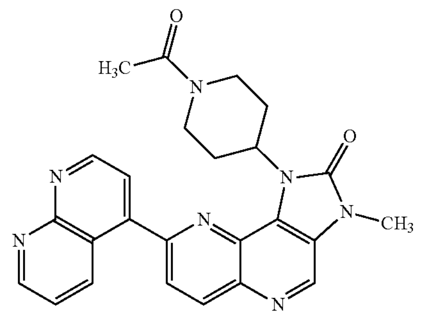 [SMILES: CC(=O)N1CCC(n2c(=O)n(C)c3cnc4ccc(-c5ccnc6ncccc56)nc4c32)CC1] | 1-(1-acetylpiperidin-4-yl)-3-methyl-8-quinolin-5-yl-1,3-dihydro-2H-imidazo[4,5-c][1,5]naphthyridin-2-one |
| 250 | J | 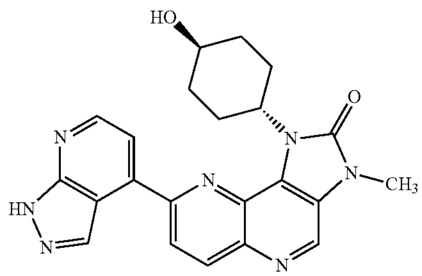 [SMILES: Cn1c(=O)n([C@H]2CC[C@H](O)CC2)c2c3nc(-c4ccnc5[nH]ncc45)ccc3ncc21] | 1-(trans-4-hydroxycyclohexyl)-3-methyl-8-(1H-pyrazolo[3,4-b]pyridin-4-yl)-1,3-dihydro-2H-imidazo[4,5-c][1,5]naphthyridin-2-one |
| 251 | C | 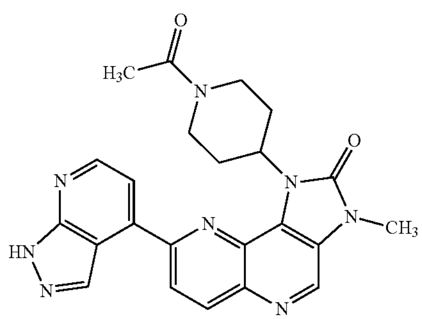 [SMILES: CC(=O)N1CCC(n2c(=O)n(C)c3cnc4ccc(-c5ccnc6[nH]ncc56)nc4c32)CC1] | 1-(1-acetylpiperidin-4-yl)-3-methyl-8-(1H-pyrazolo[3,4-b]pyridin-4-yl)-1,3-dihydro-2H-imidazo[4,5-c][1,5]naphthyridin-2-one |
| 252 | M | 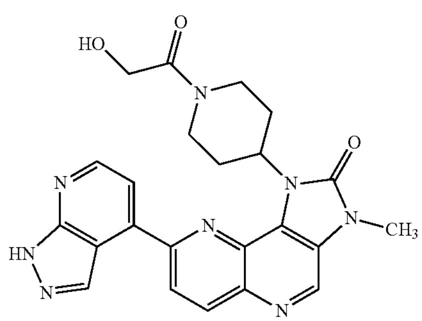 [SMILES: Cn1c(=O)n(C2CCN(C(=O)CO)CC2)c2c3nc(-c4ccnc5[nH]ncc45)ccc3ncc21] | 1-(1-glycoloylpiperidin-4-yl)-3-methyl-8-(1H-pyrazolo[3,4-b]pyridin-4-yl)-1,3-dihydro-2H-imidazo[4,5-c][1,5]naphthyridin-2-one |
| 253 | M | 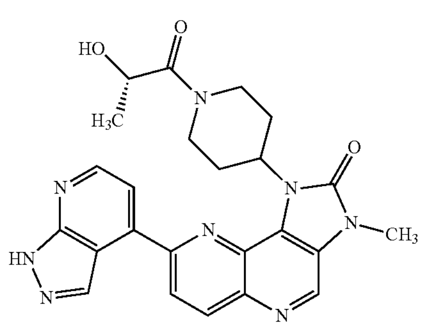 [SMILES: C[C@H](O)C(=O)N1CCC(n2c(=O)n(C)c3cnc4ccc(-c5ccnc6[nH]ncc56)nc4c32)CC1] | 1-{1-[(2S)-2-hydroxypropanoyl]piperidin-4-yl}-3-methyl-8-(1H-pyrazolo[3,4-b]pyridin-4-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 254 | C | 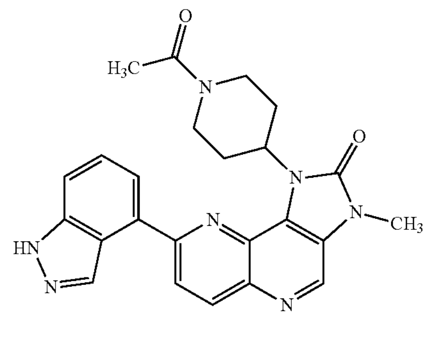 [SMILES: CC(=O)N1CCC(n2c(=O)n(C)c3cnc4ccc(-c5cccc6[nH]ncc56)nc4c32)CC1] | 1-(1-acetylpiperidin-4-yl)-8-(1H-indazol-4-yl)-3-methyl-1,3-dihydro-2H-imidazo[4,5-c][1,5]naphthyridin-2-one |
| 255 | M | 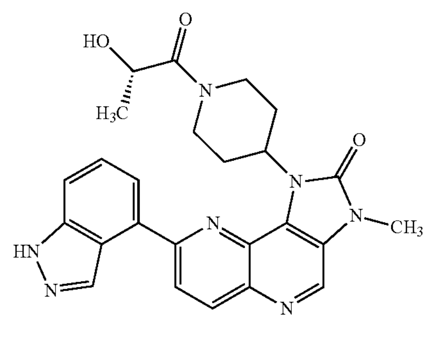 [SMILES: C[C@H](O)C(=O)N1CCC(n2c(=O)n(C)c3cnc4ccc(-c5cccc6[nH]ncc56)nc4c32)CC1] | 1-{1-[(2S)-2-hydroxypropanoyl]piperidin-4-yl}-8-(1H-indazol-4-yl)-3-methyl-1,3-dihydro-2H-imidazo[4,5-c][1,5]naphthyridin-2-one |
| 256 | M | 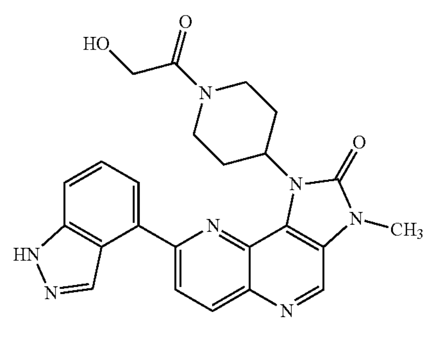 [SMILES: Cn1c(=O)n(C2CCN(C(=O)CO)CC2)c2c3nc(-c4cccc5[nH]ncc45)ccc3ncc21] | 1-(1-glycoloylpiperidin-4-yl)-8-(1H-indazol-4-yl)-3-methyl-1,3-dihydro-2H-imidazo[4,5-c][1,5]naphthyridin-2-one |
| 257 | M | 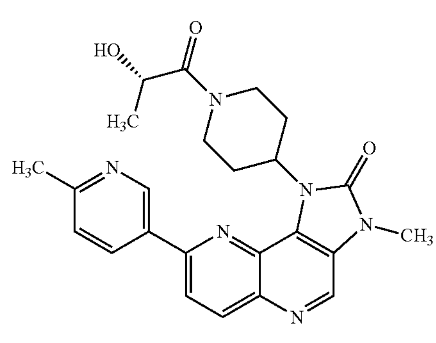 | 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 258 | F | 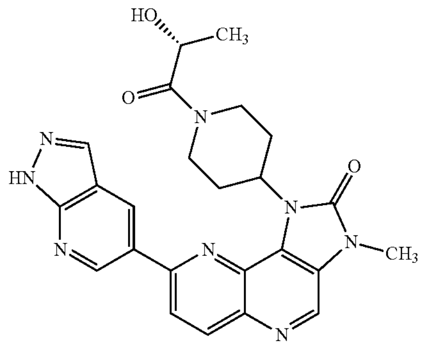 [SMILES: C[C@@H](O)C(=O)N1CCC(n2c(=O)n(C)c3cnc4ccc(-c5cnc6[nH]ncc6c5)nc4c32)CC1] | 1-{1-[(2R)-2-hydroxypropanoyl]piperidin-4-yl}-3-methyl-8-(1H-pyrazolo[3,4-b]pyridin-5-yl)-1,3-dihydro-2H-imidazo[4,5-c][1,5]naphthyridin-2-one |
| 259 | F | 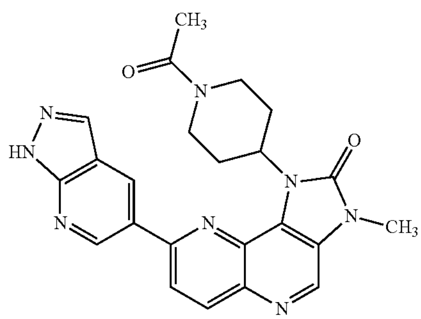 [SMILES: CC(=O)N1CCC(n2c(=O)n(C)c3cnc4ccc(-c5cnc6[nH]ncc6c5)nc4c32)CC1] | 1-(1-acetylpiperidin-4-yl)-3-methyl-8-(1H-pyrazolo[3,4-b]pyridin-5-yl)-1,3-dihydro-2H-imidazo[4,5-c][1,5]naphthyridin-2-one |
| 260 | F | 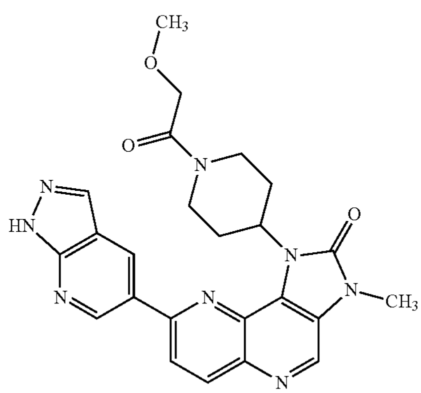 [SMILES: COCC(=O)N1CCC(n2c(=O)n(C)c3cnc4ccc(-c5cnc6[nH]ncc6c5)nc4c32)CC1] | 1-[1-(methoxyacetyl)piperidin-4-yl]-3-methyl-8-(1H-pyrazolo[3,4-b]pyridin-5-yl)-1,3-dihydro-2H-imidazo[4,5-c][1,5]naphthyridin-2-one |
| 261 | F | 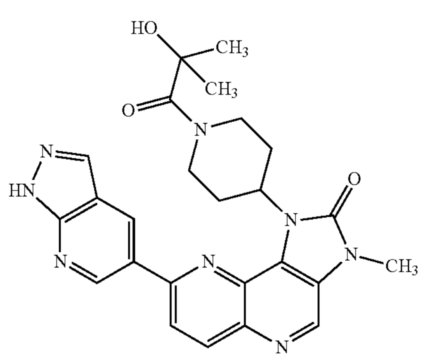 [SMILES: Cn1c(=O)n(C2CCN(C(=O)C(C)(C)O)CC2)c2c3nc(-c4cnc5[nH]ncc5c4)ccc3ncc21] | 1-[1-(2-hydroxy-2-methylpropanoyl)piperidin-4-yl]-3-methyl-8-(1H-pyrazolo[3,4-b]pyridin-5-yl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 262 | F | 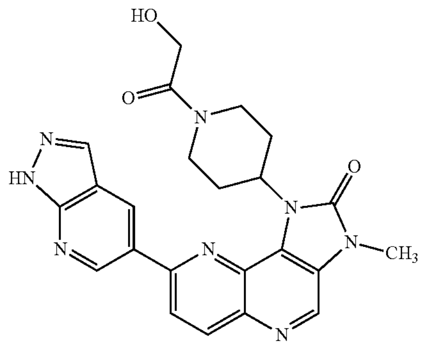 [SMILES: Cn1c(=O)n(C2CCN(C(=O)CO)CC2)c2c3nc(-c4cnc5[nH]ncc5c4)ccc3ncc21] | 1-(1-glycoloylpiperidin-4-yl)-3-methyl-8-(1H-pyrazolo[3,4-b]pyridin-5-yl)-1,3-dihydro-2H-imidazo[4,5-c][1,5]naphthyridin-2-one |
| 263 | D | 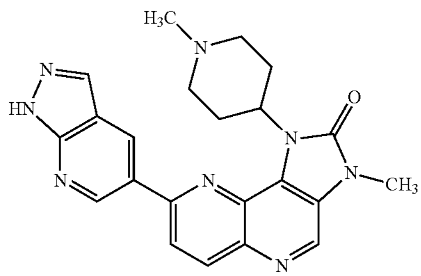 [SMILES: CN1CCC(n2c(=O)n(C)c3cnc4ccc(-c5cnc6[nH]ncc6c5)nc4c32)CC1] | 3-methyl-1-(1-methylpiperidin-4-yl)-8-(1H-pyrazolo[3,4-b]pyridin-5-yl)-1,3-dihydro-2H-imidazo[4,5-c][1,5]naphthyridin-2-one |
| 264 | C | 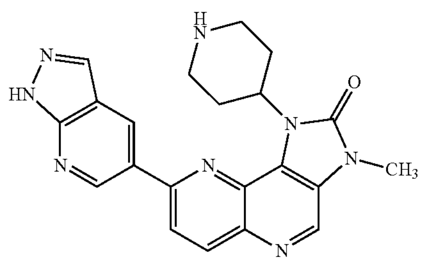 [SMILES: Cn1c(=O)n(C2CCNCC2)c2c3nc(-c4cnc5[nH]ncc5c4)ccc3ncc21] | 3-methyl-1-piperidin-4-yl-8-(1H-pyrazolo[3,4-b]pyridin-5-yl)-1,3-dihydro-2H-imidazo[4,5-c][1,5]naphthyridin-2-one |
| 265 | J | 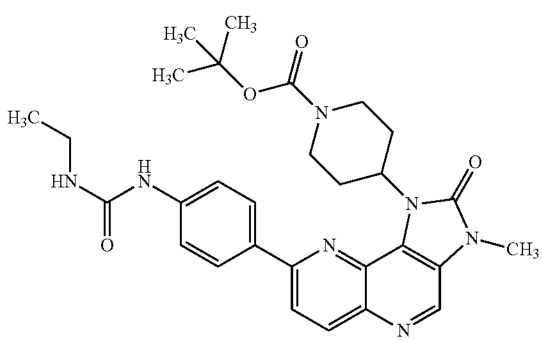 [SMILES: CCNC(=O)Nc1ccc(-c2ccc3ncc4c(c3n2)n(C2CCN(C(=O)OC(C)(C)C)CC2)c(=O)n4C)cc1] | tert-butyl 4-(8-{4-[(ethylcarbamoyl)amino]phenyl}-3-methyl-2-oxo-2,3-dihydro-1H-imidazo[4,5-c][1,5]naphthyridin-1-yl)piperidine-1-carboxylate |
| 266 | J | 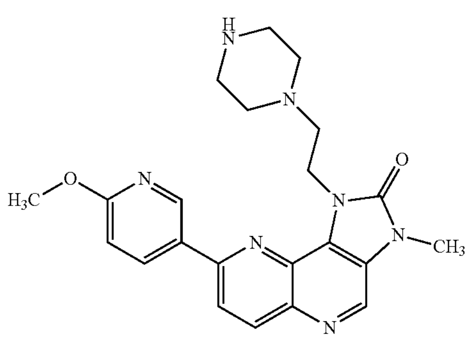 | 8-(6-methoxypyridin-3-yl)-3-methyl-1-(2-piperazin-1-ylethyl)-1,3-dihydro-2H-imidazo[4,5-c][1,5]naphthyridin-2-one |

TABLE 1-continued

| Ex. No. | Synthetic Method | Structure | Compound Name |
|---|---|---|---|
| 267 | J | 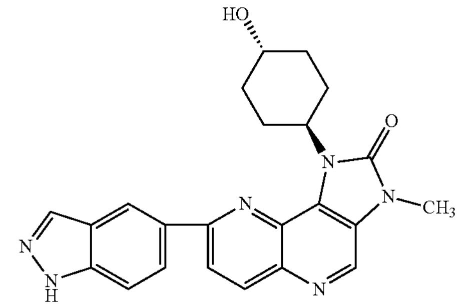 [SMILES: Cn1c(=O)n([C@H]2CC[C@H](O)CC2)c2c3nc(-c4ccc5[nH]ncc5c4)ccc3ncc21] | 1-(trans-4-hydroxycyclohexyl)-8-(1H-indazol-5-yl)-3-methyl-1,3-dihydro-2H-imidazo[4,5-c][1,5]naphthyridin-2-one |
| 268 | J | 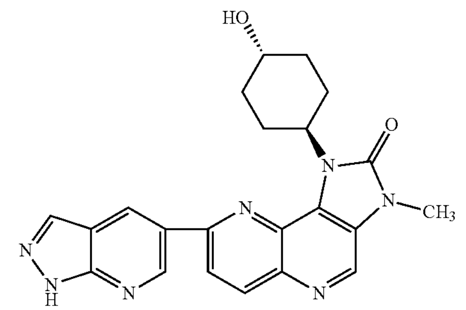 [SMILES: Cn1c(=O)n([C@H]2CC[C@H](O)CC2)c2c3nc(-c4cnc5[nH]ncc5c4)ccc3ncc21] | 1-(trans-4-hydroxycyclohexyl)-3-methyl-8-(1H-pyrazolo[3,4-b]pyridin-5-yl)-1,3-dihydro-2H-imidazo[4,5-c][1,5]naphthyridin-2-one |
| 269 | G | 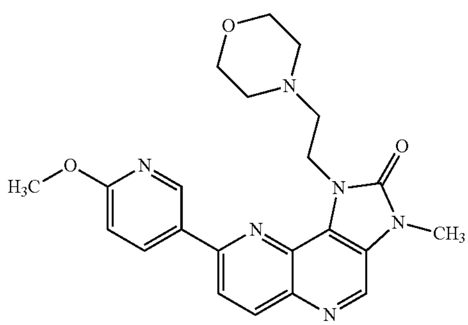 | 8-(6-methoxypyridin-3-yl)-3-methyl-1-(2-morpholin-4-ylethyl)-1,3-dihydro-2H-imidazo[4,5-c][1,5]naphthyridin-2-one |
| 270 | G | 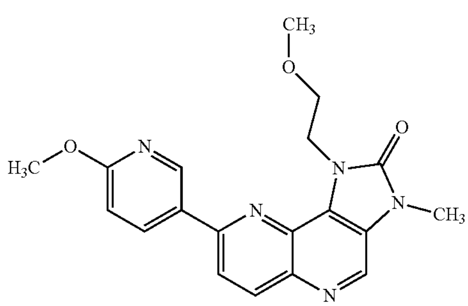 | 1-(2-methoxyethyl)-8-(6-methoxypyridin-3-yl)-3-methyl-1,3-dihydro-2H-imidazo[4,5-c][1,5]naphthyridin-2-one |
| 271 | G | 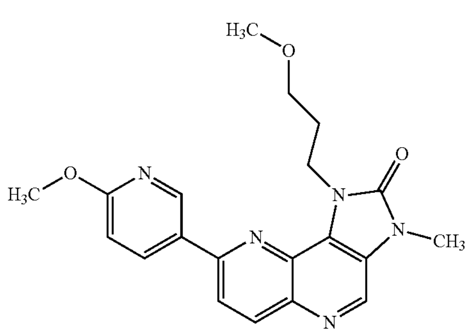 | 1-(3-methoxypropyl)-8-(6-methoxypyridin-3-yl)-3-methyl-1,3-dihydro-2H-imidazo[4,5-c][1,5]naphthyridin-2-one |

| Ex. No. | Synthetic Method | Structure | Compound Name |
|---|---|---|---|
| 272 | M | 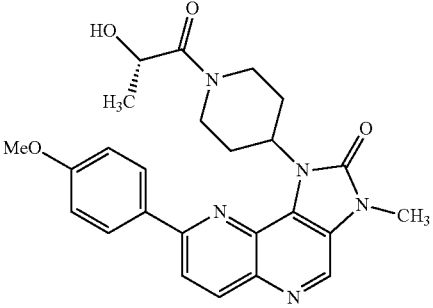 [SMILES: COc1ccc(-c2ccc3ncc4c(c3n2)n(C2CCN(C(=O)[C@H](C)O)CC2)c(=O)n4C)cc1] | 1-{1-[(2S)-2-hydroxypropanoyl]piperidin-4-yl}-8-(4-methoxyphenyl)-3-methyl-1,3-dihydro-2H-imidazo[4,5-c][1,5]naphthyridin-2-one |
| 273 | M | 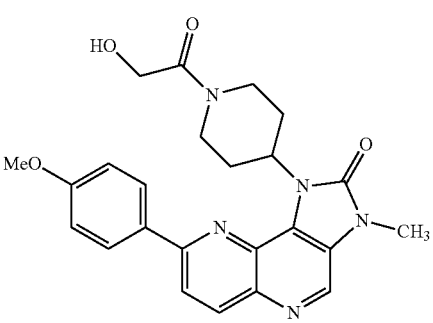 [SMILES: COc1ccc(-c2ccc3ncc4c(c3n2)n(C2CCN(C(=O)CO)CC2)c(=O)n4C)cc1] | 1-(1-glycoloylpiperidin-4-yl)-8-(4-methoxyphenyl)-3-methyl-1,3-dihydro-2H-imidazo[4,5-c][1,5]naphthyridin-2-one |
| 274 | E | 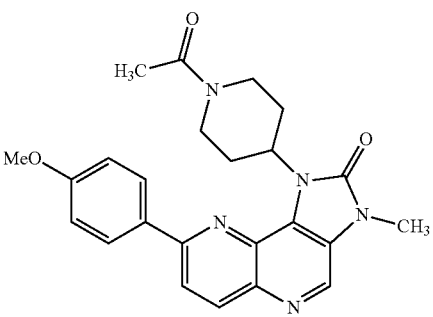 [SMILES: COc1ccc(-c2ccc3ncc4c(c3n2)n(C2CCN(C(C)=O)CC2)c(=O)n4C)cc1] | 1-(1-acetylpiperidin-4-yl)-8-(4-methoxyphenyl)-3-methyl-1,3-dihydro-2H-imidazo[4,5-c][1,5]naphthyridin-2-one |
| 275 | M | 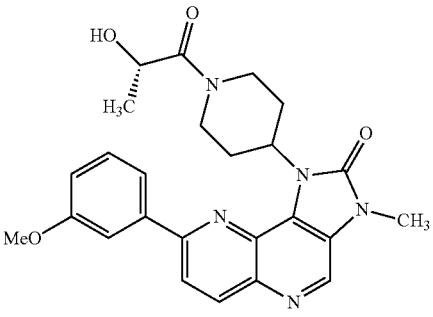 [SMILES: COc1cccc(-c2ccc3ncc4c(c3n2)n(C2CCN(C(=O)[C@H](C)O)CC2)c(=O)n4C)c1] | 1-{1-[(2S)-2-hydroxypropanoyl]piperidin-4-yl}-8-(3-methoxyphenyl)-3-methyl-1,3-dihydro-2H-imidazo[4,5-c][1,5]naphthyridin-2-one |
| 276 | M | 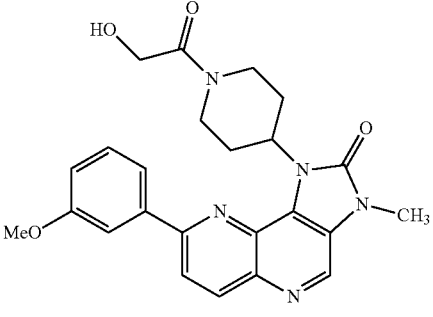 [SMILES: COc1cccc(-c2ccc3ncc4c(c3n2)n(C2CCN(C(=O)CO)CC2)c(=O)n4C)c1] | 1-(1-glycoloylpiperidin-4-yl)-8-(3-methoxyphenyl)-3-methyl-1,3-dihydro-2H-imidazo[4,5-c][1,5]naphthyridin-2-one |

TABLE 1-continued

| Ex. No. | Synthetic Method | Structure | Compound Name |
|---|---|---|---|
| 277 | E | 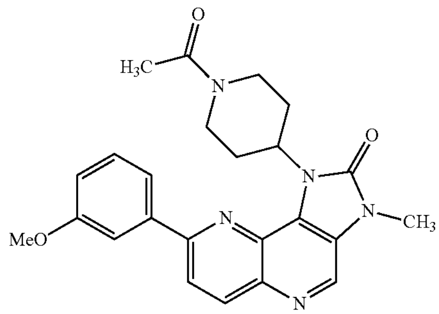 [SMILES: COc1cccc(-c2ccc3ncc4c(c3n2)n(C2CCN(C(C)=O)CC2)c(=O)n4C)c1] | 1-(1-acetylpiperidin-4-yl)-8-(3-methoxyphenyl)-3-methyl-1,3-dihydro-2H-imidazo[4,5-c][1,5]naphthyridin-2-one |
| 278 | M | 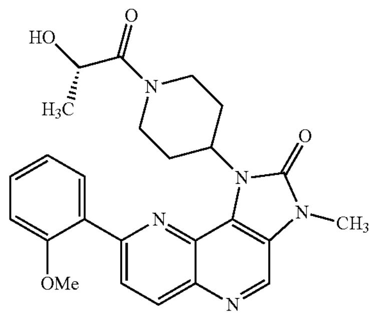 [SMILES: COc1ccccc1-c1ccc2ncc3c(c2n1)n(C1CCN(C(=O)[C@H](C)O)CC1)c(=O)n3C] | 1-{1-[(2S)-2-hydroxypropanoyl]piperidin-4-yl}-8-(2-methoxyphenyl)-3-methyl-1,3-dihydro-2H-imidazo[4,5-c][1,5]naphthyridin-2-one |
| 279 | M | 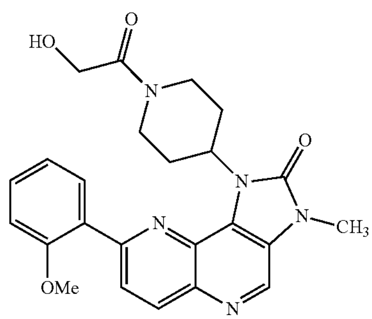 [SMILES: COc1ccccc1-c1ccc2ncc3c(c2n1)n(C1CCN(C(=O)CO)CC1)c(=O)n3C] | 1-(1-glycoloylpiperidin-4-yl)-8-(2-methoxyphenyl)-3-methyl-1,3-dihydro 2H-imidazo[4,5-c][1,5]naphthyridin-2-one |
| 280 | E | 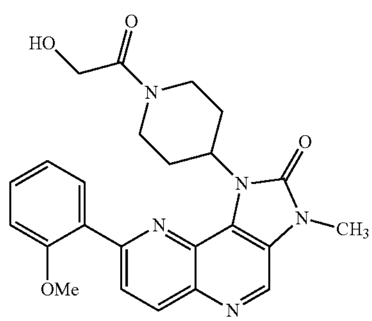 [SMILES: COc1ccccc1-c1ccc2ncc3c(c2n1)n(C1CCN(C(=O)CO)CC1)c(=O)n3C] | 1-(1-acetylpiperidin-4-yl)-8-(2-methoxyphenyl)-3-methyl-1,3-dihydro-2H-imidazo[4,5-c][1,5]naphthyridin-2-one |

Table 2 shows $^1$H NMR and LRMS m/z data for compounds listed in Table 1.

TABLE 2

| Ex. No. | LRMS m/z | $^1$H NMR |
|---|---|---|
| 103 | 437 (M + H)⁺ | (400 MHz, DMSO): δ 11.86 (s, 1H), 8.77 (s, 1H), 8.38 (m, 2H), 8.16-8.14 (d, 1H), 7.95 (m, 1H), 7.74-7.72 (d, 2H), 7.64-7.62 (d, 2H), 6.75-6.73 (d, 1H), 3.87 (s, 3H), 1.85 (s, 6H) |

TABLE 2-continued

| Ex. No. | LRMS m/z | ¹H NMR |
|---|---|---|
| 104 | 451 (M + H)⁺ | (400 MHz, DMSO): δ 9.03 (s, 1H), 8.40 (m, 2H), 8.20-8.18 (d, 1H), 7.98 (m, 1H), 7.76-7.74 (d, 2H), 7.65-7.63 (d, 2H), 6.77-6.75 (d, 1H), 3.87 (s, 3H), 3.62 (s, 3H), 1.87 (s, 6H). |
| 105 | 421 (M + H)⁺ | (400 MHz, DMSO): δ 11.88 (s, 1H), 8.81 (s, 1H), 8.70 (s, 1H), 8.40-8.40 (d, 1H), 8.25-8.22 (d, 1H), 7.90 (m, 1H), 7.74-7.72 (d, 2H), 7.65-7.63 (d, 2H), 7.21-7.19 (d, 1H), 2.47 (s, 3H), 1.86 (s, 6H). |
| 106 | 435 (M + H)⁺ | (400 MHz, DMSO): δ 9.07 (s, 1H), 8.6 (s, 1H), 8.46 (d, 1H), 8.26 (d, 1H), 7.92 (d, 1H), 7.8 (d, 2H), 7.7 (d, 2H), 7.2 (d, 1H), 3.63 (s, 3H), 2.47 (s, 3H), 1.86 (s, 6H). |
| 107 | 450.2 (M + H)⁺ | (400 MHz, DMSO): δ 11.80 (s, 1H), 8.71 (s, 1H), 8.34 (s, 1H), 8.29-8.29 (d, 1H), 8.10-8.08 (d, 1H), 7.78-7.76 (d, 1H), 7.74-7.72 (d, 2H), 7.64-7.62 (d, 2H), 6.57-6.55 (d, 1H), 3.05 (s 3H), 1.87 (s, 6H). |
| 108 | 464.1 (M + H)⁺ | (400 MHz, DMSO): δ 8.97 (s, 1H), 8.35 (s, 1H), 8.32-8.30 (d, 1H), 8.10-8.08 (d, 1H), 7.80-7.78 (d, 1H), 7.75-7.73 (d, 2H), 7.64-7.62 (d, 2H), 6.57-6.55 (d, 1H), 3.61 (s, 3 H), 3.05 (s 3H), 1.88 (s, 6H). |
| 109 | 455.2 (M + H)⁺ | (400 MHz, DMSO): δ 11.89 (s, 1H), 8.79 (s, 1H), 8.39-8.37 (d, 1H), 8.28 (s, 1H), 8.21-8.19 (d, 1H), 7.81-7.78 (d, 1H), 7.74-7.72 (d, 2H), 7.65-7.63 (d, 2H), 3.96 (s, 3H), 1.84 (s, 6H). |
| 110 | 469.4 (M + H)⁺ | (400 MHz, DMSO): δ 9.15 (s, 1H), 8.82 (s, 2H), 8.54-8.52 (d, 1H), 8.36-8.34 (d, 1H), 7.84-7.82 (d 2H), 7.73-7.71 (d, 2H), 4.02 (s, 3 H), 3.70 (s 3H), 1.96 (s, 6H). |
| 111 | 438.1 (M + H)⁺ | (400 MHz, DMSO): δ 11.88 (s, 1H), 8.81 (s, 1H), 8.74 (s, 2H), 8.43-8.41 (d, 1H), 8.24-8.22 (d, 1H), 7.75-7.73 (d, 2H), 7.65-7.63 (d, 2H), 3.93 (s 3H), 1.88 (s, 6H). |
| 112 | 451.9 (M + H)⁺ | (400 MHz, DMSO): δ 9.15 (s, 1H), 8.82 (s, 2H), 8.54-8.52 (d, 1H), 8.36-8.34 (d, 1H), 7.84-7.82 (d 2H), 7.73-7.71 (d, 2H), 4.02 (s, 3 H), 3.70 (s 3H), 1.96 (s, 6H). |
| 113 | 410.2 (M + H)⁺ | (400 MHz, DMSO): δ 11.78 (s, 1H), 8.71 (s, 1H), 8.27-8.25 (d, 1H), 7.97 (s, 1H), 7.81-7.79 (d, 1H), 7.75-7.73 (d, 2H), 7.63-7.61 (d, 2H), 7.33 (s, 1H), 3.82 (s 3H), 1.84 (s, 6H). |
| 114 | 424.0 (M + H)⁺ | (400 MHz, DMSO): δ 8.97 (s, 1H), 8.31-8.29 (d, 1H), 7.99 (s, 1H), 7.83-7.81 (d, 1H), 7.76-7.74 (d, 2H), 7.64-7.62 (d, 2H), 7.32 (s, 1H), 3.82 (s, 3H), 3.60 (s 3H), 1.85 (s, 6H). |
| 115 | 531 (M + H)⁺ | (400 MHz, DMSO-d6) δ 1.83-2.06 (m, 2 H) 2.60-2.88 (m, 2 H) 2.88-3.18 (m, 2 H) 4.17-4.42 (m, 2 H) 5.18 (s, 2 H) 6.25 (br. s, 1 H) 7.25-7.44 (m, 5 H) 7.67-7.74 (m, 1 H) 7.78-7.89 (m, 1 H) 8.11 (d, J = 8.59 Hz, 2 H) 8.48 (d, J = 9.09 Hz, 1 H) 8.55 (d, J = 8.84 Hz, 1 H) 8.75 (s, 1 H) 9.17 (d, J = 1.77 Hz, 1 H) 9.81 (d, J = 2.27 Hz, 1 H) 11.75 (br s, 1 H) |
| 116 | 545 (M + H)⁺ | (400 MHz, DMSO-d6) δ 1.85-2.06 (m, 2 H) 2.56-2.84 (m, 2 H) 2.88-3.17 (m, 2 H) 3.54 (s, 3 H) 4.30-4.38 (m, 2 H) 5.18 (s, 2 H) 7.26-7.46 (m, 5 H) 7.68-7.74 (m, 1 H) 7.83-7.88 (m, 1 H) 8.11 (d, J = 8.34 Hz, 2 H) 8.49 (d, J = 8.84 Hz, 1 H) 8.58 (d, J = 9.09 Hz, 1 H) 9.00 (s, 1 H) 9.17 (d, J = 2.02 Hz, 1 H) 9.80 (d, J = 2.27 Hz, 1 H) |
| 117 | 397 (M + H)⁺ | (400 MHz, DMSO-d6 with TFA) δ 2.22-2.33 (m, 2 H) 2.83-2.99 (m, 2 H) 3.02-3.15 (m, 2 H) 3.58-3.65 (m, 2 H) 6.27-6.41 (m, 1 H) 7.81 (t, J = 7.58 Hz, 1 H) 7.97 (t, J = 7.58 Hz, 1 H) 8.20 (d, J = 8.34 Hz, 1 H) 8.25 (d, J = 8.08 Hz, 1 H) 8.57-8.67 (m, 1 H) 8.66-8.75 (m, 2 H) 8.83 (d, J = 10.61 Hz, 1 H) 9.02 (d, J = 1.01 Hz, 1 H) 9.39 (s, 1 H) 9.84 (d, J = 2.02 Hz, 1 H) |
| 119 | 439 (M + H)⁺ | (400 MHz, DMSO-d6) δ 1.10 (t, J = 7.07 Hz, 3 H) 1.79 1.92 (m, 2 H) 2.05-2.15 (m, 2 H) 2.40-2.48 (m, 2 H) 2.74-2.96 (m, 2 H) 3.09-3.19 (m, 2 H) 3.54 (s, 3 H) 5.89 (br. s, 1 H) 7.69-7.75 (m, 1 H) 7.80-7.91 (m, 1 H) 8.11 (t, J = 8.21 Hz, 2 H) 8.52 (d, J = 8.84 Hz, 1H) 8.57 (d, J = 9.09 Hz, 1H) 8.98 (s, 1 H) 9.25 (s, 1 H) 9.92 (s, 1 H) |
| 121 | 467 (M + H)⁺ | (400 MHz, DMSO-d₆) δ 1.05 (t, J = 7.33 Hz, 3 H) 1.90-2.05 (m, 2 H) 2.35-2.47 (m, 2 H) 2.61-2.83 (m, 2 H) 3.10-3.22 (m, 1 H) 3.53 (s, 3 H) 4.10-4.20 (m, 1 H) 4.67-4.78 (m, 1 H) 6.19 (br s, 1 H) 7.66-7.73 (m, 1 H) 7.80-7.89 (m, 1 H) 8.04-8.12 (m, 2 H) 8.47 (d, J = 8.48 Hz, 1 H) 8.56 (d, J = 9.09 Hz, 1 H) 8.98 (s, 1 H) 9.14 (d, J = 1.77 Hz, 1 H) 9.77 (d, 1 H) |
| 122 | 469 (M + H)⁺ | (400 MHz, DMSO-d6) δ 1.85-2.06 (m, 2 H) 2.58-2.75 (m, 2 H) 2.89-3.10 (m, 2 H) 3.55 (s, 3 H) 3.69 (s, 3 H) 4.22-4.35 (m, 2 H) 5.69-6.42 (m, 1 H) 7.64-7.77 (m, 1 H) 7.81-7.90 (m, 1 H) 8.11 (t, J = 8.21 Hz, 2 H) 8.48 (d, J = 9.09 Hz, 1 H) 8.57 (d, J = 8.84 Hz, 1 H) 9.00 (s, 1 H) 9.15 (d, J = 1.77 Hz, 1 H) 9.78 (d, J = 2.27 Hz, 1 H) |
| 123 | 468 (M + H)⁺ | (400 MHz, DMSO-d₆) δ 1.89-1.98 (m, 2 H) 2.55-2.69 (m, 2 H) 2.64 (d, J = 4.29 Hz, 3 H) 2.80-2.90 (m, 2 H) 3.53 (s, 3 H) 4.22-4.30 (m, 2 H) 6.16 (br s, 1 H) 6.57-6.62 (m, 1 H) 7.67-7.73 (m, 1 H) 7.82-7.88 (m, 1 H) 8.07 (d, J = 7.83 Hz, 2 H) 8.12 (d, J = 8.59 Hz, 2 H) 8.48 (d, J = 8.84 Hz, 2 H) 8.57 (d, J = 8.84 Hz, 2 |

TABLE 2-continued

| Ex. No. | LRMS m/z | ¹H NMR |
|---|---|---|
| | | H) 8.97 (s, 1 H) 9.15 (d, J = 2.02 Hz, 1 H) 9.80 (d, J = 2.27 Hz, 1 H) |
| 124 | 482 (M + H)⁺ | (400 MHz, DMSO-d₆) δ 1.05 (t, J = 7.20 Hz, 3 H) 1.87-2.00 (m, 2 H) 2.52-2.70 (m, 2 H) 2.77-2.89 (m, 2 H) 3.05-3.16 (m, 2 H) 3.54 (s, 3 H) 4.22-4.34 (m, 2 H) 6.25 (br s, 1 H) 6.63 (t, J = 5.31 Hz, 1 H) 7.66-7.76 (m, 1 H) 7.82-7.91 (m, 1 H) 8.09 (d, J = 7.58 Hz, 1 H) 8.13 (d, J = 8.34 Hz, 1 H) 8.51 (d, J = 8.84 Hz, 1 H) 8.59 (d, J = 9.09 Hz, 1 H) 8.99 (s, 1 H) 9.19 (d, J = 2.02 Hz, 1 H) 9.82 (d, J = 2.27 Hz, 1 H) |
| 125 | 481 (M + H)⁺ | (400 MHz, DMSO-d6) δ 1.04 (d, J = 6.57 Hz, 6 H) 1.91-2.16 (m, 2 H) 2.59-2.78 (m, 2 H) 2.98 (qd, J = 6.74, 6.57 Hz, 1 H) 3.11-3.28 (m, 1 H) 3.54 (s, 3 H) 4.13-4.35 (m, 1 H) 4.64-4.83 (m, 1 H) 6.27 (br s, 1 H) 7.68-7.74 (m, 1 H) 7.83-7.89 (m, 1 H) 8.10 (d, J = 4.04 Hz, 1 H) 8.12 (d, J = 5.05 Hz, 1 H) 8.49 (d, J = 8.84 Hz, 1 H) 8.58 (d, J = 8.84 Hz, 1 H) 8.99 (s, 1 H) 9.17 (d, J = 1.52 Hz, 1 H) 9.80 (d, J = 2.02 Hz, 1 H) |
| 126 | 496 (M + H)⁺ | (400 MHz, DMSO-d₆) δ 1.95-2.06 (m, 2 H) 2.23 (s, 6 H) 2.52-2.60 (m, 1 H) 2.63-2.76 (m, 2 H) 3.08-3.28 (m, 3 H) 3.53 (s, 3 H) 4.31-4.41 (m, 2 H) 4.64-4.73 (m, 2 H) 6.29 (br s, 1 H) 7.68-7.76 (m, 1 H) 7.82-7.89 (m, 1 H) 8.11 (t, J = 7.58 Hz, 3 H) 8.49 (d, J = 8.84 Hz, 1 H) 8.58 (d, J = 9.09 Hz, 1 H) 8.99 (s, 1 H) 9.17 (d, J = 2.02 Hz, 1 H) 9.80 (d, J = 2.27 Hz, 1 H) |
| 127 | 483 (M + H)⁺ | (400 MHz, DMSO-d6) δ 1.23 (t, J = 7.07 Hz, 3 H) 1.90-2.04 (m, 2 H) 2.55-2.74 (m, 2 H) 2.85-3.09 (m, 2 H) 3.54 (s, 3 H) 4.14 (q, J = 7.07 Hz, 2 H) 4.22-4.36 (m, 2 H) 6.15 (br s, 1 H) 7.66-7.76 (m, 1 H) 7.83-7.90 (m, 1 H) 8.04-8.15 (m, 2 H) 8.48 (d, J = 8.51 Hz, 1 H) 8.58 (d, J = 8.53 Hz, 1 H) 8.99 (s, 1 H) 9.15 (d, J = 1.77 Hz, 1 H) 9.78 (d, J = 2.27 Hz, 1 H) |
| 128 | 497 (M + H)⁺ | (400 MHz, DMSO-d6) δ 1.23 (d, J = 6.06 Hz, 6 H) 1.85-2.08 (m, 2 H) 2.56-2.77 (m, 2 H) 2.83-3.08 (m, 2 H) 3.54 (s, 3 H) 4.15-4.44 (m, 2 H) 6.15 (br s, 1 H) 7.66-7.76 (m, 1 H) 7.83-7.90 (m, 1 H) 8.04-8.15 (m, 2 H) 8.48 (d, J = 8.34 Hz, 1 H) 8.58 (d, J = 8.14 Hz, 1 H) 9.00 (s, 1 H) 9.17 (d, J = 1.26 Hz, 1 H) 9.80 (d, J = 2.27 Hz, 1 H) |
| 129 | 425 (M + H)⁺ | (400 MHz, DMSO-d6) δ 1.76-1.90 (m, 2 H) 2.04-2.21 (m, 2 H) 2.33 (s, 3 H) 2.79-3.00 (m, 2 H) 3.00-3.10 (m, 2 H) 3.55 (s, 3 H) 5.83 (br s, 1 H) 7.67-7.79 (m, 1 H) 7.82-7.89 (m, 1 H) 8.13 (t, J = 7.20 Hz, 2 H) 8.55 (q, J = 8.93 Hz, 2 H) 8.98 (s, 1 H) 9.32 (br s, 1 H) 9.87 (d, J = 2.02 Hz, 1 H) |
| 130 | 384 (M + H)⁺ | (400 MHz, DMSO-d6) δ 3.93 (s, 3 H) 5.80 (s, 2 H) 6.93 (d, J = 8.84 Hz, 1 H) 7.20 (d, J = 7.07 Hz, 1 H) 7.23-7.30 (m, 2 H) 7.30-7.39 (m, 2 H) 8.24 (d, J = 8.84 Hz, 1 H) 8.34 (dd, J = 8.84, 2.53 Hz, 1 H) 8.42 (d, J = 8.84 Hz, 1 H) 8.75 (s, 1 H) 8.96 (d, J = 2.27 Hz, 1 H) 11.78 (br s, 1 H) |
| 131 | 436 (M + H)⁺ | (400 MHz, DMSO-d6) δ 1.18-1.47 (m, 2 H) 1.72-1.97 (m, 2 H) 2.09-2.30 (m, 2 H) 2.57-2.80 (m, 2 H) 3.37-3.49 (m, 1 H) 3.49-3.57 (m, 4 H) 3.97 (s, 3 H) 4.55-4.65 (m, 1 H) 5.79 (br s, 1 H) 7.04 (d, J = 8.84 Hz, 1 H) 8.23 (d, J = 8.84 Hz, 1 H) 8.44 (d, J = 9.09 Hz, 1 H) 8.50 (dd, J = 8.72, 2.40 Hz, 1 H) 8.70 (s, 1 H) 9.05 (d, J = 2.27 Hz, 1 H) 11.67 (br s, 1 H) |
| 132 | 392 (M + H)⁺ | (400 MHz, DMSO-d6) δ 1.19-1.47 (m, 2 H) 1.74-1.94 (m, 2 H) 1.94-2.11 (m, 2 H) 2.54-2.71 (m, 2 H) 3.49-3.65 (m, 1 H) 3.98 (s, 3 H) 4.74 (d, J = 4.55 Hz, 1 H) 5.89 (br s, 1 H) 7.05 (d, J = 8.59 Hz, 1 H) 8.24 (d, J = 8.84 Hz, 1 H) 8.43 (d, J = 8.84 Hz, 1 H) 8.52 (dd, J = 8.84, 2.53 Hz, 1 H) 8.68 (s, 1 H) 9.05 (d, J = 2.27 Hz, 1 H) 11.62 (br s, 1 H) |
| 133 | 450 (M + H)⁺ | (400 MHz, DMSO-d6) δ 1.25-1.44 (m, 2 H) 1.75-2.00 (m, 2 H) 2.14-2.30 (m, 2 H) 2.57-2.80 (m, 2 H) 3.40-3.48 (m, 1 H) 3.48-3.57 (m, 7H) 3.97 (s, 3 H) 4.42-4.63 (m, 1 H) 5.89 (br s, 1 H) 7.03 (d, J = 8.84 Hz, 1 H) 8.23 (d, J = 8.84 Hz, 1 H) 8.37-8.57 (m, 2 H) 8.93 (s, 1 H) 9.04 (d, J = 1.52 Hz, 1 H) |
| 134 | 406 (M + H)⁺ | (400 MHz, DMSO-d6) δ 1.27-1.47 (m, 2 H) 1.70-1.93 (m, 2 H) 1.94-2.11 (m, 2 H) 2.53-2.71 (m, 2 H) 3.52 (s, 3 H) 3.54-3.65 (m, 1 H) 3.98 (s, 3 H) 4.74 (br s, 1 H) 5.92 (br s, 1 H) 7.05 (d, J = 8.08 Hz, 1 H) 8.25 (d, J = 9.09 Hz, 1 H) 8.46 (d, J = 9.09 Hz, 1 H) 8.52 (dd, J = 8.59, 2.53 Hz, 1 H) 8.93 (s, 1 H) 9.05 (d, J = 2.27 Hz, 1 H) |
| 136 | 433 (M + H)⁺ | (400 MHz, DMSO-d₆) δ 1.78-1.96 (m, 2 H) 2.11 (s, 3 H) 2.59-2.92 (m, 3 H) 3.14-3.27 (m, 1 H) 3.54 (s, 3 H) 3.95 (s, 3 H) 4.02-4.12 (m, 1 H) 4.63-4.75 (m, 1 H) 6.96-7.09 (m, 1 H) 8.28 (d, J = 9.09 Hz, 1 H) 8.46 (d, J = 8.84 Hz, 1 H) 8.48-8.52 (m, 1 H) 8.96 (s, 1 H) 9.05 (d, J = 2.27 Hz, 1 H) |
| 137 | 433 (M + H)⁺ | (400 MHz, DMSO-d6) δ 1.09 (d, J = 6.57 Hz, 6 H) 1.61-1.84 (m, 2 H) 2.27-2.39 (m, 2 H) 2.79-2.91 (m, 2 H) 3.00 (m, 2 H) 3.54 (s, 3 H) 3.95 (s, 3 H) 6.94 (d, J = 8.59 Hz, 1 H) 8.30 (d, J = 9.09 Hz, 1 H) 8.46 (d, J = 8.84 Hz, 1 H) 8.75 (br s, 1 H) 8.94 (s, 1 H) 9.28 (br s, 1 H) |

TABLE 2-continued

| Ex. No. | LRMS m/z | ¹H NMR |
|---|---|---|
| 138 | 476 (M + H)⁺ | (400 MHz, DMSO-d6) δ 1.82-2.03 (m, 2 H) 2.37 (s, 6 H) 2.64-2.79 (m, 2 H) 3.06-3.22 (m, 1 H) 3.39-3.49 (m, 1 H) 3.53 (s, 3 H) 3.96 (s, 3 H) 4.13-4.24 (m, 1 H) 4.59-4.74 (m, 1 H) 7.06 (d, J = 8.59 Hz, 1 H) 8.29 (d, J = 8.84 Hz, 1 H) 8.48 (d, J = 9.09 Hz, 1 H) 8.50-8.54 (m, 1 H) 8.96 (s, 1 H) 9.06 (d, J = 2.02 Hz, 1 H) |
| 139 | 448 (M + H)⁺ | (400 MHz, DMSO-d6) δ 1.64-1.87 (m, 2 H) 2.19-2.36 (m, 2 H) 3.02 (s, 2 H) 3.05-3.14 (m, 2 H) 3.55 (s, 3 H) 3.96 (s, 3 H) 7.10 (d, J = 8.84 Hz, 1 H) 7.23 (br s, 1 H) 7.36 (br s, 1 H) 8.32 (d, J = 9.09 Hz, 1 H) 8.48 (d, J = 9.09 Hz, 1 H) 8.73 (br s, 1 H) 8.96 (s, 1 H) 9.32 (br s, 1H) |
| 140 | 392 (M + H)⁺ | (400 MHz, DMSO-d6) δ 1.71-1.84 (m, 2 H) 2.76-3.04 (m, 2 H) 3.43-3.53 (m, 2 H) 3.54 (s, 3 H) 3.96 (s, 3 H) 4.05-4.15 (m, 2 H) 5.91 (br s, 1 H) 7.04 (d, J = 8.84 Hz, 1 H) 8.30 (d, J = 8.84 Hz, 1 H) 8.47 (d, J = 8.84 Hz, 1 H) 8.68 (d, J = 7.07 Hz, 1 H) 8.95 (s, 1 H) 9.12 (d, J = 2.27 Hz, 1 H) |
| 141 | 493 (M + H)⁺ | (400 MHz, DMSO-d6) δ 1.87-1.93 (m, 2 H) 2.58-2.67 (m, 2 H) 2.73-2.87 (m, 2 H) 3.13-3.24 (m, 2 H) 3.33-3.39 (m, 2 H) 3.54 (s, 3 H) 6.08 (br s, 1 H) 7.61-7.79 (m, 1 H) 7.76-7.89 (m, 1 H) 8.13 (t, J = 8.59 Hz, 2 H) 8.50 (d, J = 9.09 Hz, 1 H) 8.57 (d, J = 8.84 Hz, 1 H) 8.98 (s, 1 H) 9.20 (d, J = 2.02 Hz, 1 H) 9.84 (d, J = 2.27 Hz, 1 H) |
| 142 | 448 (M + H)⁺ | (400 MHz, DMSO-d6) δ 1.65-1.92 (m, 2 H) 2.64 (d, J = 4.29 Hz, 3 H) 2.73-2.89 (m, 3 H) 3.54 (s, 3 H) 3.95 (s, 3 H) 4.17-4.29 (m, 2 H) 6.52-6.60 (m, 1 H) 6.99 (m, 1 H) 8.29 (d, J = 9.09 Hz, 1 H) 8.46 (d, J = 9.09 Hz, 1 H) 8.59 (d, J = 8.59 Hz, 1 H) 8.94 (s, 1 H) 9.05 (d, J = 2.27 Hz, 1 H) |
| 143 | 497 (M + H)⁺ | (400 MHz, DMSO-d6) δ 1H NMR (400 MHz, DMSO-d₆) d ppm 1.15-1.32 (m, 2 H) 1.40 (s, 6 H) 1.88-2.09 (m, 2 H) 2.55-3.10 (m, 2 H) 3.54 (s, 3 H) 4.78 (br s, 1 H) 5.16 (br s, 1 H) 5.62 (br s, 1 H) 6.22 (br s, 1 H) 7.67-7.76 (m, 1 H) 7.80-7.93 (m, 1 H) (d, J = 8.34 Hz, 2 H) 8.44-8.52 (m, 1 H) 8.52-8.62 (m, 1 H) 8.98 (s, 1 H) 9.20 (s, 1 H) 9.84 (s, 1 H) |
| 144 | 489 (M + H)⁺ | (400 MHz, DMSO-d6) δ 1.82-1.98 (m, 2 H) 2.25 (s, 6 H) 2.64-2.81 (m, 2 H) 3.14 (s, 6 H) 3.16-3.30 (m, 2 H) 3.51 (s, 3 H) 4.23-4.32 (m, 1 H) 4.65-4.74 (m, 1 H) 6.87 (d, J = 9.09 Hz, 1 H) 8.19 (d, J = 9.09 Hz, 1 H) 8.32 (dd, J = 9.09, 2.53 Hz, 1 H) 8.36 (d, J = 9.09 Hz, 1 H) 8.86 (s, 1 H) 8.98 (d, J = 2.02 Hz, 1 H) |
| 145 | 496 (M + H)⁺ | (400 MHz, DMSO-d6) δ 1.35 (s, 6 H) 1.83-2.10 (m, 2 H) 2.10-2.24 (m, 1 H) 2.57-2.85 (m, 1 H) 2.85-3.05 (m, 2 H) 3.55 (s, 3H) 5.17 (br s, 1 H) 7.69-7.79 (m, 1 H) 7.82-7.92 (m, 1 H) 8.12 (d, J = 8.34 Hz, 2 H) 8.49 (d, J = 8.84 Hz, 1 H) 8.59 (d, J = 9.09 Hz, 1 H) 9.00 (s, 1 H) 9.19 (d, J = 2.02 Hz, 1 H) 9.85 (d, J = 1.52 Hz, 1 H) |
| 146 | 426 (M + H)⁺ | (400 MHz, DMSO-d6) δ 1.34-1.53 (m, 2 H) 1.79-2.00 (m, 2 H) 2.08-2.17 (m, 2 H) 2.59-2.80 (m, 2 H) 3.58 (s, 3 H) 3.63-3.75 (m, 1 H) 4.87 (br s, 1 H) 6.03 (br s, 1 H) 7.66-7.80 (m, 1 H) 7.81-7.91 (m, 1 H) 1H 8.16 (d, J = 7.58 Hz, 1 H) 8.21 (d, J = 8.34 Hz, 1 H) 8.53 (d, 1 H) 8.61 (d, 1 H) 8.95 (s, 1 H) 9.17 (d, J = 1.52 Hz, 1 H) 9.80 (d, J = 2.27 Hz, 1 H) |
| 147 | 470 (M + H)⁺ | (400 MHz, DMSO-d6) δ 1.30-1.51 (m, 2 H) 1.86-2.07 (m, 2 H) 2.24 (d, J = 10.86 Hz, 2 H) 2.64 (br s, 2 H) 3.39-3.60 (m, 8 H) 4.62 (t, J = 5.18 Hz, 1 H) 6.09 (br s, 1 H) 7.62-7.78 (m, 1 H) 7.78-7.91 (m, 1 H) 8.12 (d, J = 7.83 Hz, 1 H) 8.16 (d, J = 8.34 Hz, 1 H) 8.49 (d, J = 8.84 Hz, 1 H) 8.58 (d, J = 8.84 Hz, 1 H) 8.98 (s, 1 H) 9.18 (s., 1 H) 9.80 (d, J = 2.02 Hz, 1 H) |
| 148 | 451 (M + H)⁺ | (400 MHz, DMSO-d6) δ 1.25-1.41 (m, 2 H) 1.85-1.99 (m, 2 H) 2.16-2.28 (m, 2 H) 2.54-2.74 (m, 2 H) 3.37-3.47 (m, 1 H) 3.51 (s, 3 H) 3.52 (m, 4 H) 4.04 (s, 3 H) 4.55-4.63 (m, 1 H) 8.29 (d, J = 8.84 Hz, 1 H) 8.51 (d, J = 8.84 Hz, 1 H) 8.96 (s, 1 H) 9.39 (s, 2 H) |
| 149 | 463 (M + H)⁺ | (400 MHz, DMSO-d6) δ 1.28-1.48 (m, 2 H) 1.79-1.98 (m, 2 H) 2.15-2.28 (m, 2 H) 2.59-2.78 (m, 2 H) 3.14 (s, 6 H) 3.46-3.57 (m, 8 H) 4.52-4.65 (m, 1 H) 6.80 (d, J = 8.84 Hz, 1 H) 8.16 (d, J = 9.09 Hz, 1 H) 8.32 (dd, J = 8.97, 2.40 Hz, 1 H) 8.37 (d, J = 8.84 Hz, 1 H) 8.86 (s, 1 H) 9.00 (d, J = 2.27 Hz, 1 H) |
| 150 | 486 (M + H)⁺ | (400 MHz, DMSO-d6) δ 1.75-1.86 (m, 2 H) 2.54-2.66 (m, 2 H) 2.75-2.99 (m, 2 H) 3.09-3.21 (m, 8 H) 3.33-3.41 (m, 2 H) 3.51 (s, 3 H) 5.86 (br s, 1 H) 6.81 (d, J = 8.84 Hz, 1 H) 8.20 (d, J = 9.09 Hz, 1 H) 8.29-8.39 (m, 1 H) 8.49 (d, J = 4.55 Hz, 1 H) 8.86 (s, 1 H) 9.04 (d, J = 2.27 Hz, 1 H) |
| 151 | 446 (M + H)⁺ | (400 MHz, DMSO-d6) δ 1.67-1.79 (m, 2 H) 2.56-2.68 (m, 2 H) 2.93-3.14 (m, 2 H) 3.15-3.23 (m, 2 H) 3.34-3.43 (m, 2 H) 3.52 (s, 3 H) 3.94 (s, 3 H) 5.24 (br s, 1 H) 7.96 (d, J = 8.84 Hz, 1H) 8.35 (d, J = 8.84 Hz, 1 H) 8.37 (br s, 1 H) 8.56 (br s, 1 H) 8.86 (s, 1 H) |
| 152 | 434 (M + H)⁺ | (400 MHz, DMSO-d6) δ 1.25-1.45 (m, 2 H) 1.79-1.96 (m, 2 H) 2.14-2.25 (m, 2 H) 2.55-2.73 (m, 2 H) 2.59 (s, 3 H) |

TABLE 2-continued

| Ex. No. | LRMS m/z | $^1$H NMR |
|---|---|---|
| | | 3.36-3.47 (m, 1 H) 3.47-3.59 (m, 7 H) 4.62 (t, J = 4.93 Hz, 1 H) 5.98 (br s, 1 H) 7.47 (d, J = 8.08 Hz, 1 H) 8.27 (d, J = 8.84 Hz, 1 H) 8.45 (dd, J = 8.08, 2.27 Hz, 1 H) 8.49 (d, J = 8.84 Hz, 1 H) 8.95 (s, 1 H) 9.31 (d, J = 1.52 Hz, 1 H) |
| 153 | 447.2 (M + H)⁺ | (400 MHz, DMSO-d₆) δ 1.91 (d, J = 2.02 Hz, 2 H), 2.55 (s, 3 H), 2.62-2.85 (m, 2 H), 3.01-3.21 (m, 1 H), 3.34 (s, 3 H), 3.52 (s, 3 H), 4.00 (d, J = 13.64 Hz, 1 H), 4.07-4.31 (m, 2 H), 4.65 (d, J = 9.85 Hz, 1 H), 6.04 (br s, 1 H), 7.46 (d, J = 8.08 Hz, 1 H), 8.29 (d, J = 9.09 Hz, 1 H), 8.36-8.43 (m, 1 H), 8.47 (d, J = 8.84 Hz, 1 H), 8.95 (s, 1 H), 9.27 (d, J = 1.52 Hz, 1 H). |
| 154 | 464.2 (M + H)⁺ | (400 MHz, DMSO-d₆) δ 1.24 (br s, 3 H), 1.96 (d, J = 9.85 Hz, 2 H), 2.53-2.89 (m, 3 H), 3.13 (br s, 1 H), 3.53 (s, 3 H), 4.03 (s, 3 H), 4.29 (t, J = 13.64 Hz, 1 H), 4.45-4.59 (m, 1 H), 4.66 (d, J = 9.09 Hz, 1 H), 4.90-5.09 (m, 1 H), 6.05 (br s, 1 H), 8.30 (d, J = 8.84 Hz, 1 H), 8.51 (d, J = 9.09 Hz, 1 H), 8.97 (s, 1 H), 9.39 (s, 2 H). |
| 155 | 448.2 (M + H)⁺ | (400 MHz, DMSO-d₆) δ 1.05 (t, J = 7.33 Hz, 3 H), 1.91 (br s, 2 H), 2.30-2.47 (m, 3 H), 2.55-2.93 (m, 2 H), 3.05-3.24 (m, 1 H), 3.54 (s, 3 H), 4.03 (s, 3 H), 4.08-4.21 (m, 1 H), 4.68 (d, J = 10.61 Hz, 1 H), 5.94 (br s, 1 H), 8.31 (d, J = 9.09 Hz, 1 H), 8.52 (d, J = 8.84 Hz, 1 H), 8.99 (s, 1 H), 9.40 (s, 2 H). |
| 156 | 4417.2 (M + H)⁺ | (400 MHz, DMSO-d₆) δ 1.44-1.67 (m, 2 H), 1.86-2.08 (m, 4 H), 2.15-2.31 (m, 1 H), 2.52-2.72 (m, 5 H), 3.53 (s, 3 H), 5.98 (br s, 1 H), 6.78 (br s, 1 H), 7.29 (br s, 1 H), 7.50 (d, J = 8.34 Hz, 1 H), 8.33 (d, J = 8.84 Hz, 1 H), 8.47-8.61 (m, 2 H), 8.97 (s, 1 H), 9.32 (d, J = 2.02 Hz, 1 H). |
| 157 | 4434.2 (M + H)⁺ | (400 MHz, DMSO-d₆) δ 1.39-1.65 (m, 2 H), 1.96 (t, J = 11.62 Hz, 4 H), 2.14-2.32 (m, 1 H), 2.51-2.69 (m, 2 H), 3.51 (s, 3 H), 4.02 (s, 3 H), 5.85 (br s, 1 H), 6.76 (br s, 1 H), 7.26 (br s, 1 H), 8.26 (d, J = 8.84 Hz, 1 H), 8.48 (d, J = 9.09 Hz, 1 H), 8.93 (s, 1 H), 9.29-9.42 (m, 2 H). |
| 158 | 4406.2 (M + H)⁺ | (400 MHz, DMSO-d₆) δ 1.48-1.72 (m, 2 H), 1.96 (dd, J = 30.32, 11.12 Hz, 4 H), 2.20-2.36 (m, 1 H), 2.49-2.64 (m, 2 H), 3.50 (s, 3 H), 3.96 (s, 3 H), 6.03 (br s, 1 H), 6.79 (br s, 1 H), 7.33 (br s, 1 H), 7.94 (d, J = 8.84 Hz, 1 H), 8.12 (s, 1 H), 8.34 (d, J = 8.84 Hz, 1 H), 8.45 (s, 1 H), 8.84 (s, 1 H). |
| 159 | 4446.2 (M + H)⁺ | (400 MHz, DMSO-d₆) δ 1.35 (d, J = 11.87 Hz, 2 H), 1.85 (br s, 2 H), 1.93-2.17 (m, 6 H), 2.43-2.76 (m, 2 H), 3.54 (d, J = 39.92 Hz, 8 H), 4.81 (br s, 1 H), 5.86 (br s, 1 H), 8.15 (br s, 1 H), 8.38 (br s, 1 H), 8.73-8.98 (m, 1 H), 9.03-9.33 (m, 2 H). |
| 160 | 4446.2 (M + H)⁺ | (400 MHz, DMSO-d₆) δ 1.37-1.69 (m, 2 H), 1.80-2.08 (m, 4 H), 2.28 (t, J = 11.62 Hz, 1 H), 2.50-2.77 (m, 2 H), 3.03-3.24 (m, 6 H), 3.50 (s, 3 H), 5.99 (br s, 1 H), 6.78 (d, J = 8.84 Hz, 2 H), 7.28 (br s, 1 H), 8.15 (d, J = 9.09 Hz, 1 H), 8.27-8.45 (m, 2 H), 8.83 (s, 1 H), 8.97 (d, J = 2.27 Hz, 1 H). |
| 161 | 4464.2 (M + H)⁺ | (400 MHz, DMSO-d₆) δ 1.94 (d, J = 9.09 Hz, 2 H), 2.52-2.98 (m, 3 H), 3.00-3.24 (m, 1 H), 3.33 (s, 3 H), 3.51 (s, 3 H), 3.88-4.09 (m, 4 H), 4.21 (br s, 2 H), 4.62 (d, J = 10.86 Hz, 1 H), 5.99 (br s, 1 H), 8.30 (d, J = 9.09 Hz, 1 H), 8.45-8.60 (m, 1 H), 8.97 (s, 1 H), 9.38 (s, 2 H). |
| 162 | 461.2 (M + H)⁺ | (400 MHz, DMSO-d₆) δ 1.37 (s, 6 H), 1.91 (br s, 2 H), 2.57 (s, 3 H), 2.62-3.18 (m, 4 H), 3.54 (s, 3 H), 4.13-6.80 (m, 4 H), 7.50 (d, J = 8.08 Hz, 1 H), 8.31 (d, J = 8.84 Hz, 1 H), 8.41-8.58 (m, 2 H), 8.97 (s, 1 H), 9.37 (br s, 1 H). |
| 163 | 477.2 (M + H)⁺ | (400 MHz, DMSO-d₆) δ 1.81 (d, J = 11.37 Hz, 2 H), 2.23 (dd, J = 10.11, 9.09 Hz, 2 H), 2.63-2.95 (m, 5 H), 2.98-3.12 (m, 5 H), 3.24 (s, 2 H), 3.52 (s, 3 H), 4.03 (s, 3 H), 5.74 (br s, 1 H), 8.29 (d, J = 8.84 Hz, 1 H), 8.48 (d, J = 8.84 Hz, 1 H), 8.95 (s, 1 H), 9.47 (s, 2 H). |
| 164 | 409.2 (M + H)⁺ | (400 MHz, DMSO-d₆) δ 1.26-1.51 (m, 2 H), 1.81 (d, J = 10.86 Hz, 2 H), 1.94-2.14 (m, 2 H), 2.51-2.82 (m, 2 H), 3.48 (s, 3 H), 3.59 (br s, 1 H), 3.83 (q, J = 5.31 Hz, 2 H), 4.24 (t, J = 5.43 Hz, 2 H), 4.76 (d, J = 4.55 Hz, 1 H), 5.02 (t, J = 5.31 Hz, 1 H), 5.90 (br s, 1 H), 7.91 (d, J = 8.84 Hz, 1 H), 8.13 (s, 1 H), 8.29 (d, J = 8.84 Hz, 1 H), 8.47 (s, 1 H), 8.78 (s, 1 H). |
| 165 | 453.2 (M + H)⁺ | (400 MHz, DMSO-d₆) δ 1.95 (d, J = 9.60 Hz, 2 H), 2.48 (br s, 3 H) 2.79 (br s, 2 H), 3.01 (t, J = 12.38 Hz, 2 H), 3.54 (s, 3 H), 5.00 (d, J = 12.38 Hz, 2 H), 5.86 (br s, 1 H), 6.72 (t, J = 4.67 Hz, 1 H), 7.36 (br s, 1 H), 8.31 (d, J = 8.84 Hz, 1 H), 8.39-8.59 (m, 4 H), 8.98 (s, 1 H), 9.29 (br s, 1 H). |
| 166 | 419.2 (M + H)⁺ | (400 MHz, DMSO-d₆) δ 1.86 (d, J = 33.85 Hz, 2 H), 2.10-3.71 (m, 17 H), 5.27 (br s, 1 H), 7.48 (d, J = 8.08 Hz, 1 H), 8.33 (d, J = 8.84 Hz, 1 H), 8.49 (d, J = 8.84 Hz, 1 H), 8.59 (br s, 1 H), 8.97 (s, 1 H), 9.55 (br s, 1 H). |
| 168 | 365.2 (M + H)⁺ | (400 MHz, DMSO-d₆) δ 1.16-1.54 (m, 2 H), 1.83 (d, J = 11.12 Hz, 2 H), 2.05 (d, J = 10.36 Hz, 2 H), 2.58 (br s, 2 H), 3.49 (s, 3 H), 3.60 (br s, 1 H), 4.79 (d, J = 4.29 Hz, 1 H), 5.96 (br s, 1 H), |

TABLE 2-continued

| Ex. No. | LRMS m/z | ¹H NMR |
|---|---|---|
| | | 8.00 (d, J = 8.84 Hz, 1 H), 8.21 (br s, 1 H), 8.33 (d, J = 8.84 Hz, 1 H), 8.52 (br s, 1 H), 8.82 (s, 1 H), 13.31 (br s, 1 H). |
| 169 | 407.2 (M + H)⁺ | (400 MHz, DMSO-d₆) δ 1.36 (d, J = 11.87 Hz, 2 H), 1.87 (br s, 2 H), 2.03 (d, J = 10.61 Hz, 2 H), 2.53-2.75 (m, 2 H), 3.52 (br s, 4 H), 4.04 (s, 3 H), 4.79 (d, J = 2.53 Hz, 1 H), 5.87 (br s, 1 H), 8.30 (d, J = 7.58 Hz, 1 H), 8.51 (d, J = 7.83 Hz, 1 H), 8.96 (br s, 1 H), 9.40 (br s, 2 H). |
| 170 | 379.2 (M + H)⁺ | (400 MHz, DMSO-d₆) δ 1.25-1.50 (m, 2 H), 1.82 (d, J = 10.86 Hz, 2 H), 2.04 (d, J = 10.36 Hz, 2 H), 2.56 (br s, 2 H), 3.49 (s, 3 H), 3.59 (br s, 1 H), 3.96 (s, 3 H), 4.77 (d, J = 4.80 Hz, 1 H), 5.90 (br s, 1 H), 7.91 (d, J = 8.84 Hz, 1 H), 8.12 (s, 1 H), 8.33 (d, J = 8.84 Hz, 1 H), 8.45 (s, 1 H), 8.82 (s, 1 H). |
| 171 | 389.2 (M + H)⁺ | (400 MHz, DMSO-d₆) δ 1.78 (d, J = 11.37 Hz, 2 H), 2.07 (t, J = 11.12 Hz, 2 H), 2.32 (s, 3 H), 2.59 (s, 3 H), 2.77-3.11 (m, 4 H), 3.44-3.64 (m, 3 H), 5.72 (br s, 1 H), 7.46 (d, J = 8.08 Hz, 1 H), 8.37 (d, J = 8.84 Hz, 1 H), 8.50 (d, J = 8.84 Hz, 1 H), 8.78 (br s, 1 H), 8.97 (s, 1 H), 9.41 (s, 1 H). |
| 172 | 433.2 (M + H)⁺ | (400 MHz, DMSO-d₆) δ 1.91 (br s, 2 H), 2.56 (s, 3 H), 2.62-2.87 (m, 3 H), 3.13 (t, J = 12.38 Hz, 1 H), 3.54 (s, 3 H), 3.85-4.02 (m, 1 H), 4.08-4.30 (m, 2 H), 4.56-4.77 (m, 2 H), 5.97 (br s, 1 H), 7.47 (d, J = 8.08 Hz, 1 H), 8.32 (d, J = 8.84 Hz, 1 H), 8.44 (dd, J = 8.08, 1.77 Hz, 1 H), 8.50 (d, J = 8.84 Hz, 1 H), 8.98 (s, 1 H), 9.29 (s, 1 H). |
| 173 | 417.2 (M + H)⁺ | (400 MHz, DMSO-d₆) δ 1.77-1.97 (m, 2 H), 2.08 (s, 3 H), 2.57 (s, 3 H), 2.60-2.86 (m, 3 H), 3.19 (t, J = 12.76 Hz, 1 H), 3.54 (s, 3 H), 4.07 (d, J = 13.64 Hz, 1 H), 4.69 (d, J = 9.09 Hz, 1 H), 5.92 (br s, 1 H), 7.47 (d, J = 7.83 Hz, 1 H), 8.31 (d, J = 9.09 Hz, 1 H), 8.44 (dd, J = 8.08, 2.02 Hz, 1 H), 8.49 (d, J = 8.84 Hz, 1 H), 8.97 (s, 1 H), 9.29 (d, J = 1.77 Hz, 1 H). |
| 174 | 365.2 (M + H)⁺ | (400 MHz, DMSO-d₆) δ 1.25-1.55 (m, 2 H), 1.84 (d, J = 10.61 Hz, 2 H), 2.04 (d, J = 10.61 Hz, 2 H), 2.53-2.73 (m, 2 H), 3.50 (s, 3 H), 3.58 (br s, 1 H), 4.77 (d, J = 3.54 Hz, 1 H), 6.00 (br s, 1 H), 6.96 (s, 1 H), 7.99 (s, 1 H), 8.27 (d, J = 8.84 Hz, 1 H), 8.40 (d, J = 8.84 Hz, 1 H), 8.88 (s, 1 H), 13.31 (br s, 1 H). |
| 176 | 432.2 (M + H)⁺ | (400 MHz, DMSO-d₆) δ 1.75 (d, J = 8.84 Hz, 2 H), 2.22 (t, J = 11.37 Hz, 2 H), 2.56 (s, 3 H), 2.75-3.26 (m, 6 H), 3.53 (s, 3 H), 5.26 (br s, 1 H), 7.22 (br s, 1 H), 7.47 (d, J = 8.08 Hz, 1 H), 7.68 (br s, 1 H), 8.30 (d, J = 9.09 Hz, 1 H), 8.40-8.50 (m, 1 H), 8.57 (d, J = 6.82 Hz, 1 H), 8.94 (s, 1 H), 9.67 (br s, 1 H). |
| 178 | 460.0 (M + H)⁺ | (400 MHz, DMSO-d₆) δ 1.91 (d, J = 9.35 Hz, 2 H), 2.21 (s, 6 H), 2.53-2.80 (m, 6 H), 2.99-3.22 (m, 3 H), 3.51 (s, 3 H), 4.29 (d, J = 12.38 Hz, 1 H), 4.66 (d, J = 10.61 Hz, 1 H), 6.14 (br s, 1 H), 7.46 (d, J = 8.08 Hz, 1 H), 8.27 (d, J = 8.84 Hz, 1 H), 8.36-8.55 (m, 2 H), 8.93 (s, 1 H), 9.27 (d, J = 1.52 Hz, 1 H). |
| 179 | 390.0 (M + H)⁺ | (400 MHz, DMSO-d₆) δ 1.23-1.46 (m, 2 H), 1.86 (d, J = 9.35 Hz, 2 H), 2.02 (d, J = 10.86 Hz, 2 H), 2.54-2.80 (m, 5 H), 3.46-3.71 (br s, 1 H), 5.97 (br s, 1 H), 7.48 (d, J = 8.34 Hz, 1 H), 8.28 (d, J = 8.84 Hz, 1 H), 8.41-8.54 (m, 2 H), 8.94 (s, 1 H), 9.33 (d, J = 1.77 Hz, 1 H). |
| 180 | 432.0 (M + H)⁺ | (400 MHz, DMSO-d₆) δ 1.89 (br s, 2 H), 2.53-2.58 (m, 3 H), 2.62-2.87 (m, 2 H), 3.01-3.29 (m, 6 H), 3.39-3.59 (m, 3 H), 4.00 (d, J = 12.88 Hz, 1 H), 4.69 (d, J = 9.85 Hz, 1 H), 6.03 (br s, 1 H), 7.45 (d, J = 8.08 Hz, 1 H), 8.27 (d, J = 8.84 Hz, 1 H), 8.35-8.42 (m, 1 H), 8.46 (d, J = 8.84 Hz, 1 H), 8.95 (s, 1 H), 9.26 (s, 1 H). |
| 181 | 432.0 (M + H)⁺ | (400 MHz, DMSO-d₆) δ 1.83 (d, J = 7.83 Hz, 2 H), 2.53-2.57 (m, 4 H), 2.61-2.86 (m, 7 H), 3.53 (s, 3 H), 4.23 (d, J = 10.86 Hz, 2 H), 6.57 (q, J = 3.87 Hz, 1 H), 7.42 (d, J = 7.07 Hz, 1 H), 8.32 (d, J = 9.09 Hz, 1 H), 8.44-8.61 (m, 2 H), 8.96 (s, 1 H), 9.30 (d, J = 2.02 Hz, 1 H). |
| 182 | 406.0 (M + H)⁺ | (400 MHz, DMSO-d₆) δ 1.77 (d, J = 9.35 Hz, 2 H), 2.06 (t, J = 11.49 Hz, 2 H), 2.33 (s, 3 H), 2.99 (d, J = 11.62 Hz, 4 H), 3.55 (s, 3 H), 4.04 (s, 3 H), 5.55 (br s, 1 H), 8.35 (d, J = 9.09 Hz, 1 H), 8.52 (d, J = 8.84 Hz, 1 H), 8.98 (s, 1 H), 9.62 (br s, 2 H). |
| 183 | 477.0 (M + H)⁺ | (400 MHz, DMSO-d₆) δ 1.86-2.11 (m, 2 H), 2.32 (s, 6 H), 2.55-2.87 (m, 2 H), 3.13 (t, J = 12.51 Hz, 1 H), 3.25-3.41 (m, 3 H), 3.53 (s, 3 H), 4.03 (s, 3 H), 4.28 (d, J = 13.14 Hz, 1 H), 4.65 (d, J = 11.37 Hz, 1 H), 6.06 (br s, 1 H), 8.32 (d, J = 8.84 Hz, 1 H), 8.53 (d, J = 8.84 Hz, 1 H), 8.99 (s, 1 H), 9.41 (s, 2 H). |
| 184 | 449.0 (M + H)⁺ | (400 MHz, DMSO-d₆) δ 1.77-2.01 (m, 2 H), 2.58-2.83 (m, 2 H), 3.12 (br s, 1 H), 3.33-3.65 (m, 4 H), 3.75-4.34 (m, 8 H), 4.66 (d, J = 10.61 Hz, 1 H), 5.85 (br s, 1 H), 8.28 (d, J = 8.84 Hz, 1 H), 8.49 (d, 1 H), 8.97 (s, 1 H), 9.36 (s, 2 H). |
| 185 | 436.0 (M + H)⁺ | (400 MHz, DMSO-d₆) δ 1.72 (d, J = 9.09 Hz, 2 H), 2.13 (t, J = 11.49 Hz, 2 H), 3.13 (d, J = 11.37 Hz, 4 H), 3.28-3.36 (m, 2 H), 3.54 (s, 3 H), 3.68 (br s, 2 H), 4.04 (s, 3 H), 4.64 (br s, 1 H), |

TABLE 2-continued

| Ex. No. | LRMS m/z | ¹H NMR |
|---|---|---|
| | | 5.32 (br s, 1 H), 8.35 (d, 1 H), 8.51 (d, J = 9.09 Hz, 1 H), 8.97 (s, 1 H), 9.70 (br s, 2 H). |
| 187 | 434.0 (M + H)⁺ | (400 MHz, DMSO-d₆) δ 1.69-2.01 (m, 2 H), 2.12 (s, 3 H), 2.55-2.86 (m, 3 H), 3.19 (t, J = 12.63 Hz, 1 H), 3.54 (s, 3 H), 4.02 (s, 3 H), 4.10 (d, J = 13.14 Hz, 1 H), 4.65 (d, J = 10.11 Hz, 1 H), 5.85 (br s, 1 H), 8.29 (d, J = 8.84 Hz, 1 H), 8.50 (d, J = 8.84 Hz, 1 H), 8.97 (s, 1 H), 9.39 (s, 2 H). |
| 188 | 392.0 (M + H)⁺ | (400 MHz, DMSO-d₆) δ 1.94 (d, J = 7.33 Hz, 2 H), 2.62-2.93 (m, 4 H), 3.32 (d, J = 8.59 Hz, 2 H), 3.52 (s, 3 H), 4.04 (s, 3 H), 5.99 (br s, 1 H), 6.55 (br s, 1 H), 8.33 (d, J = 8.84 Hz, 1 H), 8.53 (d, J = 8.84 Hz, 1 H), 8.98 (s, 1 H), 9.49 (br s, 2 H). |
| 191 | 404.0 (M + H)⁺ | (400 MHz, DMSO-d₆) δ 2.16 (d, J = 12.63 Hz, 2 H), 2.75-2.93 (m, 2 H), 2.97-3.10 (m, 2 H), 3.12-3.25 (m, 6 H), 3.27-3.43 (m, 2 H), 3.46-3.61 (m, 4 H), 6.14-6.45 (m, 1 H), 6.94 (d, J = 6.82 Hz, 1 H), 8.21 (d, J = 8.84 Hz, 1 H), 8.40 (d, J = 9.09 Hz, 2 H), 8.72-8.84 (m, 1 H), 8.88-8.97 (m, 2 H), 9.30 (d, J = 7.58 Hz, 1 H). |
| 192 | 411.0 (M + H)⁺ | (400 MHz, DMSO-d₆) δ 1.28-1.49 (m, 2 H), 1.91 (br s, 2 H), 2.03 (d, J = 12.13 Hz, 2 H), 2.59-2.77 (m, 2 H), 2.88 (br s, 1 H), 3.36 (br s, 2 H), 7.00 (br s, 2 H), 7.68-7.79 (m, 1 H), 7.82-7.96 (m, 1 H), 8.16 (d, J = 8.34 Hz, 2 H), 8.45-8.51 (m, 1 H), 8.53-8.63 (m, 1 H), 8.75 (s, 1 H), 9.20 (s, 1 H), 9.81 (d, J = 2.02 Hz, 1 H). |
| 195 | 446.00 (M + H)⁺ | (400 MHz, DMSO-d6) δ 8.99 (d, J = 2.27 Hz, 1 H) 8.87 (s, 1 H) 8.29-8.43 (m, 2 H) 8.20 (d, J = 9.09 Hz, 1 H) 6.83 (d, J = 8.59 Hz, 1 H) 4.70 (d, J = 8.84 Hz, 1 H) 4.08 (d, J = 13.14 Hz, 1 H) 3.52 (s, 3 H) 3.16-3.27 (m, 1 H) 3.13 (s, 6 H) 3.04 (d, J = 9.35 Hz, 1 H) 2.67 (dd, J = 5.81, 4.04 Hz, 1 H) 2.68 (d, J = 15.66 Hz, 1 H) 2.11 (s, 3 H) 1.80-1.98 (m, 2 H) 1.15 (t, J = 6.82 Hz, 1 H) |
| 196 | 461.0 (M + H)⁺ | (400 MHz, DMSO-d6) δ ppm 8.99 (d, J = 2.27 Hz, 1 H) 8.87 (s, 1 H) 8.44 (d, J = 11.37 Hz, 1 H) 8.36 (d, J = 9.09 Hz, 1 H) 8.21 (d, J = 9.09 Hz, 1 H) 6.80 (d, J = 7.83 Hz, 1 H) 6.59 (d, J = 4.29 Hz, 1 H) 4.24 (d, J = 9.60 Hz, 2 H) 3.52 (s, 3 H) 3.13 (s, 6 H) 2.82 (t, J = 12.00 Hz, 3 H) 2.64 (d, J = 4.29 Hz, 4 H) 1.80 (d, J = 3.03 Hz, 2 H) |
| 197 | 447.0 (M + H)⁺ | (400 MHz, DMSO-d6) δ ppm 8.96 (br s, 1 H) 8.85 (s, 1 H) 8.41 (br s, 0 H) 8.35 (d, J = 8.84 Hz, 1 H) 8.19 (d, J = 9.09 Hz, 1 H) 8.06 (d, J = 9.09 Hz, 1 H) 6.88 (d, J = 9.09 Hz, 1 H) 6.80 (d, J = 9.09 Hz, 1 H) 4.24 (d, J = 10.61 Hz, 2 H) 3.51 (br s, 3 H) 3.12 (s, 6 H) 2.82 (t, J = 11.87 Hz, 2 H) 1.90 (s, 1 H) 1.80 (br s, 2 H) |
| 198 | 448.0 (M + H)⁺ | (400 MHz, CHLOROFORM-d) δ ppm 9.60 (br s, 1 H) 8.67 (s, 1 H) 8.38 (d, J = 9.09 Hz, 1 H) 8.20 (d, J = 8.34 Hz, 1 H) 7.94 (d, J = 8.84 Hz, 1 H) 6.64 (d, J = 9.09 Hz, 1 H) 3.76 (br s, 1 H) 3.64 (s, 3 H) 3.38 (br s, 1 H) 3.26 (d, J = 11.12 Hz, 2 H) 3.21 (s, 6 H) 2.70 (br s, 2 H) 2.37 (br s, 4 H) 1.83 (br s, 2 H) |
| 199 | 351.0 (M + H)⁺ | (400 MHz, DMSO-d6) δ ppm 13.28 (br s, 1 H) 8.88 (s, 1 H) 8.68 (br s, 1 H) 8.42 (br s, 1 H) 8.36 (d, J = 8.84 Hz, 1 H) 8.05 (d, J = 8.84 Hz, 1 H) 5.40 (br s, 1 H) 4.12 (dd, J = 11.37, 4.29 Hz, 2 H) 3.59 (t, J = 11.49 Hz, 2 H) 3.54 (s, 3 H) 3.17 (d, J = 8.08 Hz, 1 H) 1.69 (d, J = 10.11 Hz, 2 H) |
| 200 | 376.1 (M + H)⁺ | (400 MHz, DMSO-d6) δ ppm 9.40 (d, J = 2.02 Hz, 1 H) 8.98 (s, 1 H) 8.62 (d, J = 7.07 Hz, 1 H) 8.50 (d, J = 8.84 Hz, 1 H) 8.35 (d, J = 9.09 Hz, 1 H) 7.48 (d, J = 8.08 Hz, 1 H) 4.10 (dd, J = 11.49, 4.17 Hz, 2 H) 3.55 (s, 3 H) 3.46-3.53 (m, 2 H) 2.89 (br s, 2 H) 2.58 (s, 3 H) 1.79 (d, J = 10.61 Hz, 2 H) |
| 201 | 393.0 (M + H)⁺ | (400 MHz, DMSO-d6) δ ppm 9.51 (s, 2 H) 8.99 (s, 1 H) 8.52 (d, J = 8.84 Hz, 1 H) 8.34 (d, J = 9.09 Hz, 1 H) 5.80 (br s, 1 H) 4.10 (dd, J = 11.49, 4.17 Hz, 2 H) 4.03 (s, 3 H) 3.50 (t, J = 12.38 Hz, 2 H) 3.55 (s, 3 H) 2.92 (br s, 2 H) 1.79 (d, J = 10.36 Hz, 2 H) |
| 202 | 351.0 (M + H)⁺ | (400 MHz, DMSO-d6) δ ppm 13.27 (br s, 1 H) 8.94 (s, 1 H) 8.43 (d, J = 8.84 Hz, 1 H) 8.31 (d, J = 8.84 Hz, 1 H) 7.94 (br s, 1 H) 7.32 (br, s, 1 H) 5.56 (br s, 0 H) 4.11 (dd, J = 11.37, 4.04 Hz, 2 H) 3.55 (s, 3 H) 3.51-3.65 (m, 2 H) 3.10 (br s, 2 H) 1.72 (d, J = 10.36 Hz, 2 H) |
| 203 | 365.2 (M + H)⁺ | (400 MHz, DMSO-d6) δ ppm 8.87 (s, 1 H) 8.62 (s, 1 H) 8.35 (d, J = 8.84 Hz, 2 H) 7.97 (d, J = 9.09 Hz, 1 H) 5.39 (br s, 0 H) 4.12 (dd, J = 11.49, 4.17 Hz, 2 H) 3.93 (s, 3 H) 3.59 (t, J = 11.49 Hz, 2 H) 3.54 (s, 3 H) 3.11 (br s, 2 H) 1.68 (d, J = 9.85 Hz, 2 H) |
| 204 | 405.2 (M + H)⁺ | (400 MHz, DMSO-d6) δ ppm 9.04 (s, 1 H) 8.87 (s, 1 H) 8.53 (br s, 1 H) 8.37 (d, J = 9.09 Hz, 1 H) 8.22 (d, J = 9.09 Hz, 1 H) 6.84 (d, J = 9.09 Hz, 1 H) 4.11 (dd, J = 11.37, 3.79 Hz, 2 H) 3.52 (s, 3 H) 3.47-3.62 (m, 2 H) 3.14 (s, 6 H) 2.90 (br s, 2 H) 1.79 (d, J = 10.61 Hz, 2 H) |
| 205 | 488.2 (M + H)⁺ | (400 MHz, DMSO-d6) δ ppm 8.97 (d, J = 2.02 Hz, 1 H) 8.87 (s, 1 H) 8.28-8.43 (m, 1 H) 8.36 (d, J = 9.09 Hz, 1 H) 8.19 (d, J = 9.09 Hz, 1 H) 6.86 (d, J = 8.59 Hz, 1 H) 4.58 (d, J = 12.63 Hz, 2 H) |

TABLE 2-continued

| Ex. No. | LRMS m/z | ¹H NMR |
|---|---|---|
| | | 3.51 (s, 3 H) 3.45-3.59 (m, 2 H) 3.13 (s, 6 H) 2.93 (t, J = 12.38 Hz, 2 H) 1.90 (br s, 2 H) 1.22 (s, 9 H) |
| 206 | 462.2 (M + H)⁺ | (400 MHz, DMSO-d6) δ ppm 9.10 (br s, 1 H) 8.83 (s, 1 H) 8.52 (d, J = 2.27 Hz, 0 H) 8.32 (d, J = 8.84 Hz, 1 H) 8.16 (d, J = 9.09 Hz, 1 H) 6.76 (d, J = 9.09 Hz, 1 H) 3.57 (br s, 2 H) 3.50 (s, 4 H) 3.27 (s, 3 H) 3.13 (s, 8 H) 3.03-3.18 (m, 2 H) 2.60 (t, J = 5.81 Hz, 2 H) 2.17 (t, J = 11.37 Hz, 2 H) 1.73 (d, J = 8.59 Hz, 2 H) |
| 207 | 418.2 (M + H)⁺ | (400 MHz, DMSO-d6) δ ppm 9.09 (d, J = 1.52 Hz, 1 H) 8.86 (s, 1 H) 8.64 (br s, 0 H) 8.36 (d, J = 9.09 Hz, 1 H) 8.22 (d, J = 9.09 Hz, 1 H) 6.78 (d, J = 9.09 Hz, 1 H) 4.10 (q, J = 5.31 Hz, 1 H) 3.52 (s, 3 H) 3.17 (d, J = 5.31 Hz, 2 H) 3.15 (s, 6 H) 3.00 (d, J = 11.62 Hz, 2 H) 2.90 (br s, 1 H) 2.32 (s, 3 H) 2.08 (t, J = 11.37 Hz, 2 H) 1.76 (d, J = 10.86 Hz, 2 H) |
| 208 | 395.2 (M + H)⁺ | (400 MHz, DMSO-d6) δ ppm 8.91 (s, 1 H) 8.67 (br s, 1 H) 8.37 (d, J = 8.84 Hz, 2 H) 8.02 (d, J = 9.09 Hz, 1 H) 4.22 (t, J = 5.56 Hz, 2 H) 4.12 (dd, J = 11.37, 4.04 Hz, 2 H) 3.81 (t, J = 5.43 Hz, 2 H) 3.59 (t, J = 11.62 Hz, 2 H) 3.54 (s, 3 H) 3.14 (br s, 2 H) 1.69 (d, J = 12.13 Hz, 2 H) |
| 209 | 490.2 (M + H)⁺ | (400 MHz, DMSO-d6) δ ppm 8.99 (d, J = 2.27 Hz, 1 H) 8.86 (s, 1 H) 8.30-8.40 (m, 2 H) 8.19 (d, J = 9.09 Hz, 1 H) 6.86 (d, J = 9.09 Hz, 1 H) 5.54 (br s, 1 H) 5.07 (br s, 1 H) 4.74 (br s, 1 H) 3.51 (s, 3 H) 3.13 (s, 6 H) 2.68 (d, J = 10.36 Hz, 3 H) 1.92 (dd, J = 5.68, 3.16 Hz, 2 H) 1.36 (s, 6 H) |
| 210 | 377.2 (M + H)⁺ | (400 MHz, DMSO-d6) δ ppm 8.95 (d, J = 2.02 Hz, 1 H) 8.87 (s, 1 H) 8.36 (d, J = 9.09 Hz, 2 H) 8.17 (d, J = 9.09 Hz, 1 H) 6.59 (d, J = 8.84 Hz, 1 H) 6.53 (d, J = 6.06 Hz, 2 H) 4.10 (dd, J = 11.37, 4.04 Hz, 2 H) 3.53 (s, 3 H) 3.47-3.59 (m, 2 H) 2.79-3.04 (m, 2 H) 1.79 (br s, 2 H) |
| 211 | 421.2 (M + H)⁺ | (400 MHz, DMSO-d6) δ ppm 8.87 (s, 1 H) 8.35 (d, J = 8.84 Hz, 2 H) 7.98 (d, J = 8.84 Hz, 1 H) 7.14 (br s, 2 H) 3.95 (s, 4 H) 3.53 (s, 4 H) 2.98-3.20 (m, 6 H) 2.20-2.40 (m, 2 H) 1.69 (d, J = 11.62 Hz, 2 H) |
| 212 | 449.2 (M + H)⁺ | (400 MHz, DMSO-d6) δ ppm 8.85 (s, 1 H) 8.24-8.40 (m, 2 H) 7.97 (d, J = 8.84 Hz, 1 H) 3.91 (s, 3 H) 3.52 (s, 3 H) 3.36 (s, 3 H) 3.16 (d, J = 2.53 Hz, 1 H) 3.14 (br s, 1 H) 3.04 (s, 4 H) 2.86 (s, 3 H) 2.37 (t, J = 10.99 Hz, 2 H) 1.66 (br s, 2 H) |
| 213 | 406.2 (M + H)⁺ | (400 MHz, DMSO-d6) δ ppm 8.88 (s, 1 H) 8.35 (d, J = 8.84 Hz, 1 H) 8.27 (br s, 1 H) 8.16 (s, 1 H) 7.97 (d, J = 8.84 Hz, 1 H) 4.71 (d, J = 9.60 Hz, 1 H) 4.07 (d, J = 13.39 Hz, 1 H) 3.95 (s, 3 H) 3.53 (s, 3 H) 3.19-3.31 (m, 3 H) 2.74 (t, J = 12.00 Hz, 2 H) 2.12 (s, 3 H) 1.82 (d, J = 8.34 Hz, 2 H) |
| 214 | 476.2 (M + H)⁺ | (400 MHz, DMSO-d6) δ ppm 8.98 (br s, 1 H) 8.88 (s, 1 H) 8.31-8.42 (m, 2 H) 8.22 (d, J = 8.84 Hz, 1 H) 6.90 (d, J = 9.09 Hz, 1 H) 5.03 (d, J = 7.83 Hz, 1 H) 4.70 (d, J = 6.57 Hz, 1 H) 4.46-4.61 (m, 0 H) 4.21-4.39 (m, 1 H) 3.52 (br s, 3 H) 3.13 (s, 8 H) 2.74 (br s, 2 H) 1.93 (br s, 2 H) 1.24 (d, J = 6.57 Hz, 3 H) |
| 215 | 450.2 (M + H)⁺ | (400 MHz, DMSO-d6) δ ppm 8.86 (s, 1 H) 8.34 (d, J = 9.09 Hz, 2 H) 8.16 (s, 1 H) 7.96 (d, J = 8.84 Hz, 1 H) 5.46 (br s, 1 H) 5.05 (br s, 1 H) 4.75 (br s, 1 H) 3.96 (s, 3 H) 3.51 (s, 4 H) 2.66 (br s, 2 H) 1.88 (s, 3 H) 1.34 (br s, 7 H) |
| 216 | 462.2 (M + H)⁺ | (400 MHz, MeOD) δ ppm 9.21 (s, 1 H) 8.73 (br s, 2 H) 8.66 (d, J = 9.09 Hz, 1 H) 8.51 (d, J = 8.84 Hz, 1 H) 7.50 (d, J = 8.08 Hz, 1 H) 4.35 (d, J = 12.63 Hz, 2 H) 4.00 (br s, 1 H) 3.67 (s, 3 H) 3.44 (s, 6 H) 3.00 (br s, 2 H) 2.65 (s, 4 H) 2.06 (br s, 2 H) |
| 217 | 421.2 (M + H)⁺ | (400 MHz, DMSO-d6) δ ppm 8.88 (s, 1 H) 8.35 (d, J = 8.84 Hz, 2 H) 8.21 (s, 1 H) 7.99 (d, J = 8.84 Hz, 1 H) 6.64 (d, J = 3.54 Hz, 1 H) 4.23 (d, J = 9.85 Hz, 2 H) 3.92 (s, 3 H) 3.53 (s, 3 H) 2.86 (t, J = 11.75 Hz, 2 H) 2.64 (d, J = 4.29 Hz, 3 H) 1.75 (d, J = 7.58 Hz, 2 H) |
| 218 | 406.2 (M + H)⁺ | (400 MHz, DMSO-d6) δ ppm 9.40 (d, J = 1.77 Hz, 1 H) 9.00 (s, 1 H) 8.62 (d, J = 7.33 Hz, 1 H) 8.49 (d, J = 8.84 Hz, 1 H) 8.34 (d, J = 8.84 Hz, 1 H) 7.48 (d, J = 8.34 Hz, 1 H) 5.88 (br s, 1 H) 5.00 (t, J = 5.56 Hz, 1 H) 4.10 (d, J = 5.05 Hz, 3 H) 4.12 (br s, 1 H) 3.74 (q, J = 5.31 Hz, 2 H) 3.52 (t, J = 11.62 Hz, 2 H) 2.89 (br s, 2 H) 2.58 (s, 3 H) 1.80 (d, J = 10.61 Hz, 2 H) |
| 219 | 422.2 (M + H)⁺ | (400 MHz, DMSO-d6) δ ppm 9.13 (d, J = 2.02 Hz, 1 H) 8.98 (s, 1 H) 8.69 (d, J = 7.83 Hz, 1 H) 8.47 (d, J = 8.84 Hz, 1 H) 8.30 (d, J = 9.09 Hz, 1 H) 7.04 (d, J = 8.84 Hz, 1 H) 4.99 (t, J = 5.56 Hz, 1 H) 4.10 (t, J = 5.05 Hz, 4 H) 3.96 (s, 3 H) 3.74 (t, J = 5.18 Hz, 2 H) 3.52 (t, J = 11.49 Hz, 2 H) 2.93 (br s, 2 H) 1.80 (d, J = 11.12 Hz, 2 H) |
| 220 | 395.2 (M + H)⁺ | (400 MHz, DMSO-d6) δ ppm 8.91-9.00 (m, 1 H) 8.64 (br s, 1 H) 8.37 (dd, J = 8.84, 2.27 Hz, 2 H) 7.95-8.06 (m, 1 H) 4.11 (t, J = 5.31 Hz, 3 H) 4.14 (d, J = 3.79 Hz, 1 H) 3.93 (s, 3 H) 3.74 (t, J = 5.31 Hz, 2 H) 3.60 (t, J = 11.37 Hz, 3 H) 3.15 (br s, 3 H) 1.70 (d, J = 9.85 Hz, 2 H) |

TABLE 2-continued

| Ex. No. | LRMS m/z | ¹H NMR |
|---|---|---|
| 221 | 381.2 (M + H)⁺ | (400 MHz, DMSO-d6) δ ppm 8.95 (s, 1 H) 8.59 (br s, 2 H) 8.37 (d, J = 8.84 Hz, 1 H) 8.07 (d, J = 8.84 Hz, 1 H) 4.11 (t, J = 5.18 Hz, 3 H) 4.15 (d, J = 4.04 Hz, 1 H) 3.74 (t, J = 5.18 Hz, 2 H) 3.60 (t, J = 11.49 Hz, 3 H) 3.20 (br s, 4 H) 1.71 (d, J = 10.36 Hz, 2 H) |
| 222 | 435.2 (M + H)⁺ | (400 MHz, DMSO-d6) δ ppm 9.04 (d, J = 2.27 Hz, 1 H) 8.90 (s, 1 H) 8.52 (br s, 1 H) 8.36 (d, J = 8.84 Hz, 1 H) 8.21 (d, J = 9.09 Hz, 1 H) 6.84 (d, J = 9.09 Hz, 1 H) 4.98 (t, J = 5.56 Hz, 1 H) 4.09 (dt, J = 11.05, 5.46 Hz, 4 H) 3.73 (q, J = 5.31 Hz, 2 H) 3.53 (t, J = 11.49 Hz, 2 H) 3.14 (s, 6 H) 2.92 (br s, 2 H) 1.79 (d, J = 10.36 Hz, 2 H) |
| 223 | 425.2 (M + H)⁺ | (400 MHz, DMSO-d6) δ ppm 8.91 (s, 1 H) 8.67 (br s, 1 H) 8.39 (br s, 1 H) 8.34 (d, J = 8.84 Hz, 1 H) 7.99 (d, J = 8.84 Hz, 1 H) 4.98 (d, J = 5.31 Hz, 2 H) 4.22 (t, J = 5.56 Hz, 2 H) 4.14 (d, J = 4.29 Hz, 1 H) 4.06-4.13 (m, 3 H) 3.81 (q, J = 5.39 Hz, 2 H) 3.73 (q, J = 5.39 Hz, 2 H) 3.60 (t, J = 11.49 Hz, 2 H) 3.31 (s, 1 H) 3.16 (br s, 2 H) 1.70 (d, J = 10.36 Hz, 2 H) |
| 224 | 423.2 (M + H)⁺ | (400 MHz, DMSO-d6) δ ppm 9.51 (s, 2 H) 9.01 (s, 1 H) 8.51 (d, J = 8.84 Hz, 1 H) 8.33 (d, J = 8.84 Hz, 1 H) 5.77 (br s, 0 H) 5.00 (t, J = 5.56 Hz, 1 H) 4.06-4.17 (m, 4 H) 4.03 (s, 3 H) 3.74 (q, J = 5.47 Hz, 2 H) 3.51 (t, J = 11.49 Hz, 2 H) 2.93 (br s, 2 H) 1.79 (d, J = 10.86 Hz, 2 H) |
| 225 | 380.2 (M + H)⁺ | (400 MHz, DMSO-d6) δ ppm 13.28 (br s, 1 H) 8.96 (s, 1 H) 8.42 (d, J = 8.84 Hz, 1 H) 8.31 (d, J = 8.34 Hz, 1 H) 7.94 (br s, 1 H) 7.34 (br s, 1 H) 4.99 (br s, 1 H) 3.74 (t, J = 5.05 Hz, 2 H) 3.51-3.65 (m, 2 H) 3.04-3.22 (m, 7 H) 1.72 (d, J = 12.63 Hz, 2 H) |
| 226 | 394.2 (M + H)⁺ | (400 MHz, DMSO-d6) δ ppm 8.86 (s, 1 H) 8.20-8.50 (m, 2 H) 7.99 (d, J = 8.84 Hz, 1 H) 4.23 (t, J = 5.43 Hz, 2 H) 3.80 (t, J = 5.43 Hz, 2 H) 3.52 (s, 5 H) 2.93 (br s, 3 H) 2.78 (t, J = 11.62 Hz, 2 H) 1.74 (br s, 2 H) |
| 227 | 377.2 (M + H)⁺ | (400 MHz, DMSO-d6) δ ppm 9.23 (br s, 2 H) 8.90 (s, 1 H) 8.41 (d, J = 9.09 Hz, 1 H) 8.29 (s, 1 H) 8.22 (d, J = 9.09 Hz, 1 H) 7.22 (s, 2 H) 3.52 (s, 3 H) 3.21 (s, 3 H) 2.67 (br s, 4 H) 1.82 (d, J = 5.05 Hz, 2 H) |
| 228 | 490.2 (M + H)⁺ | (400 MHz, DMSO-d6) δ ppm 8.99 (d, J = 2.27 Hz, 1 H) 8.86 (s, 1 H) 8.30-8.40 (m, 2 H) 8.19 (d, J = 9.09 Hz, 1 H) 6.86 (d, J = 9.09 Hz, 1 H) 5.54 (br s, 1 H) 5.07 (br s, 1 H) 4.74 (br s, 1 H) 3.51 (s, 3 H) 3.13 (s, 6 H) 2.68 (d, J = 10.36 Hz, 3 H) 1.92 (dd, J = 5.68, 3.16 Hz, 2 H) 1.36 (s, 6 H) |
| 229 | 392.2 (M + H)⁺ | (400 MHz, DMSO-d₆) δ 1.19-1.47 (m, 2 H), 1.86 (d, J = 10.11 Hz, 2 H), 2.03 (d, J = 10.61 Hz, 2 H), 2.52-2.75 (m, 2 H), 3.50 (s, 3 H), 3.54-3.67 (m, 1 H), 4.77 (d, J = 2.53 Hz, 1 H), 5.76 (br s, 1 H), 7.26 (s, 2 H), 8.19 (d, J = 8.84 Hz, 1 H), 8.40 (d, J = 9.09 Hz, 1 H), 8.88 (s, 1 H), 9.14 (s, 2 H). |
| 230 | 478.2. (M + H)⁺ | (400 MHz, DMSO-d₆) δ 1.35 (s, 6 H), 1.95 (d, J = 10.11 Hz, 2 H), 2.57-3.12 (m, 4 H), 3.52 (s, 3 H), 4.03 (s, 3 H), 4.93 (d, J = 148.04 Hz, 2 H), 5.54 (s, 1 H), 6.13 (br s, 1 H), 8.30 (d, J = 8.84 Hz, 1 H), 8.50 (d, J = 9.09 Hz, 1 H), 8.96 (s, 1 H), 9.40 (s, 2 H). |
| 231 | 350.2. (M + H)⁺ | (400 MHz, DMSO-d₆) δ 1.62 (d, J = 4.55 Hz, 3 H), 2.55 (s, 3 H), 3.54 (s, 3 H), 3.85 (br s, 1 H), 4.31 (br s, 1 H), 4.87 (br s, 1 H), 6.31 (br s, 1 H), 7.47 (d, J = 8.08 Hz, 1 H), 8.29 (d, J = 8.84 Hz, 1 H), 8.41-8.55 (m, 2 H), 8.96 (s, 1 H), 9.31 (d, J = 2.02 Hz, 1 H). |
| 232 | 339.2 (M + H)⁺ | (400 MHz, DMSO-d₆) δ 1.64 (br s, 3 H), 3.53 (s, 3 H), 3.74-4.09 (m, 4 H), 4.33 (br s, 1 H), 4.83 (t, J = 5.43 Hz, 1 H), 5.99 (br s, 1 H), 7.94 (d, J = 8.84 Hz, 1 H), 8.17 (s, 1 H), 8.34 (d, J = 8.84 Hz, 1 H), 8.45 (s, 1 H), 8.86 (s, 1 H). |
| 233 | 366.2 (M + H)⁺ | (400 MHz, DMSO-d₆) δ 1.62 (d, J = 2.27 Hz, 3 H), 3.53 (s, 3 H), 3.85 (br s, 1 H), 3.95 (s, 3 H), 4.30 (br s, 1 H), 4.89 (br s, 1 H), 6.33 (br s, 1 H), 7.02 (d, J = 8.84 Hz, 1 H), 8.23 (d, J = 9.09 Hz, 1 H), 8.43 (d, J = 8.84 Hz, 1 H), 8.51 (dd, J = 8.84, 2.53 Hz, 1 H), 8.92 (s, 1 H), 9.06 (d, J = 2.27 Hz, 1 H). |
| 234 | 386.2 (M + H)⁺ | (400 MHz, DMSO-d₆) δ 1.70 (br s, 3 H), 3.58 (s, 3 H), 3.91 (br s, 1 H), 4.31 (br s, 1 H), 5.13 (br s, 2 H), 7.77 (t, J = 7.58 Hz, 1 H), 7.86-7.99 (m, 1 H), 8.16 (dd, J = 15.66, 8.34 Hz, 2 H), 8.59-8.70 (m, 1 H), 8.72-8.85 (m, 1 H), 9.23 (s, 1 H), 9.31 (s, 1 H), 9.80 (d, J = 2.02 Hz, 1 H). |
| 235 | 352.2 (M + H)⁺ | (400 MHz, DMSO-d₆) δ 1.61 (d, J = 3.79 Hz, 3 H), 3.53 (s, 3 H), 3.84 (br s, 1 H), 4.27 (br s, 1 H), 4.87 (br s, 1 H), 6.28 (br s, 1 H), 7.16 (s, 2 H), 8.17 (d, J = 8.84 Hz, 1 H), 8.39 (d, J = 8.84 Hz, 1 H), 8.89 (s, 1 H), 9.10 (s, 2 H). |
| 236 | 407.0 (M + H)⁺ | (500 MHz, DMSO-d₆) δ 1.28 (br s, 2 H), 1.72-1.83 (m, 2 H), 1.88 (br s, 2 H), 2.63 (s, 3 H), 3.20-3.35 (m, 1 H), 3.48 (s, 2 H), 4.54 (br s, 2 H), 6.93 (br s, 1 H), 7.26 (t, J = 7.83 Hz, 1 H), 7.47 (d, J = 2.75 Hz, 1 H), 7.55 (d, J = 7.97 Hz, 1 H), 7.62 (d, J = 6.87 Hz, 1 H), 8.14 (d, J = 8.79 Hz, 1 H), 8.44 (d, J = 8.79 Hz, 1 H), 8.88 (s, 1 H), 11.35 (br s, 1 H). |
| 237 | 374.2 (M + H)⁺ | (500 MHz, DMSO-d₆) δ 1.55 (d, J = 7.14 Hz, 3 H), 2.67 (s, 3 H), 3.54 (s, 1 H), 3.71 (br s, 1 H), 4.27 (br s, 2 H), 7.08 (br s, 1 H), |

TABLE 2-continued

| Ex. No. | LRMS m/z | ¹H NMR |
|---|---|---|
| | | 7.30 (d, J = 7.97 Hz, 1 H), 7.50 (br s, 1 H), 7.57 (d, J = 8.24 Hz, 1 H), 7.63 (d, J = 7.69 Hz, 1 H), 8.17 (d, J = 8.79 Hz, 1 H), 8.48 (d, J = 8.79 Hz, 1 H), 8.93 (s, 1 H), 11.32 (br s, 1 H). |
| 238 | 376.2 (M + H)⁺ | (400 MHz, DMSO-d₆) δ 1.65 (br s, 3 H), 2.54 (br s, 1 H), 3.55 (br s, 3 H), 3.87 (br s, 1 H), 4.34 (br s, 1 H), 4.89 (br s, 1 H), 8.32 (s, 1 H), 8.37 (d, J = 8.84 Hz, 1 H), 8.51 (d, J = 8.84 Hz, 1 H), 8.96 (br s, 1 H), 9.03 (br s, 1 H), 9.44 (br s, 1 H), 13.84 (br s, 1 H). |
| 239 | 339.2 (M + H)⁺ | (400 MHz, DMSO-d₆) δ 1.63 (br s, 3 H), 3.52 (s, 3 H), 3.95 (s, 4 H), 4.32 (br s, 1 H), 4.83 (t, J = 5.18 Hz, 1 H), 6.28 (br s, 1 H), 7.94 (d, J = 8.84 Hz, 1 H), 8.17 (s, 1 H), 8.33 (d, J = 9.09 Hz, 1 H), 8.44 (s, 1 H), 8.85 (s, 1 H). |
| 240 | 386.2 (M + H)⁺ | (400 MHz, DMSO-d₆) δ 1.68 (br s, 3 H), 3.56 (s, 3 H), 3.91 (br s, 1 H), 4.34 (br s, 1 H), 4.93 (br s, 1 H), 6.42 (br s, 1 H), 7.72 (t, J = 7.45 Hz, 1 H), 7.86 (t, J = 7.71 Hz, 1 H), 8.12 (t, J = 9.47 Hz, 2 H), 8.42-8.51 (m, 1 H), 8.53-8.67 (m, 1 H), 8.99 (s, 1 H), 9.19 (s, 1 H), 9.80 (s, 1 H). |
| 241 | 366.2 (M + H)⁺ | (400 MHz, DMSO-d₆) δ 1.62 (br s, 3 H), 3.54 (s, 3 H), 3.85 (br s, 1 H), 3.96 (s, 3 H), 4.29 (br s, 1 H), 4.88 (br s, 1 H), 6.29 (br s, 1 H), 7.03 (d, J = 8.84 Hz, 1 H), 8.26 (d, J = 8.84 Hz, 1 H), 8.45 (d, J = 8.84 Hz, 1 H), 8.53 (dd, J = 8.72, 2.40 Hz, 1 H), 8.93 (s, 1 H), 9.07 (d, J = 2.27 Hz, 1 H). |
| 242 | 418.2 (M + H)⁺ | (400 MHz, DMSO-d₆) δ 1.88 (br s, 2 H), 2.11 (s, 3 H), 2.66 (br s, 3 H), 3.06-3.26 (m, 1 H), 3.52 (s, 3 H), 4.08 (d, J = 12.88 Hz, 1 H), 4.70 (d, J = 9.09 Hz, 1 H), 5.65 (br s, 1 H), 6.53 (s, 2 H), 6.61 (d, J = 8.59 Hz, 1 H), 8.16 (d, J = 9.09 Hz, 1 H), 8.21 (dd, J = 8.84, 2.27 Hz, 1 H), 8.35 (d, J = 9.09 Hz, 1 H), 8.77-8.93 (m, 2 H). |
| 243 | 474.2 (M + H)⁺ | (400 MHz, DMSO-d₆) δ 1.90 (d, J = 9.35 Hz, 2 H), 2.05-2.23 (m, 3 H), 2.59-3.14 (m, 3 H), 3.15-3.79 (m, 7 H), 4.09 (d, J = 12.38 Hz, 1 H), 4.76 (d, J = 9.85 Hz, 1 H), 6.13 (br s, 1 H), 7.70 (d, J = 8.59 Hz, 2 H), 8.20 (d, J = 8.59 Hz, 2 H), 8.26 (d, J = 8.84 Hz, 1 H), 8.44 (d, J = 9.09 Hz, 1 H), 8.94 (s, 1 H), 9.12 (br s, 1 H). |
| 244 | 504.2 (M + H)⁺ | (400 MHz, DMSO-d₆) δ 2.35 (br s, 1 H), 2.48 (d, J = 2.14 Hz, 4 H), 2.63 (br s, 15 H), 3.27 (s, 2 H), 7.59 (s, 3 H), 8.08 (s, 1 H), 8.10 (s, 1 H), 8.15 (s, 1 H), 8.17 (s, 1 H), 8.36 (s, 1 H), 8.38 (s, 1 H), 8.86 (s, 1 H). |
| 245 | 490.1 (M + H)⁺ | (400 MHz, DMSO-d₆) δ 2.49 (br s, 5 H), 2.63 (br s, 15 H), 3.26 (s, 2 H), 7.58 (s, 1 H), 8.10 (s, 1 H), 8.19 (s, 1 H), 8.38 (s, 1 H), 8.88 (s, 1 H) |
| 246 | 480.2 (M + H)⁺ | (400 MHz, DMSO-d₆) δ 1.87 (br s, 2 H), 2.02 (s, 3 H), 2.67 (d, J = 33.67 Hz, 4 H), 3.26 (br s, 2 H), 3.52 (s, 3 H), 4.01 (d, J = 11.71 Hz, 2 H), 4.69 (d, J = 9.27 Hz, 2 H), 8.12 (d, J = 8.30 Hz, 2 H), 8.33 (d, J = 8.78 Hz, 1 H), 8.41 (d, J = 8.30 Hz, 1 H), 8.53 (d, J = 8.78 Hz, 1 H), 8.98 (s, 2 H). |
| 247 | 468.1 (M + H)⁺ | (400 MHz, DMSO-d₆) δ 1.91 (t, J = 10.98 Hz, 1 H), 2.04 (s, 2 H), 2.64 (s, 1 H), 2.88 (t, J = 11.22 Hz, 1 H), 3.25 (d, J = 2.44 Hz, 3 H), 3.42 (d, J = 11.71 Hz, 1 H), 3.50 (s, 2 H), 3.99 (d, J = 14.64 Hz, 2 H), 4.60 (d, J = 11.22 Hz, 2 H), 6.56 (s, 1 H), 7.67 (t, J = 7.81 Hz, 1 H), 7.94 (d, J = 1.95 Hz, 1 H), 8.14 (d, J = 7.81 Hz, 1 H), 8.37 (d, J = 9.27 Hz, 1 H), 8.49 (d, J = 9.27 Hz, 1 H), 8.61 (d, J = 2.44 Hz, 1 H), 8.80-8.89 (m, 1 H), 8.93 (s, 1 H). |
| 248 | 426.1 (M + H)⁺ | (500 MHz, DMSO-d₆) δ 0.86 (d, J = 10.74 Hz, 2 H), 1.69 (d, J = 11.71 Hz, 4 H), 2.35 (s, 1 H), 2.63 (s, 1 H), 3.12 (d, J = 4.88 Hz, 1 H), 3.23 (d, J = 12.69 Hz, 1 H), 3.50 (s, 2 H), 3.98 (d, J = 5.86 Hz, 1 H), 4.30 (br s, 1 H), 5.53 (br s, 1 H), 7.51 (dd, J = 8.78, 3.90 Hz, 1 H), 7.86-7.93 (m, 1 H), 7.98 (d, J = 7.81 Hz, 1 H), 8.16 (d, J = 9.76 Hz, 1 H), 8.54 (d, J = 8.78 Hz, 1 H), 8.69 (br s, 1 H), 8.91-9.08 (m, 1 H). |
| 249 | 453.1 (M + H)⁺ | (500 MHz, DMSO-d₆) δ 1.81 (d, J = 13.66 Hz, 4 H), 2.08 (d, J = 10.74 Hz, 1 H), 2.35 (s, 1 H), 2.63 (s, 3 H), 3.22 (d, J = 9.76 Hz, 1 H), 3.51 (s, 2 H), 3.75 (d, J = 10.74 Hz, 1 H), 4.40 (d, J = 12.69 Hz, 1 H), 7.53 (dd, J = 8.78, 3.90 Hz, 1 H), 7.83-7.94 (m, 2 H), 7.99 (d, J = 8.78 Hz, 1 H), 8.14 (d, J = 7.81 Hz, 1 H), 8.55 (d, J = 8.78 Hz, 1 H), 8.71 (br s, 1 H), 8.94 (d, J = 3.90 Hz, 1 H), 8.99 (s, 1 H). |
| 250 | 416.2 (M + H)⁺ | (400 MHz, DMSO-d₆) δ 1.09-1.38 (m, 2 H), 1.91 (d, J = 10.36 Hz, 4 H), 2.52-2.82 (m, 2 H), 3.47 (t, J = 10.86 Hz, 1 H), 3.57 (s, 3 H), 4.24-7.63 (m, 4 H), 7.84 (d, J = 4.80 Hz, 1 H), 8.51 (d, J = 9.09 Hz, 1 H), 8.57 (s, 1 H), 8.72-8.87 (m, 2 H), 9.26 (s, 1 H), 13.99 (br s, 1 H). |
| 251 | 443.2 (M + H)⁺ | (400 MHz, DMSO-d₆) δ 1.93 (d, J = 7.83 Hz, 2 H), 2.01 (s, 3 H), 2.51-2.81 (m, 3 H), 3.04 (t, J = 12.76 Hz, 1 H), 3.54 (s, 3 H), 3.95 (d, J = 13.39 Hz, 1 H), 4.59 (d, J = 8.59 Hz, 1 H), 6.13 (br s, 1 H), 7.78 (d, J = 4.80 Hz, 1 H), 8.35 (d, J = 8.84 Hz, 1 H), 8.52-8.65 (m, 2 H), 8.72 (d, J = 4.80 Hz, 1 H), 9.03 (s, 1 H), 13.94 (s, 1 H). |

TABLE 2-continued

| Ex. No. | LRMS m/z | ¹H NMR |
|---|---|---|
| 252 | 459.1 (M + H)⁺ | (500 MHz, DMSO-d₆) δ 1.95 (br s, 1 H), 2.54 (br s, 1 H), 2.62 (br s, 2 H), 2.96 (br s, 1 H), 3.14 (d, J = 4.88 Hz, 4 H), 3.25 (s, 1 H), 3.53 (s, 2 H), 3.83 (br s, 1 H), 4.01 (d, J = 15.62 Hz, 1 H), 4.01 (d, J = 4.88 Hz, 2 H), 4.09 (d, J = 13.66 Hz, 1 H), 4.51 (t, J = 5.37 Hz, 1 H), 7.78 (d, J = 4.88 Hz, 1 H), 8.36 (d, J = 8.78 Hz, 1 H), 8.55-8.65 (m, 1 H), 8.70 (d, J = 4.88 Hz, 1 H), 9.03 (s, 1 H). |
| 253 | 473.2 (M + H)⁺ | (500 MHz, DMSO-d₆) δ 1.14 (br s, 3 H), 1.82 (s, 5 H), 1.96 (br s, 2 H), 2.94 (br s, 2 H), 4.13 (br s, 1 H), 4.42 (d, J = 21.47 Hz, 2 H), 4.55 (br s, 1 H), 6.21 (br s, 2 H), 7.77 (br s, 1 H), 8.34 (d, J = 8.78 Hz, 1 H), 8.50-8.63 (m, 2 H), 8.70 (br s, 1 H), 9.01 (s, 1 H). |
| 254 | 442.2 (M + H)⁺ | (400 MHz, CHLOROFORM-d) δ 1.88-2.04 (m, 2 H), 2.08 (br s, 3 H), 2.62 (t, J = 12.51 Hz, 1 H), 2.82 (br s, 1 H), 3.02 (br s, 1 H), 3.24 (t, J = 12.25 Hz, 1 H), 3.64 (s, 3 H), 3.95 (d, J = 13.14 Hz, 1 H), 4.85 (d, J = 12.88 Hz, 1 H), 6.28 (br s, 1 H), 7.54-7.64 (m, 1 H), 7.70 (t, J = 7.20 Hz, 2 H), 8.12 (d, J = 8.84 Hz, 1 H), 8.56 (d, J = 8.84 Hz, 2 H), 8.79 (s, 1 H), 11.02 (br s, 1 H). |
| 255 | 472.2 (M + H)⁺ | (400 MHz, DMSO-d₆) δ 1.18 (d, J = 6.32 Hz, 3 H), 1.99 (br s, 2 H), 2.55 (br s, 3 H), 2.96 (t, J = 12.63 Hz, 1 H), 3.53 (s, 3 H), 4.15 (d, J = 12.38 Hz, 1 H), 4.35-4.71 (m, 2 H), 4.91 (br s, 1 H), 6.35 (br s, 1 H), 7.49-7.63 (m, 1 H), 7.66-7.87 (m, 2 H), 8.26 (d, J = 9.09 Hz, 1 H), 8.53 (d, J = 8.84 Hz, 1 H), 8.60 (s, 1 H), 8.98 (s, 1 H), 13.35 (s, 1 H). |
| 256 | 458.2 (M + H)⁺ | (400 MHz, DMSO-d₆) δ 1.97 (br s, 2 H), 2.50-2.79 (m, 3 H), 2.94 (t, J = 11.75 Hz, 1 H), 3.54 (s, 3 H), 3.83 (d, J = 12.88 Hz, 1 H), 3.98-4.20 (m, 2 H), 4.45-4.71 (m, 2 H), 6.31 (br s, 1 H), 7.47-7.61 (m, 1 H), 7.74 (dd, J = 14.27, 7.71 Hz, 2 H), 8.27 (d, J = 8.84 Hz, 1 H), 8.54 (d, J = 8.84 Hz, 1 H), 8.59 (s, 1 H), 8.99 (s, 1 H), 13.36 (s, 1 H). |
| 257 | 447.2 (M + H)⁺ | (400 MHz, DMSO-d₆) δ 1.24 (d, J = 6.06 Hz, 3 H), 1.93 (br s, 2 H), 2.56 (s, 3 H), 2.63-3.01 (m, 3 H), 3.14 (br s, 1 H), 3.53 (s, 3 H), 4.30 (t, J = 14.15 Hz, 1 H), 4.45-4.61 (m, 1 H), 4.67 (d, J = 9.35 Hz, 1 H), 4.83-7.04 (m, 2 H), 7.34-7.62 (m, 1 H), 8.30 (d, J = 9.09 Hz, 1 H), 8.39-8.59 (m, 2 H), 8.97 (s, 1 H), 9.30 (br s, 1 H). |
| 258 | 473.2 (M + H)⁺ | (300 MHz, DMSO-d₆) δ 13.87 (s, 1 H), 9.45 (d, J = 2.07 Hz, 1 H), 9.03 (s, 1 H), 8.98 (s, 1 H), 8.50-8.56 (m, 1 H), 8.39 (d, J = 8.85 Hz, 1 H), 8.33 (s, 1 H), 6.19 (bs, 1 H), 5.02 (d, J = 6.78 Hz, 1 H), 4.63-4.75 (m, 1 H), 4.45-4.60 (m, 1 H), 4.26-4.38 (m, 1 H), 3.54 (s, 3 H), 3.09-3.25 (m, 1 H), 2.62-2.76 (m, 3 H), 2.01 (d, J = 9.23 Hz, 2 H), 1.22 (s, 3 H) |
| 259 | 443.2 (M + H)⁺ | (300 MHz, DMSO-d₆) δ 13.86 (s, 1 H), 9.43 (d, J = 1.88 Hz, 1 H), 8.92-9.03 (m, 2 H), 8.48-8.57 (m, 1 H), 8.30-8.42 (m, 2 H), 5.99 (bs, 1 H), 4.70 (s, 1 H), 4.07 (s, 1 H), 3.55 (s, 3 H), 3.22 (s, 2 H), 2.66 (s, 2 H), 2.08 (s, 3 H), 1.95 (s, 2 H) |
| 260 | 473.2 (M + H)⁺ | (300 MHz, DMSO-d₆) δ 13.86 (s, 1 H), 9.44 (d, J = 2.07 Hz, 1 H), 9.01 (d, J = 1.70 Hz, 1 H), 8.98 (s, 1 H), 8.50-8.55 (m, 1 H), 8.39 (d, J = 8.85 Hz, 1 H), 8.34 (s, 1 H), 6.13 (bs, 1 H), 4.61-4.73 (m, 1 H), 4.18 (d, J = 9.42 Hz, 2 H), 4.06 (d, J = 13.75 Hz, 1 H), 3.54 (s, 3 H), 3.32 (s, 3 H), 3.15 (t, J = 14.51 Hz, 1 H), 2.62-2.78 (m, 3 H), 1.99 (d, J = 9.80 Hz, 2 H) |
| 261 | 487.2 (M + H)⁺ | (300 MHz, DMSO-d₆) δ 13.88 (s, 1 H), 9.48 (d, J = 2.07 Hz, 1 H), 9.04 (d, J = 1.88 Hz, 1 H), 8.97 (s, 1 H), 8.53 (d, J = 9.04 Hz, 1 H), 8.39 (d, J = 9.04 Hz, 1 H), 8.32 (s, 1 H), 5.58 (s, 1 H), 4.96 (bs, 2 H), 3.54 (s, 3 H), 3.29 (s, 2 H), 2.73 (s, 2 H), 2.01 (s, 2 H), 1.34 (s, 6 H) |
| 262 | 459.2 (M + H)⁺ | (300 MHz, DMSO-d₆) δ 13.87 (s, 1 H), 9.44 (d, J = 1.88 Hz, 1 H), 8.95-9.05 (m, 2 H), 8.51-8.56 (m, 1 H), 8.40 (d, J = 9.04 Hz, 1 H), 8.33 (s, 1 H), 4.61 (s, 2 H), 4.19 (s, 2 H), 3.99 (s, 1 H), 3.55 (s, 3 H), 3.14 (s, 1 H), 2.73 (s, 3 H), 2.01 (s, 2 H) |
| 263 | 415.2 (M + H)⁺ | (300 MHz, DMSO-d₆) δ 13.90 (s, 1 H), 9.54 (s, 1 H), 9.25 (s, 1 H), 8.96 (s, 1 H), 8.49-8.56 (m, 1 H), 8.39-8.47 (m, 1 H), 8.28 (s, 1 H), 5.75 (bs, 1 H), 3.55 (s, 3 H), 3.13 (dd, J = 8.57, 3.49 Hz, 2 H), 2.89-3.05 (m, 2 H), 2.42 (s, 3 H), 2.18-2.34 (m, 2 H), 1.80-1.91 (m, 2 H) |
| 264 | 401.2 (M + H)⁺ | (300 MHz, DMSO-d₆) δ 9.44 (d, J = 1.88 Hz, 2 H) 9.03-9.08 (m, 2 H) 8.75 (s, 1 H) 8.57-8.63 (m, 1 H) 8.46 (d, J = 8.85 Hz, 1 H) 8.39 (s, 1 H) 6.34 (s, 1 H) 3.55 (s, 5 H) 2.99 (s, 2 H) 2.87 (d, J = 13.56 Hz, 2 H) 2.25 (s, 2 H). |
| 265 | 546.2 (M + H)⁺ | (300 MHz, DMSO-d₆) δ 8.95 (s, 1 H), 8.69 (s, 1 H), 8.43 (d, J = 9.04 Hz, 1 H), 8.25 (d, J = 9.23 Hz, 1 H), 8.15 (d, J = 8.67 Hz, 2 H) 7.62 (d, J = 8.67 Hz, 2 H), 6.27 (s, 1 H), 4.22 (s, 2 H), 3.85 (s, 1 H), 3.53 (s, 3 H), 3.08-3.17 (m, 2 H), 2.90 (s, 2 H), 1.92 (s, 2 H), 1.45 (s, 9 H), 1.24 (s, 2 H), 1.07 (t, J = 7.16 Hz, 3 H) |
| 266 | 420.2 (M + H)⁺ | (300 MHz, DMSO-d6) δ 9.15-9.45 (m, 3 H) 9.06 (d, J = 9.4 Hz, 1 H) 8.69 (d, J = 9.0 Hz, 1H) 7.86 (d, J = 9.4 Hz, 1 H) 5.62 (br, s, |

TABLE 2-continued

| Ex. No. | LRMS m/z | ¹H NMR |
|---|---|---|
| | | 2H), 4.60 (bs, s, 2H), 4.54 (s, 3H), 4.46 (br, s, 2H), 4.12 (br, s, 6H), 3.93 (s, 3H) |
| 267 | 415.2 (M + H)⁺ | (300 MHz, DMSO-d6) δ 1.86-2.08 (m, 2 H) 2.43 (d, J = 11.7 Hz, 2 H) 2.63 (d, J = 11.5 Hz, 2 H) 2.90-3.19 (m, 2 H) 3.98 (s, 3 H) 4.27-4.48 (m, 1H), 6.81 (br, s 1H), 8.41 (d, J = 9.0 Hz, 1H), 8.81 (d, J = 9.2 Hz, 1H), 8.95-9.05 (m, 2H), 9.08 (s, 1H), 9.20 (d, J = 3.2 Hz, 2H) |
| 268 | 416.2 (M + H)⁺ | (300 MHz, DMSO-d6) δ 1.76-2.09 (m, 2 H) 2.44 (dd, 4 H) 2.97 (q, J = 12.4 Hz, 2 H) 3.90 (s, 3 H) 4.20-4.44 (m, 1H), 6.51 (br, s 1H), 8.82 (d, J = 9.2 Hz, 1H), 9.06 (d, J = 9.2 Hz, 1H), 8.13-9.26 (m, 2H), 9.92-10.18 (m, 2H) |
| 269 | 421.2 (M + H)⁺ | (300 MHz, DMSO-d6) δ 3.56 (t, J = 11.3 Hz, 2 H) 3.92 (s, 3 H) 4.09-4.34 (m, 6 H) 4.39-4.57 (m, 5 H) 5.64 (br s, 2 H) 7.84 (d, J = 9.2 Hz, 1H), 8.66 (d, J = 9.2 Hz, 1H), ), 9.03 (d, J = 9.2 Hz, 1H), 9.21-9.41 (m, 3H) |
| 270 | 366.2 (M + H)⁺ | (300 MHz, DMSO-d6) δ 3.70 (s, 3H) 3.94 (s, 3 H) 4.41 (t, J = 4.5 Hz,, 2H) 4.53 (s, 3 H) 5.36 (br s, 2 H) 7.87 (d, J = 9.2 Hz, 1H), 8.67 (d, J = 8.7 Hz, 1H), 9.01 (d, J = 8.1 Hz, 1H), 9.22 (br, s 1 H), 9.32 (br, s, 1 H), 9.42 (d, J = 8.7 Hz, 1H) |
| 271 | 380.2 (M + H)⁺ | (300 MHz, DMSO-d6) δ 2.16-2.35 (m, 2 H) 3.31 (s, 3 H) 3.56 (t, J = 5.8 Hz, 2 H) 3.65 (s, 3 H) 4.05 (s, 3 H) 4.86 (t, 2 H), 6.91 (d, J = 8.9 Hz, 1H), 8.05 (d, J = 9.0 Hz, 1H), 8.50 (dd, J = 8.9; 2.4 Hz, 1H), 8.60 (d, J = 9.6 Hz, 1H) 8.71 (br, s, 1H), 9.04 (d, J = 2.1 Hz, 1H) |
| 272 | 462.40 (M + H)⁺ | (300 MHz, CDCl₃) δ 1.14-1.35 (m, 2 H) 1.38 (d, J = 6.59 Hz, 3 H) 1.93-2.17 (m, 2 H) 2.80-3.01 (m, 2 H) 3.15-3.38 (m, 2 H) 3.61, J = 4.71 Hz, 3 H) 3.92 (s, 3 H) 4.39-4.67 (m, 1 H) 4.81-5.08 (m, 1 H) 7.00-7.16 (m, 2 H) 7.93-8.12 (m, 3 H) 8.41 (d, J = 9.04 Hz, 1 H) 8.70 (s, 1 H) |
| 273 | 448.40 (M + H)⁺ | (500 MHz, DMSO-d6) δ 2.68-2.87 (m, 2 H) 3.07-3.19 (m, 3 H) 3.24 (s, 2 H) 3.50 (s, 3 H) 3.82 (s, 3 H) 3.86-4.02 (m, 2 H) 4.05-4.24 (m, 2 H) 4.46-4.59 (m, 1 H) 4.62-4.72 (m, 1 H) 7.09 (d, J = 7.81 Hz, 2 H) 8.10-8.24 (m, 3 H) 8.39 (d, J = 8.78 Hz, 1 H) 8.88 (s, 1 H) |
| 274 | 432.20 (M + H)⁺ | (500 MHz, DMSO-d6) δ 2.08 (s, 3 H) 2.65-2.78 (m, 4 H) 3.14-3.28 (m, 2 H) 3.53 (s, 3 H) 3.85 (s, 3 H) 3.97-4.15 (m, 2 H) 4.65-4.81 (m, 1 H) 7.14 (d, J = 8.78 Hz, 2 H) 8.21 (t, J = 8.78 Hz, 3 H) 8.42 (d, J = 8.78 Hz, 1 H) 8.91 (s, 1 H) |
| 275 | 462.20 (M + H)⁺ | (300 MHz, DMSO-d6) δ 1.22 (d, J = 6.03 Hz, 3 H) 1.88-2.12 (m, 2 H) 2.58-2.81 (m, 3 H) 3.04-3.21 (m, 1 H) 3.53 (s, 3 H) 3.88 (s, 3 H) 4.18-4.35 (m, 1 H) 4.41-4.61 (m, 1 H) 4.62-4.77 (m, 1 H) 4.84-5.04 (m, 1 H) 6.19 (br s, 1 H) 7.04-7.20 (m, 1 H) 7.45-7.62 (m, 1 H) 7.76 (br s, 1 H) 7.80-7.93 (m, 1 H) 8.30 (d, J = 9.23 Hz, 1 H) 8.49 (d, J = 9.04 Hz, 1 H) 8.97 (s, 1 H) |
| 276 | 448.40 (M + H)⁺ | (400 MHz, CDCl₃) δ 1.81-2.16 (m, 4 H) 2.83-3.03 (m, 2 H) 3.13-3.32 (m, 1 H) 3.61 (s, 3 H) 3.66-3.78 (m, 1 H) 3.90 (s, 3 H) 4.21 (br s, 2 H) 4.81-4.99 (m, 1 H) 5.23 (br s, 0 H) 7.05 (d, J = 7.58 Hz, 1 H) 7.46 (t, J = 7.71 Hz, 1 H) 7.60 (br s, 1 H) 7.67 (d, J = 7.33 Hz, 1 H) 8.01 (d, J = 8.84 Hz, 1 H) 8.45 (d, J = 8.84 Hz, 1 H) 8.73 (s, 1 H) |
| 277 | 432.20 (M + H)⁺ | (400 MHz, CDCl₃) δ 1.57-1.83 (m, 3 H) 1.90-2.07 (m, 2 H) 2.15 (s, 3 H) 2.72-2.86 (m, 1 H) 3.23-3.36 (m, 1 H) 3.62 (s, 3 H) 3.91 (s, 3 H) 3.98-4.09 (m, 1 H) 4.90-5.04 (m, 1 H) 7.05 (dd, J = 8.21, 2.40 Hz, 1 H) 7.50 (t, J = 7.96 Hz, 1 H) 7.59-7.67 (m, 1 H) 7.73 (d, J = 7.58 Hz, 1 H) 8.03 (d, J = 9.09 Hz, 1 H) 8.46 (d, J = 8.84 Hz, 1 H) 8.73 (s, 1 H) |
| 278 | 462.20 (M + H)⁺ | (300 MHz, CDCl₃) δ 1.32 (d, J = 6.59 Hz, 3 H) 1.89-2.15 (m, 2 H) 2.70-2.97 (m, 2 H) 3.06-3.24 (m, 2 H) 3.62 (s, 3 H) 3.77-3.91 (m, 2 H) 3.93 (s, 3 H) 4.30-4.54 (m, 1 H) 4.78-4.98 (m, 1 H) 5.80-6.25 (m, 1 H) 7.03-7.22 (m, 2 H) 7.39-7.59 (m, 1 H) 7.66-7.88 (m, 1 H) 8.04-8.23 (m, 1 H) 8.38 (d, J = 9.04 Hz, 1 H) 8.73 (s, 1 H) |
| 279 | 448.20 (M + H)⁺ | (300 MHz, CDCl₃) δ 1.84-2.10 (m, 4 H) 2.75-2.94 (m, 2 H) 3.08-3.17 (m, 3 H) 3.49-3.61 (m, 1 H) 3.62 (s, 3 H) 3.92 (s, 3 H) 3.96-4.06 (m, 0 H) 4.06-4.21 (m, 1 H) 4.78-4.96 (m, 1 H) 5.46-6.16 (m, 0 H) 7.02-7.18 (m, 2 H) 7.39-7.54 (m, 1 H) 7.67-7.83 (m, 1 H) 8.10 (d, J = 9.04 Hz, 1 H) 8.38 (d, J = 8.85 Hz, 1 H) 8.73 (s, 1 H) |
| 280 | 432.2 (M + H)⁺ | (500 MHz, DMSO-d6) δ 1.94 (s, 3 H) 2.24-2.45 (m, 2 H) 3.05 (t, J = 12.69 Hz, 2 H) 3.19-3.32 (m, 2 H) 3.51 (s, 3 H) 3.86 (s, 3 H) 3.89-4.07 (m, 2 H) 4.55-4.67 (m, 1 H) 7.11 (t, J = 7.32 Hz, 1 H) 7.19 (d, J = 8.78 Hz, 1 H) 7.42-7.52 (m, 1 H) 7.80 (d, J = 6.83 Hz, 1 H) 8.08 (d, J = 8.78 Hz, 1 H) 8.37 (d, J = 8.78 Hz, 1 H) 8.92 (s, 1 H) |

Example 19

PI3-Kα Biochemical Assay

Compounds of the present invention were evaluated for potency against PI3-Kα using an in vitro kinase assay. PI3-Kα activity is measured in vitro by determining the level of phosphorylation of the substrate PI(4,5)P$_2$. The formation of product PI(3,4,5)P$_3$ is monitored by binding to the Grip1 PH domain in a ligand displacement fluorescence polarization (FP) assay, in which the TAMRA-labeled PI(3,4,5)P$_3$ complexed with Grip1 PH domain is displaced by PI(3,4,5)P$_3$ formed in the PI3-Kα reaction resulting in a decrease in FP signal. Mouse PI3-Kα P110 and P85 subunits were co-expressed in insect cells and co-purified to homogeneity. PI(4,5)P$_2$ were obtained from Cayman. TAMRA-labeled PI(3,4,5)P$_3$ were from Echelon, Grip1 PH domain from Dundee and other reagents were from Sigma.

All assays were performed in a Corning solid black 96-well half area plate using LJL Analyst (Molecular Devices) at room temperature. The assay buffer contained 50 mM HEPES, pH 7.4, 150 mM NaCl, 5 mM DTT, and 0.05% CHAPS. Dry powder PI(4,5)P$_2$ was dissolved in 50 mM TRIS, pH 8 to make 1 mM stock solution. The PI(4,5)P$_2$ stock solution was then diluted in the assay buffer to 60 μM, and sonicated for 30 sec before use. To the assay plate, the following reagents were added in sequence: 10 μL of 60 μM PI(4,5)P$_2$, 5 μL of 4 nM PI3-Kα, 2 μL of compound in 25% DMSO, 3 μL of mixture containing 200 μM ATP and 33 mM MgCl$_2$. The final volume for the reaction was 20 μL. The reaction mixture was incubated at room temperature for 35 min. The reaction was then stopped by 20 μL of 20 mM EDTA. After the reaction was stopped, 15 μL of the assay mixture was transferred to a 96-well half area plate containing 15 μL detection mixture of 480 nM Grip1 PH domain and 12 nM TAMRA-labeled PI(3,4,5)P$_3$. The FP signal was allowed to develop for 40 min before reading on a LJL analyst at excitation 535 nm and emission 580 nm.

The percentage of inhibition was calculated based on the following equation $$\% \text{ inhibition} = [1 - (FP_{compound} - FP_{max})/(FP_{min} - FP_{max})] \times 100,$$

where $FP_{compound}$ is the FP reading at a given compound concentration, $FP_{min}$ is the FP signal of the PI3-Kα reaction in the absence of a compound, and $FP_{max}$ is the background FP signal in the absence of PI3-Kα and a compound. The IC$_{50}$ was determined by fitting the FP signal vs. compound concentration to a sigmoidal dose response equation using GraphPad Prism curve fitting program. The K$_i$ was calculated from IC$_{50}$ based on the equation $K_i = IC_{50}/(1+[ATP]/K_m)$, where [ATP]=30 uM and $K_m$=25 uM

Example 20 mTOR Biochemical Assay

Compounds of the present invention were evaluated for potency against mTOR using an in vitro kinase assay. mTOR activity is measured in vitro by determining the level of phosphorylation of the protein substrate 4EBP-1. The phosphorylation of GFP-4E-BP1 at tyrosine residue is recognized by Ab Tb-anti-p4E-BP1, which results in time-resolved fluorescence resonance energy transfer (TR-FRET) between GFP and terbium in the Ab—product complex. Recombinant mTOR kinase domain, GFP-4E-BP1, and Lantha Ab Tb-anti-p4E-BP1, and TR-FRET dilution buffer were from Invitrogen. All other reagents were from Sigma.

All assays were performed in a Corning white 384-well non-binding surface plate using Safire2 plate reader (TECAN) at room temperature. The assay buffer contained 50 mM HEPES pH 7.5, 0.01% polysorbate, 1 mM EGTA and 10 mM MnCl2. To the assay plate, substrate GFP-4E-BP-1 and mTOR in the assay buffer were mixed first and the reaction was initiated by addition of ATP. The final concentrations in the reactions were 1 nM mTOR, 400 nM GFP-4E-BP1 and 4 μM ATP. The total volume of the reaction was 10 μL. The reaction mixture was incubated for 20 min followed by addition of 10 μL of 20 mM EDTA, and 4 mM Ab Tb-anti-p4E-BP1 to stop the reaction and detect the product. The FRET signal was allowed to develop for 1 hour before reading on Safire2 plate reader at excitation 485 nm and emission 515 nm.

The percentage of inhibition was calculated based on the following equation $$\% \text{ inhibition} = [1 - (FRET_{compound} - FRET_{min})/(FRET_{max} - FRET_{min})] \times 100,$$

where $FRET_{compound}$ is the FRET reading at a given compound concentration, $FRET_{max}$ is the FRET signal of the mTOR reaction in the absence of a compound, and $FRET_{min}$ is the background FRET signal in the absence of mTOR and a compound. The IC$_{50}$ was determined by fitting the FP signal vs. compound concentration to a sigmoidal dose response equation using GraphPad Prism curve fitting program. The K$_i$ was calculated from IC$_{50}$ based on the equation $K_i = IC_{50}/(1+[ATP]/K_m)$, where [ATP]=4 μM and $K_m$=2.6 μM.

Example 21

PI3-Kα Cellular Assay

Compounds of the present invention were evaluated for potency against PI3-K using a cellular assay as follows. The activity of PI3-K in cells is determined by measuring the level of phosphorylation of AKT at serine 473. AKT Ser phosphorylation is measured using anti-phospho-AKT (Ser473) antibodies (Cell Signaling #4058) in an ELISA format.

Healthy growing human breast cancer cells BT20 (PI3K mutated) are used for the assay. BT20 cells are grown in 10% FBS+GLN (1:100)+PS (1:100)+1 mM Sodium Pyruvate+0.1 mM Sodium Bicarbonate+Non-Essential Amino Acids Solution (1:100) MEM medium (MEM+all). When the cells are near 85%+ confluence, the cells are rinsed with PBS once and are trypsinized with trypsin EDTA for 3 minutes. The cells are re-suspended in 10% FBS MEM all and are centrifuged down at 1400 rpm for 5 minutes. The cells are re-suspended in 0.5% FBS MEM all and are counted on a cell counter. The cells are seeded at 25,000 cells/well in volume of 100 μL/well in 10% or 0.5% FBS MEM all in a 96 well flat-bottom plate. The negative control wells receive only 100 μL of 0.5% FBS MEM all medium without cells. The plate is incubated overnight in a cell culture incubator with 5% CO$_2$ at 37° C.

On day 2, testing compounds are prepared in either 10% or 0.5% FBS MEM all medium and serially diluted at 1:3 for 11 test concentrations. Each concentration of the compounds is tested in duplicate. The compound solutions are added at 25 μL/well to the corresponded wells in cell plate, and 25 μL/well of the vehicle (0.5% DMSO in 10% or 10% or 0.5% FBS MEM all) is added to the negative control wells (no cells) and the positive control wells (cells without compounds). The plate is incubated for 1 hour in a cell culture incubator with 5% CO$_2$ at 37° C. After 1 hour of incubation, the medium is removed, 100 μL/well of cell lysis buffer is added into the cell plate, and shake for 15 minutes at room temperature. After 15 minutes, the cell lysates are transferred to ELISA plate [pre-coated with anti-phospho-AKT (Ser473) rabbit monoclonal antibody, Cell signaling, catalog #4058], and the plate is incubated with gentle shaking for 2 hours at room temperature. After 2 hours, empty the contents of the wells, wash plate 4 times with the wash buffer, and add 100 μL of anti-AKT1 mouse monoclonal detection antibody (Cell signaling, catalog #2967) into each well, incubate with gentle shaking for 1 hour at room temperature. After 1 hour, empty the contents of the wells and wash the plate 4 times with the wash buffer, and add 100 μL of anti-mouse IgG HRP-linked antibody (Cell Signaling, catalog #7076) into each well, and incubate the plate with gentle shaking for 1 hour at room temperature. After 1 hour, empty the contents of the wells, wash the plate 4 times with the wash buffer, and add 100 μL of TMB substrate solution (catalog #T0440, Sigma) into each well, and incubate with gentle shaking at room temperature for 20 minutes. After 15 minutes of color development, add 100 μL of stop solution (1N hydrochloric acid) to each well, and read the plate at 450 nm on ELISA plate reader.

Listed in Table 3 are the biological data for the compounds of the present invention.

TABLE 3

| Compound Number | PI3Ka Ki (μM) | mTOR Ki (μM) | S473 pAKT 0.5% FBS IC50 (μM) | S473 pAKT 10% FBS IC50 (μM) |
|---|---|---|---|---|
| 101 | 0.0044 | 0.00363 | 0.00647 | |
| 102 | 0.00076 | 0.00301 | 0.00354 | |
| 103 | 0.00186 | 0.00209 | 0.0115 | |
| 104 | | | | |
| 105 | | | | |
| 106 | 0.0348 | 0.0269 | 0.0244 | |
| 107 | 0.00385 | 0.00426 | 0.0676 | |
| 108 | 0.00445 | 0.00467 | 0.0309 | |
| 109 | 0.00381 | 0.00903 | 0.197 | |
| 110 | 0.00235 | 0.0266 | | 0.0907 |
| 111 | 0.0114 | 0.00154 | 0.0439 | |
| 112 | 0.00609 | | 0.0272 | |
| 113 | 0.0592 | 0.0155 | 0.0973 | |
| 114 | 0.0723 | 0.0402 | 0.116 | |
| 115 | 0.00777 | 0.0215 | 0.0322 | |
| 116 | 0.00291 | 0.00653 | 0.0134 | |
| 117 | 0.00243 | 0.0124 | | 0.353 |
| 118 | 0.00208 | 0.0132 | | |
| 119 | 0.00319 | 0.00811 | 0.0117 | |
| 120 | 0.00098 | 0.00541 | 0.00459 | |
| 121 | 0.000539 | 0.0079 | 0.00786 | |
| 122 | 0.000806 | 0.0124 | 0.00807 | |
| 123 | 0.00196 | 0.00491 | 0.00734 | |
| 124 | | 0.00404 | 0.017 | |
| 125 | 0.00106 | 0.00487 | 0.0294 | |
| 126 | 0.00255 | 0.00342 | 0.018 | |
| 127 | 0.00138 | 0.0043 | 0.0204 | |
| 128 | 0.00289 | 0.00972 | 0.0196 | |
| 129 | 0.00592 | 0.0049 | 0.0117 | |
| 130 | 0.00239 | 0.00844 | 0.0245 | |
| 131 | 0.000644 | 0.00214 | | 0.0384 |
| 132 | 0.00051 | 0.00139 | | 0.0468 |
| 133 | 0.0005 | 0.00471 | | 0.0154 |
| 134 | 0.0005 | 0.002 | | 0.00952 |
| 135 | 0.00318 | 0.0474 | | 0.0466 |
| 136 | 0.000478 | 0.00264 | | 0.0168 |
| 137 | 0.00348 | 0.0178 | | 0.0551 |
| 138 | 0.00223 | 0.0106 | | 0.0144 |
| 139 | 0.000339 | 0.00332 | | 0.00714 |
| 140 | 0.000668 | 0.00774 | | 0.0185 |
| 141 | 0.0205 | 0.00956 | | 0.0148 |
| 142 | 0.00115 | 0.0016 | | 0.00919 |
| 143 | 0.000568 | 0.00721 | | 0.028 |
| 144 | 0.0021 | 0.00799 | | 0.0153 |
| 145 | 0.00392 | 0.0133 | | 0.0117 |

TABLE 3-continued

| Compound Number | PI3Ka Ki (μM) | mTOR Ki (μM) | S473 pAKT 0.5% FBS IC50 (μM) | S473 pAKT 10% FBS IC50 (μM) |
|---|---|---|---|---|
| 146 | 0.0012 | 0.0038 | | 0.00521 |
| 147 | 0.00108 | 0.0101 | | 0.0107 |
| 148 | 0.00209 | 0.0134 | | 0.0263 |
| 149 | 0.000102 | 0.00902 | | 0.0116 |
| 150 | 0.00878 | 0.0125 | | 0.0182 |
| 151 | | 0.0977 | | 0.195 |
| 152 | 0.00168 | 0.0114 | | 0.00863 |
| 153 | 0.000922 | 0.000377 | | 0.0111 |
| 154 | 0.00259 | 0.000822 | | 0.0342 |
| 155 | | | | |
| 156 | | | | |
| 157 | 0.003 | 0.00585 | | 0.0456 |
| 158 | 0.0233 | 0.0121 | | 0.224 |
| 159 | | | | |
| 160 | | | | |
| 161 | 0.00497 | 0.00252 | | 0.0123 |
| 162 | 0.00389 | 0.0185 | | 0.0225 |
| 163 | 0.0047 | 0.0184 | | 0.037 |
| 164 | 0.0162 | 0.014 | | 0.448 |
| 165 | 0.00352 | 0.0732 | | 0.0414 |
| 166 | 0.00177 | 0.0176 | | 0.0356 |
| 167 | 0.00193 | 0.00128 | | 0.112 |
| 168 | 0.00417 | 0.000204 | | 0.0197 |
| 169 | 0.000974 | 0.00639 | | 1 |
| 170 | 0.00744 | 0.00718 | | 0.107 |
| 171 | 0.00426 | 0.0401 | | 0.0228 |
| 172 | 0.000532 | 0.000842 | | 0.0173 |
| 173 | 0.00197 | 0.00233 | | 0.0316 |
| 174 | 0.0233 | | | 0.264 |
| 175 | 0.000666 | 0.0018 | | 0.00526 |
| 176 | 0.000882 | 0.00141 | | 0.0187 |
| 177 | 0.00245 | 0.00721 | | 0.101 |
| 178 | 0.00409 | 0.00118 | | 0.0427 |
| 179 | 0.00103 | 0.00329 | | 0.0185 |
| 180 | 0.00032 | 0.00384 | | 0.0689 |
| 181 | 0.00327 | 0.00106 | | 0.0594 |
| 182 | 0.0275 | 0.00451 | | 0.159 |
| 183 | 0.0287 | 0.00896 | | 0.175 |
| 184 | 0.00393 | 0.0133 | | 0.184 |
| 185 | 0.0119 | 0.0252 | | 0.124 |
| 186 | 0.00249 | 0.00306 | | 0.0681 |
| 187 | 0.00387 | 0.00374 | | 0.0346 |
| 188 | 0.00815 | 0.0504 | | 0.333 |
| 189 | 0.00178 | 0.00195 | | 0.0272 |
| 190 | 0.00496 | 0.00976 | | 0.0903 |
| 191 | 0.0005 | 0.00841 | | 0.0246 |
| 192 | 0.00221 | 0.00333 | | 0.402 |
| 193 | 0.00161 | 0.0131 | 0.0404 | |
| 194 | 0.0023 | 0.00791 | 0.0464 | |
| 195 | 0.000391 | 0.00172 | | 0.0172 |
| 196 | 0.00076 | 0.00301 | | 0.0243 |
| 197 | 0.00105 | 0.000444 | | 0.0358 |
| 198 | 0.00313 | 0.00352 | | 0.0325 |
| 199 | 0.0113 | 0.00103 | | 0.0183 |
| 200 | 0.00111 | 0.00172 | | 0.0273 |
| 201 | 0.00896 | 0.00642 | | 0.0989 |
| 202 | 0.0283 | | | 0.309 |
| 203 | 0.00517 | 0.0723 | | 0.0718 |
| 204 | 0.000298 | 0.0127 | | 0.029 |
| 205 | 0.000281 | 0.00438 | | 0.0214 |
| 206 | 0.000802 | 0.00809 | | 0.0318 |
| 207 | 0.0267 | 0.00962 | | 0.0194 |
| 208 | 0.0244 | 0.0442 | | 0.579 |
| 209 | 0.000264 | 0.0061 | | 0.00669 |
| 210 | 0.000529 | 0.00113 | | 0.00694 |
| 211 | 0.00463 | 0.00755 | | 0.232 |
| 212 | 0.0147 | 0.0279 | | 0.248 |
| 213 | 0.00409 | 0.00781 | | 0.133 |
| 214 | 0.000397 | 0.00174 | | 0.00553 |
| 215 | 0.00467 | 0.022 | | 0.0304 |
| 216 | 0.000505 | 0.00229 | | 0.00623 |
| 217 | 0.0262 | 0.0187 | | 0.0793 |
| 218 | 0.0454 | | | 0.428 |
| 219 | 0.0757 | 0.0472 | | |
| 220 | | 0.216 | | |
| 221 | | 0.0157 | | |

TABLE 3-continued

| Compound Number | PI3Kα Ki (μM) | mTOR Ki (μM) | S473 pAKT 0.5% FBS IC50 (μM) | S473 pAKT 10% FBS IC50 (μM) |
|---|---|---|---|---|
| 222 | 0.319 | 0.0501 | | |
| 223 | | 0.555 | | |
| 224 | | 0.229 | | |
| 225 | | 0.661 | | |
| 226 | 0.0521 | 0.105 | | 3.21 |
| 227 | 0.00161 | 0.00361 | | 0.137 |
| 228 | | | | |
| 229 | 0.000273 | 0.00033 | | 0.00336 |
| 230 | | | | |
| 231 | 0.0134 | 0.0562 | | 0.269 |
| 232 | 0.143 | 0.521 | | |
| 233 | 0.00894 | 0.0238 | | 0.237 |
| 234 | 0.0573 | 0.00963 | | |
| 235 | 0.0155 | 0.00699 | | 0.331 |
| 236 | 0.00441 | 0.000404 | | 0.00961 |
| 237 | 0.0296 | 0.00666 | | 0.0553 |
| 238 | 0.000438 | 0.00444 | | 0.0838 |
| 239 | 0.102 | 0.311 | | 5.04 |
| 240 | | | | |
| 241 | 0.00408 | 0.0287 | | 0.266 |
| 242 | 0.000252 | 0.000299 | | 0.00917 |
| 243 | | | | |
| 244 | 0.00194 | 0.00178 | | 0.0815 |
| 245 | 0.00219 | 0.00203 | | |
| 246 | 0.0242 | 0.0353 | | 2.58 |
| 247 | 0.0176 | 0.00482 | | |
| 248 | | | | |
| 249 | 0.00451 | 0.442 | | 0.194 |
| 250 | | | | |
| 251 | 0.000811 | 0.00463 | | 0.14 |
| 252 | 0.000832 | 0.00177 | | |
| 253 | 0.00104 | 0.00169 | | 0.218 |
| 254 | 0.000513 | 0.00134 | | 0.0315 |
| 255 | 0.000721 | 0.00263 | | 0.0283 |
| 256 | 0.000575 | 0.00197 | | 0.0604 |
| 257 | 0.000958 | 0.00141 | | 0.0091 |
| 258 | 0.00011 | 0.000241 | | 0.0294 |
| 259 | 0.000191 | 0.000243 | | 0.0116 |
| 260 | 0.000167 | 0.000323 | | 0.0153 |
| 261 | 0.000114 | 0.000658 | | 0.00991 |
| 262 | 0.00032 | 0.00406 | | 0.0594 |
| 263 | 0.000282 | 0.00567 | | 0.0218 |
| 264 | | | | |
| 265 | 0.00502 | 0.0144 | | 0.0399 |
| 266 | 0.0078 | 0.273 | | 0.344 |
| 267 | 0.000145 | 0.000359 | | 0.0205 |
| 268 | 0.000366 | 0.000117 | | 0.0133 |
| 269 | 0.0122 | 0.0278 | | |
| 270 | 0.0135 | 0.00713 | | 0.207 |
| 271 | | 0.348 | | |
| 272 | 0.00184 | 0.00194 | | 0.014 |
| 273 | 0.00194 | 0.00342 | | 0.0174 |
| 274 | 0.00771 | 0.0146 | | 0.0113 |
| 275 | 0.00201 | 0.00851 | | 0.0344 |
| 276 | 0.00222 | 0.0102 | | 0.0304 |
| 277 | 0.00304 | 0.0103 | | 0.0577 |
| 278 | | | | |
| 279 | 0.118 | | | |
| 280 | 0.292 | | | |

We claim:

1. A compound of Formula (I)

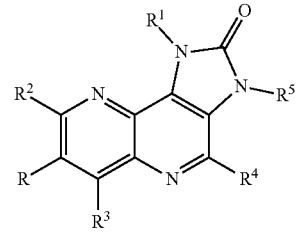

or a salt thereof, wherein:

$R^1$ is H, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl is optionally substituted with at least one $R^6$ group;

$R^2$ is H, —$(CH_2)_nC(O)OR^7$, —$(CH_2)_nC(O)N(R^{8a}R^{8b})$, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl wherein the said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl or ($C_2$ to $C_9$) heteroaryl is optionally substituted with at least one $R^6$ group;

$R^3$ is H or ($C_1$ to $C_3$) alkyl;

R and $R^4$ are independently H, halo, cyano or ($C_1$ to $C_6$) alkyl;

$R^5$ is H or ($C_1$ to $C_6$) alkyl wherein the said ($C_1$ to $C_6$) alkyl is optionally substituted with at least one $R^6$ group;

each $R^6$ is independently —OH, halogen, $CF_3$, —$(CH_2)_nNR^{8a}R^{8b}$, ($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_nOC(O)R^9$, —$(CH_2)_nNR^{8a}C(O)R^9$ or —$(CH_2)_nNR^{8a}C(O)NR^{8a}R^{8b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, ($C_3$ to $C_8$) cycloalkyl, ($C_2$ to $C_9$) cycloheteroalkyl, ($C_6$ to $C_{14}$) aryl, or ($C_2$ to $C_9$) heteroaryl is optionally substituted with at least one $R^{10}$ group;

each $R^7$ is independently H, or ($C_1$ to $C_6$) alkyl optionally substituted with at least one $R^{10}$ group;

$R^{8a}$ and $R^{8b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each of the said ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl is optionally substituted with at least one $R^{10}$ group;

each $R^9$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl wherein each of the said ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl is optionally substituted with at least one $R^{10}$ group;

each $R^{10}$ is independently —OH, halogen, $CF_3$, ($C_1$ to $C_6$) alkyl, ($C_1$ to $C_6$) alkenyl, ($C_1$ to $C_6$) alkynyl, ($C_1$ to $C_6$)

alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$(CH_2)_n NR^{11a}R^{11b}$, —$(CH_2)_n C(O)R^{12}$, —$(CH_2)_n C(O)NR^{11a}R^{11b}$, —$(CH_2)_n S(O)_m R^{12}$, —$(CH_2)_n S(O)_m NR^{11a}R^{11b}$, —$(CH_2)_n NR^{11a}S(O)_m R^{12}$, —$(CH_2)_n C(O)OR^7$, —$(CH_2)_n C(O)NR^{11a}R^{11b}$, —$(CH_2)_n OC(O)R^{12}$, —$(CH_2)_n NR^{11a}C(O)R^{12}$ or —$(CH_2)_n NR^{11a}C(O)NR^{11a}R^{11b}$;

$R^{11a}$ and $R^{11b}$ are each independently H, ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each $R^{12}$ is independently ($C_1$ to $C_6$) alkyl, ($C_3$ to $C_8$) cycloalkyl, ($C_2$ to $C_9$) cycloheteroalkyl, ($C_2$ to $C_9$) heteroaryl, or ($C_6$ to $C_{14}$) aryl;

each m is independently 1 or 2; and each n is independently 0, 1, 2, 3, or 4.

2. The compound or salt according to claim 1, wherein $R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to $C_8$) cycloalkyl, ($C_6$ to $C_{14}$) aryl, or ($C_2$ to $C_9$) cycloheteroalkyl is optionally substituted with at least one $R^6$ group.

3. The compound or salt according to claim 1, wherein $R^2$ is ($C_2$ to $C_9$) heteroaryl optionally substituted with at least one $R^6$ group.

4. The compound or salt according to claim 1, wherein one or more of $R^3$, $R^4$, R and $R^5$ is hydrogen.

5. The compound or salt according to claim 1, wherein $R^5$ is methyl.

6. The compound or salt according to claim 1, wherein each $R^6$ is independently —OH, halogen, $CF_3$, —$(CH_2)_n NR^{8a}R^{8b}$, ($C_1$ to $C_6$) alkyl, ($C_1$ to $C_6$) alkoxy, ($C_6$ to $C_{14}$) aryl, —$(CH_2)_n C(O)R^9$, —$(CH_2)_n C(O)OR^7$, or —$(CH_2)_n C(O)NR^{8a}R^{8b}$, wherein each of the said ($C_1$ to $C_6$) alkyl or ($C_6$ to $C_{14}$) aryl is optionally substituted with at least one $R^{10}$ group.

7. The compound or salt according to claim 1, wherein each $R^7$ is independently ($C_1$ to $C_6$) alkyl optionally substituted with at least one $R^{10}$ group.

8. The compound or salt according to claim 1, wherein $R^{8a}$ and $R^{8b}$ are each independently H or ($C_1$ to $C_6$) alkyl optionally substituted with at least one $R^{10}$ group.

9. The compound or salt according to claim 1, wherein each $R^9$ is independently ($C_1$ to $C_6$) alkyl optionally substituted with at least one $R^{10}$ group.

10. The compound or salt according to claim 1, wherein each $R^{10}$ is independently —OH, $CF_3$, cyano, ($C_6$ to $C_{14}$) aryl, or amino.

11. A compound selected from the group consisting of: 2-methyl-2-[4-(2-oxo-8-quinolin-3-yl-2,3-dihydro-1H-imidazo[4,5-c]-1,5-naphthyridin-1-yl)phenyl]propanenitrile; 2-methyl-2-[4-(3-methyl-2-oxo-8-quinolin-3-yl-2,3-dihydro-1H-imidazo[4,5-c]-1,5-naphthyridin-1-yl)phenyl]propanenitrile; 2-{4-[8-(6-methoxypyridin-3-yl)-2-oxo-2,3-dihydro-1H-imidazo[4,5-c]-1,5-naphthyridin-1-yl]phenyl}-2-methylpropanenitrile; 2-{4-[8-(6-methoxypyridin-3-yl)-3-methyl-2-oxo-2,3-dihydro-1H-imidazo[4,5-c]-1,5-naphthyridin-1-yl]phenyl}-2-methylpropanenitrile; 2-methyl-2-{4-[8-(6-methylpyridin-3-yl)-2-oxo-2,3-dihydro-1H-imidazo[4,5-c]-1,5-naphthyridin-1-yl]phenyl}propanenitrile; 2-methyl-2-{4-[3-methyl-8-(6-methylpyridin-3-yl)-2-oxo-2,3-dihydro-1H-imidazo[4,5-c]-1,5-naphthyridin-1-yl]phenyl}propanenitrile; 2-(4-(8-(6-(dimethylamino)pyridin-3-yl)-2-oxo-2,3-dihydroimidazo[4,5-c][1,5]naphthyridin-1-yl)phenyl)-2-methylpropanenitrile; 2-(4-(8-(6-(dimethylamino)pyridin-3-yl)-3-methyl-2-oxo-2,3-dihydroimidazo[4,5-c][1,5]naphthyridin-1-yl)phenyl)-2-methylpropanenitrile; 2-(4-(8-(5-fluoro-6-methoxypyridin-3-yl)-3-methyl-2-oxo-2,3-dihydroimidazo[4,5-c][1,5]naphthyridin-1-yl)phenyl)-2-methylpropanenitrile; 2-(4-(8-(2-methoxypyrimidin-5-yl)-2-oxo-2,3-dihydroimidazo[4,5-c][1,5]naphthyridin-1-yl)phenyl)-2-methylpropanenitrile; 2-(4-(8-(2-methoxypyrimidin-5-yl)-3-methyl-2-oxo-2,3-dihydroimidazo[4,5-c][1,5]naphthyridin-1-yl)phenyl)-2-methylpropanenitrile; 2-Methyl-2-{4-[8-(1-methyl-1H-pyrazol-4-yl)-2-oxo-2,3-dihydro-1,3,5,9-tetraaza-cyclopenta[a]naphthalen-1-yl]-phenyl}-propionitrile; benzyl4-(2-oxo-8-quinolin-3-yl-2,3-dihydro-1H-imidazo[4,5-c][1,5]naphthyridin-1-yl)piperidine-1-carboxylate; benzyl-4-(3-methyl-2-oxo-8-quinolin-3-yl-2,3-dihydro-1H-imidazo[4,5-c][1,5]naphthyridin-1-yl)piperidine-1-carboxylate; 1-(1-ethylpiperidin-4-yl)-3-methyl-8-quinolin-3-yl-1,3-dihydro-2H-imidazo[4,5-c][1,5]naphthyridin-2-one; 3-methyl-1-(1-propionylpiperidin-4-yl)-8-quinolin-3-yl-1,3-dihydro-2H-imidazo[4,5-c][1,5]naphthyridin-2-one; methyl-4-(3-methyl-2-oxo-8-quinolin-3-yl-2,3-dihydro-1H-imidazo[4,5-c][1,5]naphthyridin-1-yl)piperidine-1-carboxylate; N-methyl-4-(3-methyl-2-oxo-8-quinolin-3-yl-2,3-dihydro-1H-imidazo[4,5-c][1,5]naphthyridin-1-yl)piperidine-1-carboxamide; N-ethyl-4-(3-methyl-2-oxo-8-quinolin-3-yl-2,3-dihydro-1H-imidazo[4,5-c][1,5]naphthyridin-1-yl)piperidine-1-carboxamide; 1-(1-isobutyrylpiperidin-4-yl)-3-methyl-8-quinolin-3-yl-1,3-dihydro-2H-imidazo[4,5-c][1,5]naphthyridin-2-one; 1-[1-(N,N-dimethylglycyl)piperidin-4-yl]-3-methyl-8-quinolin-3-yl-1,3-dihydro-2H-imidazo[4,5-c][1,5]naphthyridin-2-one; ethyl 4-(3-methyl-2-oxo-8-quinolin-3-yl-2,3-dihydro-1H-imidazo[4,5-c][1,5]naphthyridin-1-yl)piperidine-1-carboxylate; isopropyl 4-(3-methyl-2-oxo-8-quinolin-3-yl-2,3-dihydro-1H-imidazo[4,5-c][1,5]naphthyridin-1-yl)piperidine-1-carboxylate; 3-methyl-1-(1-methylpiperidin-4-yl)-8-quinolin-3-yl-1,3-dihydro-2H-imidazo[4,5-c][1,5]naphthyridin-2-one; 1-benzyl-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-1,3-dihydro-2H-imidazo[4,5-c][1,5]naphthyridin-2-one; 1-(trans-4-hydroxycyclohexyl)-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-3-methyl-1,3-dihydro-2H-imidazo[4,5-c][1,5]naphthyridin-2-one; 1-(trans-4-hydroxycyclohexyl)-8-(6-methoxypyridin-3-yl)-3-methyl-1,3-dihydro-2H-imidazo[4,5-c][1,5]naphthyridin-2-one; 8-(6-methoxypyridin-3-yl)-3-methyl-1-(1-methylpiperidin-4-yl)-1,3-dihydro-2H-imidazo[4,5-c][1,5]naphthyridin-2-one; 1-(1-isopropylpiperidin-4-yl)-8-(6-methoxypyridin-3-yl)-3-methyl-1,3-dihydro-2H-imidazo[4,5-c][1,5]naphthyridin-2-one; 1-[1-(N,N-dimethylglycyl)piperidin-4-yl]-8-(6-methoxypyridin-3-yl)-3-methyl-1,3-dihydro-2H-imidazo[4,5-c][1,5]naphthyridin-2-one; 2-{4-[8-(6-methoxypyridin-3-yl)-3-methyl-2-oxo-2,3-dihydro-1H-imidazo[4,5-c][1,5]naphthyridin-1-yl]piperidin-1-yl}acetamide; 8-(6-methoxypyridin-3-yl)-3-methyl-1-(tetrahydro-2H-pyran-4-yl)-1,3-dihydro-2H-imidazo[4,5-c][1,5]naphthyridin-2-one; 3-methyl-8-quinolin-3-yl-1-[1-(2,2,2-trifluoroethyl)piperidin-4-yl]-1,3-dihydro-2H-imidazo[4,5-c][1,5]naphthyridin-2-one; 4-[8-(6-methoxypyridin-3-yl)-3-methyl-2-oxo-2,3-dihydro-1H-imidazo[4,5-c][1,5]naphthyridin-1-yl]-N-methylpiperidine-1-carboxamide; 1-[1-(2-hydroxy-2-methylpropanoyl)piperidin-4-yl]-3-methyl-8-quinolin-3-yl-1,3-dihydro-2H-imidazo[4,5-c][1,5]naphthyridin-2-one; 8-[6-(dimethylamino)pyridin-3-yl]-1-[1-(N,N-dimethylglycyl)piperidin-4-yl]-3-methyl-1,3-dihydro-2H-imidazo[4,5-c][1,5]naphthyridin-2-one; 3-methyl-1-[1-(2-methylalanyl)piperidin-4-yl]-8-quinolin-3-yl-1,3-dihydro-2H-imidazo[4,5-c][1,5]naphthyridin-2-one; 1-(trans-4- hydroxycyclohexyl)-3-methyl-8-quinolin-3-yl-1,3-dihydro-2H-imidazo[4,5-c][1,5]naphthyridin-2-one; 1-[trans-4-(2-hydroxyethoxy)cyclohexyl]-3-methyl-8-quinolin-3-yl-1,3-dihydro-2H-imidazo[4,5-c][1,5]naphthyridin-2-one; 1-[trans-4-(2-hydroxyethoxy)cyclohexyl]-8-(2-methoxypyrimidin-5-yl)-3-methyl-1,3-dihydro-2H-imidazo[4,5-c][1,5]naphthyridin-2-one; 8-[6-(dimethylamino)pyridin-3-yl]-1-[trans-4-(2-hydroxyethoxy)cyclohexyl]-3-methyl-1,3-dihydro-2H-imidazo[4,5-c][1,5]naphthyridin-2-one; 8-[6-(dimethylamino)pyridin-3-yl]-3-methyl-1-[1-(2,2,2-trifluoroethyl)piperidin-4-yl]-1,3-dihydro-2H-imidazo[4,5-c][1,5]naphthyridin-2-one; 1-[trans-4-(2-hydroxyethoxy)cyclohexyl]-3-methyl-8-(6-methylpyridin-3-yl)-1,3-dihydro-2H-imidazo[4,5-c][1,5]naphthyridin-2-one; 1-[1-(methoxyacetyl)piperidin-4-yl]-3-methyl-8-(6-methylpyridin-3-yl)-1,3-dihydro-2H-imidazo[4,5-c][1,5]naphthyridin-2-one; 1-{1-[(2S)-2-hydroxypropanoyl]piperidin-4-yl}-8-(2-methoxypyrimidin-5-yl)-3-methyl-1,3-dihydro-2H-imidazo[4,5-c][1,5]naphthyridin-2-one; trans-4-[8-(2-methoxypyrimidin-5-yl)-3-methyl-2-oxo-2,3-dihydro-1H-imidazo[4,5-c][1,5]naphthyridin-1-yl]cyclohexanecarboxamide; 1-[1-(methoxyacetyl)piperidin-4-yl]-8-(2-methoxypyrimidin-5-yl)-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(6-methylpyridin-3-yl)-1,3-dihydro-2H-imidazo[4,5-c][1,5]naphthyridin-2-one; 2-{4-[8-(2-methoxypyrimidin-5-yl)-3-methyl-2-oxo-2,3-dihydro-1H-imidazo[4,5-c][1,5]naphthyridin-1-yl]piperidin-1-yl}-N,N-dimethylacetamide; 3-methyl-8-(6-methylpyridin-3-yl)-1-(1-pyrimidin-2-ylpiperidin-4-yl)-1,3-dihydro-2H-imidazo[4,5-c][1,5]naphthyridin-2-one; 1-[1-(2-hydroxyethyl)piperidin-4-yl]-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(1H-pyrazol-4-yl)-1,3-dihydro-2H-imidazo[4,5-c][1,5]naphthyridin-2-one; 3-methyl-1-(1-methylpiperidin-4-yl)-8-(6-methylpyridin-3-yl)-1,3-dihydro-2H-imidazo[4,5-c][1,5]naphthyridin-2-one; 1-(1-glycoloylpiperidin-4-yl)-3-methyl-8-(6-methylpyridin-3-yl)-1,3-dihydro-2H-imidazo[4,5-c][1,5]naphthyridin-2-one; 1-(1-acetylpiperidin-4-yl)-3-methyl-8-(6-methylpyridin-3-yl)-1,3-dihydro-2H-imidazo[4,5-c][1,5]naphthyridin-2-one; 8-[6-(dimethylamino)pyridin-3-yl]-1-(trans-4-hydroxycyclohexyl)-3-methyl-1,3-dihydro-2H-imidazo[4,5-c][1,5]naphthyridin-2-one; 2-{4-[3-methyl-8-(6-methylpyridin-3-yl)-2-oxo-2,3-dihydro-1H-imidazo[4,5-c][1,5]naphthyridin-1-yl]piperidin-1-yl}acetamide; 1-[1-(N,N-dimethylglycyl)piperidin-4-yl]-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(6-methylpyridin-3-yl)-1,3-dihydro-2H-imidazo[4,5-c][1,5]naphthyridin-2-one; 1-(1-glycylpiperidin-4-yl)-3-methyl-8-(6-methylpyridin-3-yl)-1,3-dihydro-2H-imidazo[4,5-c][1,5]naphthyridin-2-one; N-methyl-4-[3-methyl-8-(6-methylpyridin-3-yl)-2-oxo-2,3-dihydro-1H-imidazo[4,5-c][1,5]naphthyridin-1-yl]piperidine-1-carboxamide; 4-[8-(2-methoxypyrimidin-5-yl)-3-methyl-2-oxo-2,3-dihydro-1H-imidazo[4,5-c][1,5]naphthyridin-1-yl]-N-methylpiperidine-1-carboxamide; 1-(1-acetylpiperidin-4-yl)-8-(2-methoxypyrimidin-5-yl)-3-methyl-1,3-dihydro-2H-imidazo[4,5-c][1,5]naphthyridin-2-one; 1-(1-glycoloylpiperidin-4-yl)-8-(2-methoxypyrimidin-5-yl)-3-methyl-1,3-dihydro-2H-imidazo[4,5-c][1,5]naphthyridin-2-one; 2-{4-[8-(2-methoxypyrimidin-5-yl)-3-methyl-2-oxo-2,3-dihydro-1H-imidazo[4,5-c][1,5]naphthyridin-1-yl]piperidin-1-yl}acetamide; 8-[6-(dimethylamino)pyridin-3-yl]-3-methyl-1-piperidin-4-yl-1,3-dihydro-2H-imidazo[4,5-c][1,5]naphthyridin-2-one; 3-methyl-1-[trans-4-(methylamino)cyclohexyl]-8-quinolin-3-yl-1,3-dihydro-2H-imidazo[4,5-c][1,5]naphthyridin-2-one; 1-(trans-4-aminocyclohexyl)-3-methyl-8-quinolin-3-yl-1,3-dihydro-2H-imidazo[4,5-c][1,5]naphthyridin-2-one; 1-(1-acetylpiperidin-4-yl)-8-[6-(dimethylamino)pyridin-3-yl]-3-methyl-1,3-dihydro-2H-imidazo[4,5-c][1,5]naphthyridin-2-one; 4-{8-[6-(dimethylamino)pyridin-3-yl]-3-methyl-2-oxo-2,3-dihydro-1H-imidazo[4,5-c][1,5]naphthyridin-1-yl}-N-methylpiperidine-1-carboxamide; 4-{8-[6-(dimethylamino)pyridin-3-yl]-3-methyl-2-oxo-2,3-dihydro-1H-imidazo[4,5-c][1,5]naphthyridin-1-yl}piperidine-1-carboxamide; 8-[6-(dimethylamino)pyridin-3-yl]-1-[1-(2-hydroxyethyl)piperidin-4-yl]-3-methyl-1,3-dihydro-2H-imidazo[4,5-c][1,5]naphthyridin-2-one; 3-methyl-8-(1H-pyrazol-4-yl)-1-(tetrahydro-2H-pyran-4-yl)-1,3-dihydro-2H-imidazo[4,5-c][1,5]naphthyridin-2-one; 3-methyl-8-(6-methylpyridin-3-yl)-1-(tetrahydro-2H-pyran-4-yl)-1,3-dihydro-2H-imidazo[4,5-c][1,5]naphthyridin-2-one; 8-(2-methoxypyrimidin-5-yl)-3-methyl-1-(tetrahydro-2H-pyran-4-yl)-1,3-dihydro-2H-imidazo[4,5-c][1,5]naphthyridin-2-one; 3-methyl-8-(1-methyl-1H-pyrazol-4-yl)-1-(tetrahydro-2H-pyran-4-yl)-1,3-dihydro-2H-imidazo[4,5-c][1,5]naphthyridin-2-one; 8-[6-(dimethylamino)pyridin-3-yl]-3-methyl-1-(tetrahydro-2H-pyran-4-yl)-1,3-dihydro-2H-imidazo[4,5-c][1,5]naphthyridin-2-one; 8-[6-(dimethylamino)pyridin-3-yl]-1-[1-(2,2-dimethylpropanoyl)piperidin-4-yl]-3-methyl-1,3-dihydro-2H-imidazo[4,5-c][1,5]naphthyridin-2-one; 8-[6-(dimethylamino)pyridin-3-yl]-1-[1-(2-methoxyethyl)piperidin-4-yl]-3-methyl-1,3-dihydro-2H-imidazo[4,5-c][1,5]naphthyridin-2-one; 8-[6-(dimethylamino)pyridin-3-yl]-3-methyl-1-(1-methylpiperidin-4-yl)-1,3-dihydro-2H-imidazo[4,5-c][1,5]naphthyridin-2-one; 8-[6-(dimethylamino)pyridin-3-yl]-1-[1-(2-hydroxy-2-methylpropanoyl)piperidin-4-yl]-3-methyl-1,3-dihydro-2H-imidazo[4,5-c][1,5]naphthyridin-2-one; 8-(2-aminopyrimidin-5-yl)-3-methyl-1-(tetrahydro-2H-pyran-4-yl)-1,3-dihydro-2H-imidazo[4,5-c][1,5]naphthyridin-2-one; 8-[6-(dimethylamino)pyridin-3-yl]-1-{1-[(2R)-2-hydroxypropanoyl]piperidin-4-yl}-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(1-methyl-1H-pyrazol-4-yl)-1,3-dihydro-2H-imidazo[4,5-c][1,5]naphthyridin-2-one; 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one; and N-methyl-4-[3-methyl-8-(1-methyl-1H-pyrazol-4-yl)-2-oxo-2,3-dihydro-1H-imidazo[4,5-c][1,5]naphthyridin-1-yl]piperidine-1-carboxamide, or the salt thereof.

12. A compound selected from the group consisting of: 1-(1-acetylpiperidin-4-yl)-3-methyl-8-quinolin-3-yl-1,3-dihydro-2H-imidazo[4,5-c][1,5]naphthyridin-2-one; 1-(trans-4-aminocyclohexyl)-3-methyl-8-quinolin-3-yl-1,3-dihydro-2H-imidazo[4,5-c][1,5]naphthyridin-2-one; 3-methyl-1-[trans-4-(methylamino)cyclohexyl]-8-quinolin-3-yl-1,3-dihydro-2H-imidazo[4,5-c][1,5]naphthyridin-2-one; 1-(trans-4-hydroxycyclohexyl)-8-(6-methoxypyridin-3-yl)-1,3-dihydro-2H-imidazo[4,5-c][1,5]naphthyridin-2-one; 1-[trans-4-(2-hydroxyethoxy)cyclohexyl]-8-(6-methoxypyridin-3-yl)-3-methyl-1,3-dihydro-2H-imidazo[4,5-c][1,5]naphthyridin-2-one; 1-(trans-4-hydroxycyclohexyl)-8-(6-methoxypyridin-3-yl)-3-methyl-1,3-dihydro-2H-imidazo[4,5-c][1,5]naphthyridin-2-one; 8-(6-methoxypyridin-3-yl)-3-methyl-1-(1-methylpiperidin-4-yl)-1,3-dihydro-2H-imidazo[4,5-c][1,5]naphthyridin-2-one; 1-[1-(N,N-dimethylglycyl)piperidin-4-yl]-8-(6-methoxypyridin-3-yl)-3-methyl-1,3-dihydro-2H-imidazo[4,5-c][1,5]naphthyridin-2-one; 1-(1- acetylpiperidin-4-yl)-8-(2-methoxypyrimidin-5-yl)-3-methyl-1,3-dihydro-2H-imidazo[4,5-c][1,5]naphthyridin-2-one; 4-[8-(2-methoxypyrimidin-5-yl)-3-methyl-2-oxo-2,3-dihydro-1H-imidazo[4,5-c][1,5]naphthyridin-1-yl]-N-methylpiperidine-1-carboxamide; N-methyl-4-[3-methyl-8-(6-methylpyridin-3-yl)-2-oxo-2,3-dihydro-1H-imidazo[4,5-c][1,5]naphthyridin-1-yl]piperidine-1-carboxamide; 8-[6-(dimethylamino)pyridin-3-yl]-1-[1-(2-hydroxyethyl)piperidin-4-yl]-3-methyl-1,3-dihydro-2H-imidazo[4,5-c][1,5]naphthyridin-2-one; 3-methyl-8-(1H-pyrazol-4-yl)-1-(tetrahydro-2H-pyran-4-yl)-1,3-dihydro-2H-imidazo[4,5-c][1,5]naphthyridin-2-one; 1-(trans-4-hydroxycyclohexyl)-3-methyl-8-(6-methylpyridin-3-yl)-1,3-dihydro-2H-imidazo[4,5-c][1,5]naphthyridin-2-one; 1-(1-acetylpiperidin-4-yl)-3-methyl-8-(6-methylpyridin-3-yl)-1,3-dihydro-2H-imidazo[4,5-c][1,5]naphthyridin-2-one; 1-(1-glycoloylpiperidin-4-yl)-3-methyl-8-(6-methylpyridin-3-yl)-1,3-dihydro-2H-imidazo[4,5-c][1,5]naphthyridin-2-one; 1-(trans-4-hydroxycyclohexyl)-3-methyl-8-(1H-pyrazol-4-yl)-1,3-dihydro-2H-imidazo[4,5-c][1,5]naphthyridin-2-one; 1-[1-(2-hydroxyethyl)piperidin-4-yl]-3-methyl-8-(6-methylpyridin-3-yl)-1,3-dihydro-2H-imidazo[4,5-c][1,5]naphthyridin-2-one; 8-(2-aminopyrimidin-5-yl)-3-methyl-1-(tetrahydro-2H-pyran-4-yl)-1,3-dihydro-2H-imidazo[4,5-c][1,5]naphthyridin-2-one; 1-[1-(2-hydroxy-2-methylpropanoyl)piperidin-4-yl]-3-methyl-8-(1-methyl-1H-pyrazol-4-yl)-1,3-dihydro-2H-imidazo[4,5-c][1,5]naphthyridin-2-one; 8-[6-(dimethylamino)pyridin-3-yl]-1-(1-glycoloylpiperidin-4-yl)-3-methyl-1,3-dihydro-2H-imidazo[4,5-c][1,5]naphthyridin-2-one; 1-[1-(2-hydroxy-2-methylpropanoyl)piperidin-4-yl]-3-methyl-8-(6-methylpyridin-3-yl)-1,3-dihydro-2H-imidazo[4,5-c][1,5]naphthyridin-2-one; 1-[1-(methoxyacetyl)piperidin-4-yl]-8-(2-methoxypyrimidin-5-yl)-3-methyl-1,3-dihydro-2H-imidazo[4,5-c][1,5]naphthyridin-2-one; trans-4-[8-(2-methoxypyrimidin-5-yl)-3-methyl-2-oxo-2,3-dihydro-1H-imidazo[4,5-c][1,5]naphthyridin-1-yl]cyclohexanecarboxamide; N-methyl-4-[3-methyl-8-(1-methyl-1H-pyrazol-4-yl)-2-oxo-2,3-dihydro-1H-imidazo[4,5-c][1,5]naphthyridin-1-yl]piperidine-1-carboxamide; 3-methyl-1-[1-(2-methylalanyl)piperidin-4-yl]-8-quinolin-3-yl-1,3-dihydro-2H-imidazo[4,5-c][1,5]naphthyridin-2-one; 1-[trans-4-(2-hydroxyethoxy)cyclohexyl]-8-(2-methoxypyrimidin-5-yl)-3-methyl-1,3-dihydro-2H-imidazo[4,5-c][1,5]naphthyridin-2-one; 1-{1-[(2S)-2-hydroxypropanoyl]piperidin-4-yl}-8-(2-methoxypyrimidin-5-yl)-3-methyl-1,3-dihydro-2H-imidazo[4,5-c][1,5]naphthyridin-2-one; 1-[1-(methoxyacetyp)piperidin-4-yl]-3-methyl-8-(6-methylpyridin-3-yl)-1,3-dihydro-2H-imidazo[4,5-c][1,5]naphthyridin-2-one; 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one, or the salt thereof.

13. A compound selected from the group consisting of: 1-{1-[(2S)-2-hydroxypropanoyl]piperidin-4-yl}-8-(1H-indazol-4-yl)-3-methyl-1,3-dihydro-2H-imidazo[4,5-c][1,5]naphthyridin-2-one; 1-(1-glycoloylpiperidin-4-yl)-8-(1H-indazol-4-yl)-3-methyl-1,3-dihydro-2H-imidazo[4,5-c][1,5]naphthyridin-2-one; 1-{1-[(2S)-2-hydroxypropanoyl]piperidin-4-yl}-3-methyl-8-(6-methylpyridin-3-yl)-1,3-dihydro-2H-imidazo[4,5-c][1,5]naphthyridin-2-one; and 1-{1-[(2R)-2-hydroxypropanoyl]piperidin-4-yl}-3-methyl-8-(1H-pyrazolo[3,4-b]pyridin-5-yl)-1,3-dihydro-2H-imidazo[4,5-c][1,5]naphthyridin-2-one, or the salt thereof.

14. A pharmaceutical composition, comprising at least one compound or salt according to claim 1 and a pharmaceutically acceptable carrier or diluent.

15. The compound or salt according to claim 1, wherein:
$R^1$ is ($C_1$ to $C_6$) alkyl, ($C_3$ to $C_8$) cycloalkyl, ($C_6$ to $C_{14}$) aryl, or ($C_2$ to $C_9$) cycloheteroalkyl, wherein said ($C_1$ to $C_6$) alkyl, ($C_3$ to $C_9$) cycloalkyl, ($C_6$ to $C_{14}$) aryl, or ($C_2$ to $C_9$) cycloheteroalkyl is optionally substituted with at least one $R^6$ group;
$R^2$ is ($C_2$ to $C_9$) heteroaryl optionally substituted with at least one $R^6$ group;
R, $R^3$ and $R^4$ are hydrogen;
$R^5$ is hydrogen or methyl;
each $R^6$ is independently —OH, halogen, $CF_3$, —$(CH_2)_n$ $NR^{8a}R^{8b}$, ($C_1$ to $C_6$) alkyl, ($C_1$ to $C_6$) alkoxy, ($C_6$ to $C_{14}$) aryl, —$(CH_2)_nC(O)R^9$, —$(CH_2)_nC(O)OR^7$, or —$(CH_2)_n C(O)NR^{8a}R^{8b}$, wherein each said ($C_1$ to $C_6$) alkyl or ($C_6$ to $C_{14}$) aryl is optionally substituted with at least one $R^{10}$ group;
each $R^7$ is independently ($C_1$ to $C_6$) alkyl optionally substituted with at least one $R^{10}$ group;
$R^{8a}$ and $R^{8b}$ are each independently H or ($C_1$ to $C_6$) alkyl optionally substituted with at least one $R^{10}$ group;
each $R^9$ is independently ($C_1$ to $C_6$) alkyl optionally substituted with at least one $R^{10}$ group;
each $R^{10}$ is independently —OH, $CF_3$, cyano, ($C_6$ to $C_{14}$) aryl, or —$(CH_2)_nNR^{11a}R^{11b}$; and
$R^{11a}$ and $R^{11b}$ are each independently H or ($C_1$ to $C_6$) alkyl.

16. A compound of Formula (I),

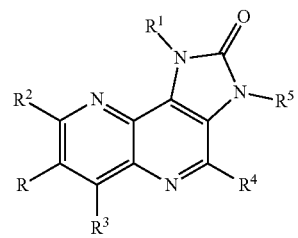

(I)

wherein:
$R^1$ is H, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, and ($C_2$ to $C_9$) heteroaryl is optionally substituted with at least one $R^6$ group;
$R^2$ is H, —$(CH_2)_nC(O)OR^7$, —$(CH_2)_nC(O)N(R^{8a}R^{8b})$, ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl, or ($C_2$ to $C_9$) heteroaryl, wherein each said ($C_1$ to $C_6$) alkyl, ($C_3$ to $C_8$) cycloalkyl, ($C_2$ to $C_8$) alkenyl, ($C_2$ to $C_8$) alkynyl, ($C_6$ to $C_{14}$) aryl, ($C_2$ to $C_9$) cycloheteroalkyl and ($C_2$ to $C_9$) heteroaryl is optionally substituted with at least one $R^6$ group;
$R^3$ is H or ($C_1$ to $C_3$) alkyl;
R and $R^4$ are independently H, halo, cyano or ($C_1$ to $C_6$) alkyl;
$R^5$ is H, or ($C_1$ to $C_6$) alkyl optionally substituted with at least one $R^6$ group;
each $R^6$ is independently —OH, halogen, $CF_3$, —$(CH_2)_n$ $NR^{8a}R^{8b}$, ($C_1$ to $C_6$) alkyl, ($C_2$ to $C_8$) alkenyl, ($C_2$ to $C_8$) alkynyl, ($C_1$ to $C_6$) alkoxy, cyano, ($C_3$ to $C_8$) cycloalkyl, ($C_2$ to $C_9$) cycloheteroalkyl, ($C_6$ to $C_{14}$) aryl, ($C_2$ to $C_9$) heteroaryl, —$(CH_2)_nC(O)R^9$, —$(CH_2)_nS(O)_mR^9$, —$(CH_2)_nS(O)_mNR^{8a}R^{8b}$, —$(CH_2)_nNR^{8a}S(O)_mR^9$, —$(CH_2)_nC(O)OR^7$, —$(CH_2)_nC(O)NR^{8a}R^{8b}$, —$(CH_2)_n$ OC(O)R$^9$, —(CH$_2$)$_n$NR$^{8a}$C(O)R$^9$ or —(CH$_2$)$_n$NR$^{8a}$C(O)NR$^{8a}$R$^{8b}$, wherein each said (C$_1$ to C$_6$) alkyl, (C$_2$ to C$_8$) alkenyl, (C$_2$ to C$_8$) alkynyl, (C$_1$ to C$_6$) alkoxy, (C$_3$ to C$_8$) cycloalkyl, (C$_2$ to C$_9$) cycloheteroalkyl, (C$_6$ to C$_{14}$) aryl, and (C$_2$ to C$_9$) heteroaryl is optionally substituted with at least one R$^{10}$ group;

each R$^7$ is independently H, or (C$_1$ to C$_6$) alkyl optionally substituted with at least one R$^{10}$ group;

R$^{8a}$ and R$^{8b}$ are each independently H, (C$_1$ to C$_6$) alkyl, (C$_3$ to C$_8$) cycloalkyl, (C$_2$ to C$_9$) cycloheteroalkyl, (C$_2$ to C$_9$) heteroaryl, or (C$_6$ to C$_{14}$) aryl wherein each said (C$_1$ to C$_6$) alkyl, (C$_3$ to C$_8$) cycloalkyl, (C$_2$ to C$_9$) cycloheteroalkyl, (C$_2$ to C$_9$) heteroaryl, and (C$_6$ to C$_{14}$) aryl is optionally substituted with at least one R$^{10}$ group;

each R$^9$ is independently (C$_1$ to C$_6$) alkyl, (C$_3$ to C$_8$) cycloalkyl, (C$_2$ to C$_9$) cycloheteroalkyl, (C$_2$ to C$_9$) heteroaryl, or (C$_6$ to C$_{14}$) aryl wherein each said (C$_1$ to C$_6$) alkyl, (C$_3$ to C$_8$) cycloalkyl, (C$_2$ to C$_9$) cycloheteroalkyl, (C$_2$ to C$_9$) heteroaryl, and (C$_6$ to C$_{14}$) aryl is optionally substituted with at least one R$^{10}$ group;

each R$^{10}$ is independently —OH, halogen, CF$_3$, (C$_1$ to C$_6$) alkyl, (C$_2$ to C$_8$) alkenyl, (C$_2$ to C$_8$) alkynyl, (C$_1$ to C$_6$) alkoxy, cyano, (C$_3$ to C$_{10}$) cycloalkyl, (C$_2$ to C$_9$) cycloheteroalkyl, (C$_6$ to C$_{14}$) aryl, (C$_2$ to C$_9$) heteroaryl, —(CH$_2$)$_n$NR$^{11a}$R$^{11b}$, —(CH$_2$)$_n$C(O)R$^{12}$, —(CH$_2$)$_n$C(O)NR$^{11a}$R$^{11b}$, —(CH$_2$)$_n$S(O)$_m$R$^{12}$, —(CH$_2$)$_n$S(O)$_m$NR$^{11a}$R$^{11b}$, —(CH$_2$)$_n$NR$^{11a}$S(O)$_m$R$^{12}$, —(CH$_2$)$_n$C(O)NR$^{11a}$R$^{11b}$, —(CH$_2$)$_n$OC(O)R$^{12}$, —(CH$_2$)$_n$NR$^{11a}$C(O)R$^{12}$ or —(CH$_2$)$_n$NR$^{11a}$C(O)NR$^{11a}$R$^{11b}$;

R$^{11a}$ and R$^{11b}$ are each independently H, (C$_1$ to C$_6$) alkyl, (C$_3$ to C$_8$) cycloalkyl, (C$_2$ to C$_9$) cycloheteroalkyl, (C$_2$ to C$_9$) heteroaryl, or (C$_6$ to C$_{14}$) aryl;

each R$^{12}$ is independently (C$_1$ to C$_6$) alkyl, (C$_3$ to C$_8$) cycloalkyl, (C$_2$ to C$_9$) cycloheteroalkyl, (C$_2$ to C$_9$) heteroaryl, or (C$_6$ to C$_{14}$) aryl;

each m is independently 1 or 2; and each n is independently 0, 1, 2, 3, or 4; or a pharmaceutically acceptable salt thereof.

17. The compound according to claim 16, wherein:

R$^1$ is (C$_1$ to C$_6$) alkyl, (C$_3$ to C$_8$) cycloalkyl, (C$_6$ to C$_{14}$) aryl, (C$_2$ to C$_9$) cycloheteroalkyl, or (C$_2$ to C$_9$) heteroaryl, wherein each said (C$_1$ to C$_6$) alkyl, (C$_3$ to C$_8$) cycloalkyl, (C$_6$ to C$_{14}$) aryl, (C$_2$ to C$_9$) cycloheteroalkyl, and (C$_2$ to C$_9$) heteroaryl is optionally substituted with at least one R$^6$ group;

R$^2$ is (C$_2$ to C$_9$) heteroaryl or (C$_6$ to C$_{14}$) aryl, each of which is optionally substituted with at least one R$^6$ group; and R, R$^3$ and R$^4$ are H; or a pharmaceutically acceptable salt thereof.

18. The compound according to claim 17, wherein:

R$^5$ is H or —CH$_3$; and each R$^6$ is independently —OH, halogen, CF$_3$, —(CH$_2$)$_n$NR$^{8a}$R$^{8b}$, (C$_1$ to C$_6$) alkyl, (C$_1$ to C$_6$) alkoxy, (C$_3$ to C$_8$) cycloalkyl, (C$_2$ to C$_9$) cycloheteroalkyl, (C$_6$ to C$_{14}$) aryl, (C$_2$ to C$_9$) heteroaryl, —(CH$_2$)$_n$C(O)R$^9$, —(CH$_2$)$_n$S(O)$_m$NR$^{8a}$R$^{8b}$, or —(CH$_2$)$_n$NR$^{8a}$C(O)NR$^{8a}$R$^{8b}$, wherein each said (C$_1$ to C$_6$) alkyl, (C$_1$ to C$_6$) alkoxy, (C$_3$ to C$_8$) cycloalkyl, (C$_2$ to C$_9$) cycloheteroalkyl, (C$_6$ to C$_{14}$) aryl, and (C$_2$ to C$_9$) heteroaryl is optionally substituted with at least one R$^{10}$ group; or a pharmaceutically acceptable salt thereof.

19. The compound according to claim 17, wherein R$^1$ is (C$_3$ to C$_8$) cycloalkyl, optionally substituted with at least one R$^6$ group, or a pharmaceutically acceptable salt thereof.

20. A pharmaceutical composition, comprising at least one compound according to claim 1, or a pharmaceutically acceptable salt thereof, and a pharmaceutically acceptable carrier.

21. A pharmaceutical composition, comprising at least one compound according to claim 11, or a pharmaceutically acceptable salt thereof, and a pharmaceutically acceptable carrier.

22. A pharmaceutical composition, comprising at least one compound according to claim 12, or a pharmaceutically acceptable salt thereof, and a pharmaceutically acceptable carrier.

23. A pharmaceutical composition, comprising at least one compound according to claim 13, or a pharmaceutically acceptable salt thereof, and a pharmaceutically acceptable carrier.

24. A pharmaceutical composition, comprising at least one compound according to claim 16, or a pharmaceutically acceptable salt thereof, and a pharmaceutically acceptable carrier.

25. A composition comprising a compound of claim 1; a second anti-cancer agent.

26. A method of treating a cancer in a subject, comprising administering to said subject an effective amount of a compound of claim 1, wherein the cancer is selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

27. A method of treating a cancer in a subject, comprising administering to said subject an effective amount of a compound of claim 1, wherein the cancer is selected from lung cancer (NSCLC and SCLC), breast cancer, ovarian cancer, colon cancer, rectal cancer, prostate cancer, cancer of the anal region, or a combination of one or more of the foregoing cancers.

28. A method of treating a non-cancerous condition in a subject, comprising administering to said subject an effective amount of a compound of claim 1, wherein the condition is selected from hyperplastic conditions comprising benign hyperplasia of the skin, psoriasis, and benign hyperplasia of the prostate.

* * * * *